(12) United States Patent
Blagg et al.

(10) Patent No.: US 6,180,627 B1
(45) Date of Patent: Jan. 30, 2001

(54) ANTITHROMBOTIC AGENTS

(75) Inventors: Julian Blagg; Alan Daniel Brown; Elisabeth Colette Louise Gautier; Julian Duncan Smith; Andrew Brian McElroy, all of Sandwich (GB)

(73) Assignee: Pfizer Inc., New York, NY (US)

( * ) Notice: Under 35 U.S.C. 154(b), the term of this patent shall be extended for 0 days.

(21) Appl. No.: 09/372,200

(22) Filed: Aug. 11, 1999

(51) Int. Cl.$^7$ .................. A61K 31/5355; C04D 413/12; C04D 403/12; A61P 7/02
(52) U.S. Cl. .................. 514/235.8; 514/252.02; 514/255.05; 514/255.01; 514/252.11; 544/120; 544/238; 544/295; 544/357; 544/405
(58) Field of Search .................. 514/252.02, 252.11, 514/255.01, 255.05, 235.8; 544/120, 238, 295, 357, 405

(56) References Cited

U.S. PATENT DOCUMENTS

| | | | |
|---|---|---|---|
| 5,958,925 | * | 9/1999 | Ross et al. .......... 514/252 |
| 6,004,966 | * | 12/1999 | Singh et al. .......... 514/258 |

FOREIGN PATENT DOCUMENTS

| | | | |
|---|---|---|---|
| 0623595 | 11/1994 | (EP) | ............ C07D/207/08 |
| 9513274 | 5/1995 | (WO) | ............ C07D/401/12 |
| 9618644 | 6/1996 | (WO) | ............ C07K/5/06 |
| 9701338 | 6/1997 | (WO) | ............ A61K/31/445 |
| 9730708 | 8/1997 | (WO) | ............ A61K/31/44 |
| 9740024 | 10/1997 | (WO) | ............ C07D/241/20 |
| 9808840 | 3/1998 | (WO) | ............ C07D/401/06 |
| 9809987 | 3/1998 | (WO) | ............ C07K/5/078 |
| 9816547 | 4/1998 | (WO) | ............ C07K/5/06 |
| 9847876 | 10/1998 | (WO) | ............ C07D/217/22 |
| 9911267 | 3/1999 | (WO) | ............ A61K/31/495 |

OTHER PUBLICATIONS

Bush, Cardiovascular Drug Rev., 9:247–263 (1991).
Sanderson et al., Bioorg. Med. Chem. Letters, 7:1497–1500 (1997).
Sanderson et al., Bioorg. Med. Chem. Letters 8:817–822 (1998).
Isaacs et al., Bioorg. Med. Chem. Letters 8:1719–1724 (1998).

* cited by examiner

Primary Examiner—Robert W. Ramsuer
Assistant Examiner—Sonya Wright
(74) Attorney, Agent, or Firm—Peter C. Richardson; Gregg C. Benson; Gregory P. Raymer

(57) ABSTRACT

Compounds of formula (I):

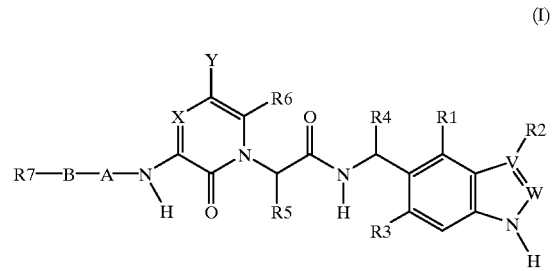

Are antithrombotic agents, having utility in a variety of therapeutic areas including the prevention and/or treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of aterio-venous shunts and blood vessel grafts (including coronary artery by-pass grafts); and restenosis and occlusion following angioplasty.

29 Claims, No Drawings

ANTITHROMBOTIC AGENTS

This application is filed claiming priority from co-pending British Provisional Application No. 9900801.3 filed Jan. 14, 1999 and British Provisional Application No. 9817819.7 filed Aug. 14, 1998.

This invention relates to a series of indole, indazole and benzimidazole derivatives, which are antithrombotic agents, having utility in a variety of therapeutic areas including the prevention and/or treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable fangina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); and restenosis and occlusion following angioplasty. They also have utility as an adjunct to thrombolytic therapy.

The compounds of the invention are potent and selective inhibitors of thrombin, which is the final serine protease enzyme in the coagulation cascade. The prime function of thrombin is the cleavage of fibrinogen to produce fibrin which forms linear insoluble polymers which, in turn, are cross-linked by factor XIIIa, itself activation of factors V and VIII earlier in the cascade. It also has important actions at the cellular level, where it acts on specific receptors to cause platelet aggregation, endothelial cell activation and fibroblast proliferation. Thus thrombin has a central regulatory role in haemostasis and thrombus formation.

Clearly then, potent, selective and orally bioavailable thrombin inhibitors represent an attractive target for the convenient therapeutic control of thrombosis. In addition, thrombin potently causes neurite retraction and therefore a thrombin inhibitor is of potential therapeutic utility in the treatment of acute and chronic neurodegenerative disorders. Furthermore, the compounds disclosed herein are of potential value in the treatment of inflammatory disorders and scarring, and in wound healing.

Because of their potential as substrate mimics, arginine derivatives have (see Cardiovascular Drug Rev., 1991, 9, 247). In turn, other research groups have sought to express the basic arginine function in alternative structures; for example, WO-A-95/13274 discloses amidinophenylalanine and amidinopyridylalanine derivatives as antithrombotic agents. Further variations on the theme of arginine mimicry amongst thrombin inhibitors are represented by, inter alia, the guanidinyl- and amidinyl-substituted heterocyclic compounds disclosed in EP-A-0623595. In general, however, compounds containing the basic arginine, amidine or guanidine function have poor oral bioavailability and are poorly selective since they inhibit trypsin as well as thrombin.

Thrombin inhibitors containing a 3-amino-2-pyridone acetamide template have been disclosed by Corvas Int Inc in PCT patent reference WO 96/18644 and COR Therapeutics Inc in WO 98/16547. Compounds of the type disclosed within WO 96/18644 and WO 98/16547 contain a guanidino function as an arginine mimic and are likely to be irreversible inhibitors of thrombin by virtue of the presence of an aldehyde or an activated carbonyl fragment.

Thrombin inhibitors containing a 3-amino-2-pyridone or pyrazinone acetamide fragment and an arginine mimic which is not a guanidine or amidine have been disclosed by Merck in PCT patent reference WO 97/40024, WO 97/01338, WO 97/30708, WO 98/09987, WO 99/11267 and in Bioorg Med Chem, Letters. 1997, 7, p1497; 1998, 8, p1719, 1998, 8, p817.

The present inventors have now found a class of non basic or weakly basic bicyclic heterocyclic arginine mimics which are highly potent, selective, reversible thrombin inhibitors with good oral bioavailability.

Accordingly, the present invention provides compound of formula (I):

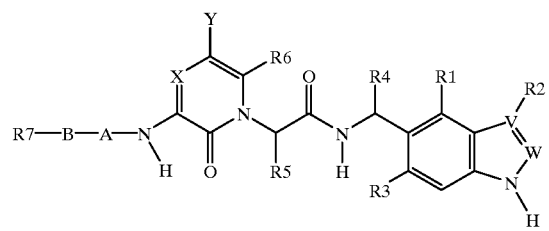

wherein:
R$^1$ is hydrogen, C$_1$–C$_4$ alkyl, perfluoro C$_1$–C$_4$ alkyl, OC$_1$–C$_4$ alkyl, fluoro or chloro;
R$^2$ is hydrogen, CH$_3$, or CF$_3$;
R$^3$ is hydrogen, C$_1$–C$_4$ alkyl, perfluoro C$_1$–C$_4$ alkyl, OC$_1$–C$_4$ alkyl, fluoro or chloro;
R$^4$ is hydrogen or C$_1$–C$_4$ alkyl;
R$^5$ is hydrogen or C$_1$–C$_4$ alkyl;
R$^6$ is hydrogen, fluoro or chloro;
C$_1$–C$_6$ alkyl, C$_3$–C$_6$ carbocyclic (eg cyclopropyl), C$_3$–C$_6$ carbocyclicC$_1$–C$_4$ alkyl wherein the alkyl and carbocyclic may optionally be substiututed by C$_1$–C$_4$ alkyl or fluoro (eg perfluoro C$_1$–C$_4$ alkyl), and wherein the carbocycle contains zero, one or more double bonds;
or R$^5$ and R$^6$ together form a bridging chain containing 2 or 3 carbon atoms;
Y is hydrogen, chloro, fluoro, bromo, methyl or CF$_3$;
W and X are independently CH, CF, CCl or N;
V is C or N;
B—A— is any one of the following fragments:
B—C(R$^8$)(R$^9$)—
B—CH$_2$—C(R$^8$)(R$^9$)—
B—C(R$^8$)(R$^9$)—CH$_2$—
B—CH$_2$—C(R$^8$)(R$^9$)—CH$_2$—
B—C(R$^8$)(R$^9$)—CH$_2$—CH$_2$—
B—CH$_2$—CH$_2$—C(R$^8$)(R$^9$)—
wherein:
R$^8$ and R$^9$ are independently hydrogen, —(CH$_2$)$_m$N(R$^{10}$)(R$^{11}$), —CH$_2$O—(CH$_2$)$_2$N(R$^{10}$)(R$^{11}$), or R$^8$ and R$^9$ together form a 4 to 6 membered ring containing a nitrogen atom present as N(R$^{12}$); and m is 0, 1 and 2 (preferably m=1) except where A represents —C(R$^8$)(R$^9$)— when m is 1 or 2;
R$^{10}$ and R$^{11}$ are independently selected from hydrogen or C$_1$–C$_4$ alkyl optionally containing an oxygen atom in the chain or at the end of the chain;
or R$^{10}$ and R$^{11}$ together with the nitrogen atom to which they are bonded form a 4 to 6 membered saturated heterocyclic ring wherein when the ring is six membered it may optionally contain one oxygen atom or a nitrogen atom present as N(R$^{12}$);
R$^{12}$ is hydrogen or C$_1$–C$_4$ alkyl optionally containing an oxygen atom in the chain or at the end of the chain;
B is phenyl or a 5 to 6 membered aromatic heterocyclic ring containing up to two heteroatoms independently selected from oxygen, sulphur and nitrogen;
R$^7$ (when B is phenyl or an aromatic heterocycle) is one or more of hydrogen, C$_1$–C$_6$ alkyl, perfluoro $C_1$–$C_6$ alkyl, $C_1$–$C_6$ alkyl, perfluoro $C_1$–$C_6$ alkyl, fluoro, chloro, or any one of the following fragments: $(CH_2)_p$—O—$(CH_2)_2N(R^{10})(R^{11})$ where $R^{10}$ and $R^{11}$ are as defined above, and p is 0 or 1;

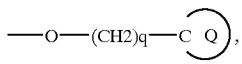

where Q, together with the C atom to which it is joined, is a 5 or 6 membered heterocyclic ring (preferably saturated) containing one nitrogen atom, said heterocyclic ring being optionally substituted by $C_1$–$C_4$ alkyl, and q is 1 or 2; —$(CH_2)_r$—$C(R^{13})(R^{14})$—$(CH_2)_s$—$N(R^{15})(R^{16})$ where r and s are independently 0, 1 or 2 and $R^{13}$ and $R^{14}$ are independently hydrogen or $C_1$–$C_4$ alkyl optionally containing one oxygen atom in the chain or at the end of the chain, or $R^{13}$ and $R^{14}$ together with the carbon atom to which they are bonded for a 4 to 6 membered carbocyclic saturated ring;

$R^{15}$ and $R^{16}$ are independently selected from hydrogen or $C_1$–$C_4$ alkyl optionally containing an oxygen atom in the chain or at the end of the chain, or $R^{15}$ and $R^{16}$ together with the nitrogen atom to which they are bonded form a 4 to 6 membered saturated heterocyclic ring;

or one of $R^{13}$ or $R^{14}$ and one of $R^{15}$ or $R^{16}$ together with the carbon and nitrogen atoms to which they are bonded form a 4 to 6 membered saturated heterocyclic ring in which case the other of $R^{13}$ or $R^{14}$ is hydrogen or $C_1$–$C_4$ alkyl, and the other of $R^{15}$ or $R^{16}$ is hydrogen or $C_1$–$C_4$ alkyl optionally containing an oxygen atom in the chain or at the end of the chain;

or wherein $R^7$—B represents any one of the following bicyclic fragments where $R^{12}$ is as defined above

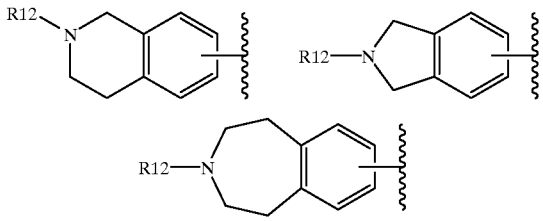

with the proviso that $R^7$, $R^8$ and $R^9$ cannot all be hydrogen, and only one of $R^7$, $R^8$ and $R^9$ contains one nitrogen atom or, when $R^8$ and $R^9$ together form a ring, said ring contains only one nitrogen atom with the proviso that one of $R^8$ or $R^9$ may be the following fragment which contains two nitrogen atoms:

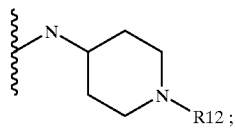

(the above proviso does not apply to the subject matter of the following paragraph) or, B is a 4 to 7 membered saturated or partially saturated heterocyclic ring containing one or two heteroatoms wherein at least one is a nitrogen and the other is independently selected from oxygen, sulphur and nitrogen; and wherein $R^7$ (when B is a saturated or partially saturated heterocycle) is one or more of $C_1$–$C_6$ alkyl or $C_3$–$C_6$ carbocyclic or $C_3$–$C_6$ carbocyclic $C_1$–$C_4$ alkyl, said carbocyclic containing zero one or more double bonds wherein said alkyl and carbocyclic optionally contain one heteratom selected from oxygen, sulphur and nitrogen (i.e. for alkyl the heteroatoms will be in the chain or at the end of the chain) and are further optionally substituted by one or more fluoro, or $C_1$–$C_4$ alkyl optionally containing an oxygen in the alkyl chain or at the end of the chain;

and pharmaceutically acceptable salts thereof.

Thus in accordance with the invention, the basic (nitrogen containing) centre can be located at various positions in formula 1 with the proviso that each compound of the invention should contain a single basic centre with a pKa (defined as the log of the ionisation constant of the corresponding conjugate acid) greater than 6 (such as 6.5).

In the above definition, unless otherwise indicated alkyl and alkoxy groups having three or more carbon atoms may be straight-chain or branched chain.

Herein $C_1$–$C_4$ alkyl or $C_1$–$C_4$ alkyl containing fragment means methyl, ethyl, n-propyl, isopropyl, n-butyl, sec-butyl, isobutyl and tert-butyl; and $C_{1-6}$ alkyl further includes the various straight and branched pentyl and hexyl fragments (although $C_1$–$C_4$ is preferred).

$C_3$–$C_6$cycloalkyl (used hereinafter means cyclopropyl, cyclobutyl, cyclopenyl and cyclohexyl.

Herein $C_1$–$C_6$ alkyl optionally containing an oxygen atom in the chain or at the end of the chain includes moieties of the formula —$(CH_2)_t$—O—$(CH_2)_u$—$CH_3$ where t is 1 to 5 and u is 0 to 4 and in $C_1$–$C_4$ alkyl of the same definition, t is 1,2 or 3 and u is 0,1 or 2.

The following independently represent preferred subclasses of the compounds of formula I.

$R^1$ is hydrogen or methyl (most preferably hydrogen);

$R^2$ is hydrogen or methyl;

$R^3$ is hydrogen or methyl (most preferably hydrogen);

$R^4$ is hydrogen.

$R^5$ is hydrogen $R^6$ is $C_1$–$C_6$ alkyl (eg methyl), $C_3$–$C_6$ carbocyclic optionally substituted by fluoro, or $R^5$ and $R^6$ together form a bridging chain containing 2 or 3 carbon atoms.

Y is hydrogen, chloro or bromo.

V is C

W is CH or N.

X is CH or N.

$R^{10}$ and $R^{11}$ independently represent hydrogen, $C_1$–$C_4$ alkyl optionally containing an oxygen atom in the chain, or $R^{10}$ and $R^{11}$ together with the nitrogen to which they are bonded form a 5 to 6 membered heterocyclic ring wherein when the ring is six membered it may optionally contain one oxygen or a nitrogen atom present as $N(R^{12})$.

$R^{12}$ is hydrogen or $C_1$–$C_4$ alkyl optionally containing an oxygen atom in the chain or at the end of the chain.

B is phenyl or a six membered aromatic heterocyclic ring containing one nitrogen atom, wherein said phenyl or heterocyclic ring may optionally be substituted by fluoro, chloro, $C_1$–$C_4$ alkyl or $OC_1$–$C_4$ alkyl.

Also in a preferred subclass of the compounds of formula (I), B—A-represents B—$CH_2$—$C(R^8)(R^9)$ —$(CH_2)_m$N$(R^{10})(R^{11})$, —$CH_2$O —$(CH_2)_2N(R^{10})(R^{11})$, where $R^8$ and $R^9$ are independently hydrogen, or $R^8$ and $R^9$ together form a 4 to 6 membered ring containing $N(R^{12})$ m is 0, 1 and 2, and $R_{10}$ and $R_{11}$ are as defined above. More preferably, B is preferably phenyl when B—A represents B—$CH_2$—$(R^8)$ $(R^9)$.

When C* is chiral in B—CH$_2$—C*(R$^8$)(R$^9$), then the S-enantiomer is preferred.

In a preferred sub-class of compounds B is phenyl and R$^7$ is —(CH$_2$)$_r$—C(R$^{13}$)(R$^{14}$ (CH$_2$)$_s$—N(R$^{15}$)(R$^{16}$) wherein r, s, and R$^{13}$ to R$^{16}$ are as defined hereinbefore.

When B is phenyl, preferably R$^7$ is connected at the 3 position of the phenyl ring (relative to connection to the 'A' moiety at position 1).

In another preferred sub-class of compounds B is a saturated or partially saturated 4 to 7 membered heterocyclic ring containing one or two heteroatoms, at least one of which is nitrogen and the other is selected from oxygen, sulphur and nitrogen; and R$^7$ is R$_{17}$ which is substituted on the nitrogen of the heterocyclic ring and is selected from one or more of C$_1$–C$_6$ alkyl, C$_3$–C$_6$ carbocyclic or C$_3$–C$_6$ carbocyclic C$_1$–C$_4$ alkyl, said carbocyclic containing zero, one or more double bonds wherein said alkyl and carbocyclic optionally contain one heteroatom selected from oxygen, sulphur and nitrogen and are further optionally substituted by one or more fluoro atoms or C$_1$–C$_4$ alkyl optionally containing an oxygen in the alkyl chain or at the end of the chain. More preferably the saturated or partially saturated heterocycle is furthermore optionally substituted by R$_{18}$ which is independently selected from one or more of C$_1$–C$_6$ alkyl, per fluoro C$_1$–C$_6$ alkyl wherein said alkyl optionally contains an oxygen atom in the chain or at the end of the chain. Still more preferably the heterocyclic ring is a 5 to 6 membered saturated heterocyclic ring, and B—A is B—C (R$^8$)(R$^9$) wherein R$^8$ and R$^9$ are as defined hereinbefore. Preferably also, the heterocyclic ring is connected at the 2-position (i.e. adjacent the nitrogen) to the 'A' moiety. Preferably C$_3$–C$_6$ carbocyclic and C$_3$–C$_6$ carbocyclic C$_1$–C$_4$ alkyl moiety of R$^{17}$ is an optionally substituted C$_3$–C$_6$ cycloalkyl (such as cyclopentyl) or C$_3$–C$_6$ cycloalkyl C$_1$–C$_4$ alkyl, (such as cyclopropylmethyl). More preferably R$^{17}$ is cyclopropylmethyl. More particularly, preferred radicals of R$^7$—B—A are:

and (a)

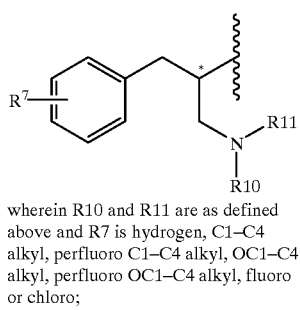

wherein R10 and R11 are as defined above and R7 is hydrogen, C1–C4 alkyl, perfluoro C1–C4 alkyl, OC1–C4 alkyl, perfluoro OC1–C4 alkyl, fluoro or chloro;

(b)

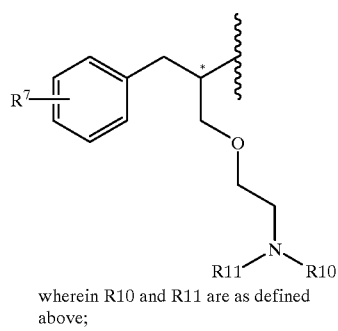

wherein R10 and R11 are as defined above;

(c)

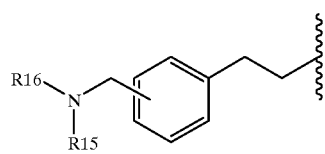

wherein R15 and R16 are as defined above;

(d)

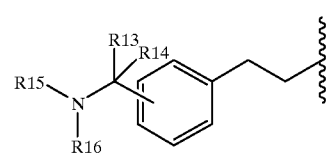

wherein R13 to R16 are as defined above;

(e)

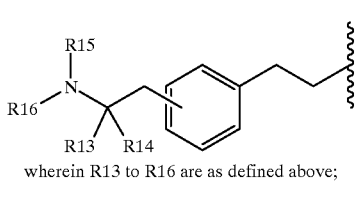

wherein R13 to R16 are as defined above;

(f)

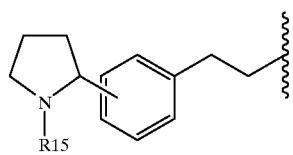

wherein R15 is hydrogen or C1–C4 alkyl optionally containing oxygen in the chain or at the end of the chain;

(g)

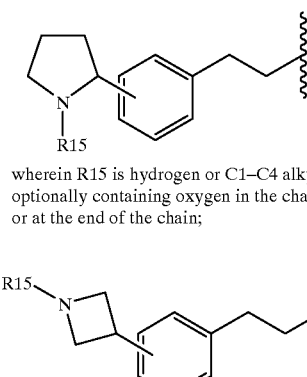

wherein R15 is hydrogen or C1–C4 alkyl optionally containing oxygen in the chain or at the end of the chain;

(h)

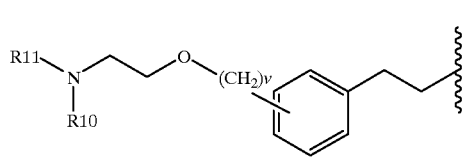

wherein R10 and R11 are as defined above, and v is 0 or 1:

(i)

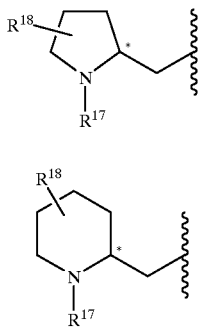

(j)

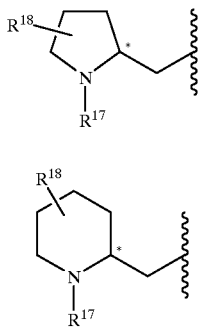

(k)
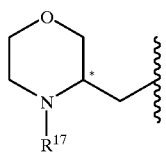
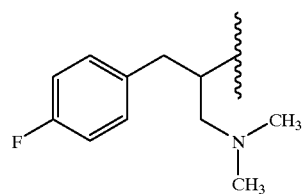
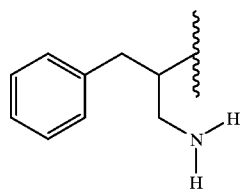
Wherein R17 and R18 in (i), (j) and (k) are as defined herebefore. Examples of radicals (a) to (k) are shown below.
radical (b)
radical (a)
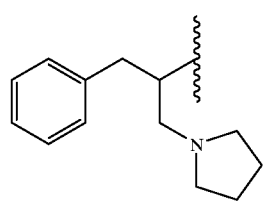
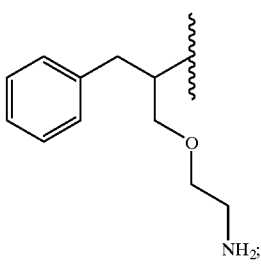
(wherein the S-enantiomer is preferred for fragments (a) and (b)).
radical (c)
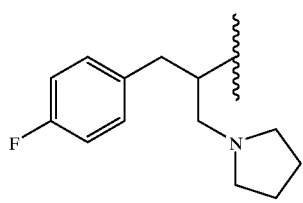
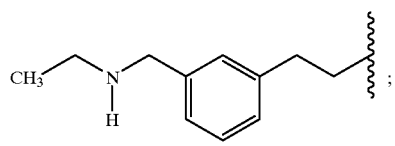
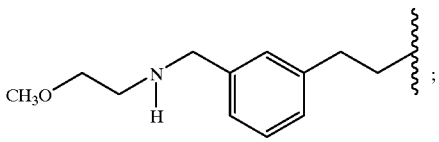
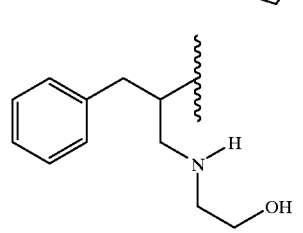
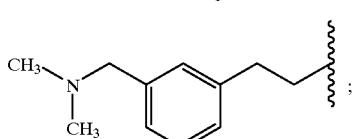
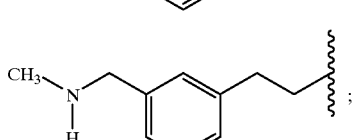
radical (d)
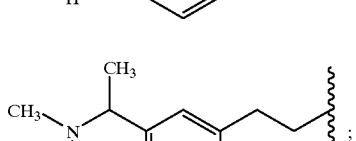
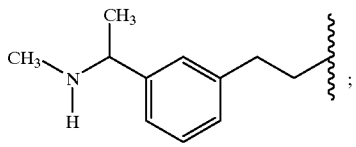

-continued radical (e)
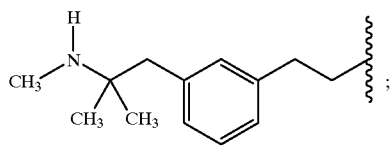

radical (f)
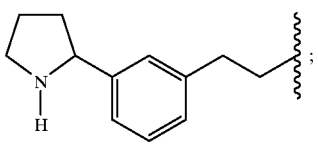

radical (g)
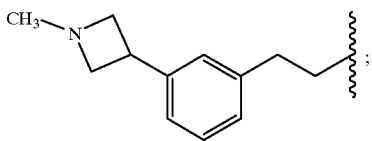

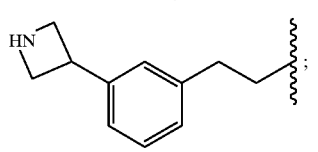

radical (h)
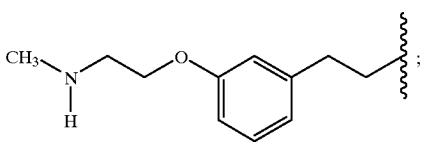

radical (l)
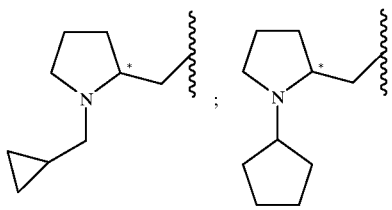

radical (j)
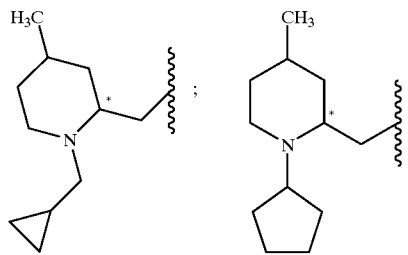

radical (k)
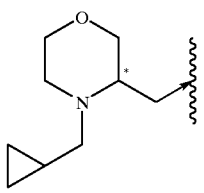

Preferred compounds according to the invention are as follows:

(R,S)-2-[3-[(2-amino-1-benzylethyl)amino]-6-methyl-2-oxo-1(2H)-pyridinyl]-N-(1H-indol-5-ylmethyl)acetamide;

2-[3-(3-[(dimethylamino)methyl]phenethylamino)-6-methyl-2-oxo-1(2H)-pyrazinyl]-N-(1H-indol-5-ylmethyl)acetamide;

2-[3-chloro-5-(3-[(dimethylamino)methyl]phenethylamino)-2-methyl-6-oxo-1(6H)-pyrazinyl]-N-(1H-indol-5-ylmethyl)acetamide;

2-[3-[(1S)-1-benzyl-2-(dimethylamino)ethyl]amino-6-methyl-2-oxo-1(2H)-pyrazinyl]-N-(1H-indol-5-ylmethyl)acetamide;

2-[3-[(1S)-1-benzyl-2-(dimethylamino)ethyl]amino-5-chloro-6-methyl-2-oxo-1(2H)-pyrazinyl]-N-(1H-indol-5-ylmethyl)acetamide;

2-[3-{[(2R,S)-3-(dimethylaminoy2-phenylpropyl]amino}-6-methyl-2-oxo-1(2H)-pyrazinyl]-N-(1H-indol-5-ylmethyl)acetamide;

N-[(3-Methyl-1H-indol-5-yl)methyl]-2-[6-methyl-3-([3-[(methylamino)methyl]phenethyl]amino)-2-oxo-1(2H)-pyrazinyl]acetamide;

2-[3{[(1S)-1-benzyl-2-(dimethylamino)ethyl]amino}-6-methyl-2-oxo-1(2H)-pyrazinyl]-N-[(6-methyl-1H-indazol-5-yl)methyl]acetamide;

2-[3-{[3-(3-azetidinyl)phenethyl]amino}-6-methyl-2-oxo-1H (2H)-pyrazinyl]-N-[(3-methyl-1H-indol-5-yl)methyl]acetamide;

N-[(3-methyl-1H-indol-5-yl)methyl]-2-[6-methyl-3-{[3-(1-methyl-3-azetidinyl)phenethyl]amino}-2-oxo-1(2H)-pyrazinyl]acetamide;

2-[3-[(3-{[(2-methoxyethyl)amino]methyl}phenethyl)amino]-methyl-2-oxo-1(2H)-pyrazinyl]-N-[(3-methyl-1H-indol-5-yl)methyl]acetamide;

2-[3-({[(2R)-1-(cyclopropylmethyl)pyrrolidinyl]methyl}amino)-6-metbyl-2-oxo-1(2H)-pyrazinyl]-N-[(3-methyl-1H-indol-5-yl)methyl]acetamide;

2-[3-({[(2R)-1-cyclopentyl pyrrolidinyl]methyl}amino)-6-methyl-2-oxo-1(2H)-pyrazinyl]-N-[(3-methyl-1H-indol-5-yl)methyl]acetamide;

N-[(3-methyl-1H-indol-5-yl)methyl]-2-[6-methyl-2-oxo-3-({[(2R)-1-tetrahydro-2H-pyran-4-ylpyrrolidinyl]methyl}amino)-1(2H)-pyrazinyl]acetamide;

N-[(3-methyl-1H-indol-5-yl)methyl]-2-[6-methyl-3-[({(2R)-1-[(1-methylcyclopropyl)methyl]pyrrolidinyl}methyl)amino]-2-oxo-1(2H)-pyrazinyl]acetamide;

2-[3-({[(2R)-1-(2-methoxyethyl)pyrrolidinyl]methyl}amino)-6-methyl-2-oxo-1(2H)-pyrazinyl]-N-[(3-methyl-1H-indol-5-yl)methyl]acetamide;

N-[(3-methyl-1H-indol-5-yl)methyl]-2-[6-methyl-3-({[(2R)-1-neopentylpyrrolidinyl]methyl}amino)-2-oxo-1(2H)-pyrazinyl]acetamide;

2-[3-({[(2R)-1-isobutylpyrrolidinyl]methyl}amino)-6-methyl-2-oxo-1(2H)-pyrazinyl]-N-[(3-methyl-1H-indol-5-yl)methyl]acetamide;

2-[3-({[(2R)-1-(2-methoxyethyl)pyrrolidinyl]methyl}amino)-6-methyl-2-oxo-1(2H)-pyrazinyl]-N-[(3-methyl-1H-indol-5-yl)methyl]acetamide;

2-[3-({[(2R)-1-cyclopentyl pyrrolidinyl]methyl}amino)-6-methyl-2-oxo-1(2H)-pyrazinyl]-N-[(3-methyl-1H-indol-5-yl)methyl]acetamide;

2-[3-({[(2R)-1-(cyclopropylmethyl)piperidinyl]methyl}amino)-6-methyl-2-oxo-1(2H)-pyrazinyl]-N-[(3-methyl-1H-indol-5-yl)methyl]acetamide;

and pharmaceutically acceptable salts thereof.

Preferably the compounds of the invention are selected from:

2-[3-(3-[(dimethylamino)methyl]phenethylamino)-6-methyl-2-oxo-1(2H)-pyrazinyl]-N-(1H-indol-5-ylmethyl)acetamide;

2-[3-[(1S)-1-benzyl-2-(dimethylamino)ethyl]amino-6-methyl-2-oxo-1(2H)-pyrazinyl]-N-(1H-indol-5-ylmethyl)acetamide;

N-[(3-Methyl-1H-indol-5-yl)methyl]-2-[6-methyl-3-([3-[(methylamino)methyl]phenethyl]amino)-2-oxo-1(2H)-pyrazinyl]acetamide;

2-[3-[(3-{[(2-methoxyethyl)amino]methyl}phenethyl)amino]-6-methyl-2-oxo-1(2H)-pyrazinyl]-N-[(3-methyl-1H-indol-5-yl)methyl]acetamide;

2-[3-({[(2R)-1-(cyclopropylmethyl)pyrrolidinyl]methyl}amino)-6-methyl-2-oxo-1(2H)-pyrazinyl]-N-[(3-methyl-1H-indol-5-yl)methyl]acetamide;

2-[3-({[(2R)-1-cyclopentyl pyrrolidinyl]methyl}amino)6-methyl-2-oxo-1(2H)-pyrazinyl]-N-[(3-methyl-1H-indol-5-yl)methyl]acetamide;

2-[3-({[(2R)-1-isobutylpyrrolidinyl]methyl}amino)-6-methyl-2-oxo-1(2H)-pyrazinyl]-N-[(3-methyl-1H-indol-5-yl)methyl]acetamide;

and pharmaceutically acceptable salts thereof.

It will be appreciated that many compounds of formula (I) contain one or more asymmetric centres and will therefore exist in the form of optical isomers. The present invention also includes within its scope all such enantiomers and mixtures thereof, including racemic mixtures thereof. In addition all possible diastereomeric forms (individual diastereoisomers and mixtures thereof) of compounds of formula I are included within the scope of the invention. Thus, for example, when $R^8$ and $R^9$ are different, then C* of the following fragment. B—C*($R^8$)($R^9$)—, B—CH$_2$—C*($R^8$)($R^9$)—, B—C*($R_8$)($R^9$)—CH$_2$—, B—CH$_2$—C*($R^8$)($R^9$)—CH$_2$—, B—C($R^8$)($R^9$)—CH$_2$—CH$_2$—, and B—CH$_2$—CH$_2$—C*($R^8$)($R^9$) will form an asymmetric centre.

In compounds containing the fragment B—C*($R^8$)($R^9$)—, the S-enantiomer has been found to be substantially more active than the R-enantiomer. In radicals (a) and (b), the S-enantiomer is preferred, in radicals (i) and (j) the R-enantiomer is preferred (wherein the chiral carbon is indicated by an asterix) while in radical (k) the S enantiomer is preferred.

A further aspect of the invention provides compounds of formula(I ):

(Iα)

wherein:

$R^1$ is hydrogen, $C_1$–$C_4$ alkyl, perfluoro $C_1$–$C_4$ alkyl, $OC_1$–$C_4$ alkyl, fluoro or chloro;

$R^2$ is hydrogen, $CH_3$, or $CF_3$;

$R^3$ is hydrogen, $C_1$–$C_4$ alkyl, perfluoro $C_1$–$C_4$ alkyl, $OC_1$–$C_4$ alkyl, fluoro or chloro;

$R^4$ is hydrogen or $C_1$–$C_4$ alkyl;

$R^5$ is hydrogen or $C_1$–$C_4$ alkyl;

$R^6$ is hydrogen, cyclopropyl, $C_1$–$C_4$ alkyl, perfluoro $C_1$–$C_4$ alkyl, fluoro or chloro;

or $R^5$ and $R^6$ together form a bridging chain containing 2 or 3 carbon atoms;

Y is hydrogen, chloro, fluoro, bromo, methyl or $CF_3$;

W and X are independently CH, CF, CCl or N;

B—A— is any one of the following fragments:

B—C($R^8$)($R^9$)—

B—CH$_2$—C($R^8$)($R^9$)—

B—C($R^8$)($R^9$)—CH$_2$—

B—CH$_2$—C($R^8$)($R^9$)—CH$_2$—

B—C($R^8$)($R^9$)—CH$_2$—CH$_2$—

B—CH$_2$—CH$_2$—C($R^8$)($R^9$)— wherein:

$R^8$ and $R^9$ are independently hydrogen, —(CH$_2$)$_m$N($R^{10}$)($R^{11}$), —CH$_2$O—(CH$_2$)$_2$N($R^{10}$)($R^{11}$), or $R^8$ and $R^9$ together form a 4 to 6 membered ring containing a nitrogen atom present as N($R^{12}$); and m is 0,1 and 2 (preferably m=1) except where A represents —C($R^8$)($R^9$)— when m is 1 or2;

$R^{10}$ and $R^{11}$ are independently selected from hydrogen or $C_1$–$C_4$ alkyl optionally containing an oxygen atom in the chain or at the end of the chain; or $R^{10}$ and $R^{11}$ together with the nitrogen atom to which they are bonded form a 4 to 6 membered saturated heterocyclic ring wherein when the ring is six membered it may optionally contain one oxygen atom or a nitrogen atom present as N($R^{12}$);

$R^{12}$ is hydrogen or $C_1$–$C_4$ alkyl optionally containing an oxygen atom in the chain or at the end of the chain;

B is phenyl or a 5 or 6 membered aromatic heterocyclic ring containing up to two heteroatoms independently selected from oxygen, sulphur and nitrogen;

$R^7$ is one or more of hydrogen, $C_1$–$C_4$ alkyl, perfluoro $C_1$–$C_4$ alkyl, $OC_1$–$C_4$ alkyl, perfluoro $OC_1$–$C_4$ alkyl, fluoro, chloro, or any one of the following fragments:
—O—(CH$_2$)$_2$N($R^{10}$)($R^{11}$) where $R^{10}$ and $R^{11}$ are as defined above —(CH$_2$)r—C($R^{13}$)($R^{14}$)—(CH$_2$)S—N($R^{15}$)($R^{16}$) where r and s are independently 0, 1 or 2 and $R^{13}$ and $R^{14}$ are independently hydrogen or $C_1$–$C_4$ alkyl, or $R^{13}$ and $R^{14}$ together with the carbon atom to which they are bonded form a 4 to 6 membered carbocyclic saturated ring;

$R^{15}$ and $R^{16}$ are independently selected from hydrogen or $C_1$–$C_4$ alkyl optionally containing an oxygen atom in the chain or at the end of the chain, or together $R^{15}$ and $R^{16}$ together with the nitrogen atom to which they are bonded form a 4 to 6 membered saturated hetorocyclic ring;

or one of $R^{13}$ or $R^{14}$ and one of $R^{15}$ or $R^{16}$ together with the carbon and nitrogen atoms to which they are bonded form a 4 to 6 membered saturated heterocyclic ring in which case the other of $R^{13}$ or $R^{14}$ is hydrogen or $C_1$–$C_4$ alkyl, and the other of $R^{15}$ or $R^{16}$ is hydrogen or $C_1$–$C_4$ alkyl optionally containing an oxygen atom in the chain or at the end of the chain;

or wherein $R^7$—B represents any one of the following bicyclic fragments where $R^{12}$ is as defined above

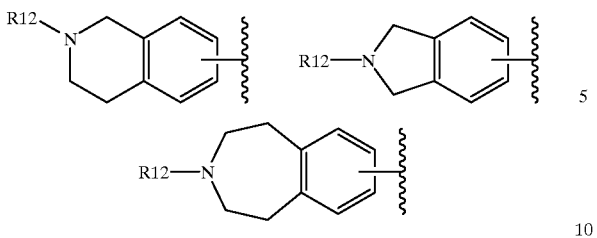

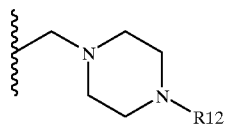

with the proviso that $R^7$, $R^8$ and $R^9$ cannot all be hydrogen, and only one of $R^7$, $R^8$ and $R^9$ contains one nitrogen atom or, when $R^8$ and $R^9$ together form a ring, said ring contains only one nitrogen atom with the proviso that one of $R^8$ or $R^9$ may be the following fragment which contains two nitrogen atoms:

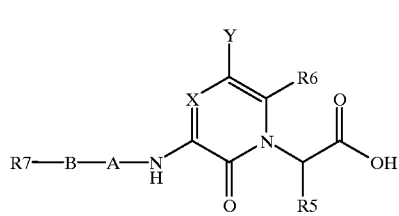

and pharmaceutically acceptable salts thereof.

Another aspect of the present invention provides processes for the preparation of compounds of the general formula (I), their pharmaceutically acceptable salts and acceptable solvates of either entity, as illustrated below. It will be appreciated by persons skilled in the art that, within the various processes described, the order of the synthetic steps employed may be varied and will depend, inter alia on factors such as the nature of other functional groups present in a particular substrate, the availability of key intermediates, and the protecting group strategy (if any) to be adopted. Clearly, such factors will also influence the choice of reagent for use in the said synthetic steps. It will also be appreciated that various standard transformations within certain compounds of formula (I) will provide other compounds of formula (I); examples are reductive alkylations of N-unsubstituted and N-monosubstituted amines with an appropriate aldehyde or ketone and dealkylation of N-methylamines by treatment with α-chloroethylchloroformate followed by methanolysis.

Moreover, persons skilled in the art will be aware of variations of, and alternatives to, those processes described hereinafter in the Examples and Preparations section which allow the compounds defined by formula (I) to be obtained.

Accordingly in a further aspect of the present invention there is provided processes for preparing the compounds of general formula (I) and (1 ), and pharmaceutically acceptable salts thereof comprising:

(a) coupling of an acid of formula (II)

(II)

with a heterocyclic amine of formula (III)

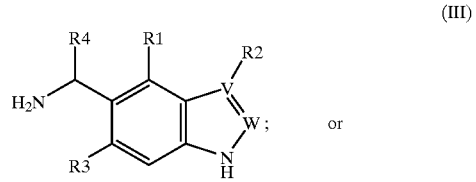

(III)

or (b) coupling a heterocycle of formula (XII)

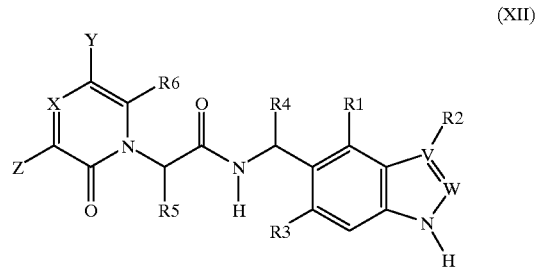

(XII)

wherein Z is a suitable leaving group, such as halogen, with an amine of formula (V)

$$R_7—B—A—NH_2 \quad (V);$$

or (c) coupling a heterocycle of formula (1c)

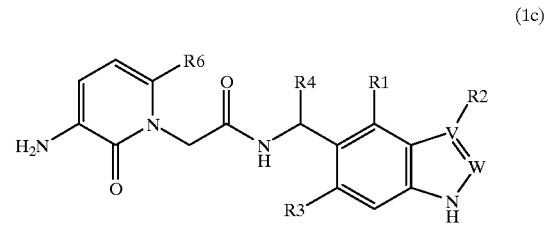

(1c)

with a carbonyl of formula (XXXVII)

$$R_7—B—A_1—C(O)—R_8 \quad (XXXVII);$$

wherein $A_1$ is $C(R^8)(R^9), CH_2C(R^8)(R^9)$ or $C(R^8)(R^9)CH_2$ in the presence of a reducing agent; and optionally converting into a pharmaceutically acceptable salt.

General Method A

Compounds of the general formula (Ia) (Scheme I) may be prepared by coupling of the acid (II) with the appropriate heterocyclic amine (III) (Scheme 1). The coupling may be achieved using conventional amide bond forming techniques, in particular any one of a number of amino acid coupling variations. For example, the acid (II) may be activated using a carbodiimide such as 1-(3-dimethylaminopropyl)-3-ethylcarbodiimide hydrochloride optionally in the presence of 1-hydroxybenzotriazole hydrate and or a catalyst such as 4-dimethylaminopyridine. Such couplings may be performed in a suitable solvent such as dichloromethane or N,N-dimethylacetamide, optionally in the presence of a tertiary amine such as N-methylmorpholine or N,N-diisopropylamine at 0° C.

Compounds of the general formula (II) may be prepared from compounds of the general formula (IV) by hydrolysis or hyrogenation of the carboxylic acid ester and dechlorination of the pyrazinone ring (where $R^{17}$ is as an aryl moiety or an alkyl moiety susceptible to hydrolysis to form the corresponding carboxylic acid). This conversion may be achieved in a single step where the carboxylic acid ester is removed by catalytic hydrogenation (eg $R^{17}$=benzyl). For example a compound of the general formula (II) can be obtained from a compound of the general formula (IV) where $R^{17}$=benzyl by treatment with a catalytic quantity of Pearlmans catalyst under an atmosphere of hydrogen (preferably 60 psi) in a suitable solvent such as methanol, at room temperature for 2 to 24 hours. Alternatively a compound of the general formula (IV) may be subject to ester hydrolysis according to the plethora of methods currently available. For example treatment with lithium hydroxide or sodium hydroxide in a mixture of methanol, THF and water at room temperature. Subsequent reduction of the pyrazinone chlorine substituent may be carried out by treatment with a suitable active metal catalyst under an atmosphere of hydrogen for example: Pearlmans catalyst under an atmosphere of hydrogen as described above or by transfer hydrogenation methodology for example: treatment with ammonium formate in methanol, ethanol or isopropanol in the presence of a catalytic amount of palladium on carbon catalyst.

Compounds of the general formula (IV) may be prepared by treatment of compounds of the general formula (VI) with a primary amine (V) in a solvent such as ethyl acetate or THF at reflux for 6 to 24 hrs in the presence of a suitable tertiary amine base for example triethylamine or N,N-diisopropylethylamine.

Compounds of the general formula (VI) may be prepared from a suitable ester derivative of glycine (VIII) according to the method of Hoornaert (J. Het Chem. 1983, 20, 919,).

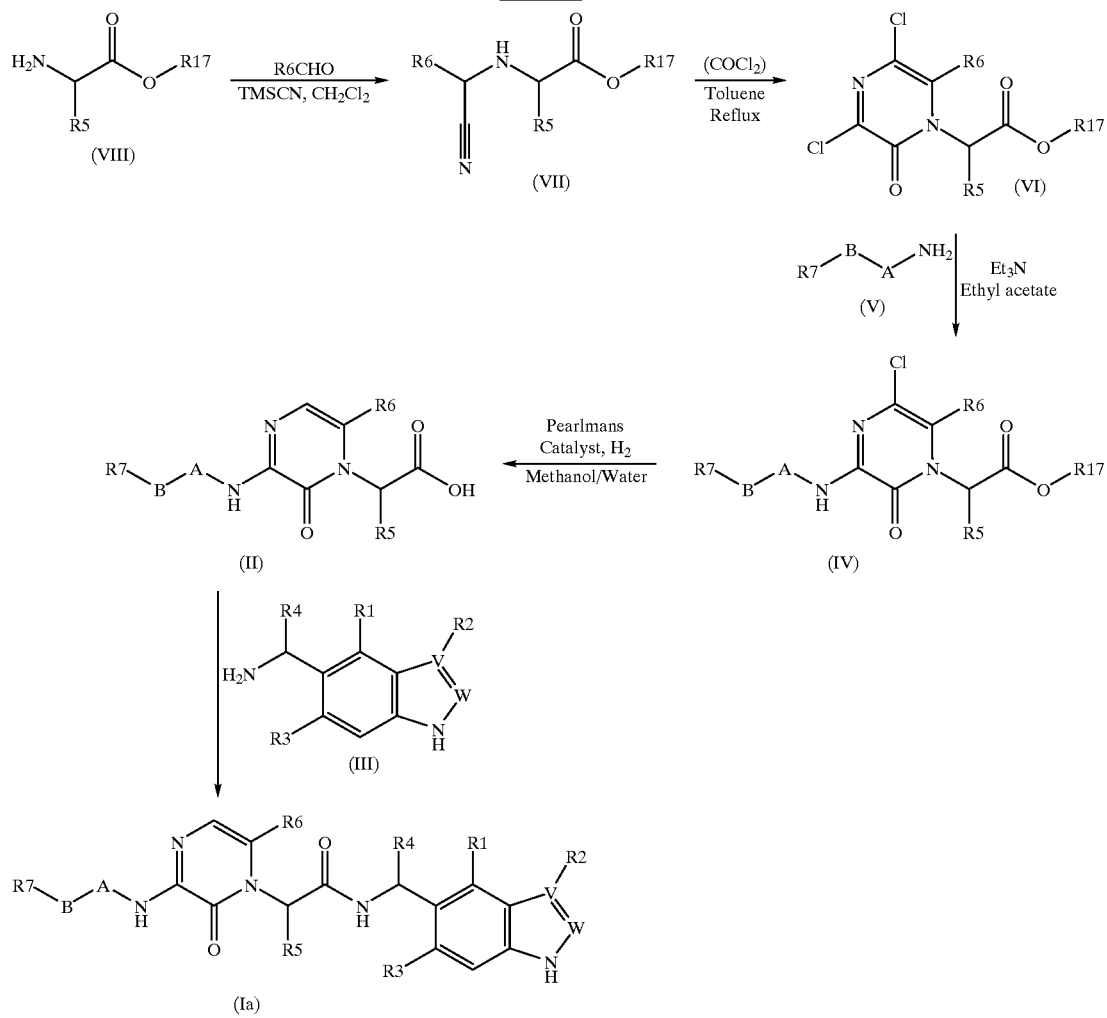

Compounds of the general formula (III) may be prepared by reduction of compounds of the general formula (IX) (Scheme 2). Such a reduction may be performed with a variety of reagents; for example, lithium aluminum hydride or hydrogen over Raney Nickel catalysis. Preferred conditions involve the use of Raney Nickel with methanol as solvent which contains 20% ammonia. The reaction is carried out at a temperature of up to 50° C. in an autoclave charged with hydrogen at a pressure up to 50 bar. Compounds of the general formula (IX) where W=CH, V=C and R1=R2=R3=R4=H are commercially available whilst compounds of the general formula (IX) where W=N or CH, V=C or N, R1=R2=R4=H and R3=Me may be prepared from the precursor (X) according to the method of H. D. Porter and W. D Peterson, (*Org Synthesis*, Coll Vol III p660).

Compounds of the general formula (IX) where W=CH, V=C, R2=CH3 and R1=R3=R4=H may be prepared from commercially available 5-cyano-1H-indole by formylation at the 3-position according to the method of P. N. James and H. R. Snyder, (*Org Synthesis* Coll Vol IV, p539) followed by simultaneous reduction of the formyl and cyano groups using a suitable reducing agent such as lithium aluminum hydride in an aprotic solvent for example tetrahydrofuran or diethyl ether.

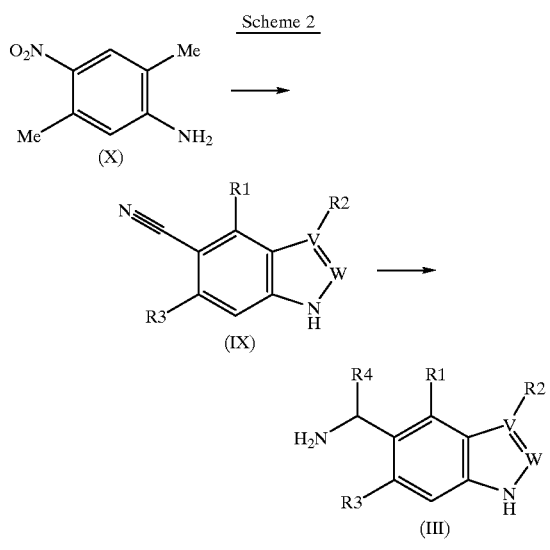

General Method B

An alternative method of preparation of compounds of the general formula (Ia) (Scheme 3) involves dechlorination of compounds of the general formula (XI) by reduction. Typically this procedure may be performed by treatment with a suitable active metal catalyst under an atmosphere of hydrogen, for example, Pearlmans catalyst under an atmosphere of hydrogen as described above (General Method A); or by transfer hydrogenation methodology, for example; treatment with ammonium formate in methanol, ethanol or isopropanol in the presence of a catalytic amount of palladium on carbon catalyst (General Method A). In scheme 3, Y has been indicated as chloro as a preferred embodiment but it will be appreciated that the reaction scheme is applicable for other components of Y, and therefore as a general principle Y can be indicated generally in scheme 3. Furthermore the chloro leaving group (in position 3) in scheme 3, as a general principle can be indicated as a "leaving group" (formula XII) such as a halogen.

Compounds of the general formula (XI) may be prepared by treatment of compounds of the general formula (XIIA) with a primary amine of the general formula (V) according to the conditions described above in General Method A. Compounds of the general formula (XIIA) may be prepared from the carboxylic acid (XIII) and a suitable amine of the general formula (III) according to the general methods described above (General Method A). Compound (XIII) may be prepared from a compound of the general formula (VI) according to the plethora of methods for the hydrolysis of a carboxylic acid ester (General Method A).

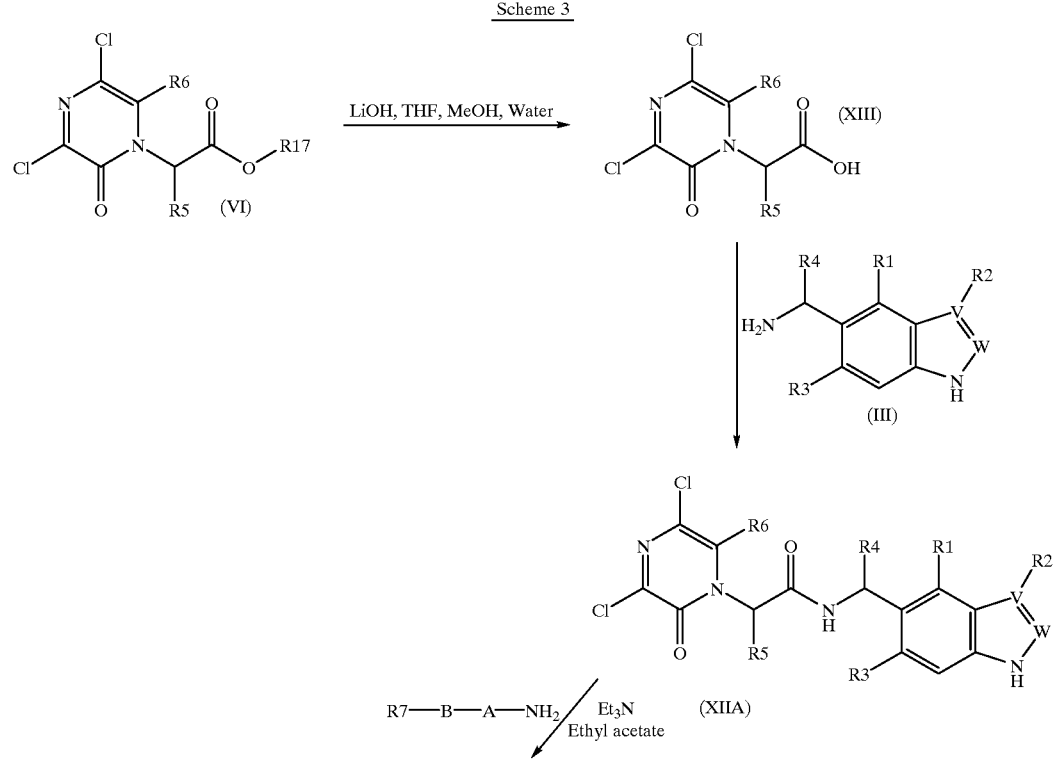

-continued

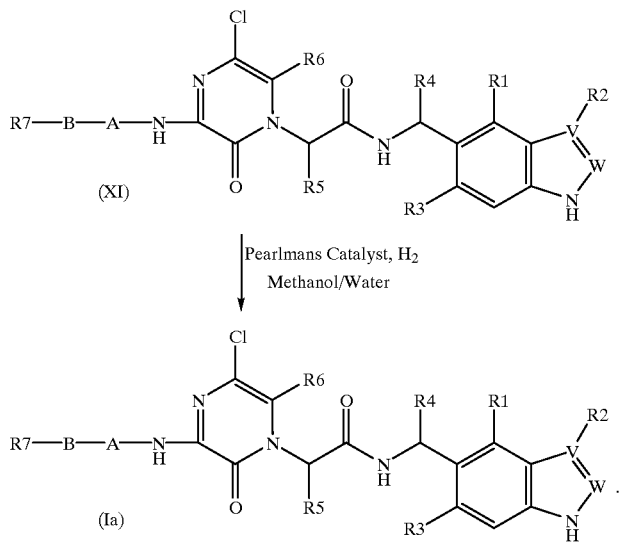

Amines of the general formula (V) may be prepared from a variety of precursors. Preferred routes include preparation from the corresponding nitrile such as illustrated by formula (XIV) (Scheme 4). Preparation of the amines (Va) from the nitriles (XIV) may be achieved by reduction of the appropriate nitriles using Raney nickel under an atmosphere of hydrogen. Compounds of the general formula (XIV) may be prepared from compounds of the general formula (XV) by palladium catalysed functionalisation of the halo substituent preferably a bromo substituent (shown for convenience). For example, treatment of compound (XV) with a palladium catalyst (palladium acetate or tris triphenyphosphinepalladium) in the presence of sodium formate under an atmosphere of carbon monoxide gives compound (XIV) where R7=CHO. Subsequent treatment with a primary or secondary amine in the presence of a suitable reducing agent (eg sodium triacetoxyborohydride) in a protic solvent system (eg acetic acid, methanol) gives a compound of the general formula (XIV) where $R7=CH_2NR_{15}R_{16}$. Alternatively the reaction may be carried out under conventional catalytic hydrogenation conditions. This synthetic methodology allows the preparation of preferred compounds of type (d). In a related methodology palladium catalysed cross coupling of (XV) with the zincate derived from N-Boc-3-iodoazetidine, by direct analogy to the procedure of S. Billotte, (*Synlett*, 1998, p379), gives a compound of the general formula (XIV) where R7=N-BOC-azetidine-3-yl. Deprotection of the nitrogen using standard methodology such as protonolysis using trifluoroacetic acid or hydrogen chloride and, if required, subsequent reductive alkylation with an appropriate aldehyde or ketone allows the preparation of preferred compounds of type (g). In the case of an aldehyde or ketone precursor the reaction may be carried out in the presence of a suitable reducing agent (e.g. sodium triacetoxyborohydride) in a protic solvent system (e.g. acetic acid, methanol). Alternatively the reaction may be carried out under conventional catalytic hydrogenation conditions. Intermediate (XV) can be transmetalated with an appropriate organolithium such as butyllithium and reacted in situ with an N-substituted 2-pyrrolidone and the resulting intermediate (XIV) with R7=an N-substituted-2-hydroxypyrrolidin-2-yl fragment may be reduced directly using for example platinum oxide under an atmosphere of hydrogen, by direct analogy with the synthetic methodology of H. Malmberg, M. Nilllsson and C. Ullenius, (*Acta Chemica Scandinavia*, B, 35, 1981, p625), to allow the preparation of intermediate (Va) with R7=an N-substituted pyrrolidine-2-yl fragment. This synthetic methodology allows the preparation of preferred compounds of type (G).

Scheme 4

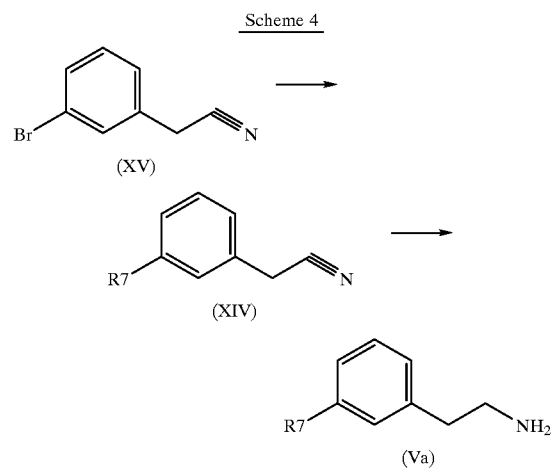

Amines of the general formula (Vb) may be prepared from a variety of precursors. Preferred routes include preparation from amino acid derivatives (XVI) (Scheme 5) and from the nitrile derivatives (XIV). Preparation from the amino acid derivatives (XVI) where P is a suitable protecting group for an amine (preferably BOC), may be achieved by reduction of the amide bond using lithium aluminum hydride, borane or lithium borohydride in the presence of trimethylsilyl chloride in an aprotic solvent such as diethyl ether or tetrahydrofuran. Subsequent removal of the nitrogen protecting group may be achieved using trifluoroacetic acid in dichloromethane or dichloromethane saturated with HCl. Amides of the general formula (XVI) may be prepared by coupling of the appropriate amine $HNR_{10}R_{11}$ with the commercially available amino acid derivatives (XVII). The coupling may be achieved using conventional amide bond forming techniques, in particular any one of a number of amino acid coupling variations described under General Method A. This synthetic methodology allows the preparation of preferred compounds of type (a).

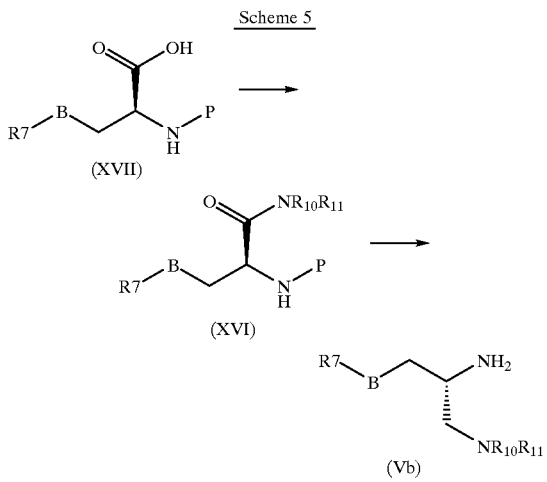

Amines of the general formula (Vc) (Scheme 6) may be prepared by treatment of compounds of the general formula (XVIII) where P is a suitable nitrogen protecting group (preferably BOC) with, for example, bromoacetonitrile and a suitable base in an aprotic polar solvent such as tetrahydrofuran, followed by reduction of the nitrile and removal of the nitrogen protecting group using, for example, ether saturated with HCl or trifluoroacetic acid in dichloromethane. Compounds of the general formula (XVIII) are commercially available. This synthetic methodology allows preparation of preferred compounds of the type (b).

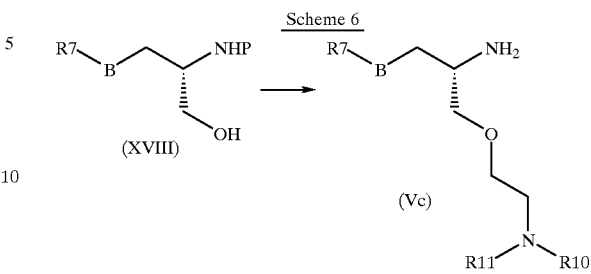

Amines of the general formula (Vd) (Scheme 7) may be prepared from intermediates of the general formula (XIX) by reduction according to the methods described above. Compounds of the general formula (XIX) may be prepared from compounds of the general formula (XX) by reaction of compounds of the general formula (XX) with sodium cyanide in suitable solvent for example, tetrahydrofuran or acetonitrile. Compounds of the general formula (XX) may be prepared from compounds of the general formula (XXI) by bromination using for example, N-bromosuccinimide as reviewed by L. Homer and E. H. Winkelmann in *Angewandte Chemie* 1959, 71, 349. Intermediates (XXI) may be prepared from compounds of the general formula (XXII) by nucleophilic attack onto the carbon atom of the cyano group according to the method of Ciganeck (*J. Org. Chem.* 1992, 57, 4521) or the method of Calderwood, (*Tetrahedron Letters*, 1997, 38, 1241). This synthetic methodolgy allows the preparation of preferred compounds of the type (d).

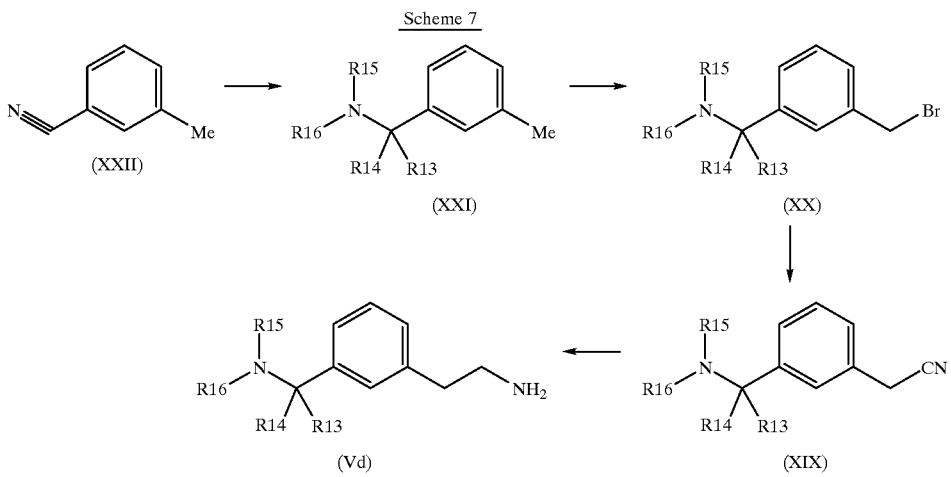

Amines of the general formula (Ve) (Scheme 8) may be prepared by reduction of the commercially available nitrile (XXIII) using the method of F. Vogtle et al (*Chem Ber*, 1984, 117, 1487). One of the amines in intermediate (XXIV) may be protected with a 20 suitable protecting group P (preferably BOC) using the method of Adamczyk et al; (*Org Prep Proc Int*, 1998, 30(3) 339) or the method of Krapcho et al, (*Syn Comm*, 1990, 20, 2559) to give compounds of the general structure (XXV). Reductive amination of the unprotected primary amine of compounds of the formula (XXV) and subsequent removal of the protecting group P gives compounds of the general formula (Ve). This synthetic methodology allows the preparation of preferred compounds of type (e).

nickel in ethanol saturated with ammonia. Compounds of the general formula (XXVI) may be prepared from compounds of the general formula (XXVII) by removal of the nitrogen protecting group P and subsequent reductive amination. Compounds of the general formula (XXVII) can be prepared by alkylation of the phenol (XXVIII) (or hydroxy methyl phenyl) with a suitably protected alcohol (XXIX) according to the method of O. Mitsonubu, (*Synthesis*, 1981, 1). Compound (XXVIII) is prepared from commercially available (XXX) by demethylation using for example, a solution of boron tribromide in dichloromethane. This methodology is also applicable for compounds where there is a methylene between the benzene and oxygen, such as shown

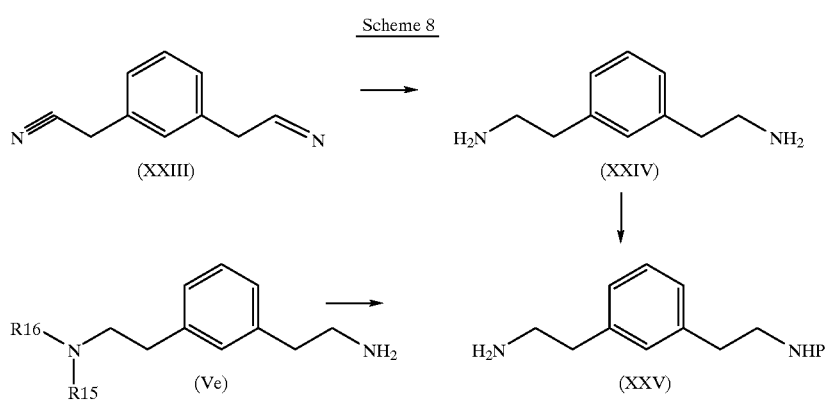

Amines of the general formula (Vf) (Scheme 9) may be prepared from intermediates of the general formula (XXVI) by reduction of the nitrile group using for example, Raney in the accompanying examples 27 and 28. This said methodology allows the preparation of preferred compounds of the general type (h).

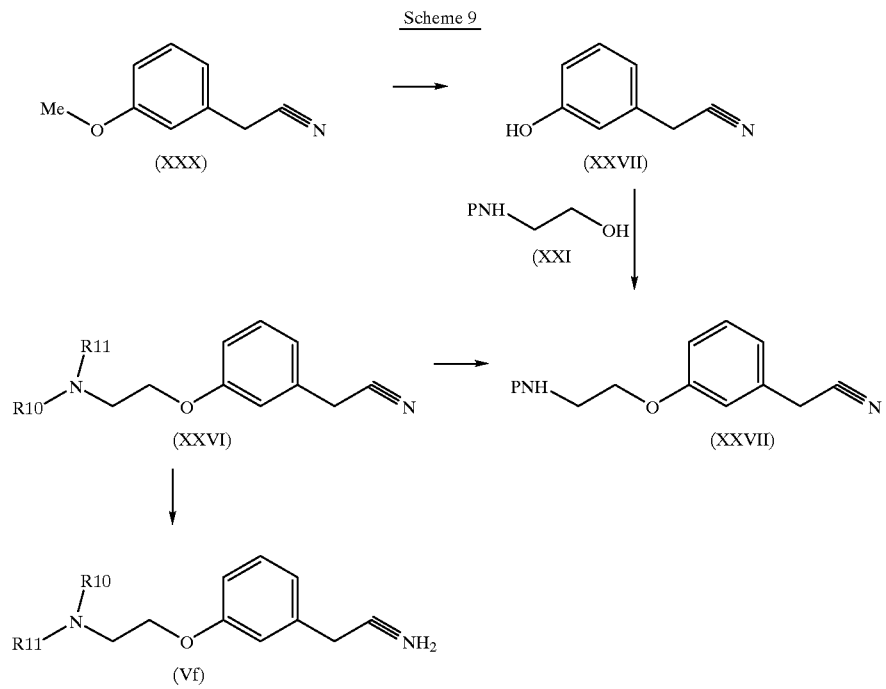

Amines of the general formula (Vg) (Scheme 10 and Scheme 11) may be prepared according to the method described by J. Permattam et al (Tett, Let, 1991, 32, p7183). For example, commercially available D-prolinamide (XXXI) can be treated with an aldehyde in the presence of a suitable reducing agent (eg sodium triacetoxyborohydride) in a protic solvent system (eg acetic acid or methanol) or by alkylation with a suitable alkylating agent as described by J. Permattam et al (Tett, Let, 1991, 32, p7183) to give a compound of formula (XXXII). Subsequent reduction of the amide with a suitable reducing agent (for example lithium aluminum hydride) in a suitable aprotic solvent (for example, diethyl ether or tetrahydrofuran) as described by J. Permattam et al (Tett Let, 1991, 32, p7183) gives a compound of the general formula Vg. This synthetic methodology allows the synthesis of preferred compounds of type (i) and (j).

Scheme 10

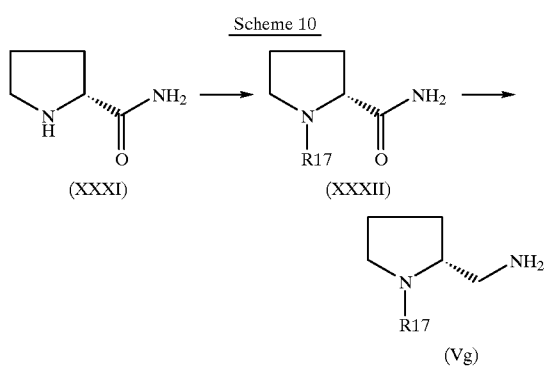

Preferred compounds of the type (k) may be made according to the general method described in Scheme 11. Carboxylic acid (XXXIII) may be prepared according to the method described by G. R. Brown et. Al. in J. Chem. Soc. Perkin Trans I, 1985, 2577. Subsequent formation of the primary amide (XXXIV) may be performed using a suitable carboxylic acid activating agent (for example oxalyl chloride) in a suitable solvent system (for example, dichloromethane with a trace of dimethyl formamide). Reduction of (XXXIV) using a suitable reducing agent (for example lithium aluminum hydride) in a suitable aprotic solvent (for example diethyl ether or tetrahydrofuran) provides compounds of the type (k).

Scheme 11

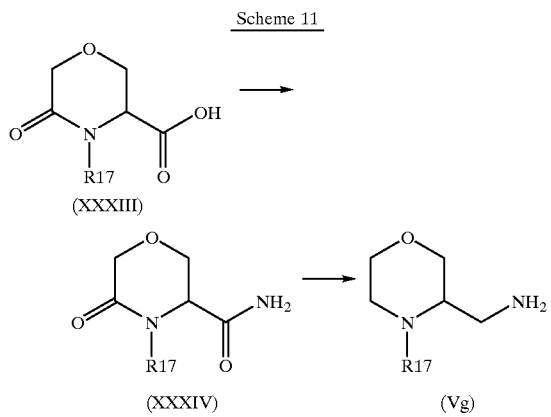

General Method C

As a general principle, pyridone derivatives of formula (I)—i.e. formula (1b) in scheme 12, can be formed by coupling the heterocycle of formula (1c) with a carbonyl of formula (XXXVII) in the presence of a reducing agent (see hereinbefore). Compounds of the general formula (Ib) may also be prepared by coupling of the acid (XXXV) with the appropriate heterocyclic amine (III) (Scheme 12). The coupling may be achieved using conventional amide bond forming techniques, in particular any one of a number of amino acid coupling variations. For example, the acid (XXXV) may be activated using a carbodiimide such as 1-ethyl-3-(3-dimethylamino-1-propyl)carbodiimide optionally in the presence of 1-hydroxybenzotriazole and or a catalyst such as 4-dimethylaminopyridine. Such couplings may be performed in a suitable solvent such as dichloromethane, optionally in the presence of a tertiary amine such as N-methylmorpholine or N,N-diisopropylamine at 0° C.

Compounds of the general formula (XXXV) may be prepared from compounds of the general formula (XXXVI) where P is a suitable carboxylic acid protecting group (preferably P is the tert-butyl group) by hydrolysis of the carboxylic acid ester using, for example if P=tert-butyl, trifluoroacetic acid in a suitable solvent such as dichloromethane at, for example, a temperature between 0° C. and room temperature.

Compounds of the general formula (XXXVI) may be prepared by the reaction of the amine (XXXVIII) with the desired carbonyl compound (XXXVII) in the presence of a suitable reducing agent. Preferred conditions involve the use of sodium triacetoxyborohydride in tetrahydrofuran and acetic acid.

Compound (XXXVIII) may be prepared from the carbamate (XXXIX) by removal of the carbamate protecting group using a suitable catalyst under an atmosphere of hydrogen. Typical conditions involve the use of 10% palladium on carbon, at room temperature in ethyl acetate under a hydrogen pressure of 2 to 20 psi.

Compound (XXXIX) may be prepared by alkylation of compound (XXXX) using a suitably protected haloacetic acid derivative (XXXXI) where P is the acid protecting group (preferably P=tert-butyl) and a suitable base, for example potassium carbonate, sodium carbonate, caesium carbonate, sodium hydride or potassium hydride in a polar solvent such as acetone, THF, dimethyl formamide or 2-butanone. Preferred conditions involve the use of potassium carbonate in 2-butanone at room temperature.

Compound (XXXXI) is prepared from commercially available (XXXXII) following the procedure described for a closely related compound by D. J. Wolanin and C. A. Veale et al, (J. Med Chem 1994, 37, 3303).

Scheme 12

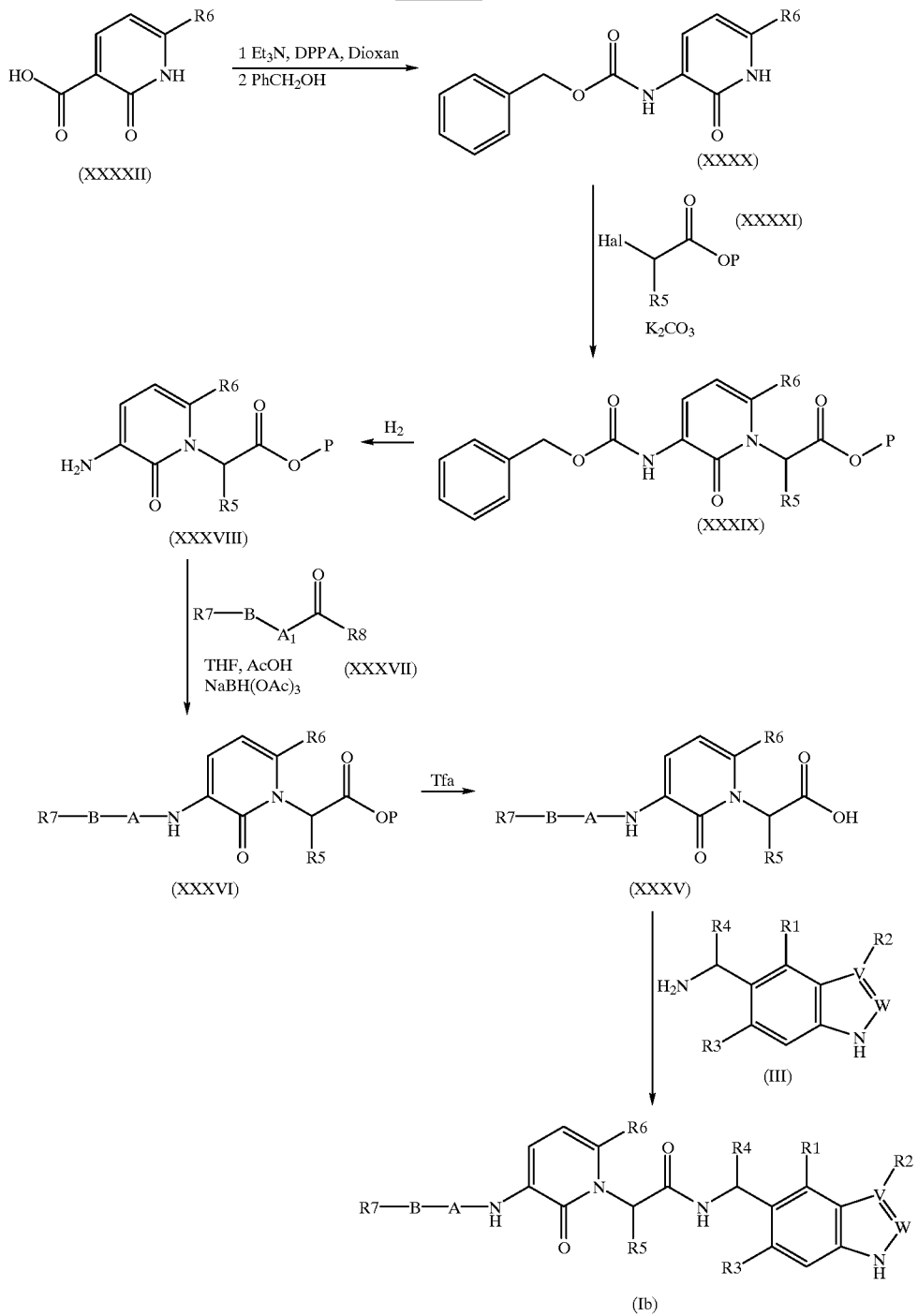

Carbonyl compounds of the general formula (XXXVII) may be prepared by oxidation of alcohols of the general formula (XXXXIII) where $A_1$ is C(R8)(R9), $CH_2C(R8)(R9)$, or $C(R8)(R9)CH_2$, (Scheme 13). Such an oxidation may be performed by a variety of agents known to oxidise an alcohol including $CrO_3/H_2SO_4$ in acetone (Jones Reagent), $CrO_3Pyr_2$ (Collins Reagent), $MnO_2$ or the methods of Swern or Dess-Martin. A preferred method is that of Swern involving the use of dry DMSO and oxalyl chloride in dichloromethane as solvent at −60° C. under a nitrogen atmosphere.

Scheme 13

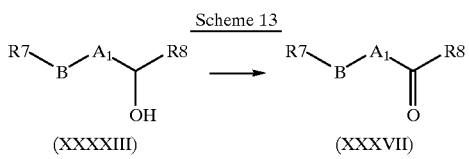

General Method D

Compounds of the general formula (XXXVII) may also be prepared from compounds of the general formula (XXXVIII) by treatment with a suitable triflate of the general formula (XXXXIV) in the presence of a base; for example pyridine, triethylamine or N-ethyl-diisopropylamine in a non protic solvent such as dichloromethane, THF or diethyl ether (scheme 14). Preferred conditions for this reaction involve the use of N-ethyl-diisopropylamine as the base in dichloromethane.

Scheme 14

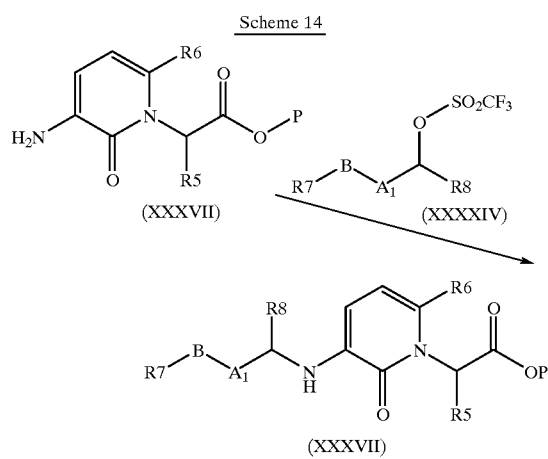

Triflates of the general formula (XXXXIV) may be prepared from alcohols of the general formula (XXXXV) by treatment with trifluoromethanesulfonic anhydride in the presence of a suitable base; for example pyridine, triethylamine or N-ethyl-diisopropylamine in a non protic solvent such as dichloromethane, THF or diethyl ether. Preferred conditions include the use of trifluoromethane sulfonic anhydride in dichloromethane with pyridine as the solvent at 0° C. to room temperature (scheme 15).

Scheme 15

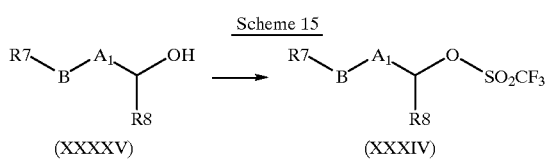

Scheme 16

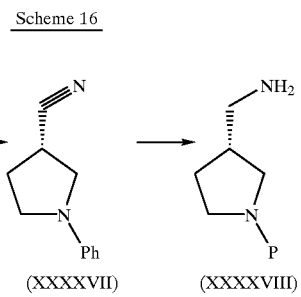

Preperation of compounds of the type of example 24 (ie wherein the pyrollidine is attached at the 3-position to the methyl amino moiety), can be prepared according to scheme 16.

Amines of the general formula (XXXXVIII) may be made according to the general method described in scheme 16. The mesylate (XXXXVI) may be prepared in a 2-step procedure from (3R)-pyrrolidinol, by suitable protection of the amine (preferably Boc), following such methods as described in "Protective groups in Organic synthesis", by T W Greene and PGM Wutz (1991) or "Protecting Groups" by P J Kocienski (1994), followed by mesylation of the intermediate alcohol. The alcohol is treated with methanesulphonyl chloride in the presence of a suitable base, such as triethylamine or pyridine, in a non protic solvent such as dichloromethane, at between 0° to room temperature. Amines of general formula (XXXXVII) may be prepared by reaction of compounds of formula (XXXXVI) with potassium cyanide in a suitable high boiling solvent, preferably DMSO, at between room temperature and 100° C. Amines of general formula (XXXXVIII) may be obtained from the nitrile of formula (XXXXVII) by reduction using Raney® nickel in an alcoholic solvent, (eg methanol), under an atmosphere of hydrogen.

Scheme 17

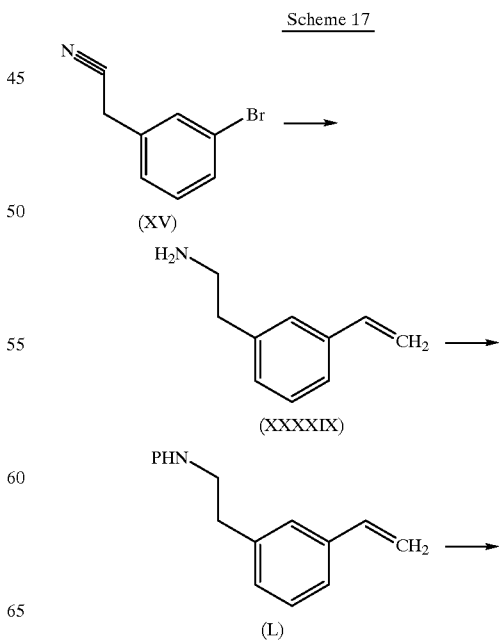

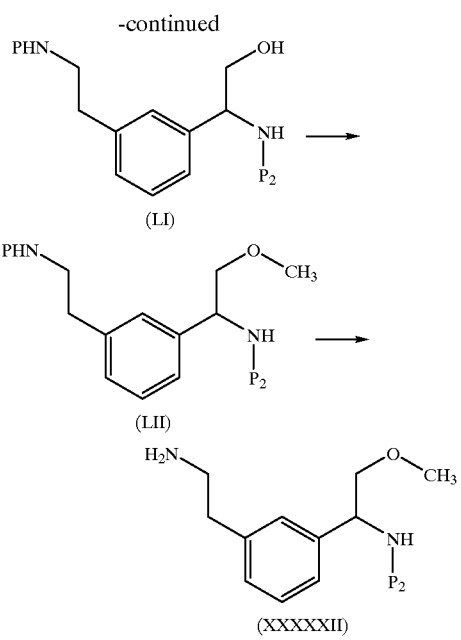

This following synthetic methodology allows the preparation of preferred compounds of the type analogous to example 29.

Palladium catalysed cross coupling of (XV) with vinyl tributyl tin, by analogy with methods described in (Org. React. 1997; 50) gave the vinyl acetonitrile, and subsequently the vinyl amine (XXXXIX), by employing a selective reducing agent (eg $AlCl_3/LiAlH_4$) in a non protic solvent (eg tetrahydrofuran). Protection of the amine with a suitable protecting group (preferably CBz) following methods described in "Protective groups in Organic synthesis", by T W Greene and PGM Wutz (1991) or "Protecting Groups" by P J Kocienski (1994), followed by asymmetric aminohydroxylation (AA), according to the method of O'Brien et al (J.Chem. Soc.Perk. Trans.1, 1998, 2519) provided the hydroxyamine of general formula (LI). Subsequent methylation, using an alkylating agent (eg methyl iodide), under phase transfer conditions, using a catalyst such as benzyltriethylammonium chloride, provided the compound of general formula (LII)

Removal of the initial nitrogen protecting group may be achieved by, for example, hydrogenation in the presence of a palladium on carbon catalyst in methanol, at a pressure of, typically 15 psi.

Compounds of formula (I) and the various intermediates and reagents required for the processes hereinbefore disclosed, when neither commercially available nor subsequently described, can be obtained either by analogy with the reactions described in the Examples and Preparations sections or by conventional synthetic procedures, in accordance with standard textbooks on organic chemistry or literature precedent, from readily accessible starting materials using appropriate reagents and reaction conditions.

The novel intermediates described herein form a further aspect of the invention. Where keto/enol tautomerism is present the keto and enol forms are claimed separately and together (as a mixture).

Suitable pharmaceutical and physiologically acceptable salts will be apparant to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, benzoic, p-toluenesulphonic, methanesulphonic or napthalenesulphonic acid. Other non-physiologically acceptable salts eg. oxalates may be used, for example in the isolation of compounds of formula (I) and are included within the scope of this invention.

The acid addition salts of the compounds of formula (I) may be prepared in a conventional manner. For example a solution of the free base is treated with the appropriate acid, either neat or in a suitable solvent, and the resulting salt isolated either by filtration or by evaporation under reduced pressure of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The subject invention also includes pharmaceutially acceptable solvates (including hydrates), and polymorphs of the compounds of the invention. It will be further appreciated that certain moieties known as "pro-moieties", for example as described in "Design of Prodrugs" by H. Bundgaard, Elsevier, 1985 (the disclosured of which is hereby incorporated by reference), may be placed on appropriate functionalities of the compounds of formula 1. Such prodrugs are included within the scope of the invention.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention and pharmaceutically acceptable salts of said compounds or which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

In therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example intravenously, intramuscularly or subcutaneously. For parenteral administration, they are best used in the form of a sterile aqueous solution which may contain other substances, for example enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I) and their pharmaceutically acceptable salts and solvates may contain from 1 to 1000 mg (in single or divided doses). Thus tablets or capsules may contain from 0.5 to 500 mg of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention.

The following formulation examples are illustrative only and are not intended to limit the scope of the invention. "Active ingredient means a compound according to formula 1 or a pharmaceutically acceptable salt thereof.

Formulation 1: A tablet is prepared using the following ingredients:

|  | Quantity (mg/tablet) |
|---|---|
| Active ingredient | 250 |
| cellulose, microcrystalline | 400 |
| silicon dioxide, fumed | 10 |
| stearic acid | 5 |
| total | 665 mg | the components are blended and compressed to form tablets each weighing 665 mg.

Formulation 2: An intrvenous formulation may be prepared as follows:

|  |  |
|---|---|
| Active ingredient | 100 mg |
| isotonic saline | 1,000 ml |

Further aspects of the invention are as follows below.

(i) Pharmaceutical composition comprising a compound of formula (I), or a pharmaceutically acceptable salt thereof together with a pharmaceutically acceptable diluent or carrier.

(ii) A compound of formula (I), or a pharmaceutically acceptable salt thereof for use as a medicament.

(iii) Use of a compound of formula (I), or a pharmaceutically acceptable salt thereof for the manufacture of a medicament for the curative or prophylactic treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring.

(iv) A method of treating a mammal (including a human being) to cure or prevent deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring; which comprises treating said mammal with an effective amount of a compound of formula (I) or a pharmaceutically acceptable salt thereof.

It will be appreciated that all references herein to treatment include curative, palliative and prophylactic treatment.

The syntheses of the compounds of the invention and of the intermediates for use therein are illustrated by the following examples. The purity (Rf) of the compounds was routinely monitored by thin layer chromatography using Merck Kieselgel 60 $F_{254}$ plates and the following solvent systems (SS):

1. isobutyl methyl ketone:glacial acetic acid:water, 2:1:1 (upper phase);
2. hexane:ethyl acetate, 1:1;
3. hexane:ethyl acetate, 7:3;
4. dichloromethane:methanol:0.880 aqueous ammonia, 85:15:2;
5. dichloromethane:methanol:0.880 aqueous ammonia, 84:14:2;
6. hexane:ethyl acetate, 6:4;
7. dichloromethane:methanol:0.880 aqueous ammonia, 93:7:1;
8. dichloromethane:methanol, 90:10;
9. dichloromethane:methanol:0.880 aqueous ammonia, 93:7:2;
10. dichloromethane:methanol:0.880 aqueous ammonia, 90:10:1;
11. dichloromethane:methanol, 95:5;
12. dichloromethane:methanol:0.880 aqueous ammonia, 193:7:1;
13. ethyl acetate;
14. hexane:ether, 1:1;
15. hexane:ether, 1:3;
16. dichloromethane:methanol:0.880 aqueous ammonia, 80:20:5;
17. chloroform:methanol, 95:5;
18. hexane:ethyl acetate, 3:7;
19. methanol:ethyl acetate:glacial acetic acid:0.880 aqueous ammonia:water, 60:12:4:4:8.

[1]H Nuclear magnetic resonance (NMR) spectra were recorded using either a Varian Inova 300 or a Varian Inova 400 spectrometer and were in all cases consistent with the proposed structures.

Mass spectra were obtained with a Fisons Instrument Trio 1000 spectrometer using thermospray ionisation.

Room temperature means 20–25° C.

EXAMPLE 1

(R,S)-2-[3-[(2-Amino-1-benzylethyl)amino]-6-methyl-2-oxo-1(2H)-pyridinyl]-N-(1H-indol-5-ylmethyl)acetamide

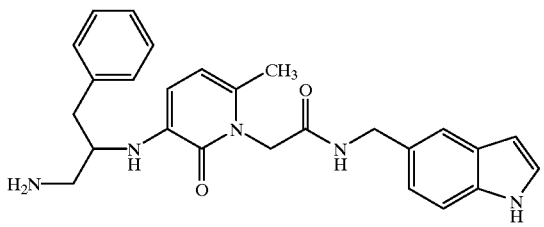

Preparation 1

(R,S)-Benzyl N-(2-hydroxy-3-phenylpropyl)carbamate

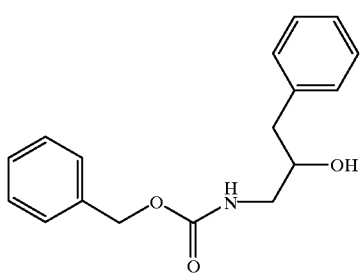

1-Amino-3-phenyl-2-propanol (3.9 g, 25.79 mmol; prepared as described in *J. Amer. Chem. Soc.* 1946, 203) was dissolved in $CH_2Cl_2$ (200 ml) and treated with triethylamine (0.35 ml, 2.58 mmol) followed by 1-[(benzyloxy)carbonyl]oxydihydro-1H-pyrrole-2,5-dione (6.43 g, 25.79 mmol) and the resultant mixture stirred at room temperature (72 hr). The resultant mixture was washed with aq citric acid (1N, 200 ml), sat aq brine (2×200 ml) and dried over $MgSO_4$. Removal of the drying agent by filtration followed by evaporation of the solvent gave the desired product as a viscous clear oil (5.18 g, 78%). $^1H$ NMR ($CDCl_3$) d 1.60 (m, 1H), 2.20 (s, br, 1/2H), 2.70 (m, 1H), 2.80 (m, 3/2H), 3.20 (m, 1/2H), 3.45 (m, 1/2H), 3.95 (m, 1H), 5.10 (s, br, 2H), 5.30 (m, 1H), 7.19–7.35 (m, 10H). LRMS m/z=286.3 (M+1).

Preparation 2

Benzyl N-(2-oxo-3-phenylpropyl)carbamate

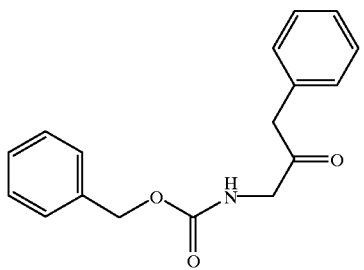

Dry DMSO (3.0 ml, 43.54 mmol) in $CH_2Cl_2$ (6.9 ml) was added dropwise to a solution of oxalyl chloride (1.73 ml, 19.91 mmol) in $CH_2Cl_2$ (35 ml) at −60° C. under a nitrogen atmosphere. After stirring for 2 mins at −60° C. a solution of (RS)-benzyl-N-(2-hydroxy-3-phenylpropyl)carbamate (preparation 1) (5.18 g, 18.15 mmol) in $CH_2Cl_2$ (17 ml) was added dropwise over 10 mins followed by triethylamine (17.63 ml, 90.74 mmol). The resultant mixture was allowed to warm to room temperature, whereupon water (100 ml) was added. The aqueous mixture was extracted with $CH_2Cl_2$ (3×100 ml) and the combined organic extracts washed with sat aq brine (2×250 ml) and dried over $MgSO_4$. Filtration away from the drying agent followed by evaporation of the solvent gave the crude product which was purified by chromatography ($SiO_2$; eluting with 40:60 hexane:ethyl acetate) to give the desired product (yellow crystalline solid, 4.41 g, 86%). $^1H$ NMR ($CDCl_3$) δ:3.72 (s, 2H), 4.11 (d, 2H), 5.09 (s, 2H), 5.45 (s, br, 1H), 7.20–7.37 (m, 10H). LRMS m/z=301.0 $(M+18)^+$.

Preparation 3

Benzyl N-(6-methyl-2-oxo-1,2-dihydro-3-pyridinyl)carbamate

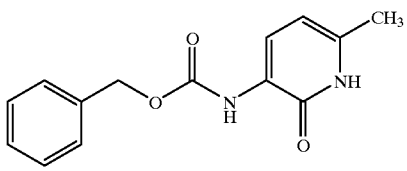

A suspension of 6-methyl-2-oxo-2,3-dihydro-3-pyridinecarboxylic acid (20 g, 0.13 mol) in dioxan (400 ml) was treated with triethylamine (22 ml, 0.15 mol) followed by diphenylphosphoryl azide (30.8 ml, 0.14 mol) and heated under reflux for 2 hr. A further portion of diphenylphosphoryl azide (3 ml) and triethylamine (2 ml) were added and heated under reflux for a further 1 hr. The resultant mixture was then treated with benzyl alcohol (18.8 ml, 0.18 mol) and heated under reflux for 18 hr. The resultant mixture was cooled, evaporation of the solvent gave a crude solid which was triturated with water. The solid was collected by filtration, washed with HCl (1N, 300 ml) then water. The solid was triturated with diethyl ether, filtered, washed with diethyl ether and dried to give the desired product (22 g, 65%). $^1H$ NMR ($CDCl_3$) δ 1.20 (s, 1H), 2.30 (s, 3H), 5.20 (s, 2H), 6.05 (d, 1H), 7.40 (m, 5H), 7.70 (s, 1H), 8.00 (d, 1H). LRMS m/z=259.2 $(M+1)^+$.

Preparation 4 tert-Butyl 2-[3-[(benzyloxy)carbonyl]amino-6-methyl-2-oxo-1(2H)-pyridinyl]acetate

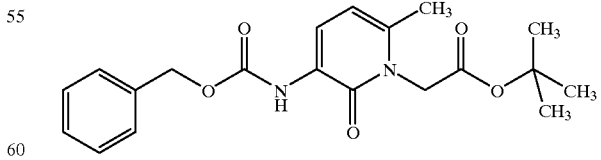

A slurry of benzyl N-(6-methyl-2-oxo-1,2-dihydro-3-pyridinyl)carbamate (preparation 3) (20 g, 78 mmol) in 2-butanone (500 ml) was treated with $K_2CO_3$ (53.9 g, 94 mmol) and further 2-butanone (100 ml). The resultant mixture was treated cautiously with tert-butyl 2-bromoacetate (15.2 ml, 94 mmol) and stirred at room temperature for 18 hr. The solvent was evaporated and the crude material was partitioned between ethyl acetate and water. The aqueous layer was washed with ethyl acetate, the combined organic layers washed with sat aq brine and dried over $Na_2SO_4$. Removal of the drying agent by filtration followed by evaporation of the solvent gave the crude product which was purified by recrystallisation from ethyl acetate:hexane to give the desired product (white solid, 15.1 g, 52%). $^1$H NMR ($CDCl_3$) δ: 1.40 (s, 9H), 2.20 (s, 3H), 4.70 (s, 2H), 5.20 (s, 2H), 6.05 (d, 1H), 7.40 (m, 5H), 7.70 (s, br, 1H), 7.90 (d, 1H). LRMS m/z=373.6 (M+1)$^+$.

Preparation 5 tert-Butyl 2-[3-amino-6-methyl-2-oxo-1(2H) pyridinyl]acetate

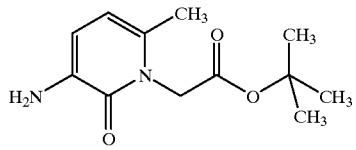

tert-Butyl-2-[3-[(benzyloxy)carbonyl]amino-6-methyl-2-oxo-1(2H)-pyridinyl]acetate (preparation 4) (5 g, 13 mmol) was dissolved in ethyl acetate (70 ml), treated with 10% Pd on carbon catalyst (400 mg) and stirred under a hydrogen atmosphere (2 psi, room temperature, 3 hr). The catalyst was removed by filtration, and the solvent evaporated to dryness to give the desired product as a cream solid (3.08 g, 99%). $^1$H NMR ($CDCl_3$) δ 1.40 (s, 9H), 2.20 (s, 3H), 4.00 (s, br, 2H), 4.70 (s, 2H), 5.90 (d, 1H), 6.45 (d, 1H). LRMS m/z=239.5 (M+1)$^+$.

Preparation 6

(R,S)-tert-Butyl 2-[3-[(1-benzyl-2-[(benzyloxy) carbonyl]aminoethyl)amino]-6-methyl-2-oxo-1(2H)-pyridinyl]acetate

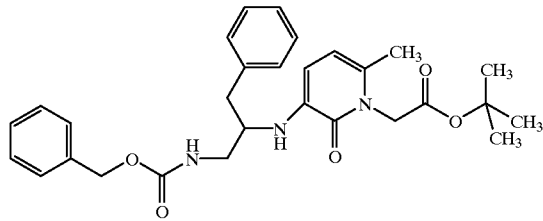

tert-Butyl-2-[3-amino-6-methyl-2-oxo-1(2H)-pyridinyl] acetate (preparation 5) (0.476 g, 2.00 mmol) and benzyl N-(2-oxo-3-phenylpropyl)carbamate (preparation 2) (0.68 g, 2.4 mmol) was dissolved in THF (10 ml) and acetic acid (0.132 g, 2.2 mmol). This mixture was treated with sodium triacetoxyborohydride (0.634 g, 3.0 mmol) and the resultant mixture stirred (18 hr, room temperature). A further quantity of benzyl N-(2-oxo-3-phenylpropyl)carbamate (0.46 g, 1.6 mmol) was added followed by sodium triacetoxyborohydride (0.634 g, 3.0 mmol) and the mixture stirred (room temperature, 18 hr). The resultant mixture was diluted with $CH_2Cl_2$ (100 ml) and washed with sat aq $NaHCO_3$ (100 ml), sat aq brine (100 ml) and dried over $MgSO_4$. Filtration away from the drying agent and evaporation of the solvent gave a pale yellow oil which was purified by chromatography ($SiO_2$, gradient elution 100% hexane; 90:10 hexane:ethyl acetate; 80:20 hexane:ethyl acetate; 75:25 hexane:ethyl acetate). The desired product was isolated impure (pale yellow oil, 1.0 g). $^1$H NMR ($CDCl_3$) δ 1.45 (s, 9H), 2.15 (s, 3H), 2.70 (m, 1H), 2.80 (m, 1H), 3.15 (m, 1H), 3.40 (m, 1H), 3.65 (m, 1H), 4.70 (m, 2H), 5.10 (m, 3H), 5.90 (d, 1H), 6.25 (d, 1H), 7.10–7.40 (m, 11 H). LRMS m/z=506.3 (M+1).

Preparation 7

(R,S)-2-[3-[(1-Benzyl-2-[(benzyloxy)carbonyl] aminoethyl)amino]-6-methyl-2-oxo-1(2H)-pyridinyl] acetic acid

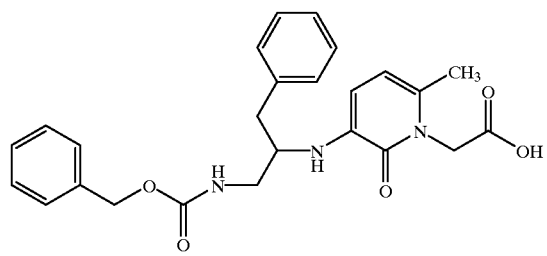

(R,S)-tert-Butyl-2-[3-[(1-benzyl-2-[(benzyloxy) carbonyl]aminoethyl)amino]-6-methyl-2-oxo-1(2H)-pyridinyl]acetate (preparation 6) (1.0 g, 1.98 mmol), was dissolved in $CH_2Cl_2$ (16 ml) and treated with TFA (8.0 ml). After stirring at room temperature for 5 hr, the resultant mixture was evaporated to dryness and azeotroped with $CH_2Cl_2$ (×3). Chromatography ($SiO_2$, gradient elution 100% $CH_2Cl_2$; 95:5 $CH_2Cl_2$:MeOH; 90:10 $CH_2Cl_2$:MeOH) gave the desired product (white powder, 0.358 g, 40%). $^1$H NMR ($d^6$-DMSO) δ 2.05 (s, 3H), 2.75 (m, 1H), 2.85 (m, 1H), 2.90 (m, 1H), 3.15 (m, 1H), 3.50 (m, 1H), 4.45 (s, br, 2H), 4.95 (d, 1H), 5.0 (s, 2H), 5.90 (d, 1H), 6.25 (d, 1H), 7.10–7.30 (m, 10H), 7.45 (t, br, 1H). LRMS m/z=450.8 (M+1)+. Found C 56.30, H 4.87, N 7.24%; $C_{25}H_{27}N_3O_5$ requires C 56.42, H 5.33, N 7.50%.

Preparation 8

1H-Indol-5-ylmethylamine

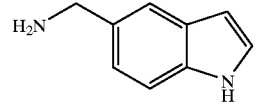

A stirred solution of 1H-indole-5-carbonitrile (4.0 g, 28.1 mmol) in THF (50 ml) at 0° C. was treated dropwise with lithium aluminum hydride in THF (1M, 98 ml, 98 mmol). The resultant mixture was stirred, warming to room temperature overnight. Sat. aq. $NaHCO_3$ (60 ml) was added at 0° C. and resultant mixture was filtered through filter agent celite 521 and washed with THF. Evaporation of the solvent gave the crude product which was purified by chromatography ($SiO_2$, gradient elution with 95:5 $CH_2Cl_2$:MeOH; 90:10 $CH_2Cl_2$:MeOH; 90:10:1 $CH_2Cl_2$:MeOH:$NH_3$) to give the desired product (white powder, 12.9 g, 71%). $^1$H NMR ($CD_3OD$) δ 4.10 (s, 2H), 6.50 (d, 1H), 7.15 (d, 1H), 7.30 (d, 1H), 7.40 (d, 1H), 7.60 (s, 1H). LRMS m/z=147.2 (M+1)$^+$.

Preparation 9

(R,S)-Benzyl N-2-[(1-2-[(1H-indol-5-ylmethyl)amino]-2-oxoethyl-6-methyl-2-oxo-1,2dihydro-3-pyridinyl)amino]-3-phenylpropylcarbamate

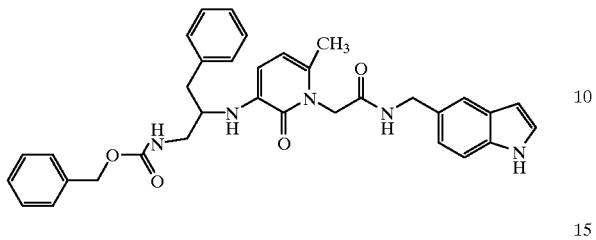

(R,S)-2-[3-[(1-benzyl-2-[(benzyloxy)carbonyl]aminoethyl)amino]-6-methyl-2-oxo-1(2H)-pyridinyl]acetic acid (preparation 7) (157 mg, 0.349 mmol), 1H-indol-5-ylmethylamine (preparation 8) (50 mg, 0.349 mmol), HOBT (49 mg, 0.349 mmol), WSCDI.HCl (75 mg, 0.391 mmol), N-methylmorpholine (145 mg, 1.40 mmol) and DMF (5.0 ml) were stirred at room temperature for 18 hr. The reaction mixture was diluted with water (20 ml) and ethyl acetate (20 ml) and shaken in a separatory funnel. The organic layer was separated, washed with sat aq brine (20 ml), dried over MgSO$_4$. Filtration away from the drying agent followed by evaporation of the solvent gave the crude product which was purified by chromatography (SiO$_2$, gradient elution 50:50 hexane:ethyl acetate; 100% ethyl acetate) to give the desired product (white foam, 0.153 g, 76%). $^1$H NMR (CDCl$_3$) δ 2.35 (s, 3H), 2.78 (d, 2H), 3.15 (m, 1H), 3.35 (m, 1H), 3.65 (m, 1H), 4.50 (d, 2H), 4.75 (AB Quartet, 2H), 5.0 (s, br, 1H), 5.05 (s, 2H), 5.95 (d, 1H), 6.30 (d, 1H), 6.50 (s, 1H), 6.95 (s, br, 1H), 7.0 (d, 1H), 7.10–7.35 (m, 13H), 7.45 (s, 1H), 8.15, (s, br, 1H). LRMS m/z=578.4 (M+1).

Preparation 10

(R,S 2-[3-[(2-Amino-1-benzylethyl)amino]-6-methyl-2-oxo-1(2H)-pyridinyl]-N-(1H-indol-5-ylmethyl)acetamide

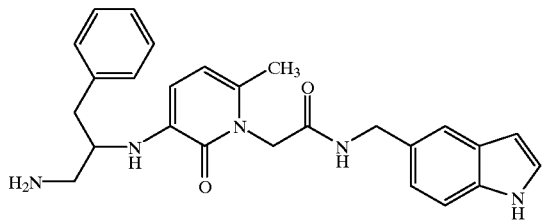

(R,S)-Benzyl-N-2-[(1-2-[(1H-indol-5-ylmethyl)amino]-2-oxoethyl-6-methyl-2-oxo-1,2-dihydro-3-pyridinyl)amino]-3-phenylpropylcarbamate (preparation 9) (0.15 g, 0.259 mmol) was dissolved in ethanol (10 mL), treated with 10% Pd on carbon catalyst (50 mg) and stirred under a hydrogen atmosphere (15 psi, room temperature, 18 hr). A further 50 mg of 10% Pd on carbon was added and stirring under hydrogen (15 psi) continued for 18 hr. The catalyst was removed by filtration, the solvent evaporated to dryness and the resultant crude product purified by chromatography (SiO$_2$, gradient elution 90:10 CH$_2$Cl$_2$:MeOH; 90:10:0.5 CH$_2$Cl$_2$:MeOH:NH$_3$; 90:1 0:1 CH$_2$Cl$_2$:MeOH:NH$_3$) to give, recovered starting material as the first eluted fraction (8 mg at 53%) and the desired product as the second eluted fraction (white solid, 28 mg at 24%). $^1$H NMR (CD$_3$OD) δ 2.25 (s, 3H), 2.75–2.90 (m, 3H), 3.0 (dd, 1H), 3.75 (s, 1H), 4.50 (s, 2H), 4.75 (d, 1H), 4.90 (d, 1H), 6.1 0(d, 1H), 6.40(d, 1H), 6.45 (d, 1H), 7.05 (d, 1H), 7.10–7.30 (m, 6H), 7.35 (d, 1H), 7.50 (s, 1H). LRMS m/z=444.2 (M+1)$^+$.

EXAMPLE 2

2-[3-(3-[(Dimethylamino)methyl]phenethylamino)-6-methyl-2-oxo-1(2H)-pyrazinyl]-N-(1H-indol-5-ylmethyl)acetamide

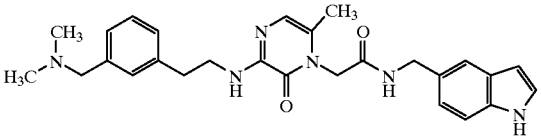

Preparation 11

Methyl 3-[(methylamino)carbonyl]benzoate

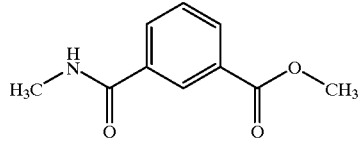

A slurry of methyl isophthalate (5.10 g, 0.028 mol) in CH$_2$Cl$_2$ (100 ml) at room temperature was treated with oxalyl chloride (6.0 ml) followed by DMF (3 drops). The resultant mixture was stirred under reflux (90 mins). The resultant mixture was cooled to room temperature, the solvent removed by evaporation and the residue azeotroped with CH$_2$Cl$_2$. The resultant mixture was dissolved in THF (100 ml), cooled to 0° C. and treated with a solution of methylamine (2M, 28 ml,56 mmol) in THF. The mixture was allowed to warm to room temperature overnight, solvent removed by evaporation and resultant mixture was partitioned between ethyl acetate (200 ml) and water (200 ml). The organic layer separated and washed with sat aq NaHCO$_3$, sat aq brine, and dried over MgSO$_4$. Removal of the drying agent by filtration followed by evaporation of the solvent gave the desired product (white solid, 4.60 g, 79%). $^1$H NMR (CDCl$_3$) δ 3.00 (d, 3H), 4.00 (s, 3H), 6.30 (s, br, 1H), 7.50 (t, 1H), 8.00 (d, 1H), 8.20 (d, 1H), 8.40 (s, 1H). LRMS m/z=211.1 (M+18)$^+$.

Preparation 12

3-[(Methylamino)methyl]phenylmethanol

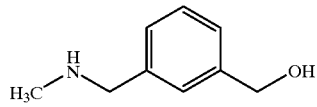

A stirred solution of methyl 3-[(methylamino)carbonyl]benzoate (preparation 11) (5.0 g, 20.7 mmol) in THF (120 ml) was treated dropwise with a solution of lithium aluminum hydride (1M, 30 ml,30 mmol) in THF. The resultant slurry was stirred under reflux overnight, cooled and treated with water (1.1 ml), 15%NaOH (1.8 ml) and water (2.5 ml).

The resultant gel was removed by filtration, the liquors concentrated in vacuo and taken up in ethyl acetate (120 ml). The organic layer was washed with sat aq brine (100 ml) and dried over MgSO$_4$. Removal of the drying agent by filtration followed by evaporation of the solvent gave an oil which was purified by chromatography (SiO$_2$, gradient elution with CH$_2$Cl$_2$; 95:5 CH$_2$Cl$_2$:MeOH; 90:10 CH$_2$Cl$_2$:MeOH; 90:10:1 CH$_2$Cl$_2$:MeOH:NH$_3$; 85:15:1 CH$_2$Cl$_2$:MeOH:NH$_3$). The second eluted material proved to be the correct product (2.9 g, 69%,). $^1$H NMR (CDCl$_3$) δ 2.20 (s, 2H), 2.40 (s, 3H), 3.70 (s, 2H), 4.60 (s, 2H), 7.20–7.40 (m, 4H). LRMS m/z=152.4 (M+1)$^+$.

Preparation 13 tert-Butyl N-[3-(bromomethyl)benzyl]-N-methylcarbamate

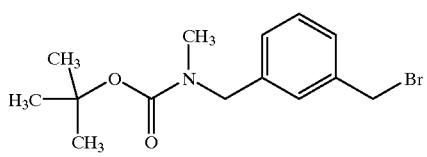

A milky suspension of 3-[(methylamino)methyl]phenylmethanol (preparation 12) (2.7 g, 17.9 mmol) in THF (60 ml) and water (60 ml) was treated with di-t-butylpyrocarbonate (5.4 g, 24.7 mmol) and the mixture stirred at room temperature overnight. The THF was evaporated and the aqueous residue treated with ethyl acetate (250 ml). The organic layer was washed with sat aq brine (100 ml) a and dried over MgSO$_4$. Filtration away from the drying agent followed by evaporation of the solvent gave the crude product which was purified by chromatography (SiO$_2$, eluting with 95:5CH$_2$Cl$_2$:MeOH) to give the intermediate tert-butyl N-[3-(hydroxymethyl)benzyl]-N-methylcarbamate(4.2 g) which was used directly in the next step. A stirred solution of tert-butyl-N-[3-(hydroxymethyl)benzyl]-N-methylcarbamate (4.2 g, 16.7 mmol) in CH$_2$Cl$_2$ (150 ml) at 0° C., was treated with carbon tetrabromide (8.0 g, 24.1 mmol) and triphenyl phosphine (6.35 g, 24.21 mmol). The resultant solution was warmed to room temperature and stirred for 4 days. The resultant mixture was evaporated to dryness and the residue purified by chromatography (SiO$_2$, gradient elution with 100% hexane; 99:1 hexane:ethyl acetate; 95:5 hexane:ethyl acetate) to give the desired product (3.32 g, 60%). $^1$H NMR (CDCl$_3$) δ 1.50 (s, 9H), 2.80 (s, br, 3H), 4.20 (s, 2H), 4.30 (s, 2H), 7.15 (m, 1H), 7.25 (m, 1H), 7.30 (m, 2H). LRMS m/z=333.2 (M+18)$^+$.

Preparation 14 tert-Butyl N-[3-(cyanomethyl)benzyl]-N-methylcarbamate

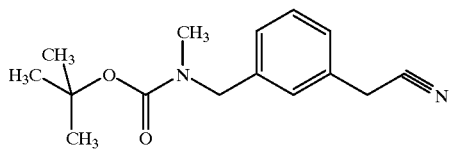

tert-Butyl-N-[3-(bromomethyl)benzyl]-N-methylcarbamate (preparation 13) (3.2 g, 10.18 mmol) was dissolved in acetonitrile (50 ml) and treated with sodium cyanide (1.23 g, 25.10mmol) followed by benzyl triethylammonium bromide (220 mg, 0.8 mmol) and the resultant mixture stirred at room temperature for 4 days. The resultant slurry was diluted with ethyl acetate (200 ml) washed with water, sat aq brine and dried over MgSO$_4$. Removal of the drying agent by filtration followed by evaporation of the solvent gave a pale yellow solid which was purified by chromatography (SiO$_2$, eluting with 100% CH$_2$Cl$_2$) to give the desired product with a trace of impurity (3.0 g). $^1$H NMR (CDCl$_3$) δ 1.50 (s, 9H), 2.80 (s, b, 3H), 3.75 (s, 2H), 4.40 (s, 2H), 7.20 (m, 3H), 7.35 (t, 1H). LRMS m/z=278.1 (M+18)$^+$.

Preparation 15 tert-Butyl N-[3-(2-aminoethyl)benzyl]-N-methylcarbamate

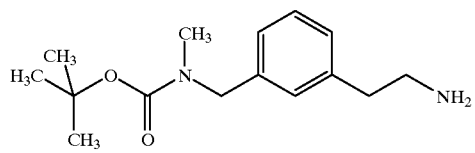

tert-Butyl-N-[3-(cyanomethyl)benzyl]-N-methylcarbamate (preparation 14) (3 g, 11.5 mmol, slightly impure) was dissolved in ethanol saturated with NH$_3$ (300 ml), treated with Raney® Nickel (500 mg) and stirred under a hydrogen atmosphere (60 psi, room temperature, 18 hr). The catalyst was removed by filtration under nitrogen, the solvent evaporated to dryness and the resultant crude product purified by chromatography (SiO$_2$, gradient elution with 100% CH$_2$Cl$_2$; 95:5 CH$_2$Cl$_2$:MeOH; 90:10 CH$_2$Cl$_2$:MeOH) to give the desired product (2.40 g, 78%). $^1$H NMR (CDCl$_3$) δ 1.20 (s, 2H), 1.50 (s, 9H), 2.70–2.90 (m, 5H), 3.00 (s, 2H), 4.20 (s, br, 2H), 7.05 (s, br, 3H), 7.25 (s, br, 1H). LRMS m/z=265.1 (M+1)$^+$.

Preparation 16

(R,S)-Benzyl 2-[(1-cyanoethyl)amino]acetate hydrochloride

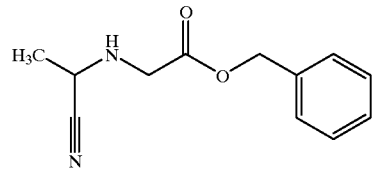

A cooled solution of glycine benzylester free base (12.9 g, 78.09 mmol from the HCl salt by partition between ethyl acetate and brine basified with sat Na$_2$CO$_3$ solution) in CH$_2$Cl$_2$ (100 ml) with 3 Å molecular sieves was treated with a solution of acetaldehyde (4.36 ml, 78.09 mmol) in CH$_2$Cl$_2$ (5 ml). After 30 mins the mixture was treated dropwise with a solution of TMSCN (10.40 ml, 78.09 mmol) cautiously, and the temperature maintained at 5° C. The resultant mixture was stirred at room temperature for 3 hr, washed with water, the aqueous layer extracted with CH$_2$Cl$_2$ (×2). the combined organic layers dried over MgSO$_4$ and the solvent evaporated. The resultant pale yellow oil was taken up in ether (150 ml) treated with a solution of HCl in ether (1M, 78 ml) to precipitate a solid which was collected by filtration, dried to give the desired product (17.85 g, 89%).

¹H NMR (CD₃OD) δ 1.70 (d, 3H), 4.20 (s, 2H), 4.70 (q, 1H), 5.30 (s, 2H), 7.40 (m, 5H). LRMS m/z=236.3 (M+18)⁺.

Preparation 17

Benzyl 2-[3,5-dichloro-2-methyl-6-oxo-1(6H)-pyrazinyl]acetate

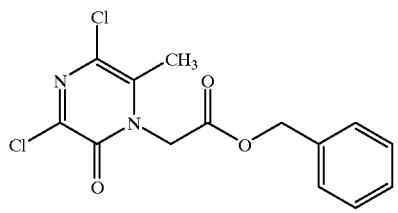

A suspension of benzyl-2-[(1-cyanoethyl)amino]acetate hydrochloride (preparation 16) (17.8 g, 69.88 mmol) in toluene (120 ml) was treated cautiously with oxalyl chloride (24.38 ml). Once effervescence had ceased the reaction was heated at 100° C. (24 hr). The reaction was cooled, solvent evaporated to dryness and the resultant crude product purified by chromatography (SiO₂, gradient elution with 70:30 pentane:ethyl acetate; 50:50 pentane:ethyl acetate; 30:70 pentane:ethyl acetate; 100% ethyl acetate). Chromatography again, (SiO₂, eluting with 100% CH₂Cl₂) gave the desired product as an off-white solid (9.40 g, 41%). ¹H NMR (CD₃OD) δ 2.35 (s, 3H), 4.90 (s, 2H), 5.25 (s, 2H), 7.40 (m, 5H).

Preparation 18

Benzyl 2-[3-[(3-[(tert-butarbonyl)(methyl)amino]methylphenethyl)amino]-5-chloro-6-methyl-2-oxo-1(2H)-pyrazinyl]acetate

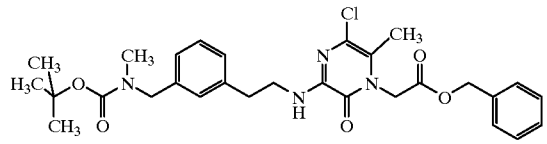

tert-Butyl-N-[3-(2-aminoethyl)benzyl]-N-methylcarbamate (preparation 15) (0.5 g, 1.89 mmol), benzyl-2-[3,5-dichloro-2-methyl-6-oxo-1(6H)-pyrazinyl]acetate (preparation 17) (0.6 g, 1.83 mmol) and triethylamine (0.5 ml, 3.66 mmol) in ethyl acetate (30 ml) were stirred at reflux for 24 hr. The resultant mixture was diluted with ethyl acetate (20 ml) and washed with water, sat aq brine, dried over MgSO₄. Removal of the drying agent by filtration followed by evaporation of the solvent gave a red oil which was purified by chromatography (SiO₂, gradient elution with 100% CH₂Cl₂; 99:1 CH₂Cl₂:MeOH; 98:2 CH₂Cl₂:MeOH) to give the desired product (0.76 g, 75%). ¹H NMR (CDCl₃) δ 1.45 (s, 9H), 2.20 (s, 3H), 2.80 (s, br, 3H), 2.90 (t, 2H), 3.70 (m, 2H), 4.20 (s, br, 2H), 4.80 (s, 2H), 5.20 (s, 2H), 6.10 (m, br, 1H), 7.10 (m, 3H), 7.25 (m, 1H), 7.35 (m, 5H). LRMS m/z=555.3 (M+1)⁺. Found C 62.50, H 6.34, N 9.98%; C₂₉H₃₅N₄O₅Cl requires C 62.75, H 6.36, N 10.09%.

Preparation 19

Benzyl 2-[3-chloro-2-methyl-5-(3-[(methylamino)methyl]phenethylamino)-6-oxo-1(6H)-pyrazinyl]acetate

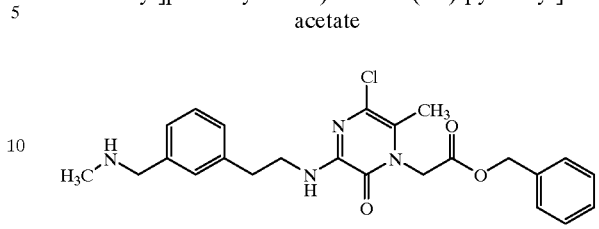

Benzyl-2-[3-[(3-[(tert-butoxycarbonyl)(methylphenethyl)amino]-5-chloro-6-methyl-2-oxo-1(2H)-pyrazinyl]acetate (preparation 18) (0.7 g, 1.26 mmol) was dissolved in CH₂Cl₂ (10 ml) and treated with TFA (1.0 ml). After stirring at room temperature for 3 hr, the reaction mixture was evaporated to dryness then dissolved in ethyl acetate (200 ml) washed with sat. aq NaHCO₃, sat aq brine, dried over MgSO₄. Removal of the drying agent by filtration followed by evaporation of the solvent gave a dark brown oil which was purified by chromatography (SiO₂, gradient elution with 100% CH₂Cl₂; 98:2 CH₂Cl₂:MeOH; 95:5 CH₂Cl₂:MeOH; 95:5:1 CH₂Cl₂:MeOH:NH₃) to give the desired product (0.38 g, 65%). ¹H NMR (CDCl₃) δ 2.00 (s, br, 1H), 2.20 (s, 3H), 2.45 (s, 3H), 2.90 (t, 2H), 3.70 (m, 2H), 3.75 (s, 2H), 4.80 (s, 2H), 5.20 (s, 2H), 6.10 (m, br, 1H), 7.10 (m, 1H), 7.15 (m, 2H), 7.25 (m, 1H), 7.35 (m, 5H). LRMS m/z=455.0, 457.2 (M+1)⁺.

Preparation 20

Benzyl 2-[3-chloro-5-(3-[(dimethylamino)methyl]phenethylamino)-2-methyl-6-oxo-1(6H)-pyrazinyl]acetate

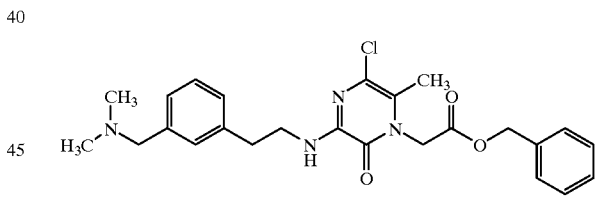

A stirred solution of benzyl 2-[3-chloro-2-methyl-5-(3[(methylamino)methyl]phenethylamino)-6-oxo-1(6H)-pyrazinyl]acetate (preparation 19) (0.38 g, 0.83 mmol) in CH₂Cl₂ (10 ml) was treated with formaldehyde (0.31 ml). After stirring at room temperature for 45 mins, the resultant cloudy -mixture was treated with sodium triacetoxyborohydride (253 mg, 1.19 mmol) and stirred at room temperature for a further 2 days. The reaction mixture was diluted with CH₂Cl₂ (200 ml) and washed with sat. aq NaHCO₃, sat aq brine and dried over MgSO₄. Removal of the drying agent by filtration followed by evaporation of the solvent gave a crude solid which was purified by chromatography (SiO₂, gradient elution with 100% CH₂Cl₂; 95:5 CH₂Cl₂:MeOH; 90:10 CH₂Cl₂:MeOH) to give the desired product (0.30 g, 77%). ¹H NMR (CDCl₃) δ 2.20 (s, 3H), 2.25 (s, 6H), 2.90 (t, 2H), 3.40 (s, 2H), 3.70 (m, 2H), 4.80 (s, 2H), 5.20 (s, 2H), 6.10 (m, br, 1H), 7.10–7.20 (m, 3H), 7.25 (m, 1H), 7.35 (m, 5H). LRMS m/z=469.2, 471.2 (M+1).

Preparation 21

2-[3-(3-[(Dimethylamino)methyl]phenethylamino)-6-methyl-2-oxo-1(2H)-pyrazinyl]acetic acid

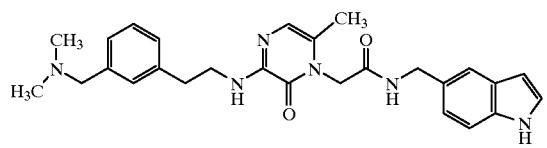

Benzyl-2-[3-chloro-5-3-[(dimethylamino)methyl]phenethylamino)-2-methyl-6-oxo-1(6H-pyrazinyl]acetate (preparation 20) (137 mg, 0.29 mmol) was dissolved in methanol:water (10:2, 20 ml), treated with Pearlman's catalyst (10 mg) and stirred under a hydrogen atmosphere (60 psi, room temperature, 2.5 hr). The catalyst was removed by filtration, followed by evaporation of the solvent and azeotroping with $CH_2Cl_2$ to yield a crude yellow solid. To the crude mixture, 1H-indol-5-ylmethylamine (preparation 8) (43 mg, 0.29 mmol), HOBT (46 mg, 0.34 mmol), WSCDI.HCl (74 mg, 0.39 mmol), N-methylmorpholine (0.061 ml, 0.55 mmol) and DMF (5 ml) were stirred at room temperature for 18 hr. The resultant mixture was evaporated to dryness and azeotroped with $CH_2Cl_2$. Water (2 ml) was added followed by aq $Na_2CO_3$ (a few drops) and the residue treated with ethyl acetate and methanol. The organic layer was separated, dried over $MgSO_4$. Filtration away from the drying agent followed by evaporation of the solvent gave the crude product which was purified by chromatography ($SiO_2$, gradient elution with 100% $CH_2Cl_2$; 95:5 $CH_2Cl_2$:MeOH; 95:5:0.5 $CH_2Cl_2$:MeOH:$NH_3$) to give the desired product (10 mg, 7%). $^1$H NMR ($CDCl_3$) δ 2.10 (s, 3H), 2.20 (s, 6H), 2.90 (t, 2H), 3.45 (s, 2H), 3.60 (t, 2H), 4.45 (s, 2H), 4.70 (s, 2H), 6.40 (m, br, 2H), 6.70 (m, 1H), 7.05 (m, 2H), 7.10–7.30 (m, 4H), 7.35 (m, 2H), 7.50 (m, 2H). LRMS m/z=473.2 (M+1)$^+$.

EXAMPLE 3

2-[3-Chloro-5-(3-[(dimethylamino)methyl]phenethylamino)-2-methyl-6-oxo-1(6H)-pyrazinyl]-N-(1H-indol-5-ylmethyl)acetamide

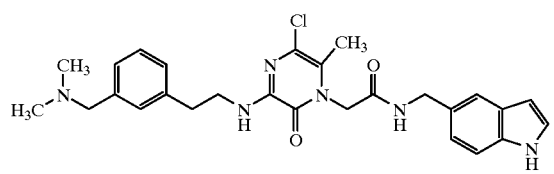

Preparation 22

2-[3-Chloro-5-(3-[(dimethylamino)methyl]phenethylamino)-2-methyl-6-oxo-1(6H)-pyrazinyl]acetic acid hydrochloride

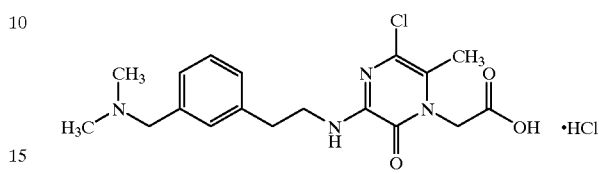

Benzyl-2-[3-chloro-5-(3-[(dimethylamino)methyl]phenethylamino)-2-methyl-6-oxo-1(6H-pyrazinyl]acetate (preparation 20) (100 mg, 0.21 mmol) was dissolved in ethanol (10 ml), treated with 10% Pd on carbon catalyst (20 mg), aq HCl (1 m, 0.1 ml) and stirred under a hydrogen atmosphere (20 psi, room temperature, 2 hr). The catalyst was removed by filtration, the solvent evaporated to dryness and the residue azeotroped with $CH_2Cl_2$ to give the desired product, slightly impure (white solid, 85 mg). $^1$H NMR ($CD_3OD$) δ 2.30 (s, 3H), 2.80 (s, 6H), 3.00 (t, 2H), 3.60 (t, 2H), 4.20 (s, 2H), 4.70 (s, 2H), 7.30 (m, 2H), 7.40 (m, 2H). LRMS m/z=379.1 (M+1)$^+$.

Preparation 23

2-[3-Chloro-5-(3-[(dimethylamino)methyl]phenethylamino)-2-methyl-6-oxo-1(6H)-pyrazinyl]-N-(1H-indol-5-ylmethyl)acetamide

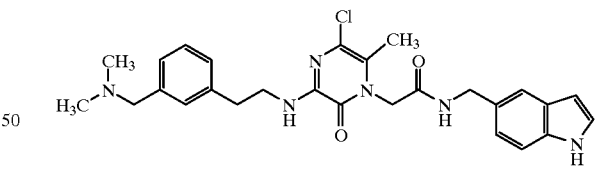

The title compound was prepared by a similar method to preparation 9 from 2-[3-chloro-5-(3-[(dimethylamino)methyl]phenethylamino)-2-methyl-6-oxo-1(6H)-pyrazinyl] acetic acid hydrochloride (preparation 22) (85 mg, 0.20 mmol) and 1H-indol-5-ylmethylamine (preparation 8) (35 mg, 0.24 mmol) to give the title compound (100 mg, 0.19 mmol, 98%). $^1$H NMR ($CD_3OD$) δ 2.20 (s, 3H), 2.70 (s, 6H), 3.00 (m, 2H), 3.60 (m, 2H), 4.20 (s, 2H), 4.50 (s, 2H), 4.80 (m, 2H), 7.05 (m, 1H), 7.10–7.55 (m, 9H), 7.75 (m, 1H), 7.85 (m, 1H). LRMS m/z=507.3, 509.3 (M+1)$^+$.

EXAMPLE 4

2-[3-[(1S)-1-Benzyl-2-(dimethylamino)ethyl]amino-6-methyl-2-oxo-1(2H)-pyrazinyl]-N-(1H-indol-5-ylmethyl)acetamide

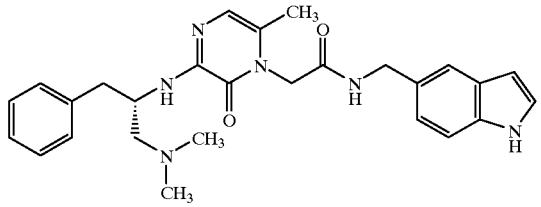

Preparation 24

Benzyl 2-[3-[(1S)-1-benzyl-2-(dimethylamino)ethyl]amino-5-chloro-6-methyl-2-oxo-1(2H)-pyrazinyl]acetate

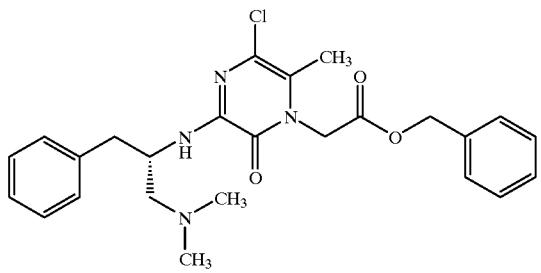

The title compound was prepared by a similar method to preparation 18 from N-[(2S)-2-amino-3-phenylpropyl]-N,N-dimethylamine (190 mg, 1.07 mmol; prepared as described in *Chem. Pharm. Bull.* 1970, 18,1731–1736) and benzyl 2-[3,5-dichloro-2-methyl-6-oxo-1(6H)-pyrazinyl]acetate (preparation 17) (361 mg, 1.10 mmol). The crude product was purified by chromatography (SiO$_2$; gradient elution 100% hexane; 80:20 hexane:ethyl acetate; 60:40 hexane:ethyl acetate; 40:60 hexane:ethyl acetate; 20:80 hexane:ethyl acetate) to give the desired product (yellow solid, 260 mg, 50%). $^1$H NMR (CDCl$_3$) δ 2.20 (m, 9H), 2.30 (m, 1H), 2.20 (m, 1H), 2.85 (m, 1H), 3.10 (m, 1H), 4.25 (m, 1H), 4.80 (s, 2H), 5.20 (s, 2H), 6.20 (m, 1H), 7.20 (m, 5H), 7.35 (m, 5H). LRMS m/z=469.2, 471.3 (M+1)$^+$.

Preparation 25

2-[3-[(1S)-1-Benzyl-2-(dimethylamino)ethyl]amino-6-methyl-2-oxo-1(2H)-pyrazinyl]-N-(1H-indol-5-ylmethyl)acetamide

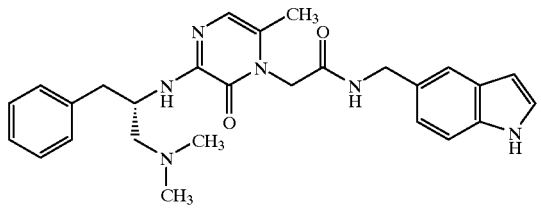

The title compound was prepared by a similar method to Example 2 from benzyl 2-[3-[(1S)-1-benzyl-2-(dimethylamino)ethyl]amino-5-chloro-6-methyl-2-oxo-1(2H)-pyrazinyl]acetate (preparation 24) (240 mg, 0.51 mmol) which was treated with Pearlman's catalyst (see example 2) to give a crude acid (168 mg, 95%). The crude acid (100 mg, 0.26 mmol) was coupled with 1H-indol-5-ylmethylamine (preparation 8) (41 mg, 0.29 mmol), to give a crude mixture which was purified by chromatography (SiO$_2$, eluting with 100% CH$_2$Cl$_2$; 95:5 CH$_2$Cl$_2$:MeOH; 95:5:0.5 CH$_2$Cl$_2$:MeOH:NH$_3$) to give example 5 as the first eluted fraction (yellow foam, 8 mg, 6% from crude acid) and desired product as the second eluted fraction (white foam 86 mg, 70% from crude acid). $^1$H NMR (CDCl$_3$) δ 2.20 (s, 6H), 2.25 (m, 4H), 2.40 (m, 1H), 2.85 (m, 1H), 3.00 (m, 1H), 4.30 (m, 1H), 4.50 (m, 2H), 4.55–4.70 (m, 2H), 6.00 (m, 1H), 6.50 (s, 1H), 6.70 (m, 2H), 7.10 (m, 1H), 7.20 (m, 6H), 7.35 (m, 1H), 7.50 (m, 1H), 8.20 (s, br, 1H). LRMS m/z=473.4 (M+1)$^+$; Found C 63.45, H 6.46, N 15.88%; C$_{27}$H$_{32}$N$_6$O$_2$.0.6 CH$_2$Cl$_2$ requires C 63.32, H 6.39, N 16.05%.

EXAMPLE 5

2-[3-[(1S)-1-Benzyl-2-(dimethylamino)ethyl]amino-5-chloro-6-methyl-2-oxo-1(2H)-pyrazinyl]-N-(1H-indo-5-ylmethyl)acetamide

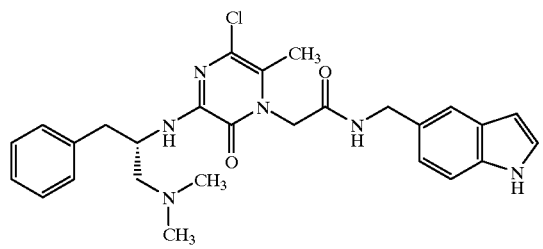

$^1$H NMR (CDCl$_3$) δ 2.20 (s, 7H), 2.35 (s, 3H), 2.50 (m, 1H), 2.80 (m, 1H), 3.00 (m, 1H), 4.30 (m, 1H), 4.40–4.60 (m, 3H), 4.65 (m, 1H), 6.30 (s, br, 1H), 6.50 (s, 1H), 6.80 (s, br, 1H), 7.05 (m, 1H), 7.15–7.40 (m, 7H), 7.50 (s, 1H), 8.30 (s, br, 1H). LRMS m/z=507.4, 509.6 (M+1)$^+$.

EXAMPLE 6

2-[3-{[(2R,S)-3-(Dimethylamino)-2-phenylpropyl]amino}-6-methyl-2-oxo-1(2H)-pyrazinyl]-N-(1H-indol-5-ylmethyl)acetamide

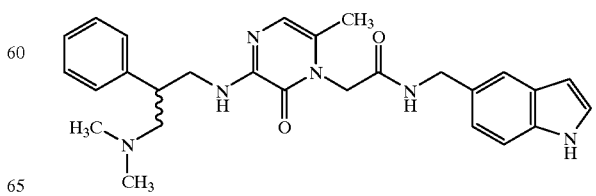

Preparation 26

Ethyl (2R,S)-3[-(benzyloxy)carbonyl]amino-2-phenylpropanoate

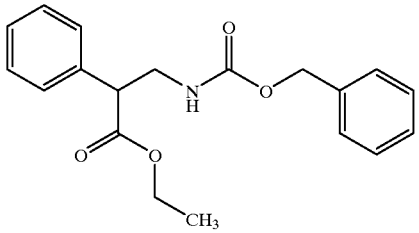

Ethyl (2R,S)-3-amino-2-phenylpropanoate (1.0 g, 5.18 mmol; prepared as described in *J Org. Chem.* 1961, 4062), 1-[(benzyloxy)carbonyl]oxydihydro-1H-pyrrole-2,5-dione (1.55 g, 6.21 mmol) and triethylamine (1.08 ml, 7.77 mmol) in $CH_2Cl_2$ (20 ml) were stirred at room temperature for 65 hr. The reaction mixture was washed with aq citric acid (1N), aq $NaHCO_3$, sat aq brine and dried over $MgSO_4$. Filtration away from the drying agent followed by evaporation of the solvent gave the crude product which was purified by chromatography ($SiO_2$; eluting with 98:2 $CH_2Cl_2$:MeOH) to give the desired product, slightly impure (colourless oil, 1.8 g). $^1$H NMR ($CDCl_3$) δ 1.20 (t, 3H), 3.50 (d, 1H), 3.60 (m, 1H), 3.65 (m, 1H), 3.90 (m, 1H), 4.15 (m, 2H), 5.10 (s, 2H), 7.20–7.40 (m, 10H). LRMS m/z=328.2 $(M+1)^+$.

Preparation 27

Benzyl (2R,S)-N-[3-(dimethylamino)-2-phenylpropyl]carbamate

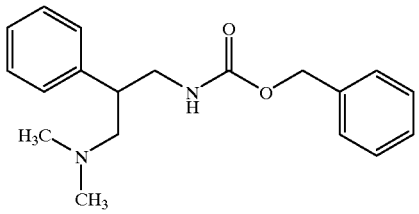

A solution of ethyl-(2R,S)-3-[(benzyloxy)carbonyl]amino-2-phenylpropanoate (preparation 26) (1.8 g, 5.50 mmol) in toluene (10 ml) was cooled to –75° C. and treated with a solution of DIBAL (1M, 11 ml, 11 mmol) in toluene, keeping the temperature below –65° C. The reaction mixture was stirred for 30 mins, then quenched by the addition of methanol. Aq potassium sodium tartrate was added and mixture warmed to room temperature, partitioned between ethyl acetate and water, the organic layers were separated and dried over $MgSO_4$. Filtration away from the drying agent followed by evaporation of the solvent gave the crude product which was purified by chromatography ($SiO_2$; eluting with 98:2 $CH_2Cl_2$:MeOH) to give the intermediate benzyl N-(3-oxo-2-phenylpropyl)carbamate (colourless oil, 933 mg 60%). Benzyl N-(3-oxo-2-phenylpropyl)carbamate (930 mg, 3.28 mmol) and dimethylamine hydrochloride (321 g, 3.94 mmol) were dissolved in $CH_2Cl_2$ (20 ml) and stirred for 1 hr. This mixture was treated with sodium triacetoxyborohydride (1.04 g, 4.92 mmol) and the resultant mixture stirred (2 hr, room temperature). The resultant mixture was washed with sat aq $NaHCO_3$, sat aq brine and dried over $MgSO_4$. Filtration away from the drying agent and evaporation of the solvent gave the crude product which was purified by chromatography ($SiO_2$; eluting with 90:10 $CH_2Cl_2$:MeOH) to give the desired product (colourless oil, 741 mg 72%). $^1$H NMR ($CDCl_3$) δ 2.20 (s, 6H), 2.40 (m, 1H), 2.65 (m, 1H), 3.00 (m, 1H), 3.40 (m, 1H), 3.55 (m, 1H), 5.05 (s, 2H), 5.85 (s, br, 1H), 7.15 (m, 2H), 7.25 (m, 2H), 7.30 (m, 6H). LRMS m/z=313.3 $(M+1)^+$.

Preparation 28

N-(2R,S)-(3-Amino-2-phenylpropyl)-N,N-dimethylamine

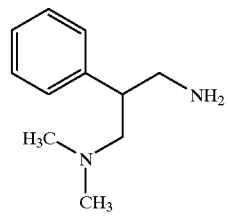

Benzyl-(2R,S)-N-[3-(dimethylamino)-2-phenylpropyl] carbamate (preparation 27) (740 mg, 2.61 mmol) was dissolved in ethanol (20 ml), treated with 10% Pd on carbon catalyst (100 mg) and stirred under a hydrogen atmosphere (10 psi, room temperature, 1 hr). The catalyst was removed by filtration, the solvent evaporated to dryness to give the desired product (colourless oil, 350 mg, 75%). $^1$H NMR ($CDCl_3$) δ 2.20 (s, 6H), 2.40 (m, 1H), 2.60 (m, 1H), 2.80 (m, 2H), 3.10 (m, 1H), 7.20–7.40 (m, 5H). LRMS m/z=179.4 $(M+1)^+$.

Preparation 29

Benzyl 2-[3-chloro-5-{[(2R,S)-3-(dimethylamino)-2-phenlpropyl]amino}-2-methyl-6-oxo-1(6H)pyrazinyl]acetate

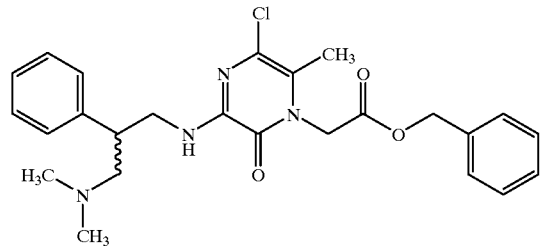

The title compound was prepared by a similar method to preparation 18 from N-(2R,S)-(3-amino-2-phenylpropyl)-N,N-dimethylamine (preparation 28) (261 mg, 1.47 mmol) and benzyl 2-[3,5-dichloro-2-methyl-6-oxo-1(6H-pyrazinyl] acetate (preparation 17) (400 mg, 1.22 mmol). The crude product was purified by chromatography ($SiO_2$; eluting with 95:5 $CH_2Cl_2$:MeOH) to give the desired product (off-white solid, 325 mg 57%). $^1$H NMR ($CDCl_3$) δ 2.20 (s, 3H), 2.30 (s, 6H), 2.50 (m, 1H), 2.80 (m, 1H), 3.15 (m, 1H), 3.70 (m, 2H), 4.80 (s, 2H), 5.20 (s, 2H), 7.20–7.40 (m, 10H), 7.55 (s, br, 1H). LRMS m/z=469.2, 471.2 $(M+1)^+$.

Preparation 30

2-[3-{[(2R,S)-3-(Dimethylamino)-2-phenylpropyl]amino}-6-methyl-2-oxo-1(2H-pyrazinyl]-N-(1H-indol-5-ylmethyl)acetamide

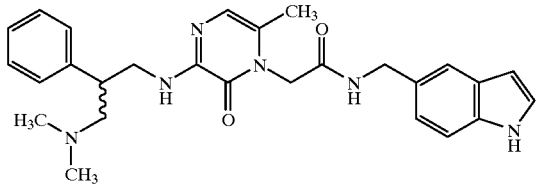

The title compound was prepared by a similar method to example 2 from benzyl 2-3-chloro-5-[(2R,S)-(dimethylamino)-2-phenylpropyl]amino-2-methyl-6-oxo-1(6H)-pyrazinyl]acetate (preparation 29) (320 mg, 0.68 mmol) which was treated with Pearlman's catalyst (see example 2) to give a crude acid (233 mg, 99%). The crude acid (230 mg, 0.67 mmol) was coupled with 1H-indol-5-ylmethylamine (preparation 8) (149 mg, 0.80 mmol) to give a crude product which was purified by chromatography (SiO$_2$, eluting with 90:10:1 CH$_2$Cl$_2$:MeOH:NH$_3$) to give the desired product (90 mg, 28%). $^1$H NMR (d$^6$-DMSO) δ 2.00 (s, 3H), 2.15 (s, 6H), 2.35 (m, 1H), 2.60 (m, 1H), 3.20 (m, 1H), 3.40 (m, 1H), 3.60 (m, 1H), 4.30 (d, 2H), 4.60 (s, 2H), 6.40 (m, 1H), 6.60 (m, 1H), 6.75 (s, 1H), 7.00 (m, 1H), 7.20–7.35 (m, 7H), 7.40 (s, 1H), 8.60 (m, 1H), 11.00 (s, br, 1H). LRMS m/z=473.5 (M+1)$^+$.

EXAMPLE 7

2-[3-{[(1S)-1-Benzyl-2-(dimethylamino)ethyl]amino-6-methyl-2-oxo-1(2H)-pyrazinyl]-N-[(6-methyl-1H-indazol-5-yl)methyl]acetamide

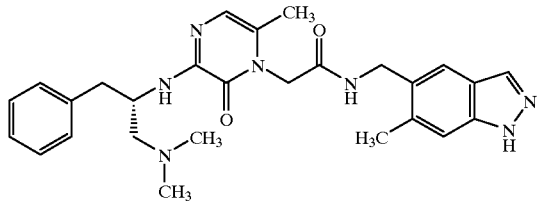

Preparation 31

4-Amino-2,5-dimethylbenzonitrile

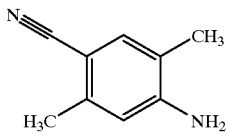

2,5-Dimethyl-4-nitrobenzonitrile (500 mg, 2.84 mmol; purchased from Salor) was dissolved in ethanol (20 ml), treated with 10% Pd on carbon catalyst (50 mg) and stirred under a hydrogen atmosphere (10 psi, room temperature, 3 hr). The catalyst was removed by filtration and the solvent evaporated to dryness. The resultant mixture was dissolved in CH$_2$Cl$_2$ and washed with HCl (2N, 4×15 ml), aqueous layer was treated with NaHCO$_3$ then extracted repeatedly with CH$_2$Cl$_2$. Solvent was evaporated from the organic layer to give the desired product (brown solid, 350 mg, 84%). $^1$H NMR (CD$_3$OD) δ 2.10 (s, 3H), 2.30 (s, 3H), 6.60 (s, 1H), 7.20 (s, 1H). LRMS m/z=147.4 (M+1)$^+$. Found C 72.12, H 6.86, N 18.53%; C$_9$H$_{10}$N$_2$.0.2H$_2$O requires C 72.16, H 7.00, N 18.70%.

Preparation 32

6-Methyl-1H-indazole-5-carbonitrile

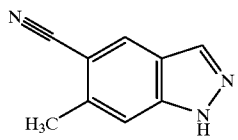

A solution of 4-amino-2,5-dimethylbenzonitrile (preparation 31) (111 mg, 0.76 mmol) in acetic acid (5 ml) was treated with a solution of sodium nitrite (53 mg, 0.76 mmol) in water (1 ml). The resultant mixture was stirred at room temperature for 10 mins then left to stand for 48 hrs. The solvent was removed by evaporation and the residue purified by chromatography (SiO$_2$, eluting with 50:50 hexane: ethyl acetate) to give the desired product (25 mg, 21%). $^1$H NMR (CD$_3$OD) δ 2.60 (s, 3H), 7.50 (s, 1H), 8.15 (s, 1H), 8.20 (s, 1H). LRMS m/z=158.1 (M+1)$^+$.

Preparation 33

(6-ethyl-1H-indazol-5-yl)methylamine

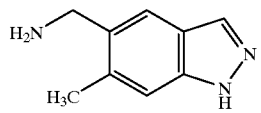

A solution of 6-methyl-1H-indazole-5-carbonitrile (preparation 32) (230 mg, 1.47 mmol) in THF (10 ml) under nitrogen was treated with a solution of lithium aluminum hydride (1N, 3.66 ml, 3.66 mmol) in THF at 0° C. The resultant mixture was stirred for 16 hr warming to room temperature, then treated with MeOH (12 ml), H$_2$O (0.8 ml), NaOH (4N, 2 ml) and H$_2$O (4 ml). The resultant precipitate was removed by filtration, washed with THF and purified by chromatography (SiO$_2$, eluting with 90:10:1 CH$_2$Cl$_2$:MeOH:NH$_3$) to give the desired product (71 mg, 30%). $^1$H NMR (CD$_3$OD) δ 2.40 (s, 3H), 3.95 (s, 2H), 7.35 (s, 1H), 7.70 (s, 1H), 7.95 (s, 1H). LRMR m/z=162.0 (M+1)$^+$.

Preparation 34

2-[3-{[(1S)-1-Benzyl-2-(dimethylamino)ethyl]amino}-6-methyl-2-oxo-1(2H)-pyrazinyl]-N-[(6-methyl-1H-indazol-5-yl)methyl]acetamide

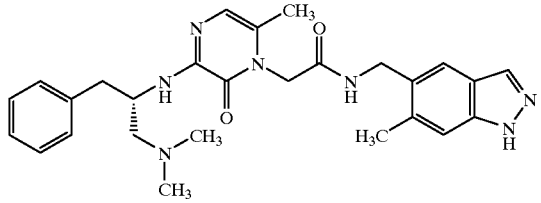

The title compound was prepared by a similar method to Example 2 from benzyl 2-[3-[(1S)-1-benzyl-2-(dimethylamino)ethyl]amino-5-chloro-6-methyl-2-oxo-1(2H)-pyrazinyl]acetate (preparation 24) (240 mg, 0.51 mmol) which was treated with Pearlman's catalyst (see example 2) to give a crude acid (168 mg, 95%). The crude acid (48 mg, 0.13 mmol) was then coupled with (6-methyl-1H-indazol-5-yl)methylamine (preparation 33) (22.4 mg, 0.14 mmol) to give a crude mixture which was purified by chromatography ($SiO_2$, eluting with 90:10 $CH_2Cl_2$: MeOH; 90:10:0.2 $CH_2Cl_2$:MeOH:$NH_3$; 90:10:0.4 $CH_2Cl_2$:MeOH:$NH_3$) to give the desired product (yellow solid, 28 mg, 46% from crude acid). $^1$H NMR ($CDCl_3$) δ 2.15–2.40 (m, 14H), 2.80 (m, 1H), 3.05 (m, 1H), 4.20–4.65 (m, 4H), 4.80 (m, 1H), 6.00–6.30 (m, br, 1H), 6.75 (s, 1H), 7.10 (s, 1H), 7.15–7.30 (m, 6H), 7.50 (s, 1H), 7.80 (s, b, 1H). LRMS m/z=488.2 (M+1)$^+$.

EXAMPLE 8

N-[(3-Methyl-1H-indol-5-yl)methyl]-2-[6-methyl-3-({3-[(methylamino)methyl]phenethyl}amino)-2-oxo-1(2H)-pyrazinyl]acetamide

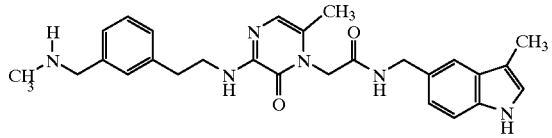

Preparation 35

3-Formyl-1H-indole-5-carbonitrile

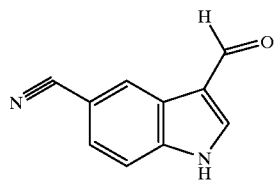

Phophoyl chloride (4.24 ml, 45.48 mmol) was added dropwise to dimethylformamide (3.52 ml, 45.48 mmol) and stirred for 30 mins at room temperature. A solution of 1H-indole-5-carbonitrile (5.39 g, 37.9 mmol) in dimethylformamide (10 ml) was added dropwise. A solid precipitated, further dimethylformamide (10 ml) was added to aid stirring and the reaction mixture was then stirred at room temperature for 3 hr. Water was s added to quench the reaction mixture which was then stirred for 18 hr. The stirring was stopped and the reaction mixture was left to stand, after 24 hr a pink solid had precipitated in the organic layer. The layers were separated and organic layer filtered, washed with water and dried to give the desired product (5.44 g, 84%). $^1$H NMR (DMSO) δ 7.60–7.80 (m, 2H), 8.20–8.30 (m, 2H), 10.00 (s, 1H), 12.20–12.35 (s, br, 1H).

Preparation 36

(3-Methyl-1H-indol-5-yl)methylamine

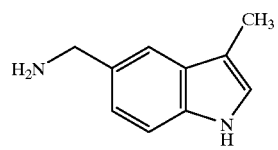

The title compound was prepared by a similar method to preparation 8 from 3-formyl-1H-indole-5-carbonitrile (preparation 35) (5.44 g, 32 mmol) to give the desired product as a white solid (2.57 g, 50%). $^1$H NMR ($CDCl_3$) δ 2.35 (s, 3H), 4.00 (s, 2H), 7.00 (s, 1H), 7.15 (d, 1H), 7.35 (d, 1H), 7.50 (s, 1H), 7.80–8.00 (s, br, 1H).

Preparation 37

Benzyl 2-[3-chloro-2-methyl-5-[(3-{[methyl(2,2,2-trifluoroacetyl)amino]methyl}phenethyl)amino]-6-oxo-1(6H)-pyrazinyl]acetate

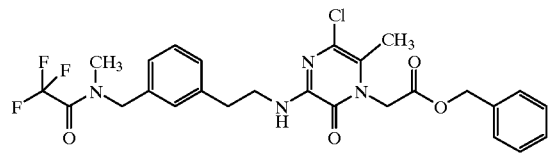

A solution of 2-[3-chloro-2-methyl-5-(3[(methylamino)methyl]phenethylamino)-6-oxo-1(6H)-pyrazinyl]acetate (preparation 19) (1.77 g, 3.90 mmol) in $CH_2Cl_2$ (75 ml) was treated with pyridine (0.65 ml) and trifluoroacetic anhydride (1 ml). After stirring at room temperature for 24 hr, the reaction mixture was evaporated to dryness and azeotroped with dichloromethane (×3). The residue was dissolved in dichloromethane (400 ml) washed with water, sat aq brine and dried over $MgSO_4$. Removal of the drying agent by filtration followed by evaporation of the solvent gave a pale orange solid which was recrystallised from boiling methanol to give the desired product. The mother liquors were concentrated under reduced pressure and purified by chromatography ($SiO_2$, gradient elution with 100% pentane; 3:1 pentane:ethyl acetate) to give further product (1.47 g, 68%). $^1$H NMR ($CDCl_3$) δ 2.20 (s, 3H), 3.90 (m, 3H), 3.05 (s, 2H), 3.60–3.70 (m, 2H), 4.60 (s, 2H), 4.80 (s, 2H), 5.20 (s, 2H), 6.05–6.15 (m, 1H), 7.00–7.15 (m, 2H), 7.15–7.25 (m, 1H), 7.25–7.40 (m, 7H). LRMS m/z=551.8 (M+1)$^+$.

Preparation 38

2,2,2-Trifluoro-N-methyl-N-[3-(2-{[5-methyl-4-(2-{[(3-methyl-1H-indol-5-yl)methyl]amino}-2-oxoethyl)-3-oxo-3,4-dihydro-2-pyrazinyl]amino}ethyl)benzyl]acetamide

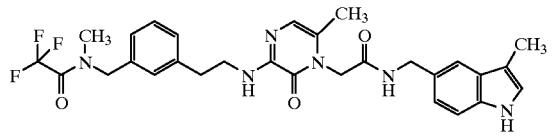

Benzyl-2-[3-chloro-2-methyl-5-[(3{[methyl(2,2,2-trifluoroacetyl)amino]methyl}phenethyl)amino]-6-oxo-1(6H pyrazinyl]acetate (preparation 37) (200 mg,0.36 mmol) was dissolved in methanol (80 ml), treated with Pearlman's catalyst (80 mg) and stirred under a hydrogen atmosphere (60 psi, room temperature, 2.5 hr). The catalyst was removed by filtration, followed by evaporation of the solvent and azeotroping with CH$_2$Cl$_2$ to yield a crude solid. To the crude mixture, (3-methyl-H-indol-5yl)methylamine (preparation 36) (60 mg, 0.37 mmol), HOBT (56 mg, 0.41 mmol), WSCDI.HCl (91 mg, 0.47 mmol), N-methylmorpholine (0.073 ml, 0.66 mmol) and DMF (10 ml) were added and stirred at room temperature for 18 hr. The resultant mixture was evaporated to dryness and triturated with water. The brown solid was filtered, dried, then purified by chromatography (SiO$_2$, gradient elution with 1:2 ethyl acetate:hexane; 2:1 ethyl acetate:hexane) to give the desired product (42 mg, 20%). $^1$H NMR (CD$_3$OD) δ 2.15 (s, 3H), 2.30 (s, 3H), 2.85–3.20 (m, 3H), 3.35 (s, 2H), 3.60 (m, 2H), 4.50 (s, 2H), 4.60–4.65 (m, 2H), 4.75 (s, 2H), 6.65 (s, 1H), 6.95–7.50 (m, 8H). LRMS m/z=596.5 (M+1)$^+$.

Preparation 39

N-[(3-Methyl-1H-indol-5-yl)methyl]-2-[6-methyl-3-({3-[(methylamino)methyl]phenethyl}amino)-2-oxo-1(2H)-pyrazinyl]acetamide

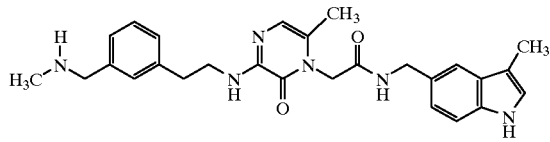

2,2,2-Trifluoro-N-methyl-N-[3-(2-{[5-methyl-4-(2-{[(3-methyl-1H-indol-5-yl)methyl]amino}-2-oxoethyl)-3-oxo-3,4-dihydro-2-pyrazinyl]amino}ethyl)benzyl]acetamide (preparation 38) (40 mg, 0.07 mmol) was dissolved in hot methanol (15 ml) and treated with an aq. solution of Na$_2$CO$_3$ (0.6 ml, 0.46 mol) followed by an additional portion of water (1.5 ml). The resultant cloudy mixture was stirred at room temperature for 18 hr, then evaporated to dryness and dried. The resultant white solid was purified by chromatography (SiO$_2$, gradient elution with 90:10 CH$_2$Cl$_2$:MeOH; 90:10:1 CH$_2$Cl$_2$:MeOH:NH$_3$) to give the desired product (34 mg, 100%). $^1$H NMR (CDCl$_3$) δ 2.15 (s, 3H), 2.30 (s, 3H), 2.50 (s, 3H), 2.90 (t, 2H), 3.60 (t, 2H), 3.90 (s, 2H), 4.50 (s, 2H), 4.75 (s, 2H), 6.70 (s, 1H), 7.00 (s, 1H), 7.05 (d, 1H), 7.20–7.40 (m, 5H), 7.45 (s, 1H). LRMS m/z=473.4 (M+1)$^+$.

EXAMPLE 9

2-[3-{[3-(3-Azetidinyl)phenethyl]amino}-6-methyl-2-oxo-1(2H)-pyrazinyl]-N-[(3-methyl-1H-indol-5-yl)methyl]acetamide

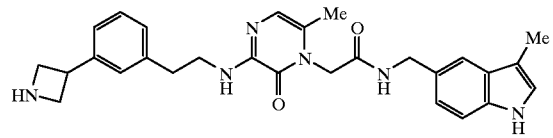

Examples 9 and 10 were prepared following the general methods outlined above, in particular those described for compounds of type (g) and more particularly in accordance with example 8.

$^1$H NMR (CD$_3$OD, 300 MHz) δ: 2.18 (s, 3H), 2.28 (s, 3H), 3.05 (t, 2H), 3.78 (m, 2H), 4.17–4.40 (m, 5H), 4.54 (m, 2H), 4.80 (s, 2H), 6.58 (m, 1H), 6.99 (m, 1H), 7.05 (d, 1H), 7.18–7.57 (m, 6H). LRMS m/z=485 (M+1)$^+$.

EXAMPLE 10

N-[(3-Methyl-1H-indol-5-yl)methyl]-2-[6-methyl-3-{[3-(1-methyl-3-azetidinyl)phenethyl]amino}-2-oxo-1(2H)-pyrazinyl]acetamide

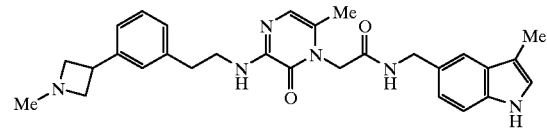

$^1$H NMR (CD$_3$OD, 300 MHz) δ: 2.14 (s, 3H), 2.27 (s, 3H), 2.39 (s, 3H), 2.90 (t, 2H), 3.20–3.38 (m, 3H), 3.58 (t, 2H), 3.78 (m, 2H), 4.49 (s, 2H), 4.75 (s, 2H), 6.66 (s, 1H), 6.98 (s, 1H), 7.02 (d, 2H), 7.12 (m, 2H), 7.18–7.30 (m, 3H), 7.42 (s, 1H). LRMS m/z=499 (M+1)$^+$.

EXAMPLE 11

2-[3-[(3-{[(2-Methoxyethyl)amino]methyl}phenethyl)amino]-6-methyl-2-oxo-1(2H)-pyrazinyl]-N-[(3-methyl-1H-indol-5-yl)methyl]acetamide

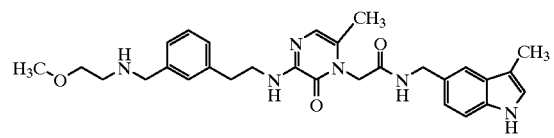

Preparation 40

3-(Cyanomethyl)-N-(methoxymethyl)benzamide

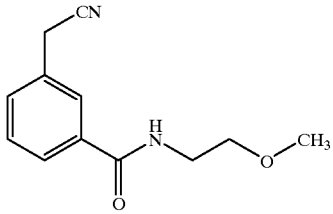

2-(3-Bromophenyl)acetonitrile (40 g, 0.20 mol) was added to a solution of 2-methoxyethylamine (61.3 g, 0.81 mol), triphenylphosphine (8.0 g, 0.03 mol), palladium acetate (4.0 g, 0.01 mol) and triethylamine (62 g, 0.61 mol) in tetrahydrofuran (400 ml). The reaction mixture was heated to 100° C. in a sealed vessel under carbon monoxide @100 psi for 18 hrs, after which time the solvent was removed under reduced pressure. The crude product was purified by column chromatography on silica gel using an elution gradient of dichloromethane:pentane (90:10) changing to dichloromethane (100%) and then to dichloromethane:methanol (98:2) to afford the title compound, 14.57 g (33%).

$^1$H-NMR (300 MHz, DMSO): δ [ppm] 3.26 (3H, s), 3.41 (4H, m), 4.09 (2H, s), 7.65–7.43 (2H, m), 7.78 (1H, m), 7.83 (1H, s), 8.55 (1H, bs). LRMS: m/z=219 (MH$^+$).

Preparation 41

3-(2-aminoethyl)-N-(2-methoxyethyl)benzamide

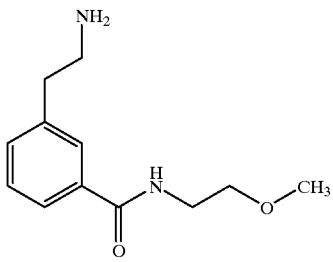

Borane (1N in tetrahydrofuran, 467 ml, 0.467 mol) was added dropwise to a solution of 3-(cyanomethyl)-N-(methoxymethyl)benzamide (14.57 g, 0.067 mol) [see preparation 40] in tetrahydrofuran (30 ml) over 20 minutes. The reaction mixture was then stirred at room temperature for 18 hrs and then heated to reflux for 2 hrs, after which time the solvent was evaporated under reduced pressure and the residue acidified with hydrochloric acid (2N). The resultant mixture was heated to reflux for 10 minutes after which time it was basified with sodium hydroxide. The product was extracted with dichloromethane (3×30 ml), the combined organic layers were dried over MgSO$_4$ and the solvent evaporated under reduced pressure. The crude product was purified by column chromatography on silica gel using an elution gradient of dichloromethane:methanol:0.88 ammonia (95:5:0.5) changing to (92.5:7.5:0.25) changing to (90:10:1) to afford the title compound, 6.15 g, (44%).

$^1$H-NMR (300 MHz, DMSO): δ [ppm] 1.60 (2H, bs), 2.62 (4H, m), 2.73 (2H, m), 3.22 (3H,s), 3.40 (2H, t), 3.65 (2H, s), 7.05 (1H, d), 7.10 (2H, d), 7.22 (1H, d). LRMS; m/z=209 (MH$^+$).

Preparation 42

Benzyl 2-[3-chloro-5-[(3-{[(2-methoxyethyl)amino]methyl}phenethyl)amino]-2-methyl-6-oxo-1(6H)-pyrazinyl]acetate

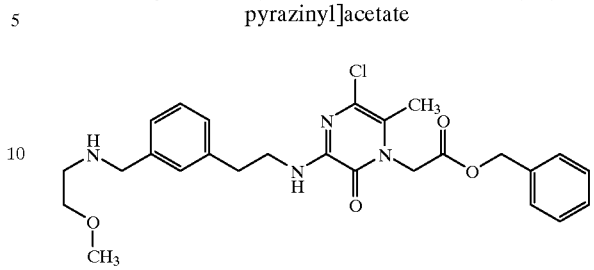

Benzyl 2-(3,5-dichloro-2-methyl-6-oxo-1(6I-)-pyrazinyl] acetate (400 mg, 1.22 mmol) [see preparation 17] was added to a solution of 3-(2-aminoethyl 1)-N-(2-methoxyethyl) benzamide (260 mg, 1.25 mmol) [see preparation 41] and triethylamine (0.34 ml, 2.4 mmol) in ethyl acetate (5 ml). The reaction mixture was heated to reflux for 4 hrs, after which time the mixture was cooled to room temperature and stirred for a further 56 hrs, the mixture was partitioned between ethyl acetate (20 ml) and water (20 ml). The organic layer was washed with water (2×20 ml), brine (20 ml) and dried over MgSO$_4$ the solvent was evaporated under reduced pressure. The crude product was purified by trituration with diethyl ether to afford the title compound, 365 mg, (60%).

$^1$H-NMR (300 MHz, DMSO): δ [ppm] 2.20 (3H, s), 2.60 (2H, t), 2.80 (2H, t), 3.30 (3H, s), 3.38 (2H, t), 3.45 (2H, m), 3.70 (2H, s), 4.85 (2H, s), 5.20 (2H, s), 7.07–7.25 (4H, m), 7.35 (5H, m), 7.50 (1H, t). LRMS: m/z=499 (M$^+$).

Preparation 43

Benzyl 2-[3-chloro-5-[(3-{[(2-methoxyethyl)(2,2,2-trifluoroacetyl)amino]methyl}phenethyl)amino]-2-methyl-6-oxo-1(6H)-pyrazinyl]acetate

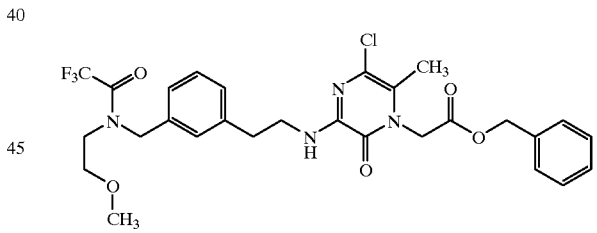

Trifluoroacetic anhydride (0.17 ml, 0.766 mmol) was added to a solution of benzyl 2-[3-chloro-5-[(3-{[(2-methoxyethyl)amino]methyl}phenethyl)amino-2-methyl-6-oxo-1(6H)-pyrazinyl]acetate (365 mg, 0.73 mmol) [see preparation 42] and pyridine (0.077 ml, 0.95 mmol) in dichloromethane (5 ml). The reaction mixture was stirred at room temperature for 18 hrs, after which time the mixture was partitioned between dichloromethane (20 ml) and water (20 ml), the organic layer was washed with brine (20 ml) and dried over MgSO$_4$ and the solvent was evaporated under reduced pressure. The crude product was purified by recrystallisation from methanol to afford the title compound as a white solid, 260 mg, (60%).

$^1$H-NMR (300 MHz, DMSO): δ [ppm] 2.20 (3H, s), 2.88 (2H, q), 3.20 (3H, m), 3.40–3.55 (6H, m), 4.65 (2H, d), 4.86 (2H, s), 5.20 (2H, s), 7.03–7.40 (9H, m), 7.55 (1H, m). LRMS: m/z 596 (MH$^+$).

Preparation 44

2-[3-[(3-{[(2-Methoxyethyl)(2,2,2-trifluoroacetyl)amino]methyl}phenethyl)amino]-6-methyl-2-oxo-1(2H)-pyrazinyl]acetic acid

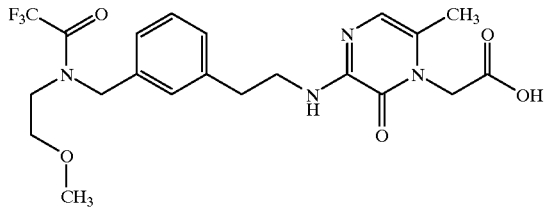

Benzyl 2-[3-chloro-5-[(3-{[(2-methoxyethyl)(2,2,2-trifluoroacetyl)amino]methyl}phenethyl)amino]-2-methyl-6-oxo-1(6H) pyrazinyl] acetate [see preparation 43] (260 mg, 0.437 mmol) was dissolved in methanol (10 ml) and palladium hydroxide catalyst (30 mg) added. The reaction mixture was hydrogenated at 60 psi for 4 hrs. The catalyst was filtered off and the solvent evaporated under reduced pressure to afford the title compound as a oil, 190 mg, (92%). LRMS: m/z=471 (MH$^+$).

Preparation 45

2,2,2-Trifluoro-N-(2-methoxyethyl)-N-[3-(2-{[-methyl-4-(2{[-methyl-1H-indol-5-yl)methyl]amino)}-2-oxoethyl)-3-oxo-3,4-dihydro-2-pyrazinyl]amino}ethyl)benzyl]acetamide

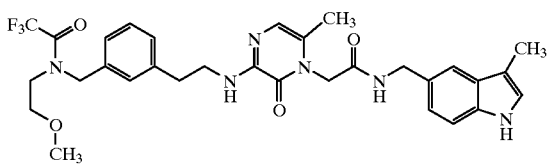

Hydroxybenzotriazole hydrate (60 mg, 0.44 mmol) and WSCDI.HCl (93 mg, 0.47 mmol) were added to a solution of 2-[3-[(3-{[(2-methoxyethyl)(2,2,2-trifluoroacetyl)amino]methyl}phenethyl)amino]-6-methyl-2-oxo-1(2H)-pyrazinyl]acetic acid (190 mg, 0.40 mmol) [see preparation 44] in N,N-dimethylformamide (3.0 ml). N-methylmorpholine (123 mg, 1.2 mmol) was added followed by (3-methyl-1H-indol-5-yl)methylamine (72 mg, 0.45 mmol) [see preparation 36]. The reaction mixture was stirred at room temperature for 18 hrs, after which time the mixture was partitioned between ethyl acetate (30 ml) and water (30 ml). The organic layer was washed with water (3×30 ml), brine (30 ml) and dried over MgSO$_4$ and the solvent evaporated under reduced pressure. The crude product was purified by column chromatography on silica gel using an elution gradient of dichloromethane:methanol:0.88 ammonia (99:1:0.1) changing to (98:2:0.2) to afford the title compound as a oil, 113 mg (53%).

$^1$H-NMR (300 MHz, CDCl$_3$): δ [ppm] 2.93 (3H, m), 3.45–3.70 (12H, m), 4.50 (2H, d), 4.67 (2H, s), 4.73 (3H, m), 5.90 (1H, m), 6.60 (1H, m), 6.78 (1H, s), 6.95–7.30 (8H, m), 7.41 (1H, s), 7.92 (1H, m). LRMS: m/z=613 (MH$^+$).

Preparation 46

2-[3-[(3{[(2-Methoxyethyl)amino]methyl}phenethyl)amino]-6-methyl-2-oxo-1(2H)-pyrazinyl]-N-[(3-methyl-1H-indol-5-yl)methyl]acetamide

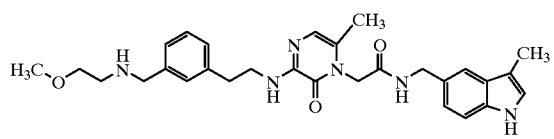

2,2,2-Trifluoro-N-(2-methoxyethyl)N-[3-(2-{[5-methyl-4-(2-{[(3-methyl-1H-indol-5-yl)methyl]amino}-2-oxoethyl)-3-oxo-3,4-dihydro-2 pyrazinyl]amino}ethyl)benzyl]acetamide (preperation 45) (110 mg, 0.18 mmol) was dissolved in methanol(15 ml) and sodium carbonate solution in water (1.5 ml, 0.765 m, 1.15 mmol) was added. The reaction mixture was stirred for 56 hrs, after which time the reaction was heated to 50° C. and sodium carbonate (1.5 ml, 1.15 mmol) was added. The mixture was heated for 18 hrs and then partitioned between ethyl acetate and water, the organic layer was washed with brine, dried over MgSO$_4$ and the solvent evaporated under reduced pressure. The crude product was triturated with diethyl ether:methanol (1:1) to afford the title compound, 23 mg, (25%).

$^1$H-NMR (400 MHz, CDCl$_3$): δ [ppm] 2.08 (3H, s), 2.21 (3H, s), 2.60 (1H, t), 2.81 (2H, m), 3.20 (3H, s), 3.30 (3H, m), 3.39 (1H, t), 3.50 (3H, m), 3.57 (1H, m), 4.35 (2H, d), 4.60 (2H, m), 6.64 (1H, s), 6.78 (1H, t), 6.94–7.30 (7H, m), 8.60 (1H, t), 10.21 (1H, bs). LRMS: m/z=517 (MH$^+$). Found C, 65.55; H, 6.78; N, 15.48; C$_{29}$H$_{36}$N$_6$O$_3$.H$_2$O requires C, 65.15; H, 7.16; N, 15.72%.

EXAMPLE 12

2-[3-({[(2R)1-(Cyclopropylmethyl)pyrrolidinyl]methyl}amino)-6-methyl-2-oxo-1(2H)-pyrazinyl]-N-[(3-methyl-1H-indol-5-yl)methyl]acetamide

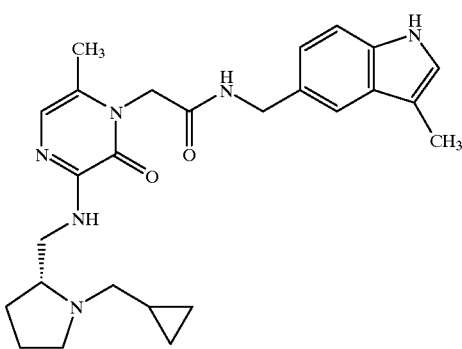

Preparation 47

Benzyl 2-[3-chloro-5-({[(2R)-1-(cyclopropylmethyl)pyrrolidinyl]methyl}amino)-2-methyl-6-oxo-1(6H)-pyrazinyl]acetate

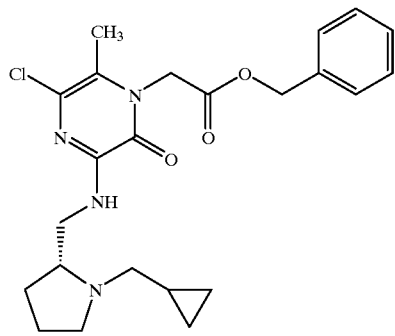

The title compound was prepared by a similar method to preparation 42 from benzyl 2-[3,5-dichloro-2-methyl-6-oxo-1(6H)-pyrazinyl]acetate [see preparation 17] and [(2R)-1-(cyclopropylmethyl)pyrrolidinyl]methylamine [see WO 9839295 A1], to afford the product as a orange oil (100%).

LRMS: m/z=445 (MH$^+$).

Preparation 48

2-[3-({[(2R)-1-(cyclopropylmethyl)pyrrolidinyl]methyl}amino)-6-methyl-2-oxo-1(2H)-pyrazinyl]acetic acid hydrochloride

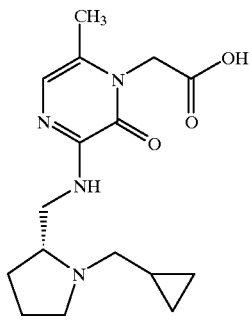

The title compound was prepared by a similar method to preparation 44 from benzyl 2-[3-chloro-5-({[(2R)-1-(cyclopropylmethyl)pyrrolidinyl]methyl}amino)-2-methyl-6-oxo-1(6H)-pyrazinyl]acetate [see preparation 47] and palladium hydroxide to afford the product as a oil, 352 mg, (100%).

$^1$H-NMR (300 MHz, CDCl$_3$): δ [ppm] 7.40 (1H, t), 6.65 (1H, s), 4.66 (2H, s), 3.75–3.00 (7H, m), 2.87 (1H, m), 2.08 (3H, s), 1.96–1.71 (4H, m), 1.10 (1H, m), 0.58 (2H, d), 0.35 (2H, m). $^1$HMR (300 MHz, CDCl$_3$): δ [ppm} 0.35(2H,m), 0.58(2H,d), 1.10(1H,m), 1.91–1.96(4H,m), 2.08(3H,s), 2.87 (1H,m),3.00–3.75(7H,m), 4.66(2H,s), 6.65(1H, s), 7.40(1H, t).

Preparation 49

2-[3-({[(2R)-1-(Cyrlopropylmethyl)pyrrolidinyl]methyl}amino)-6-methyl-2-oxo-1(2H)-pyrazinyl]-N-[(3-methyl-1H-indol-5-yl)methyl]acetamide

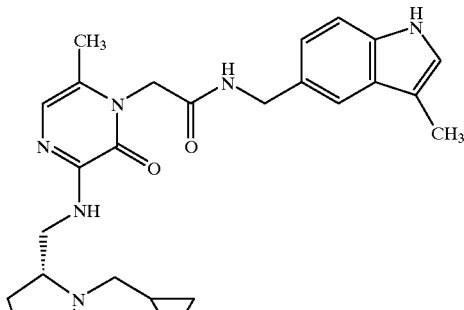

The title compound was prepared by a similar method to preparation 45 from 2-[3-({[(2R)-1-(cyclopropylmethyl)pyrrolidinyl]methylamino)-6-methyl-2-oxo- 1(2H)-pyrazinyl]acetic acid hydrochloride [see preparation 48] and (3-methyl-1H-indol-5-yl)methylamine (72 mg, 0.45 mmol) [see preparation 36]. The crude product was purified by column chromatography on silica gel using dichloromethane:methanol:0.88 ammonia (96:3.5:0.5) as the eluant to afford the title compound as a yellow solid, 245 mg, (55%).

$^1$H-NMR (300 MHz, MeOD): δ [ppm] 0.27 (2H, d), 0.53 (1H, t), 0.94 (1H, m), 1.70 (1H, m), 1.75 (2H, t), 1.90–2.00 (1H, m), 2.18 (4H, m), 2.20–2.40 (5H, m), 2.80 (2H, m), 3.30 (3H, m), 3.45–3.40 (2H, m), 4.46 (4H, m), 4.73 (1H, s), 6.68 (1H, s), 6.98 (1H, s), 7.06 (1H, m), 7.26 (1H. m), 7.45 (1H, d). LRMS=463 (MH$^+$).

The hydrochloride salt of the product of preparation 49 was prepared by dissolving the product in methanol (5 ml) and adding hydrochloric acid (1N, 0.53 ml, 0.53 mmol). to afford (2R)-1-(cyclopropylmethyl)-2-({[5-methyl-4-(2-{[(3-methyl-1H-indol-5-yl)methyl]amino)-2-oxoethyl)-3-oxo-3,4-dihydro-2-pyrazinyl]amino}methyl)pyrrolidinium hydrochloride as a solid.

$^1$H-NMR consistent with free base.

EXAMPLE 13

2-[3-({[(2R)-1-Cyclopentyl pyrrolidinyl]methyl}amino)-6-methyl-2-oxo-1(2H)-pyrazinyl]-N-[(3-methyl-1H-indol-5-yl)methyl]acetamide

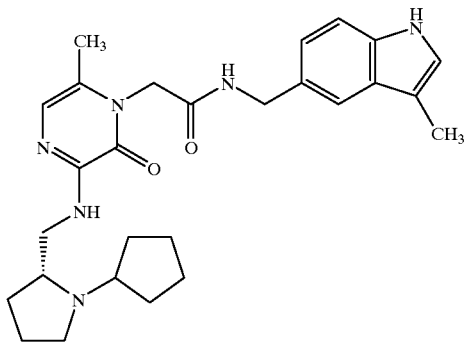

Preparation 50 tert-Butyl (2R)-2-({[(4-methylphenyl)sulfonyl]oxy}methyl)-1-pyrrolidinecarboxylate

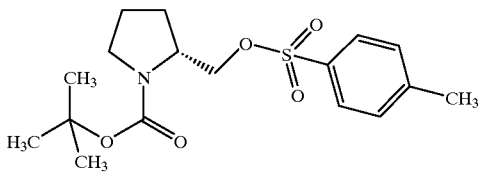

4-Methylbenzenesulfonyl chloride (8.83 g, 46.32 mmol) was added to a solution of tert-butyl (2R)-2-(hydroxymethyl)-1-pyrrolidinecarboxylate (5.48 g, 27.24 mmol) in pyridine (25 ml). The reaction mixture was stirred for 2.5 hrs, after which time the reaction was diluted with ethyl acetate (100 ml) and washed with water (100 ml), saturated copper sulphate solution (100 ml), dried over MgSO$_4$ and the solvent was evaporated under reduced pressure. The crude product was purified by column chromatography on silica gel using ethyl acetate:pentane (20:80) as the eluant to afford the title compound as a clear oil, 9.2 g, (95%).

LRMS: m/z=356 (MH$^+$). Found, C, 57.44; H, 7.09; N, 3.94; C$_{17}$H$_{25}$NO$_5$S requires C, 57.22; N, 7.15; N, 3.79%

Preparation 51 tert-Butyl (2R)-2-(azidomethyl)-1-pyrrolidinecarboxylate

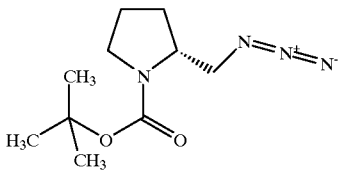

Sodium azide (2.52 g, 38.80 mmol) was added to a solution of tedt-butyl (2R)-2-({[(4-methylphenyl)sulfonyl]oxy}methyl)-1-pyrrolidinecarboxylate (9.20 g, 25.90 mmol) [see preparation 50] in dimethylsulphoxide (100 ml). The reaction mixture was heated to 80° C. for 18 hrs. after which time the cooled mixture was partitioned between diethyl ether (200 ml) and water (200 ml). The aqueous was washed with diethyl ether (200 ml). The combined organic layers were dried over MgSO$_4$ and the solvent evaporated under reduced pressure to afford the title compound as a clear oil, 5.74 g, (98%).

$^1$H-NMR (400 MHz, CDCl$_3$): δ [ppm] 1.48 (9H, s), 1.50 (1H, s), 1.80–2.06 (4H, m), 3.35 (4H, m), 3.90 (1H, m). LRMS: m/z=227 (MH$^+$).

Preparation 52 tert-butyl (2R)-2-(aminomethyl)-1-pyrrolidinecarboxylate

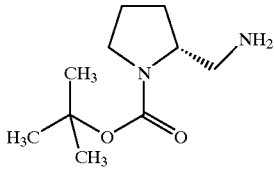

10% Palladium on charcoal (750 mg) was added to a solution of tert-butyl (2R)-2-(azidomethyl)-1-pyrrolidinecarboxylate (preperation 51)(5.74 g, 25.39 mmol) in ethanol (100 ml). The reaction mixture was hydrogenated @15 psi for 2.5 hrs, after which time the catalyst was filtered off and the solvent evaporated under reduced pressure. The crude product was purified by column chromatography on silica gel using dichloromethane:methanol:0.88 ammonia (90:10:0.5) as the eluant, to afford the title compound and some starting material. The mixture was dissolved in ethanol (100 ml) and 10% palladium on charcoal (500 mg) was added, the mixture was hydrogenated at 30 psi for 18 hrs, after which time the catalyst was filtered off and the solvent evaporated under reduced pressure to afford the title compound as a clear oil, 4.32 g, (85%).

$^1$H-NMR (300 MHz, CDCl$_3$): δ [ppm] 1.30 (2H, bs), 1.45 (9H, s), 1.72–2.00 (4H, m), 2.65–2.90 (2H, m), 3.26–3.33 (2H, m), 3.75 (1H, m). LRMS: m/z=201 (MH$^+$).

Preparation 53 tert-Butyl (2R)-2-[({4-[2-(benzyloxy)-2-oxoethyl]-6-chloro-5-methyl-3-oxo-3,4-dihydro-2-pyrazinyl}amino)methyl]-1-pyrrolidinecarboxylate

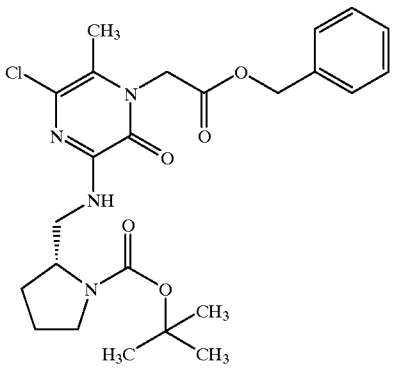

The title compound was prepared by a similar method to preparation 42 from benzyl 2-[3,5-dichloro-2-methyl-6-oxo-1(6H)-pyrazinyl]acetate (preperation 17) and tert-butyl (2R-2-(aminomethyl)-1-pyrrolidinecarboxylate [see preparation 52]. The crude product was purified by column chromatography on silica gel using an elution gradient of ethyl acetate-:pentane (10:90) changing to (80:20) in 10% increments to afford the title compound as a clear oil, (80%).

$^1$H-NMR (300 MHz, CDCl$_3$): δ [ppm] 1.43 (9H, s), 1.70–2.08 (4H, m), 2.18 (2H, s), 2.35 (1H, s), 3.26–3.65 (4H, m), 4.00–4.20 (1H, m), 4.80 (2H, s), 5.25 (2H, s), 7.26–7.40 (5H, m). LRMS: m/z=491 (MH$^+$).

Preparation 54

2-[3-({[(2R)-1-(tert-butoxycarbonyl)pyrrolidinyl]methyl}amino)-6-methyl-2-oxo-1(2H)-pyrazinyl]acetic acid

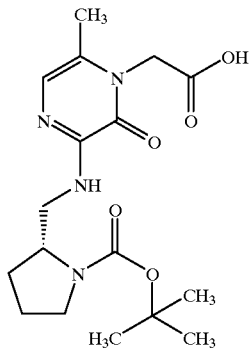

The title compound was prepared by a similar method to preparation 44 from tert-butyl (2R)-2-[((4-[2-(benzyloxy)-2-oxoethyl]-6-chloro-5-methyl-3-oxo-3,4-dihydro-2-pyrazinyl}amino)methyl]-1-pyrrolidinecarboxylate [see preparation 53] and palladium hydroxide to afford the product as a white foam, (68%).

$^1$H-NMR (400 MHz, DMSO): δ [ppm] 1.40 (9H, s), 1.68–1.86 (4H, m), 2.00 (2H, s), 3.06–3.25 (4H, m), 3.40 (1H, bs), 3.95 (1H, m), 4.13–4.30 (2H, m), 5.72 (2H, s), 6.48 (1H, s). LRMS: m/z=367 (MH$^+$).

Preparation 55 tert-butyl (2R)-2-({[5-methyl-4-(2-{[(3-methyl-1H-indol-5-yl)methyl]amino}-2-oxoethyl)-3-oxo-3,4-dihydro-2-pyrazinyl]amino}methyl)-1-pyrrolidinecarboxylate

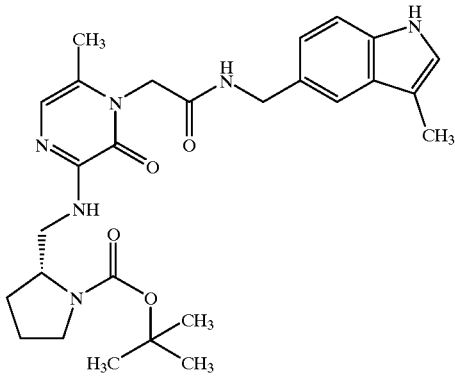

The title compound was prepared by a similar method to preparation 45 from 2-[3-({[(2R)-1-(tert-butoxycarbonyl)pyrrolidinyl]methyl}amino)-6-methyl-2-oxo-1(2H)-pyrazinyl]acetic acid [see preparation 54] and (3-methyl-1H-indol-5-yl)methylamine (72 mg, 0.45 mmol) [see preparation 36]. The crude product was purified by column chromatography on silica gel using an elution gradient of dichloromethane:methanol (100:0) changing to (95:5) in 1% increments $^1$H-NMR indicated starting chloro compound material. A mixture of this product with 10% palladium on charcoal (39.6 mg) and ammonium formate (439.5 mg, 6.98 mmol) in dichloromethane (50 ml), was then stirred at room temperature overnight. Additional, 10% Palladium on charcoal (49 mg) was added and the mixture was heated under reflux for 48 hrs, after which time the catalyst was filtered off and the solvent evaporated under reduced pressure. The residue was partitioned between ethyl acetate (100 ml) and water (100 ml). The organic layer was separated and dried over MgSO$_4$ and the solvent evaporated under reduced pressure to afford the title compound as a off-white solid, (44%).

$^1$H-NMR (400 MHz, DMSO): δ [ppm] 1.40 (9H, s), 170–1.86 (4H, m), 2.06 (2H, s), 2.21 (3H, s), 3.23 (4H, m), 3.43 (1H, m), 4.35 (2H, d), 4.63 (2H, s), 6.59 (1H, s), 6.98 (1H, d), 7.07 (1H, s), 7.25 (1H, d), 7.35 (1H, s), 8.60 (1H, m), 10.65 (1H, bs). LRMS: m/z=509 (MH$^+$).

Preparation 56

N-[(3-Methyl-1H-indol-5-yl)methyl]-2-[6-methyl-2-oxo-3-{[(2R)pyrrolidinylmethyl]amino}-1(2H)-pyrazinyl]acetamide

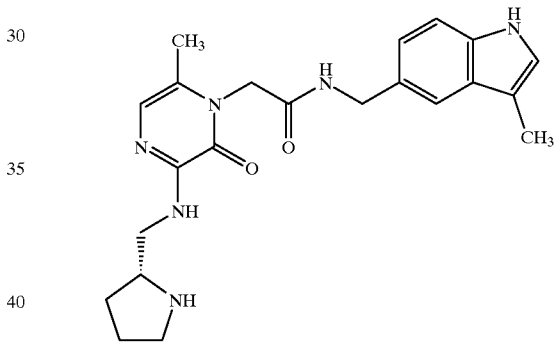

tert-Butyl (2R)-2-({[5-methyl-4-(2{[(3-methyl-1H-indol-5-yl)methyl]amino}-2-oxoethyl)-3-oxo-3,4-dihydro-2-pyrazinyl]amino}methyl)-1-pyrrolidinecarboxylate (1.08 g, 2.14 mmol) [see preparation 55] was dissolved in methanol (10 ml) and hydrochloric acid (6N, 10 ml, 60 mmol) was added. The reaction mixture was stirred for 18 hrs, after which time the pH was adjusted to 10 with sodium hydroxide (1N). The product was then extracted with dichloromethane (100 ml) followed by dichloromethane:methanol (90:10) (100 ml). Aqueous and organic layers were then concentrated under reduced pressure and the residue triturated with isopropanol (3×100 ml) to afford the title compound as a off-white solid, 629 mg, (72%).

$^1$H-NMR (400 MHz, DMSO): δ [ppm] 1.58–1.85 (4H, m), 2.06 (2H, s), 2.21 (3H, s), 2.77–2.90 (2H, m), 3.15–3.40 (5H, m), 4.35 (2H, d), 4.61 (2H, s), 6.60 (1H, s), 6.80 (1H, m), 6.98 (1H, d), 7.06 (1H, s), 7.26 (1H, d), 7.37 (1H, s), 8.65 (1H, m), 10.68 (1H, s). LRMS: m/z=409 (MH$^+$).

Preparation 57

2-[3-({[(2R)-1-Cyclopentyl pyrrolidinyl]
methyl}amino)-6-methyl-2-oxo-1(2H)-pyrazinyl]-N-
[(3-methyl-1H-indol-5-yl)methyl]acetamide

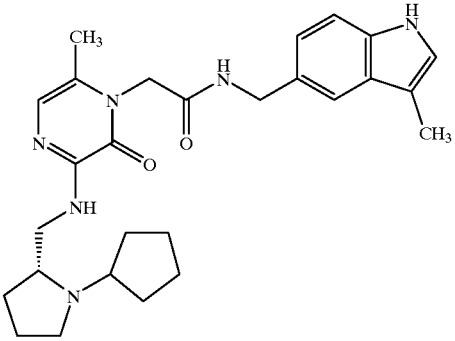

N-[(3-Methyl-1H-indol-5-yl)methyl]-2-[6-methyl-2-oxo-3 {[(2R)pyrrolidinylmethyl]amino}1(2H)-pyrazinyl] acetamide (52.3 mg, 0.129 mmol) [see preparation 56] and cyclopentanone (22 ml, 0.248 mmol) were stirred together in N,N-dimethylformamide (2 ml). Sodium triacetoxyborohydride (27.3 mg, 0.129 mmol) was added. The reaction mixture was stirred for 18 hrs, after which time the mixture was quenched with water and basified. The product was then extracted with ethyl acetate (4×50 ml), the combined organic layers were dried with MgSO₄ and the solvent evaporated under reduced pressure. The crude product was purified by column chromatography on silica gel using an elution gradient of dichloromethane:methanol (100:0) changing to (90:10) and then dichloromethane:methanol:0.88 ammonia (90:10:1) changing to (84:14:2) to afford the title compound as a white solid, 19.4 mg, (32%).

¹H-NMR (300 MHz, CD₃OD): δ [ppm] 1.40–2.00 (12H, m), 2.11 (3H, s), 2.28 (3H, s), 2.55–2.65 (1H, q), 3.00–3.17 (3H, m), 3.20–3.35 (1H, m), 3.47–3.55 (1H, 2×d), 4.46 (2H, s), 4.71 (2H, s), 6.65 (1H, s), 6.98 (1H, s), 7.03 (1H, d), 7.25 (1H, d), 7.41 (1H, s). LRMS: m/z=477 (MH⁺).

EXAMPLES 14–19

The compounds of the following tabulated examples with the general formula:

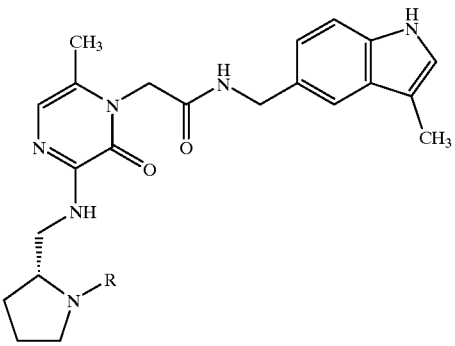

were prepared using a similar method to preparation 57 from N-[(3-methyl-1H-indol-5-yl)methyl]-2-[6-methyl-2-oxo-3-[(2R)pyrrolidinylmethyl]amino}-1(2H)-pyrazinyl] acetamide [see preparation 56] and the corresponding carbonyl compound.

| Example | Starting material prep. No. | R | Yield | Analytical Data |
|---|---|---|---|---|
| 14 | | * ⟨tetrahydropyran-4-yl⟩ | 37% | ¹H-NMR(400 MHz, CDCl₃): δ [ppm] 1.58–1.85(4H, m), 2.25(3H, s), 2.30(3H, s), 2.55(1H, q), 2.72(1H, t), 3.00(1H, m), 3.15(2H, m), 3.35(2H, q), 3.98(2H, t), 4.50(2H, d), 4.61(2H, d), 6.30(1H, bs), 6.70(1H, s), 6.72(1H, bs), 6.95(1H, s), 7.02(1H, d), 7.28(1H, m), 7.40(1H, s), 8.16(1H, bs). LRMS: m/z = 493(MH⁺). |
| 15 | 58 Tetra- hedron (1996), 2515 | H₃C— ⟨1-methylcyclopropyl⟩ * | 10% | ¹H-NMR(400 MHz, CD₃OD): δ [ppm] 1.07(3H, s), 1.28(1H, m), 1.56–1.90(8H, m), 2.22(3H, s), 2.30(3H, s), 2.67(1H, m), 3.20(1H, d), 3.21–3.37(2H, m), 3.48–3.62(2H, m), 4.50(2H, s), 4.67(2H,s), 6.50(1H, bs), 6.70(1H, s), 6.95(1H, s), 7.05(1H, d), 7.21(1H, d), 7.89(1H, d), 7.89(1H, s), 8.10(1H, bs). LRMS: m/z = 475(MH⁺). |
| 16 | | * ⟨CH₂CH₂OCH₃⟩ H₃C—O | 20% | ¹H-NMR(400 MHz, CD₃OD): δ [ppm] 0.90(1H, t), 1.30(1H, m), 1.61(1H, m), 1.75(2H, m), 1.93(1H, m), 2.13(3H, s), 2.26(3H, s), 2.32(1H, m), 2.52(1H, m), 2.80(1H, m), 3.00(1H, m), 3.18–3.51(10H, m), 4.47(2H, s), 4.73(2H, s), 6.63(1H, s), 6.98(1H, s), 7.03(1H, d), 7.27(1H, d), 7.43(1H, s). LRMS: m/z = 467(MH⁺). |
| 17 | | H₃C⟩C(CH₃)CH₃ * ⟨tert-butyl-methyl⟩ | 29% | ¹H-NMR(400 MHz, DMSO): δ [ppm] 1.04(9H, s), 1.72(1H, m), 1.88(1H, m), 1.93–2.10(5H, m), 2.23(3H, s), 3.05(1H, m), 3.20(1H, m), 3.66(4H, bs), 4.35(2H, d), 4.65(2H, d), 6.62(1H, s), 6.97(1H, d), 7.16(1H, s), 7.25(1H, d), 7.35(1H, s), 7.50(1H, bs), 8.66(1H, t), 9.47(1H, bs). LRMS: m/z = 479(MH⁺). |

Preparation 58

1-Methylcyclopropanecarbaldehyde

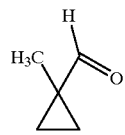

To a solution of 1-methylcyclopropane methanol (4.86 g, 56.4 mmol) in dichloromethane (200 ml) under an atmosphere of nitrogen was added 4 Å molecular sieves and N-methylmorpholine-N-oxide (9.916 g, 84.64 mmol). The reaction mixture was stirred at room temperature for 20 mins, after which time tetrahydrofuran-n-propylammonium perruthenate(VII) (0.992 g, 2.82 mmol) was added. The mixture was stirred for a further 4 hrs, and then filtered through a plug of silica eluting with dichloromethane to afford the crude product which was fractionally distilled to afford the title compound (100%).

EXAMPLE 18

2-[3-({[(2R)-1-Isobutylpyrrolidinyl]methyl}amino)-6-methyl-2-oxo-1(2H)-pyrazinyl]-N-[(3-methyl-1H-indol-5-yl)methyl]acetamide

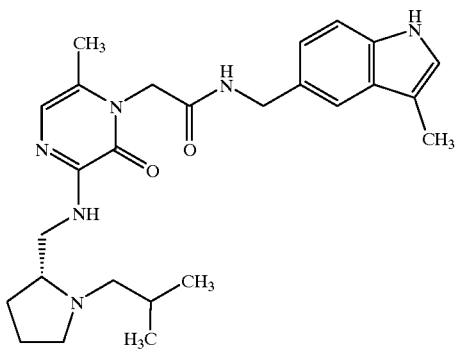

Preparation 59

(2R)-1-1-sobutyl-2-pyrrolidinecarboxamide

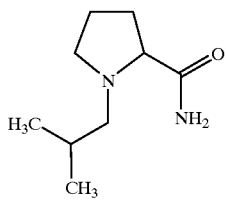

The title compound was prepared by a similar method to preparation 57 from R-prolinamide and 3-methylbutanal. The crude compound was purified by column chromatography on silica gel using dichloromethane:methanol:0.88 ammonia (96:3.5:0.5) as the eluant, to afford the product as a white solid, (87%).

$^1$H-NMR (400 MHz, CDCl$_3$): δ [ppm] 0.88 (3H, d), 0.97 (3H, d), 1.68–1.93 (4H, m), 2.12–2.35 (4H, m), 3.00 (1H, m), 3.17 (1H, m), 6.67 (1H, bs), 7.37 (1H, bs). LRMS: m/z=171 (MH$^+$).

Preparation 60

[(2R)-1-isobutylpyrrolidinyl]methanamine

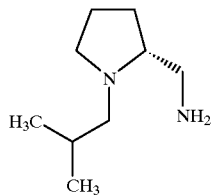

Lithium aluminum hydride [1.0mol soln. in tetrahydrofuran] (11.52 ml, 11.52 mmol) was added to a solution of (2R)-1-isobutyl-2-pyrrolidinecarboxamide (1.3 g, 7.68 mmol) [see preparation 59] in tetrahydrofuran (5 ml) @0° C. The reaction mixture was stirred for 10 mins and then heated to reflux for 6 hrs. Water (0.5 ml) was added to the cooled mixture followed by sodium hydroxide (1.5 ml) and water (1.5 ml). Tetrahydrofuran (10 ml) was added and the mixture was stirred at room temperature for 1 hr. The aluminum salts were removed by filtration and washed well with diethyl ether. The filtrate was then evaporated under reduced pressure to afford the title compound as a white solid, 705 mg, (58%).

$^1$H-NMR (400 MHz, CDCl$_3$): δ [ppm] 0.86 (3H, d), 0.92 (3H, d), 1.78–1.86 (5H, 2.04–2.10 (2H, m), 2.26–2.38 (2H, m), 2.60 (1H, 2×d), 2.72 (1H, m), 3.09 (1H, m). LRMS m/z=157 (MH$^+$).

Preparation 61

Benzyl 2-[3-chloro-5-({[(2R)-1-isobutylpyrrolidinyl]methyl}amino)-2-methyl-6-oxo-1(6H)-pyrazinyl]acetate

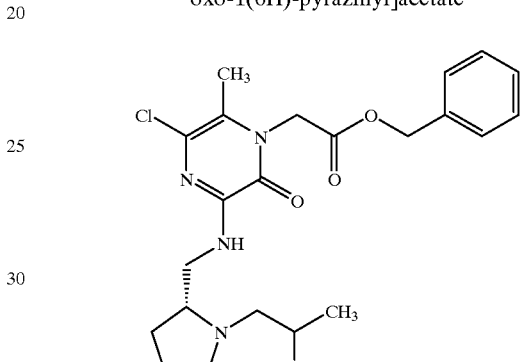

The title compound was prepared by a similar method to preparation 42 from benzyl 2-[3,5-dichloro-2-methyl-6-oxo-1(6H)-pyrazinyl]acetate (preperation 170 and [(2R)-1-isobutylpyrrolidinyl]methanamine [see preparation 60]. The crude product was purified by column chromatography on silica gel using ethyl acetate as the eluant, to afford the product as a yellow oil, (94%).

$^1$H-NMR (400 MHz, CDCl$_3$): δ [ppm] 0.90 (6H, 2×d), 1.60 (1H, m), 1.70 (3H, m), 1.85 (1H, m), 2.08 (2H, m), 2.20 (3H, s), 2.30 (1H, m), 2.62 (1H, m), 3.12 (1H, m), 3.27 (1H, m), 3.55 (1H, m), 4.78 (2H, m), 5.20 (2H, s), 6.66 (1H, m), 7.32 (5H, m). LRMS m/z=447 (MH$^+$).

Preparation 62

2-[3-({[(2R)-1-isobutylpyrrolidinyl]methyl}amino)-6-methyl-2-oxo-1(2H)-pyrazinyl]acetic acid hydrochloride

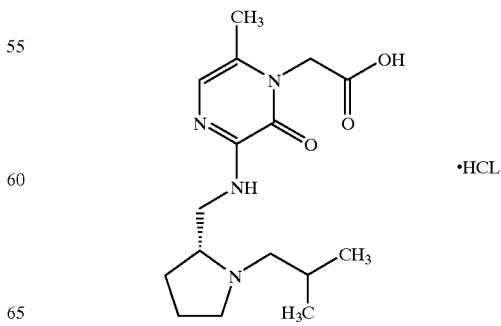

71

The title compound was prepared by a similar method to preparation 44 from benzyl 2-[3-chloro-5-({[(2R)-1-isobutylpyrrolidinyl]methyl}amino)-2-methyl-6-oxo-1(6H)-pyrazinyl]acetate [see preparation 61] and palladium hydroxide, to afford the product as a oil. LRMS: 323 (MH⁺)

Preparation 63

2-[3-({[(2R)-1-isobutylpyrrolidinyl]methyl}amino)-6-methyl-2-oxo-1(2H)-pyrazinyl]-N-[(3-methyl-1H-indol-5-yl)methyl]acetamide

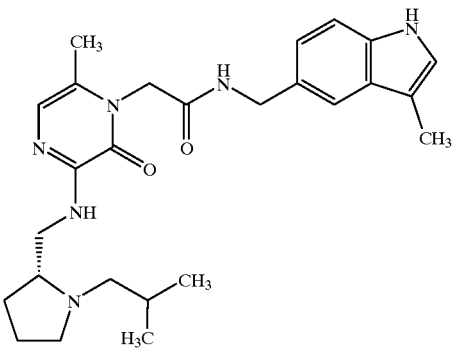

The title compound was prepared by a similar method to preparation 49 from 2-[3-({[(2R)-1-isobutylpyrrolidinyl]methyl}amino)-6-methyl-2-oxo-1(2H)-pyrazinyl]acetic acid hydrochloride [see preparation 62] and (3-methyl-1H-indol-5-yl)methylamine (72 mg, 0.45 mmol) [see preparation 36]. The crude product was purified by column chromatography on silica gel using dichloromethane:methanol:0.88 ammonia (92:7:1) as the eluant, to afford the product as a foam. This was dissolved in methanol (5 ml) and hydrochloric acid (1M, 0.58 ml, 0.58 mmol), to afford the product, (56%).

¹H-NMR (400 MHz, DMSO): δ [ppm] 0.95 (6H, 2×d), 1.72–2.10 (7H, m), 2.21 (3H, s), 2.86–3.20 (4H, m), 3.33–3.50 (4H, m), 4.35 (2H, d), 4.63 (2H, s), 6.60 (1H, s), 6.98 (1H, d), 7.06 (1H, s), 7.25 (1H, d), 7.35 (1H, s), 7.42 (1H, bs), 8.68 (1H, t), 8.80 (1H, bs), 10.68 (1H, bs). LRMS: m/z=465 (MH⁺).

EXAMPLE 19 and 20

The compounds of the following tabulated examples with the general formula:-

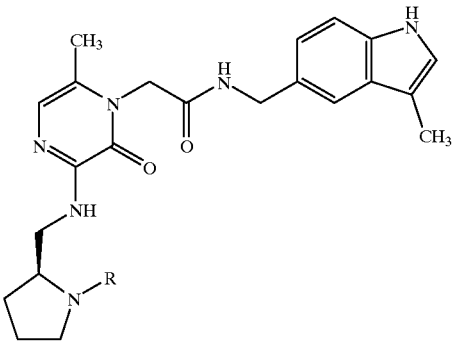

Were prepared using a similar method to preparation 57 from N-[(3-methyl-1H-indol-5-yl)methyl]-2-[6-methyl-2-oxo-3-{[(2S)pyrrolidinylmethyl]amino}-1(2H)-pyrazinyl]

72 acetamide [see preparation 67] and the corresponding carbonyl compound.

| Example No. | Starting material prep No. | R | Yield | Data |
|---|---|---|---|---|
| 19 | 67 | * ~O~CH₃ | 61% | ¹H-NMR(400 MHz, DMSO): δ [ppm] 1.45–1.81(4H, m), 2.06(3H, s), 2.21(3H, s), 2.89–3.00(1H, m), 3.01–3.50(11H, m), 4.35(2H, d), 4.60(2H, s), 6.55–6.62(2H, m), 6.98(1H, d), 7.08(1H, s), 7.25(1H, d), 7.38(1H, s), 8.60(1H, t), 10.62(1H, s). LRMS: m/z = 466(M⁺). |
| 20 | 67 | * cyclopentyl | 77% | ¹H-NMR(400 MHz, DMSO): δ [ppm] 1.35–1.88(12H, m), 2.05(3H, s), 2.22(3H, s), 2.80–2.96(2H, m), 3.25–3.37(4H, m), 4.35(2H, d), 4.61(2H, s), 6.60(2H, bs), 6.96(1H, d), 7.06(1H, s), 7.25(1H, d), 7.35(1H, s), 8.60(1H, m), 10.64(1H, s). LRMS: m/z = 476(M⁺) |

Preparation 64 tert-Butyl (2S)-2-[({4-[2-(benzyloxy)-2-oxoethyl]-6-chloro-5-methyl-3-oxo-3,4-dihydro-2-pyrazinyl}amino)methyl]-1-pyrrolidinecarboxylate

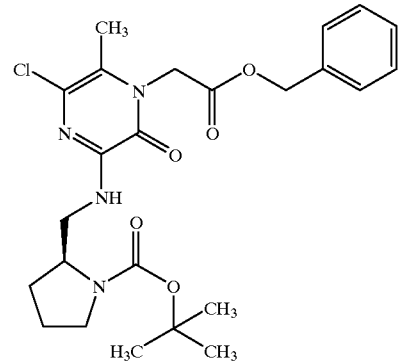

The title compound was prepared by a similar method to preparation 42 from benzyl 2-[3,5-dichloro-2-methyl-6-oxo-1(6H)-pyrazinyl]acetate (preperation 17) and tert-butyl (2S)-2-(aminomethyl)-1-pyrrolidinecarboxylate [JP 63183560 A2], to afford the product as a colourless oil, (100%).

¹H-NMR (400 MHz, DMSO): δ [ppm] 1.38 (9H, s), 1.68–1.86 (4H, m), 2.19 (3H, s), 3.20–3.30 (3H, m), 3.40 (1H, m), 4.01 (1H, m), 4.86 (2H, s), 5.19 (2H, s), 7.35 (5H, m), 7.45–7.60 (1H, m). LRMS: m/z=491 (MH⁺).

Preparation 65

2-[3-({[(2S)-1-(tedt-Butoxycarbonyl)pyrrolidinyl]methyl}amino)-5-chloro-6-methyl-2-oxo-1(2H)-pyrazinyl]acetic acid

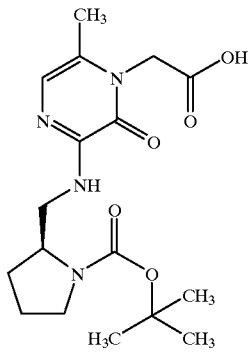

The title compound was prepared by a similar method to preparation 44 from tert-butyl (2S)-2-[({4-[2-(benzyloxy)-2-oxoethly]-6-chloro-5methyl-3-oxo-3,4-dihydro-2-pyrazinyl}amino)methyl]-1-pyrrolidinecarboxylate [see preparation 64] and palladium hydroxide. The title compound was purified by column chromatography on silica gel using an elution gradient of dichloromethane:methanol:0.88 ammonia (90:10:0.5) changing to (80:20:3), to afford the product as a colourless oil, (44%).

$^1$H-NMR (400 MHz, DMSO): δ [ppm] 1.40 (9H, s), 1.68–1.86 (4H, m), 2.00 (3H, s), 3.05–3.27 (3H, m), 3.41 (1H, bs), 3.99 (1H, m), 4.30 (2H, m), 6.50 (1H, s), 6.61–6.80 (1H, m). LRMS: m/z=367 (MH$^+$).

Preparation 66 tert-Butyl (2S)-2-({[6-chloro-5-methyl-4-(2-{[(3-methyl-1H-indol-5-yl)methyl]amino}-2-oxoethyl)-3-oxo-3,4-dihydro-2-pyrazinyl]amino}methyl)-1-pyrrolidinecarboxylate

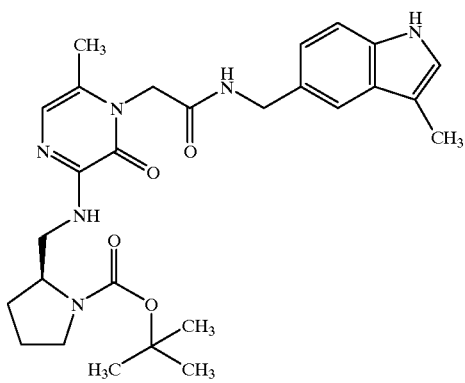

The title compound was prepared by a similar method to preparation 45 from 2-[3-({[(2S)-1-(tert-butoxycarbonyl)pyrrolidinyl]methyl}amino)-6-methyl-2-oxo-1(2H)-pyrazinyl]acetic acid [see preparation 65] and (3-methyl-1H-indol-5-yl)methylamine (72 mg, 0.45 mmol) [see preparation 36], to afford the product as a colourless oil, (89%).

$^1$H-NMR (400 MHz, DMSO): δ [ppm] 1.39 (9H, s), 1.66–1.87 (4H, m), 2.05 (3H, s), 2.21 (3H, s), 3.13–3.30 (4H, m), 3.40 (1H, bs), 4.00 (1H, m), 3.37 (2H, d), 4.61 (2H, s), 6.58 (1H, s), 6.97 (1H, d), 7.07 (1H, s), 7.25 (1H, d), 7.45 (1H, s), 8.60 (1H, t). LRMS: m/z=509 (MH$^+$).

Preparation 67

N-[(3-Methyl-1H-indol-5-yl)methyl]-2-[6-methyl-2-oxo-3-{[(2S)pyrrolidinylmethyl]amino}-1(2H)-pyrazinyl]acetamide

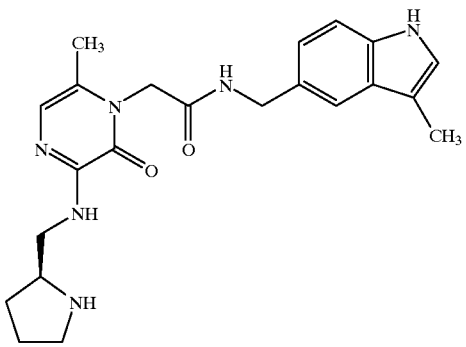

The title compound was prepared by a similar method to preparation 56 from tert-butyl (2S)-2-({[6-chloro-5-methyl-4-(2{[(3-methyl-1H-indol-5-yl)methyl]amino}-2-oxoethyl)-3-oxo-3,4-dihydro-2-pyrazinyl]amino}methyl)-1-pyrrolidinecarboxylate [see preparation 66] and 6N hydrochloric acid, to afford the product as a white solid, (60%).

$^1$H-NMR (400 MHz, DMSO): δ [ppm] 1.35 (1H, m), 1.53–1.78 (3H, m), 2.05 (3H, s), 2.22 (3H, s), 2.75 (2H, m), 3.08–3.32 (4H, m), 4.34 (2H, d), 4.61 (2H, s), 6.60 (1H, s), 6.66 (1H, m), 6.98 (1H, d), 7.06 (1H, s), 7.27 (1H, d), 7.39 (1H, s), 8.61 (1H, t), 10.63 (1H, bs). LRMS: m/z=409 (MH$^+$).

EXAMPLE 21

2-[3-({[(2R)-1-(Cyclopropylmethyl)piperidinyl]methyl}amino)-6-methyl-2-oxo-1(2H)-pyrazinyl]-N-[(3-methyl-1H-indol-5-yl)methyl]acetamide

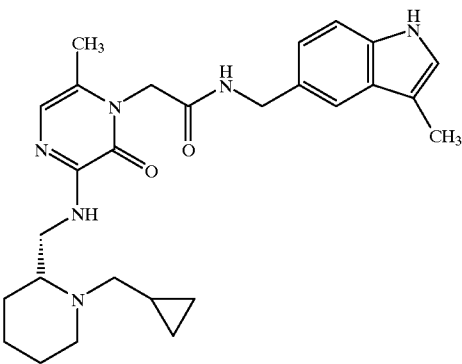

Preparation 68

(2R)-2-Piperidinecarboxamide

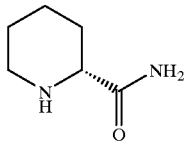

(2R)-2-(Methoxycarbonyl)piperidinium chloride (2.6 g, 14.5 mmol) was dissolved in ammonia (0.88M, 30 ml). The reaction mixture was heated at 60° C. for 1.5 hr. The mixture was partitioned between ethyl acetate (100 ml) and sodium hydroxide (1N, 100 ml, 100 mmol), the aqueous was washed with ethyl acetate (3×100 ml). The combined organic layers were dried over sodium sulphate and the solvent evaporated under reduced pressure. Aqueous layer was acidified with hydrochloric acid and evaporated to dryness under reduced pressure. The resultant white solid was triturated with dichloromethane:methanol (9:1), the remaining solid was removed by filtration and the filtrate evaporated under reduced pressure to afford the title compound as a white solid, 1.14 g, (61%).

LRMS: m/z=129 (MH+).

Preparation 69

(2R)-1-(Cyclopropylmethyl)-2-piperidinecarboxamide

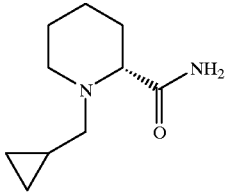

The title compound was prepared by a similar method to preparation 57 from (2R)-2-piperidinecarboxamide [see preparation 68] and cyclopropylcarboxaldehye. The crude compound was purified by column chromatography on silica gel using dichloromethane:methanol:0.88 ammonia (92:7:1) as the eluant to afford the product as a white solid, (44%).

$^1$H-NMR (300 MHz, CDCl$_3$): δ [ppm] 0.00–0.20 (2H, m), 0.40–0.61 (2H, m), 0.79–0.93 (1H, m), 1.18–1.38 (1H, m), 1.40–1.80 (5H, m), 1.87–2.14 (3H, m), 2.56 (1H, 2×d), 2.71 (1H, 2×d), 3.30 (1H, m), 5.29 (1H, bs), 6.64 (1H, bs). LRMS: m/z=183 (MH+).

Preparation 70

[(2R)-1-(Cyclopropylmethyl)piperidinyl]methylamine

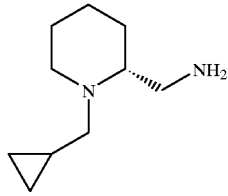

The title compound was prepared by a similar method to preparation 60 from (2R)-1-(cyclopropylmethyl)-2-piperidinecarboxamide [see preparation 69] and lithium aluminum hydride. The crude product was purified by column chromatography on silica gel using dichloromethane:methanol:0.88 ammonia (90:10:0.1) as the eluant, to afford the product as a yellow oil, (71%).

$^1$H-NMR (300 MHz, CDCl$_3$): δ [ppm] 0.09 (2H, m), 0.49 (2H, m), 0.82 (1H, m), 1.21–1.80 (9H, m), 2.17–2.27 (3H, m), 2.60 (1H, 2×d), 2.70 (1H, 2×d), 2.87 (1H, 2×d), 3.16 (1H, m). LRMS: m/z=169 (MH+).

Preparation 71

Benzyl 2-[3-chloro-5-({[(2R)-1-(cyclopropylmethyl)piperidinyl]methyl}amino)-2-methyl-6-oxo-1(6H)-pyrazinyl]acetate

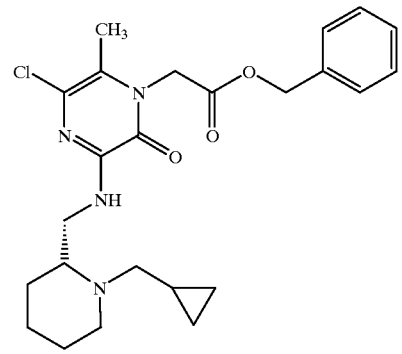

The title compound was prepared by a similar method to preparation 42 from benzyl 2-[3,5-dichloro-2-methyl-6-oxo-1(6H)-pyrazinyl]acetate (preperation 17) and [(2R)-1-(cyclopropylmethyl)piperidinyl]methylamine [see preparation 70]. The crude product was purified by column chromatography on silica gel using dichloromethane:methanol (95:5), to afford the product as a yellow oil, (87%).

$^1$H-NMR (400 MHz, CDCl$_3$): δ [ppm] 0.100(2H, m), 0.45 (2H, m), 0.92 (1H, m), 1.20–1.79 (5H, m), 2.20–2.31 (5H, m), 2.57 (2H, m), 3.17 (1H, m), 3.46 (2H, m), 4.80 (2H, s), 5.21 (2H, s), 6.63 (1H, m), 7.18 (1H, d), 7.39 (5H, m). LRMS: m/z=459 (MH+).

Preparation 72

2-[3-chloro-5-({[(2R)-1-(cyclopropylmethyl)piperidinyl]methyl}amino)-2-methyl-6-oxo-1(6H)-pyrazinyl]acetic acid

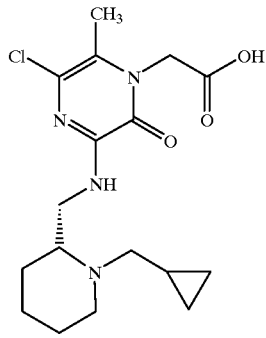

The title compound was prepared by a similar method to preparation 44 from benzyl 2-[3-chloro-5-({[(2R)-1-(cyclopropylmethyl)piperidinyl]methyl}amino)-2-methyl-6-oxo-1(6H)-pyrazinyl]acetate [see preparation 71] and palladium hydroxide. To afford the product as a yellow foam, (100%).

LRMS: m/z=369 (MH⁺).

Preparation 73

2-[3-Chloro-5-({[(2R)-1-(cyclopropylmethyl)piperidinyl]methyl}amino)-2-methyl-6-oxo-1(6H)-pyrazinyl]-N-[(3-methyl-1H-indol-5-yl)methyl]acetamide

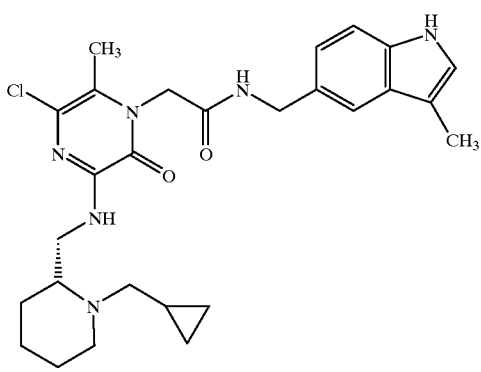

The title compound was prepared by a similar method to preparation 45 from 2-[3-chloro-5-({[(2R)-(cyclopropylmethyl)piperidinyl]methyl}amino)-2-methyl-6-oxo-1(6H)-pyrazinyl]acetic acid [see preparation 72] and (3-methyl-1H-indol-5-yl)methylamine (preperation 36) to afford the product as a white solid, (14%).

LRMS: m/z=511 (M⁺).

Preparation 74

2-[3-({[(2R)-1-(cyclopropylmethyl)piperidinyl]methyl}amino)-6-methyl-2-oxo-1(2H)-pyrazinyl]-N-[(3-methyl-1H-indol-5-yl)methyl]acetamide

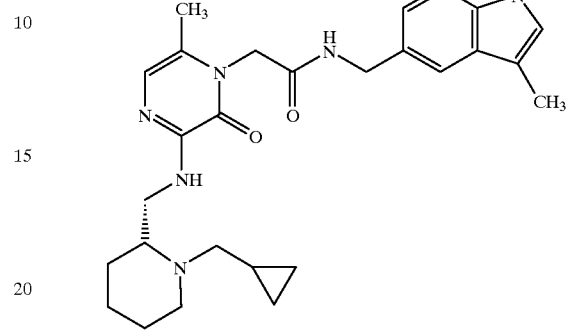

The title compound was prepared by a similar method to preparation 44 from 2-[3-chloro-5-({[(2R)-1-(cyclopropylmethyl)piperidinyl]methyl}amino)-2-methyl-6-oxo-1(6H) pyrazinyl]-N-[(3-methyl-1H-indol-5-yl)methyl]acetamide [see preparation 73] and palladium hydroxide. The crude product was purified by column chromatography on silica gel using dichloromethane:methanol:0.88 ammonia (90:10:1) as the eluant to afford the product as a white solid, (36%).

¹H-NMR (400 MHz, CD₃OD): δ [ppm] 0.15 (2H, m), 0.53 (2H, m), 0.96 (1H, m), 1.32–1.88 (6H, m), 2.15 (3H, s), 2.29 (3H, s), 2.40 (2H, s), 2.70 (3H, m), 3.20 (1H, m), 3.30 (3H, m), 3.33 (1H, m), 3.39–3.57 (2H, m), 4.48 (2H, s), 4.75 (2H, s), 6.65 (1H, s), 6.98 (1H, s), 7.06 (1H, d), 7.27 (1H, d), 7.43 (1H, s). LRMS: m/z=477 (MH⁺).

EXAMPLE 22

2-[3-({[(2S)-1-(Cyclopropylmethyl)pyrrolidinyl]methyl}amino)-6-methyl-2-oxo-1(2H)-pyrazinyl]-N-[(3-methyl-1H-indol-5-yl)methyl]acetamide

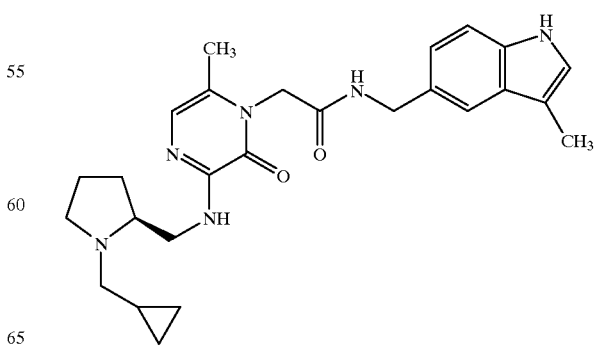

Preparation 75

Benzyl 2-[3-chloro-5-({[(2S)-1-(cyclopropylmethyl) pyrrolidinyl]methyl}amino)-2-methyl-6-oxo-1(6H)-pyrazinyl]acetate

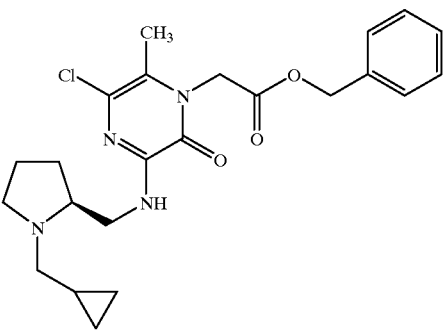

A mixture of benzyl 2-[3,5-dichloro-2-methyl-6-oxo-1 (6H)-pyrazinyl]acetate (preparation 17) (400 mg, 1.22 mmol) and [(2S)-1-(cyclopropylmethyl)pyrrolidinyl] methylamine (WO 87,07271) (190 mg, 1.22 mmol) and triethylamine (0.51 ml, 3.67 mmol) in ethyl acetate (20 ml) was heated under reflux for 18 hrs. The cooled mixture was partitioned between water and ethyl acetate, the phases separated, and the organic layer dried over MgSO$_4$ and concentrated under reduced pressure. The residual orange oil was purified by column chromatography on silica gel using dichloromethane:methanol:0.88 ammonia (96:3.5:0.5) as eluant to give the desired product as a yellow oil, (476 mg, 88%).

$^1$H NMR (CDCl$_3$, 300 MHz) δ: 0.15 (m, 2H), 0.48 (m, 2H), 0.92 (m, 1H), 1.58–1.94 (m, 5H), 2.03 (m, 1H), 2.23 (s, 3H), 2.70 (m, 2H), 3.30 (m, 2H), 3.60 (m, 1H), 4.80 (s, 2H), 5.22 (s, 2H), 6.62 (s, br,1H), 7.38 (m, 5H).

Preparation 76

2-[5-({[(2S)-1-(Cyclopropylmethyl)pyrrolidinyl] methyl}amino)-2-methyl-6-oxo-1(6H)-pyrazin acetic acid hydrochloride

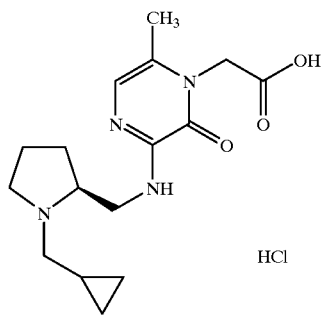

A mixture of benzyl 2-[3-chloro-5-({[(2)-1-(cyclopropylmethyl)pyrrolidinyl]methyl}amino)-2-methyl-6-oxo-1(6H)-pyrazinyl]acetate (preparation 75) (470 mg, 1.06 mmol) and palladium hydroxide (230 mg) in methanol (20 ml) was hydrogenated at room temperature and 60 psi for 3 hrs. The reaction mixture was filtered through Arbocel®, washing through with ethanol, and the combined filtrate evaporated under reduced pressure, to give the title compound as a yellow foam, (388 mg, 100%).

$^1$H NMR (d$_6$-DMSO, 300 MHz) δ: 0.38 (m, 2H), 0.60 (m, 2H), 0.97 (m, 1H), 1.77–1.99 (m, 4H), 2.07 (s, 3H), 2.96 (m, 1H), 3.06–3.76 (m, 6H), 4.66 (s, 2H), 6.64 (s, 1H), 7.40 (t, br,1H), 10.05 (s, br,1H).

Preparation 77

2-[3-({[(2S)-1-(Cyclopropylmethyl)pyrrolidinyl] methyl}amino)-6-methyl-2-oxo-1(2H)-pyrazinyl]-N-[(3-methyl-1H-indol-5-yl)methyl]acetamide

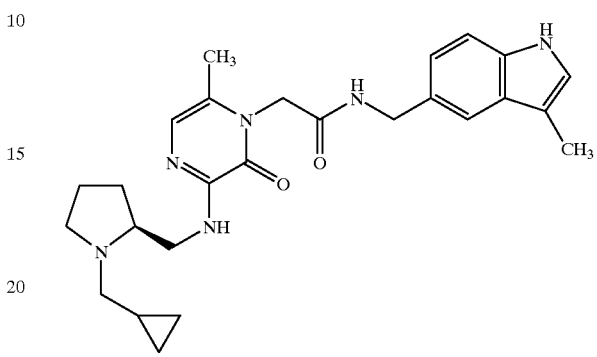

A mixture of 2-[5-({[(2S)-1-(cyclopropylmethyl) pyrrolidinyl]methyl}amino)-2-methyl-6-oxo-1(6H)-pyrazinyl]acetic acid hydrochloride (preparation 76) (380 mg, 1.07 mmol), (3-methyl-1H-indol-5-yl)methylamine (preparation 36) (171 mg, 1.07 mmol), HOBT (216 mg, 1.60 mmol), WSCDI.HCl (255 mg, 1.33 mmol) and N-methylmorpholine (0.38 ml, 3.46 mmol) in N,N-dimethylformamide (4 ml), was stirred at room temperature for 24 hrs under a nitrogen atmosphere. The reaction mixture was evaporated under reduced pressure and the residue purified by column chromatography on silica gel using dichloromethane:methanol:0.88 ammonia (96:3.5:0.5) as eluant. This product was further purified using a Biotage™ (KP-Sil[\T] 60 Å silica gel) cartridge and dichloromethane:methanol:0.88 ammonia (96:3.5:0.5) as eluant to give the title compound as a white solid, (145 mg, 29%).

$^1$H NMR (CDCl$_3$, 300 MHz) δ: 0.10 (m, 2H), 0.48 (m, 2H), 0.88 (m, 1H), 1.58–1.90 (m, 5H), 2.00 (m, 1H), 2.22 (s, 3H), 2.30 (s, 3H), 2.60–2.80 (m, 2H), 3.25 (m, 2H), 3.25 (m, 1H), 4.52 (d, 2H), 4.62 (s, 2H), 6.37 (s, br,1H), 6.69 (m, 2H), 6.98 (s, 1H), 7.02 (d, 1H), 7.24 (m, 1H), 7.40 (s, 1H), 8.10 (s, 1H). LRMS: m/z=463 (M+1)$^+$.

EXAMPLE 23

2-[3-({[(3R)-1-(Cyclopropylmethyl)pyrrolidinyl] methyl}amino)-6-methyl-2-oxo-1(2H)-pyrazinyl]-N-[(3-methyl-1H-indol-5-yln)methyl]acetamide

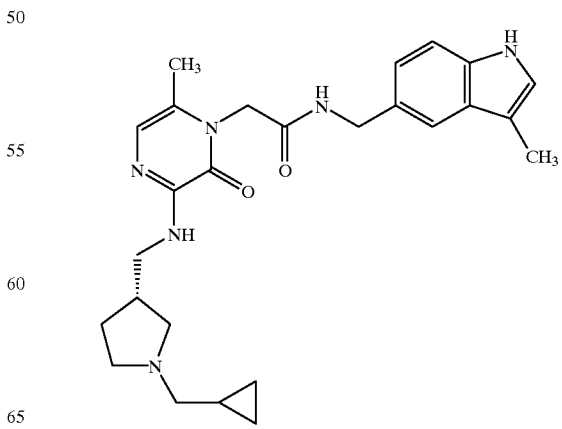

Preparation 78 tert-Butyl (3S)-3-[(methylsulphonyl)oxy]-1-pyrrolidinecarboxylate

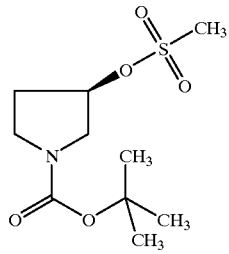

Triethylamine (8.7 ml, 62.4 mmol) was added to a solution of (3R)-3-pyrrolidinol (5.16 g, 41.7 mmol) in dichloromethane (30 ml), and the solution stirred for 10 mins. Di-tert-butyl dicarbonate (9.11 g, 41.7 mmol) was added and the reaction stirred at room temperature for 20 hrs. The reaction mixture was concentrated under reduced pressure and the residue partitioned between water and ethyl acetate, and the layers separated. The organic phase was washed with 1N citric acid, water, and brine, then dried over $MgSO_4$, and evaporated under reduced pressure to give a pale yellow oil, 7.14 g.

This intermediate alcohol was dissolved in dichloromethane (100 ml), triethylamine (6.4 ml, 45.9 mmol) added and the solution cooled in an ice-bath. Methanesulphonyl chloride (3.25 ml, 41.9 mmol) was added slowly, and the reaction stirred for 2 hrs. The reaction mixture was washed with 1N citric acid, saturated $NaHCO_3$ solution, brine, the dried over $Na_2SO_4$ and evaporated under reduced pressure to afford the title compound as an oil, (9.36 g, 85%).

$^1$H NMR ($CDCl_3$, 300 MHz) δ: 1.40 (s, 9H), 2.03–2.28 (m, 2H), 2.99 (s, 3H), 3.36–3.60 (m, 4H), 5.18 (m, 1H). LRMS: m/z=283 (M+18)$^+$.

Preparation 79 tert-Butyl (3R)-3-cyano-1-pyrrolidinecarboxylate

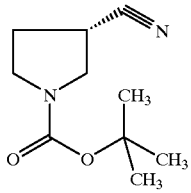

Potassium cyanide (5.80 g, 89.0 mmol) was added to a solution of tedt-butyl (3S)-3-[(methylsulphonyl)oxy]-1-pyrrolidinecarboxylate (preparation 78) (9.35 g, 35.3 mmol) in dimethylsulphoxide (100 ml), and the reaction stired at room temperature for 18 hrs, and then at 100° C. for a further 24 hrs. The cooled mixture was poured into water and extracted well with ethyl acetate. The combined organic extracts were washed with brine, dried over $MgSO_4$ and concentrated under reduced pressure. The residue was purified by column chromatography on silica gel using ethyl acetate:pentane (20:80) as eluant to give the title compound as an oil, (4.28 g, 62%).

$^1$H NMR ($CDCl_3$, 300 MHz) d: 1.46 (s, 9H), 2.21 (m, 2H), 3.10 (m, 1H), 3.39–3.78 (m, 4H). LRMS: m/z=214 (M+18)$^+$.

Preparation 80 tert-Butyl (3R)-3-aminomethyl-1-pyrrolidinecarboxylate

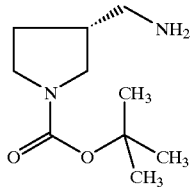

A mixture of tert-butyl (3R)-3-cyano-1-pyrrolidinecarboxylate (preparation 79) (1.60 g, 8.13 mmol) and Raney® Nickel (1 g) in 0.88 ammonia (20 ml) and ethanol (150 ml), was hydrogentaed at 60 psi and room temperature for 8 hrs. The mixture was filtered through Arbocel®, and the filtrate concentrated under reduced pressure. The crude product was purified by column chromatography on silica gel using an elution gradient of dichloromethane:methanol:0.88 ammonia (100:0:0 to 90:10:1) to yield the desired product as an oil, (1.59 g, 98%).

$^1$H NMR ($CDCl_3$, 300 MHz) δ: 1.39 (s, 2H), 1.48 (s, 9H), 1.59 (m, 1H), 2.00 (m, 1H), 2.22 (m, 1H), 2.74 (m, 2H), 3.00 (m, 1H), 3.30 (m, 1H), 3.38–3.59 (m, 2H). LRMS: m/z=201 (M+1)$^+$.

Preparation 81 tert-Butyl (3R)-3-[({4-[2-(benzyloxy)-2-oxoethyl]-6-chloro-5-methyl-3-oxo-3,4-dihydro-2-pyrazinyl}amino)methyl]-1-pyrrolidinecarboxylate

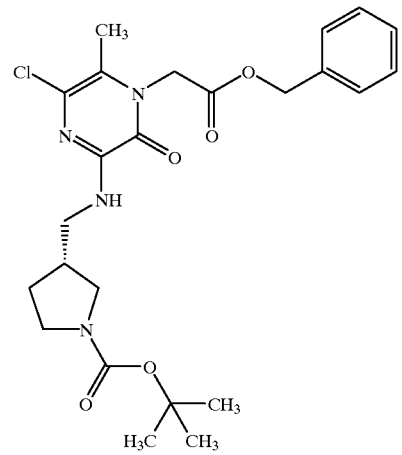

A mixture of benzyl 2-[3,5-dichloro-2-methyl-6-oxo-1 (6H)-pyrazinyl]acetate (preparation 17) (647 mg, 1.98 mmol), tert-butyl (3R)-3-aminomethyl-1-pyrrolidinecarboxylate (preparation 80), (398 mg, 1.98 mmol) and triethylamine (830 ml, 5.95 mmol) in ethyl acetate (25 ml) was heated under reflux for 18 hrs. The cooled mixture was washed consecutively with water, 1N citric acid solution, brine, then dried over $MgSO_4$, and evaporated under reduced pressure to give the desired compound as a gum, (952 mg, 98%).

$^1$H NMR ($CDCl_3$, 300 MHz) δ: 1.44 (s, 9H), 1.66 (m, 1H), 2.01 (m, 1H), 2.21 (s, 3H), 2.56 (m, 1H), 3.01 (m, 1H), 3.28–3.59 (m, 5H), 4.80 (s, 2H), 5.22 (s, 2H), 6.15 (t, br,1H), 7.39 (m, 5H).

Preparation 82

2-[3-({[(3R)-1-(tert-Butoxycarbonyl)pyrrolidinyl]methyl}amino)-6-methyl-2-oxo-1(2H)-pyrazinyl]acetic acid

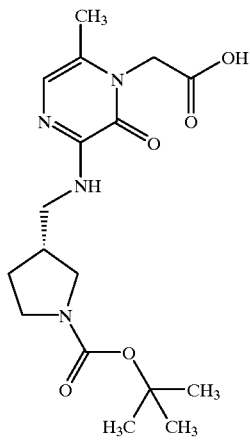

A mixture of tert-butyl (3R)-3-[({4-[2-(benzyloxy)-2-oxoethyl]-6-chloro-5-methyl-3-oxo-3,4-dihydro-2-pyrazinyl}amino)methyl]-1-pyrrolidinecarboxylate (preparation 81) (922.3 mg, 1.89 mmol), ammonium formate (1.19 g, 18.9 mmol) and 10% palladium on charcoal (166.8 mg) in methanol (50 ml), was stirred at room temperature under a nitrogen atmosphere for 20 hrs. The mixture was filtered through Arbocel®, and the filtrate evaporated under reduced pressure. The residue was triturated with a 10% dichloromethane:methanol solution, and the resulting solid removed by filtration. The filtrate evaporated under reduced pressure to afford the title compound as a white solid, slightly impure, 703 mg.

$^1$H NMR ($d_6$-DMSO, 300 MHz) δ: 1.39 (s, 9H), 1.58 (m, 1H), 1.83 (m, 1H), 2.00 (s, 3H), 2.97 (m, 1H), 3.10–3.38 (m, 6H), 4.19 (s, 2H), 6.46 (s, 1H). LRMS: m/z=367 (M+1)$^+$.

Preparation 83 tert-Butyl (3R)-3-({[5-methyl-4-(2-{[(3-methyl-1H-indol-5-yl)methyl]amino}-2-oxoethyl)-3-oxo-3,4-dihydro-2-pyrazinyl]amino}methyl)-1-pyrrolidinecarboxylate

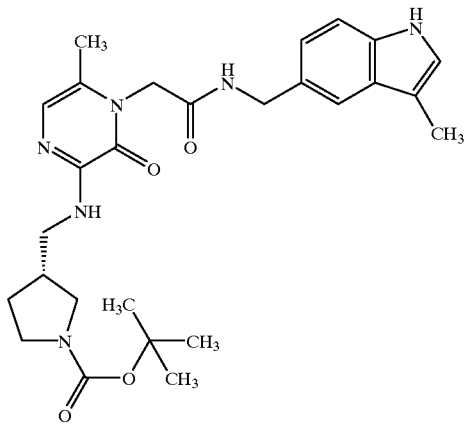

A mixture of 2-[3-({[(3R)-1-(tert-butoxyarbonyl)pyrrolidinyl]methyl}amino)-6-methyl-2-oxo-1(2H)-pyrazinyl]acetic acid (preparation 82) (698.2 mg, 1.91 mmol), 3-methyl-1H-indol-5-yl)methylamine (preparation 36) (306.1 mg, 1.91 mmol), HOBT (291.2 mg, 1.90 mmol), WSCDI.HCl (367.2 mg, 1.92 mmol) and N-methylmorpholine (4.2 ml, 3.82 mmol) in N,N-dimethylformamide (30 ml), was stirred at room temperature for 66 hrs. The reaction was diluted with water, and this mixture extracted with ethyl acetate. The combined organic extracts were washed with 1N citric acid, saturated aqueous NaHCO$_3$, and brine, then dried over MgSO$_4$ and evaporated under reduced pressure to afford the title compound as an off-white solid, (402 mg, 42%).

$^1$H NMR ($d_6$-DMSO, 300 MHz) δ: 1.39 (s, 9H), 1.58 (m, 1H), 1.83 (m, 1H), 2.04 (s, 3H), 2.21 (s, 3H), 2.73 (s, 2H), 2.86 (s, 2H), 2.98 (m, 1H), 3.14–3.34 (m, 4H), 4.38 (d, 2H), 4.62 (s, 2H), 6.60 (s, 1H), 6.99 (m, 2H), 7.06 (s, 1H), 7.24 (d, 1H), 7.37 (s, 1H), 8.61 (m, 1H), 10.65 (s, 1H). LRMS: m/z=531 (M+23)$^+$.

Preparation 84

N-[(3-Methyl-1H-indol-5-yl)methyl]-2-[6-methyl-2-oxo-3-{[(3R)-pyrrolidinylmethyl]amino}-1(2H)-pyrazinyl]acetamide

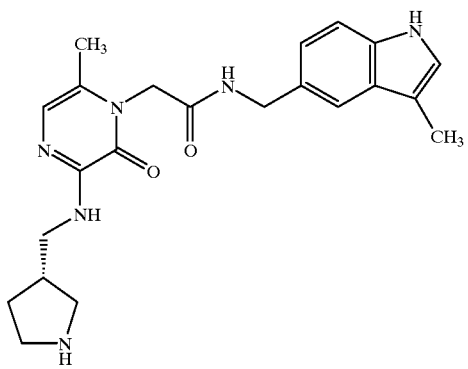

tert-Butyl (3R)-3-({[5-methyl-4-(2-{[(3-methyl-1H-indol-5-yl)methyl]amino}-2-oxoethyl)-3-oxo-3,4-dihydro-2-pyrazinyl]amino}methyl)-1-pyrrolidinecarboxylate (preparation 83) (400 mg, 0.79 mmol) was dissolved in a solution of methanol (50 ml) and 6N hydrochloric acid (50 ml), and the reaction stirred at room temperature for 1½ hrs. The reaction was neutralised using NaOH solution, the mixture extracted with dichloromethane, and the combined organic extracts evaporated under reduced pressure. The residue was purified by column chromatography on silica gel using an elution gradient of dichloromethane:methanol:0.88 ammonia (100:0:0 to 95:5:0 to 90:10:1), to provide the title compound.

The remaining aqueous solution was evaporated under reduced pressure, the residue triturated with i propanol, and the filtrate concentrated under reduced pressure .This crude product was purified by column chromatography on silica gel using an elution gradient of dichloromethane:methanol:0.88 ammonia (90:10:1 to 84:14:2 to 80:20:5) to afford more of the desired product as a glass-like solid, (126 mg, 39% in total).

$^1$H NMR (CD$_3$OD, 300 MHz) δ: 1.66–1.80 (m, 1H), 2.04–2.18 (m, 4H), 2.30 (s, 3H), 2.66 (m, 1H), 2.96 (m, 1H), 3.15 (m, 1H), 3.25 (m, 3H), 3.40 (m, 2H), 4.50 (s, 2H), 4.77 (s, 2H), 6.66 (s, 1H), 6.99 (s, 1H), 7.04 (d, 1H), 7.28 (d, 1H), 7.43 (s, 1H). LRMS: m/z=409 (M+1)$^+$.

Preparation 85

2-[3-({[(3R)-1-(Cyclopropylmethyl)pyrrolidinyl]methyl}amino)-6-methyl-2-oxo-1(2H)-pyrazinyl]-N-[(3-methyl-1H-indol-5-yl)methyl]acetamide

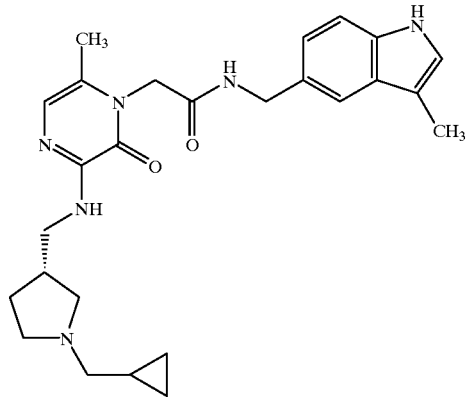

A mixture of N-[(3-methyl-1H-indol-5-yl)methyl]-2-[6-methyl-2-oxo-3-{[(3R)-pyrrolidinylmethyl]amino}-1(2H)-pyrazinyl]acetamide (preparation 84) (66.8 mg, 0.16 mmol), cyclopropanecarboxaldehyde (0.12 ml, 1.60 mmol) and sodium triacetoxyborohydride (35 mg, 0.165 mmol) in N,N-dimethylformamide (5 ml) was stirred at room temperature for 72 hrs. The reaction was diluted with water, basified, and then extracted with ethyl acetate. The combined organic extracts were washed with brine, dried over MgSO$_4$ and evaporated under reduced pressure. The residue was purified by column chromatography on silica gel using an elution gradient of dichloromethane:methanol:0.88 ammonia (90:10:0.1 to 90:10:1) to yield the title compound, (36 mg, 48%).

$^1$H NMR (d$_6$-DMSO, 300 MHz) δ: 0.07 (m, 2H), 0.42 (m, 2H), 0.82 (m, 1H), 1.42 (m, 1H), 1.82 (m, 1H), 2.04 (s, 3H), 2.22 (s, 3H), 2.36–2.62 (m, 5H), 3.20 (m, 2H), 4.38 (d, 2H), 4.61 (s, 2H), 6.60 (s, 1H), 6.94 (m, 1H), 6.99 (d, 1H), 7.07 (s, 1H), 7.23 (d, 1H), 7.38 (s, 1H), 8.60 (s, 1H), 10.64 (s, 1H). LRMS: m/z=463 (M+1)$^+$.

EXAMPLE 24

2-[3-{2-[(2R,4R)-1-(Cyclopropylmethyl)-4-methylpiperidinyl]methyl}amino)-6-methyl-2-oxo-1(2H)-pyrazinyl]-N-[(3-methyl-1H-indol-5-yl)methyl]acetamide

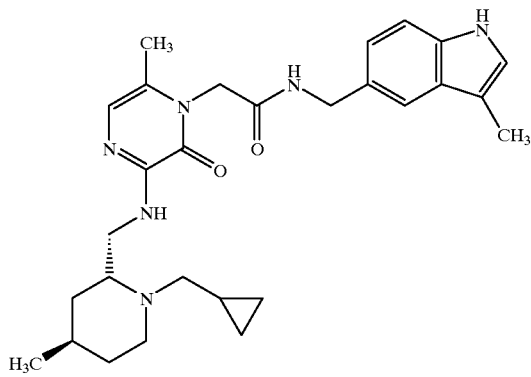

Preparation 86

(2R,4R)-1-Benzyl-4-methyl-2-piperidinecarboxamide

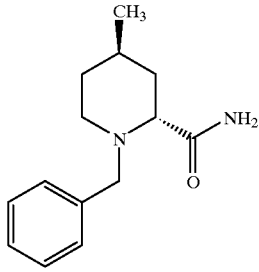

HCl gas was bubbled through a solution of (2R,4R)-4-methyl-2-piperidine carboxylic acid (Biochem.Biophys.Res.Comm.1981, 440) (4.2 g, 29.0mmol) in methanol (120 ml) for 15 mins, and the resulting solution stirred at room temperature overnight. The reaction was concentrated under reduced pressure and azeotroped with dichloromethane to give a pale yellow oil.

A solution of this intermediate methyl ester (5.6 g, 29 mmol) in 0.88 ammonia solution (100 ml) was stirred for 2 hrs at 50° C., followed by a further 18 hrs at room temperature. The reaction mixture was concentrated under reduced pressure, the residue azeotroped with toluene, and then dichloromethane, to give a white solid. Benzyl bromide (3.5 ml, 29.0 mol) was added to a solution of the intermediate carboxamide and triethylamine (8.1 ml, 58.0 mmol) in dichloromethane (100 ml), and the reaction stirred at room temperature for 4 days. The mixture was diluted with dichloromethane (100 ml), then washed with water, brine, dried over MgSO$_4$, and evaporated under reduced pressure. The crude product was purified by column chromatography on silica gel using an elution gradient of dichloromethane:methanol (100:0 to 95:5) to give the desired product as a viscous oil, (3.5 g, 52%).

$^1$H NMR (CDCl$_3$, 300 MHz) δ: 0.97 (d, 3H), 1.29–1.50 (m, 3H), 2.04 (m, 1H), 2.63 (m, 1H), 2.84 (m, 1H), 3.22 (t, 1H), 3.68 (d, 1H), 3.89 (d, 1H), 5.88 (s, br,1H), 7.17 (s, 1H), 7.30 (m, 5H). LRMS: m/z=233 (M+1)$^+$.

Preparation 87

[(2R,4R)-1-Benzyl-4-methylpiperidinyl]methylamine

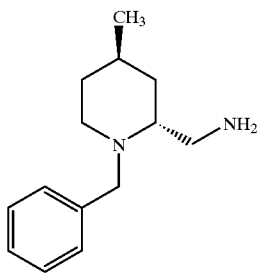

87

Lithium aluminum hydride (9.2 ml, 1M in tetrahydrofuran, 9.2 mmol) was added to a solution of (2R,4R)-1-benzyl-4-methyl-2-piperidinecarboxamide (preparation 86) (3.5 g, 15.0 mmol) in tetrahydrofuran (60 ml), and the reaction heated under reflux overnight. The reaction was cooled in an ice-bath, water (0.4 ml), 15% NaOH solution (0.4 ml), and water (1.2 ml) were added consecutively, and the resulting precipitate filtered off. The filtrate was concentrated under reduced pressure, re-dissolved in dichloromethane and washed with brine, dried over $Na_2SO_4$ and evaporated under reduced pressure. The crude product was purified by column chromatography on silica gel using an elution gradient of dichloromethane:methanol:0.88 ammonia (100:0:0 to 85:15:1) to give the title compound as a yellow oil, (650 mg, 20%).

$^1$H NMR ($CDCl_3$, 300 MHz) δ: 0.88 (d, 3H), 1.19–1.54 (m, 3H), 1.63 (m, 1H), 2.14 (s, br, 2H), 2.46–2.75 (m, 4H), 2.94 (m, 1H), 3.77 (d, 2H), 7.17–7.37 (m, 5H). LRMS: m/z=219 (M+1)$^+$.

Preparation 88

Benzyl 2-[3-({[(2R,4R)-1-benzyl-4-methylpiperidinyl]methyl}amino)-5-chloro-6-methyl-2-oxo-1(2H)-pyrazinyl]acetate

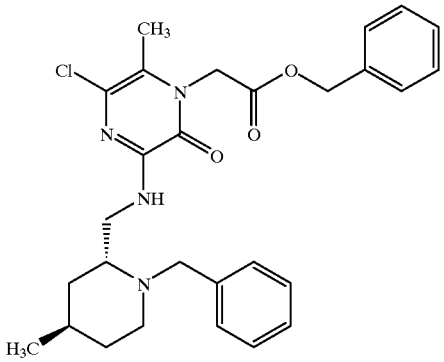

A mixture of benzyl 2-[3-({[(2R,4R)-1-benzyl-4-methylpiperidinyl]methyl}amino)-5-chloro-6-methyl-2-oxo-1(2H)-pyrazinyl]acetate (preparation 87) (650 mg, 2.98 mmol), benzyl 2-[3,5-dichloro-2-methyl-6-oxo-1(6H)-pyrazinyl]acetate (preparation 17) (970 mg, 3.0 mmol) and triethylamine (0.42 ml, 3.0 mmol) in ethyl acetate (50 ml), was heated under reflux for 24 hrs. The cooled reaction was diluted with ethyl acetate, washed with water, brine, then dried over $MgSO_4$, and evaporated under reduced pressure. The residual orange oil was purified by column chromatography on silica gel using an elution gradient of ethyl acetate-:pentane (0:100 to 28:72) to give the title compound as an orange oil, (1.2 g, 80%).

$^1$H NMR ($CDCl_3$, 300 MHz) δ: 0.95 (d, 3H), 1.22–1.56 (m, 5H), 1.79 (m, 1H), 2.20 (s, 3H), 2.60 (m, 1H), 2.78 (m, 1H), 2.98 (m, 1H), 3.41–3.60 (m, 2H), 3.80 (d, 1.5H), 4.82 (d, 1.5H), 5.22 (s, 2H), 6.61 (m, 1H), 7.19–7.42 (m, 10H). LRMS m/z=510 (M+1)$^+$.

88

Preparation 89

Benzyl 2-[3-({[(2R,4R)-4-methylpiperidinyl]methyl}amino)-5-chloro-6-methyl-2-oxo-1(2H)-pyrazinyl]acetate

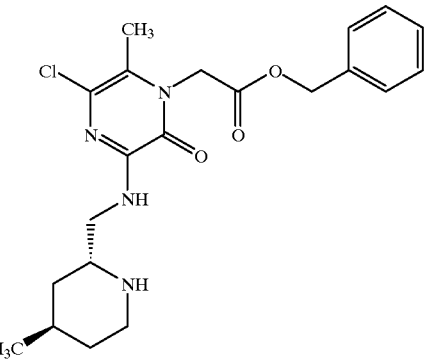

1-Chloroethyl chloroformate (0.28 ml, 2.57 mmol) was added to an ice-cooled solution of benzyl 2-[3-({[(2R,4R)-1-benzyl-4-methylpiperidinyl]methyl}amino)-5-chloro-6-methyl-2-oxo-1(2H)-pyrazinyl]acetate (preparation 88) (1.2 g, 2.36 mmol) and 1,8-bis(dimethylamino)naphthalene (100 mg) in dichloromethane (15 ml), and the reaction stirred at room temperature overnight. Additional 1-chloroethyl chloroformate (0.30 ml, 2.75 mmol) and 1,8-bis(dimethylamino) naphthalene (700 mg) were added and the reaction stirred for a further 4 hrs. The solution was diluted with dichloromethane (200 ml), washed with 0.5M citric acid solution (6×50 ml), water and then brine, dried over $MgSO_4$ and evaporated under reduced pressure. The residue was dissolved in methanol (80 ml), and the solution heated under reflux for 1½ hrs, concentrated under reduced pressure and azeotroped with dichloromethane to give the desired product as a brown foam, slightly impure, 1.1 g.

LRMS m/z=419 (M+1)$^+$.

Preparation 90

Benzyl 2-[3-({[(2R,4R)-4-methyl-1-(2,2,2-trifluoroacetyl)piperidinyl]methyl}amino)-5chloro-6-methyl-2-oxo-1(2H)-pyrazinyl]acetate

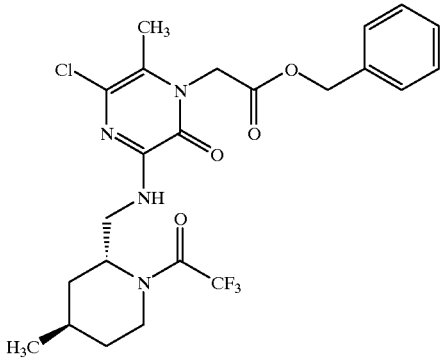

Pyridine (0.39 ml, 4.58 mmol) followed by trifluoroacetic anhydride (0.42 ml, 3.0 mmol) were added to a solution of benzyl 2-[3-({[(2R,4R)-4-methylpiperidinyl]methyl}amino)-5-chloro-6-methyl-2-oxo-1(2H)-pyrazinyl]acetate (preparation 89) (1.0 g, 2.3 mmol) in dichloromethane (30 ml), and the reaction stirred at room temperature for an hour. The solution was concentrated under reduced pressure and the residual oil was purified by column chromatography on silica gel using an elution gradient of ethyl acetate:pentane (0:100 to 34:66) to give the title compound, (910 mg, 77%).

¹H NMR (Consistent with rotamers) (CDCl₃, 300 MHz) δ: 0.97 (d, 3H), 1.10–1.40 (m, 3H), 1.78 (m, 2H), 1.99 (m, 1H), 2.21 (d, 3H), 3.03 (m, ⅓H), 3.40 (m, ⅔H), 3.53–3.91 (m, 4H), 4.77–4.98 (m, 3H), 5.21 (s, 2H), 6.16 (m, ⅓H), 6.26 (m, ⅔H), 7.38 (m, 10H). LRMS: m/z=516 (M+1)⁺.

Preparation 91

2-[3-({[(2R,4R)-4-Methyl-1-(2,2,2-trifluoroacetyl)piperidinyl]methyl}amino)-6-methyl-2-oxo-1(2H)-pyrazinyl]acetic acid

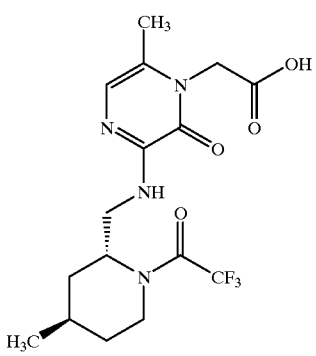

10% Palladium on charcoal (200 mg), followed by ammonium formate (1.1 g, 17.4 mmol) were added to a solution of benzyl 2-[3-({[(2R,4R)-4-methyl-1-(2,2,2-trifluoroacetyl)piperidinyl]methyl}amino)-5-chloro-6-methyl-2-oxo-1(2H)-pyrazinyl]acetate (preparation 90) (900 mg, 1.74 mmol) in methanol (20 ml) and the reaction was stirred at room temperature overnight. Additional 10% palladium on charcoal (50 mg) was added and the reaction stirred for a further 24 hrs. The mixture was filtered through Whatman® fibre and the filtrate concentrated under reduced pressure. The residue was suspended in a methanol:dichloromethane (10:90) solution, the resulting precipitate filtered off, and the filtrate evaporated under reduced pressure to provide the title compound as a white solid, (600 mg, 92%).

LRMS: m/z=391 (M+1)⁺.

Preparation 92

N-[(3-Methyl-1H-indol-5yl)methyl]-2-[6-methyl-3-{2-[(2R,4R)-4-methyl-1-(2,2,2-trifluoroacetyl)piperidinyl]ethyl}-2-oxo-1(2H)-pyrazinyl]acetamide

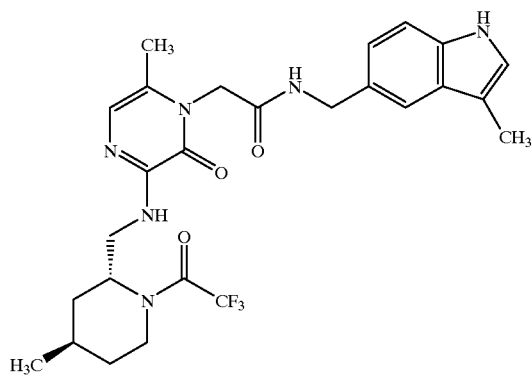

A mixture of 2-[3-({[(2R,4R)-4-methyl-1-(2,2,2-trifluoroacetyl)piperidinyl]methyl}amino)-6-methyl-2-oxo-1(2H)-pyrazinyl]acetic acid (preparation 91) (600 mg, 1.60 mmol), (3-methyl-1H-indol-5-yl)methylamine (preparation 36) (256 mg, 1.60 mmol), HOBT (256 mg, 1.90 mmol), WSCDI.HCl (364 mg, 1.90 mmol) and N-methylmorpholine (3.5 ml, 3.18 mmol) in N,N-dimethylformamide (5 ml), was stirred at room temperature overnight. The solution was diluted with water (50 ml), and the resulting precipitate filtered off and dried under vacuum. The solid was purified by column chromatography on silica gel using an elution gradient of pentane:ethyl acetate (100:0 to 34:66) to give the title compound, (360 mg, 42%).

¹H NMR (Consistent with rotamers) (CDCl₃, 300 MHz) δ: 0.97 (d, 3H), 1.06–1.38 (m, 3H), 1.78 (m, 2H), 1.95 (m, 1H), 2.22 (d, 3H), 2.30 (s, 3H), 3.00 (m, ⅓H), 3.30 (m, ⅔H), 3.50–3.88 (m, 3H), 4.23 (m, ⅓H), 4.39–4.72 (m, 3H), 4.94 (m, ⅔H), 5.90 (m, ⅓H), 6.00 (t, br,⅔H), 6.70 (m, 2H), 6.98 (s, 1H), 7.03 (d, 1H), 7.26 (m, 1H), 7.40 (s, 1H), 7.97 (s, br,1H). LRMS: m/z=534 (M+2)⁺.

Preparation 93

N-[(3-Methyl-1H-indol-5-yl)methyl]-2-[6-methyl-3-{2-[(2R,4R)-4-methylpiperidinyl]ethyl}-2-oxo-1(2H)-pyrazinyl]acetamide

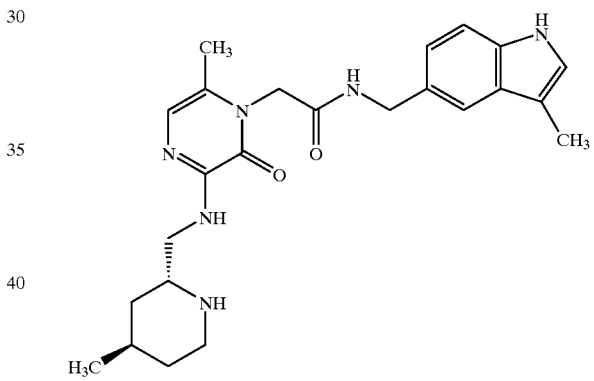

A mixture of N-((3-methyl-1H-indol-5-yl)methyl]-2-[6-methyl-3-{2-[(2R,4R)-4-methyl-1-(2,2,2-trifluoroacetyl)piperidinyl]ethyl}-2-oxo-1(2H)-pyrazinyl]acetamide (preparation 92) (360 mg, 0.68 mmol) and aqueous Na₂CO₃ solution (6 ml, 0.76M, 4.6 mmol) in methanol (50 ml) and water (10 ml) was stirred at room temperature for 3 days, followed by a further 3 hrs, heating under reflux. The solution was concentrated under reduced pressure and extracted with a dichloromethane:methanol (90:10) solution (3×100 ml), and the combined organic extracts evaporated under reduced pressure. The crude product was purified by column chromatography on silica gel using an elution gradient of dichloromethane:methanol:0.88 ammonia (100:0:0 to 90:10:1) to afford the title compound, (300 mg, 100%).

¹H NMR (CD₃OD, 300 MHz) δ: 1.06 (d, 3H), 1.44 (m, 1H), 1.60 (m, 1H), 1.75–1.95 (m, 2H), 2.03 (m, 1H), 2.18 (s, 3H), 2.30 (s, 3H), 3.08 (m, 1H), 3.20 (m, 1H), 3.55 (m, 2H), 3.70 (m, 1H), 4.50 (s, 2H), 4.78 (s, 2H), 6.70 (s, 1H), 6.99 (s, 1H), 7.04 (d, 1H), 7.27 (d, 1H), 7.42 (s, 1H). LRMS: m/z=437 (M+1)⁺.

Preparation 94

2-[3-{2-[(2R,4R)-1-(Cyclopropylmethyl)-4-methylpiperidinyl]methyl}amino)-6-methyl-2-oxo-1(2H)-pyrazinyl]-N-[(3-methyl-1H-indol-5-yl)methyl]acetamide

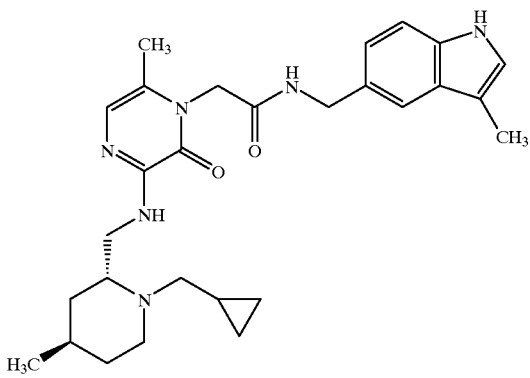

The title compound was obtained as a white solid, (56%) from N-[(3-methyl-1H-indol-5-yl)methyl]-2-[6-methyl-3-{2-[(2R,4R)-4-methylpiperidinyl]ethyl}-2-oxo-1-(2H)-pyrazinyl]acetamide (preparation 93) and cyclopropanecarboxaldehyde, following the procedure described in preparation 85.

$^1$H NMR (CD$_3$OD, 300 MHz) δ: 0.18 (m, 2H), 0.54 (m, 2H), 0.94 (m, 4H), 1.22–1.42 (m, 2H), 1.52–1.66 (m, 2H), 1.78 (m, 1H), 2.15 (s, 3H), 2.30 (s, 3H), 2.42 (m, 1H), 2.70 (m, 2H), 2.82 (m, 1H), 3.20 (m, 1H), 3.48 (m, 2H), 4.48 (s, 2H), 4.75 (s, 2H), 6.64 (s, 1H), 6.99 (s, 1H), 7.04 (d, 1H), 7.26 (d, 1H), 7.42 (s, 1H). LRMS: m/z=513 (M+23)$^+$.

EXAMPLE 25

2-[3-({[(3R)-4-(Cyclopylmethyl)morpholinyl]methyl}amino)-6-methyl-2-oxo-1(2H)-pyrazinyl]-N-[(3-methyl-1H-indol-5-yl)methyl]acetamide

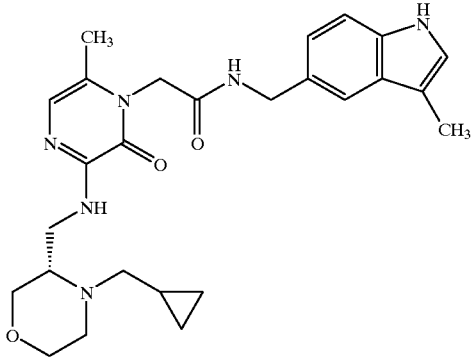

Preparation 95

[(3R)-4-Benzylmorpholinyl]methylamine

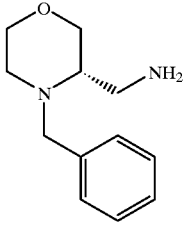

Oxalyl chloride (4 ml, 45.8 mmol) was added carefully to a slurry of 4-benzyl-(2R)-5-oxo-2-morpholinecarboxylic acid (J.Chem.Soc.Perk.I; 1985;2577) (7.3 g, 31 mmol) in dichloromethane (90 ml), followed by N,N-dimethylformamide (3 drops), and the reaction stirred at room temperature for 2 hrs. The mixture was concentrated under reduced pressure, azeotroped with dichloromethane (3×), and the resulting oil, dried under vacuum.

Ammonia gas was bubbled through an ice-cold solution of this intermediate acid chloride in ether (50 ml), for 15 minutes, and the resulting solution stirred at room temperature for 72 hrs. The reaction mixture was evaporated under reduced pressure to give a buff-coloured solid, 8.6 g.

Lithium aluminum hydride (35.8 ml, 1M in tetrahydrofuran, 35.8 mmol) was added carefully to a slurry of this amide in tetrahydrofuran (100 ml), and the resulting mixture stirred at room temperature for 30 minutes, and then heated under reflux for 24 hrs. Additional lithium aluminum hydride (25 ml, 1M in tetrahydrofuran, 25 mmol) was added, and the reaction heated under reflux for a further 48 hrs. The mixture was then cooled in an ice-bath, and treated sequentially, with stirring, with water (2.7 ml), 15% NaOH solution (2.7 ml), and water (8 ml), and the resulting precipitate filtered off. The filtrate was concentrated under reduced pressure and the residual gum purified by column chromatography on silica gel using an elution gradient of dichloromethane:methanol:0.88 ammonia (100:0:0 to 85:15:1) to afford the title compound, (4.2 g, 65%).

LRMS: m/z=207 (M+1)$^+$.

Preparation 96

Benzyl 2-[3-({[(3R)-4-benzylmorpholinyl]methyl}amino)-5-chloro-6-methyl-2-oxo-1(2H)-pyrazinyl]acetate

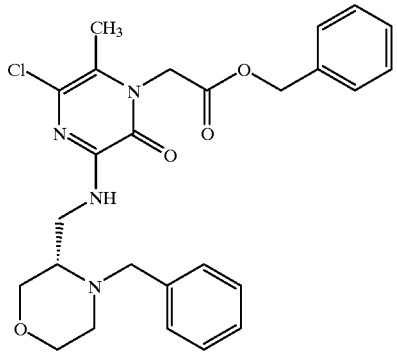

A solution of [(3R)-4-benzylmorpholinyl]methylamine (preparation 95) (4.2 g, 20.4 mmol), benzyl 2-[3,5-dichloro- 2-methyl-6-oxo-1(6H)-pyrazinyl]acetate (preparation 17) (1 g, 3.06 mmol), and triethylamine (0.7 ml, 5.0 mmol) in ethyl acetate (25 ml) was heated under reflux for 18 hrs. The cooled reaction mixture was diluted with ethyl acetate, washed with water, then brine, dried over MgSO$_4$ and concentrated under reduced pressure. The residual brown oil was purified by column chromatography on silica gel using an elution gradient of ethyl acetate:pentane (0:100 to 100:0) to give the title compound as a white solid, (500 mg, 32%).

LRMS: m/z=515 (M+18)$^+$.

Preparation 87

Benzyl 2-[3-({[(3R)-morpholinyl]methyl}amino)-5-chloro-6-methyl-2-oxo-1(2H)-pyrazinyl]acetate

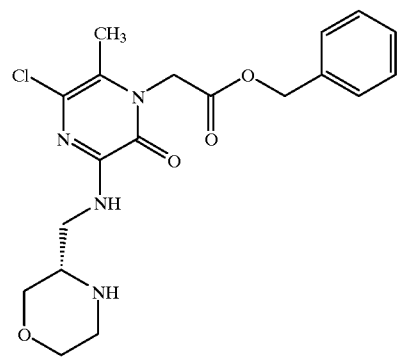

1,8-Bis(dimethylamino)naphthalene (250 mg, 1.17 mmol) was added to a solution of benzyl 2-[3-({[(3R)-4-benzylmorpholinyl]methyl}amino)-5-chloro-6-methyl-2-oxo-1(2H)-pyrazinyl]acetate (preparation 96) (570 mg, 1.1 mmol) in dichloromethane (15 ml), followed by 1-chloroethyl chloroformate (120 ml, 1.1 mmol), and the reaction stirred at room temperature for 18 hrs. Additional 1,8-bis(dimethylamino)naphthalene (250 mg, 1.16 mmol) and 1-chloroethyl chloroformate (120 ml, 1.1 mmol), were added and the reaction stirred for a further 4 days at room temperature and under reflux for the final 24 hrs. The solution was diluted with dichloromethane (200 ml), and washed with 0.5N citric acid (5×), brine, then dried over MgSO$_4$, and concentrated under reduced pressure. The crude brown solid was heated under reflux in methanol (30 ml), overnight, the cooled mixture filtered, the filtrate concentrated under reduced pressure and azeotroped with dichloromethane to yield the desired product as a brown foam, slightly impure, 520 mg.

LRMS: m/z 406 (M)$^+$.

Preparation 98

Benzyl 2-[3-chloro-2-methyl-6-oxo-5-({[(3R)-4-(2,2,2-trifluoroacetyl)morpholinyl]methyl}amino)-1(6H)-pyrazinyl]acetate

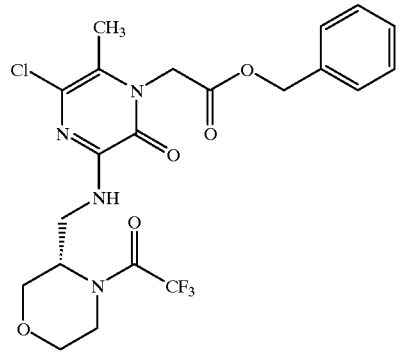

Pyridine (31 ml, 0.38 mmol) followed by trifluoroacetic anhydride (44 ml, 0.31 mmol) were added to an ice-cold solution of benzyl 2-[3-({[(3R)-morpholinyl]methyl}amino)-5-chloro-6-methyl-2-oxo-1(2H)-pyrazinyl]acetate (preparation 97) (120 mg, 0.29 mmol) in dichloromethane (7 ml), and the reaction stirred at 0° C. for 10 mins, and then at room temperature for a further 2 hrs. The reaction was quenched with water, the layers separated, and the organic phase dried over MgSO$_4$ and evaporated under reduced pressure. The residue was purified by column chromatography on silica gel using ethyl acetate:pentane (30:70) as eluant to give the title compound as a yellow solid, (83 mg, 56%).

$^1$H NMR (CDCl$_3$, 300 MHz) δ: 2.20 (s, 3H), 3.40–4.20 (m, 9H), 4.80 (s, 2H), 5.21 (s, 2H), 6.20 (m, 1H), 7.36 (m, 5H). LRMS: m/z=502 (M)$^+$.

Preparation 99

2-[3-Chloro-2-methyl-6-oxo-5-({[(3R)-4-(2,2,2-trifluoroacetyl)morpholinyl]methyl}amino)-1(6H)-pyrazinyl]-N-[(3-methyl-1H-indol-5-yl)methyl] acetamide

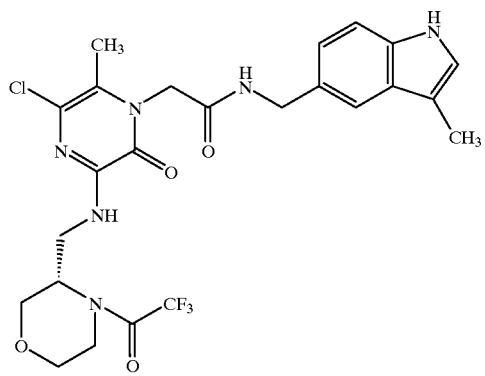

A mixture of benzyl 2-[3-chloro-2-methyl-6-oxo-5-({[(3R)-4-(2,2,2-trifluoroacetyl)morpholinyl]methyl}amino)-1(6H)-pyrazinyl]acetate (preparation 98) (300 mg, 0.60 mmol), and palladium hydroxide (80 mg) in methanol (4 ml), was hydrogenated at room temperature and 15 psi for 18 hrs. The reaction mixture was filtered through What-

Preparation 100

2-[3-Chloro-2-methyl-5-{[(3R)morpholinylmethyl]amino}-6-oxo-1(6H)-pyrazinyl]-N-[(3-methyl-1H-indol-5-yl)methyl]acetamide

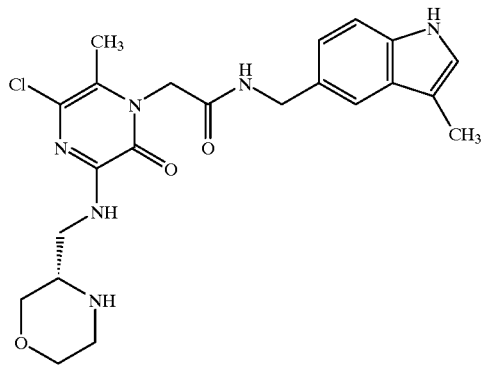

man® fibre, and the filter pad washed well with ethyl acetate. The combined filtrate was evaporated under reduced pressure to give a pale yellow solid, 180 mg.

(3-Methyl-1H-indol-5-yl)methylamine (preparation 36) (76 mg, 0.48 mmol), HOBT (64 mg, 0.48 mmol), WSCDI·HCl (91 mg, 0.48 mmol) and N-methylmorpholine (79 mg, 0.71 mmol), were added to a solution of the intermediate acid in N,N-dimethylformamide (4 ml), and the reaction stirred at room temperature for 72 hrs. The reaction mixture was purified directly by column chromatography on silica gel using dichloromethane:methanol (90:10) as eluant to afford the title compound as an off-white solid, (162 mg, 52%).

$^1$H NMR (CDCl$_3$, 400 MHz) δ: 2.30 (s, 3H), 2.38 (s, 2H), 2.40 (s, 1H), 3.50 (m, 1H), 3.62 (m, 2H), 3.75 (m, 1H), 3.92–4.26 (m, 4H), 4.42–4.59 (m, 3H), 4.65 (m, 2H), 6.25 (m, 1H), 6.55 (m, ⅓H), 6.65 (m, ⅔H), 6.98 (s, 1H), 7.02 (m, 1H), 7.27 (m, 1H), 7.40 (s, 1H), 7.99 (s, 1H). LRMS: m/z=555 (M+1)$^+$.

A mixture of 2-[3-chloro-2-methyl-6-oxo-5-({[(3R)-4-(2,2,2-trifluoroacetyl)morpholinyl]methyl}amino)-1(6H)-pyrazinyl]-N-[(3-methyl-1H-indol-5-yl)methyl]acetamide (preparation 99) (162 mg, 0.31 mmol) and Na$_2$CO$_3$ (600 mg, 5.66 mmol) in water (8 ml), and methanol (6 ml), was stirred at 40° C. for 18 hrs. The cooled reaction was concentrated under reduced pressure to remove the methanol, and the remaining aqueous solution extracted with ethyl acetate. The combined organic extracts were dried over MgSO$_4$, and evaporated under reduced pressure to give the title compound, (140 mg, slightly impure).

$^1$H NMR (CDCl$_3$, 400 MHz) δ: 2.30 (s, 3H), 2.39 (s, 3H), 2.90 (m, 2H), 3.08 (m, 1H), 3.30 (m, 2H), 3.49 (m, 1H), 3.60–4.00 (m, 3H), 4.54 (d, 2H), 4.62 (s, 2H), 6.34 (m, 1H), 6.54 (m, 1H), 6.98 (s, 1H), 7.03 (d, 1H), 7.28 (d, 1H), 7.40 (s, 1H), 7.96 (s, 1H). LRMS: m/z=459,461 (M+1)$^+$.

Preparation 101

2-[3-Chloro-5-({[(3R)-4-(cyclopropylmethyl)morpholinyl]methyl}amino)-2-methyl-6-oxo-1(6H)-pyrazinyl]-N-[(3-methyl-1H-indol-5-yl)methyl]acetamide

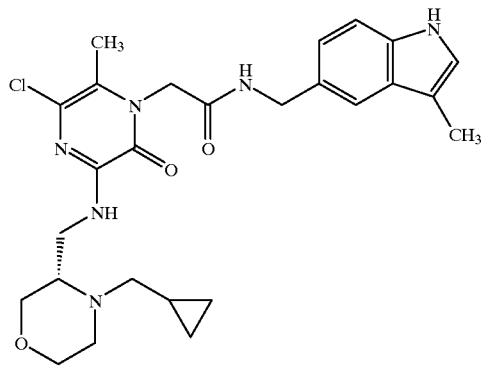

A mixture of 2-[3-chloro-2-methyl-6-oxo-5-({[(3R)-4-morpholinyl]methyl}amino)-1(6H)-pyrazinyl]-N-[(3-methyl-1H-indol-5-yl)methyl]acetamide (preparation 100) (140 mg, 0.33 mmol), cyclopropanecarboxaldehyde (26 ml, 0.35 mmol) and sodium triacetoxyborohydride (105 mg, 0.49 mmol) in tetrahydrofuran (4 ml) was stirred at room temperature under a nitrogen atmosphere for 16 hrs. The solution was partitioned between water and ethyl acetate, the layers separated, and the organic phase dried over MgSO$_4$ and evaporated under reduced pressure. The crude product was purified by column chromatography on silica gel using an elution gradient of dichloromethane:methanol (95:5 to 90:10) to afford the title compound (121 mg, 72%).

$^1$H NMR (CDCl$_3$, 400 MHz) δ: 0.10 (m, 2H), 0.45 (m, 2H), 0.86 (m, 1H), 2.19 (m, 1H), 2.30 (s, 3H), 2.40 (s, 3H), 2.48 (m, 1H), 2.60–2.75 (m, 2H), 3.02 (m, 1H), 3.42 (m, 3H), 3.62 (m, 1H), 3.74 (m, 1H), 3.80 (m, 1H), 4.56 (m, 2H), 4.66 (s, 2H), 6.48 (m, 1H), 6.56 (m, 1H), 6.98 (s, 1H), 7.05 (d, 1H), 7.30 (d, 1H), 7.42 (s, 1H), 7.92 (s, 1H). LRMS: m/z=513, 515 (M+1)$^+$.

Preparation 102

2-[3-({(3R)-4-(Cyclopropylmethyl)morpholinyl]methyl}amino)-6-methyl-2-oxo-1(2H)-pyrazinyl]-N-[(3-methyl-1H-indol-5-yl)methyl]acetamide

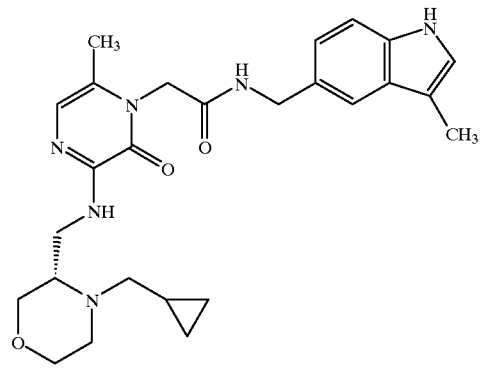

A mixture of 2-[3-chloro-5-({[(3R)-4-(cyclopropylmethyl)morpholinyl]methyl}amino)-2-methyl- 6-oxo-1(6H)-pyrazinyl]-N-[(3-methyl-1H-indol-5-yl)methyl]acetamide (preparation 101) (120 mg, 0.23 mmol), ammonium formate (44 mg, 0.7 mmol) and 10% palladium on charcoal (catalytic) in methanol (5 ml) was stirred at room temperature under a nitrogen atmosphere for 64 hrs. The reaction mixture was filtered through a Whatman® filter, washing through with ethyl acetate. The combined filtrate was evaporated under reduced pressure and the residue purified by column chromatography on silica gel using dichloromethane:methanol:0.88 ammonia (90:10:0.5) as eluant to give the title compound as a white solid, (15 mg, 14%).

$^1$H NMR (CDCl$_3$, 400 MHz) δ: 0.12 (m, 2H), 0.50 (m, 2H), 0.86 (m, 1H), 2.18 (m, 1H), 2.24 (s, 3H), 2.30 (s, 3H), 2.46 (m, 1H), 2.65 (m, 2H), 3.02 (m, 1H), 3.40 (m, 2H), 3.46–3.83 (m, 4H), 4.55 (m, 2H), 4.64 (s, 2H), 6.35 (s, br,1H), 6.60 (s, br,1H), 6.72 (s, 1H), 6.98 (s, 1H), 7.04 (d, 1H), 7.18 (m, 1H), 7.60 (s, 1H), 7.94 (s, br,1H). LRMS: m/z=478 (M+1)$^+$.

EXAMPLE 26

2-[3-({3-[(2-Aminoethoxy)methyl]phenethyl}amino)-6-methyl-2-oxo-1(2H)-pyrazinyl]-N-[(3-methyl-1H-indol-5-yl)methyl]acetamide

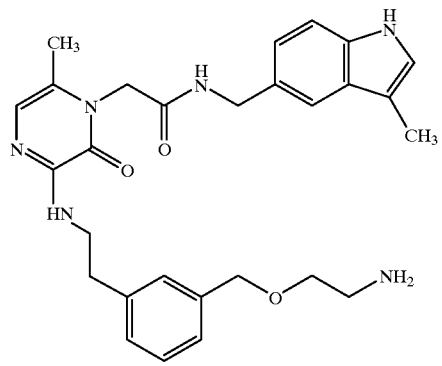

Preparation 103 tert-Butyl 2-{[3-(bromomethyl)benzyl]oxy}ethylcarbamate

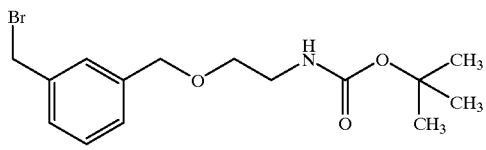

Sodium hydride (125 mg, 60% dispersion in mineral oil, 3.13 mmol) was added portionwise to an ice-cooled solution of tert-butyl 2-hydroxyethylcarbamate (500 mg, 3.10 mmol), and 1,3-bis(bromomethyl)benzene (8.2 g, 31.0 mmol) in tetrahydrofuran (15 ml), and the reaction stirred at 0° C. for an hour under a nitrogen atmosphere, then allowed to warm to room temperature. Saturated ammonium chloride solution (10 ml) was added, and the mixture partitioned between water and ethyl acetate, and the layers separated. The organic phase was then dried over MgSO$_4$, and evaporated under reduced pressure. The residue was purified by column chromatography on silica gel using an elution gradient of ethyl acetate:pentane (15:85 to 75:25) to give the title compound as a colourless oil, (796 mg, 74%).

$^1$H NMR (CDCl$_3$, 300 MHz) δ: 1.42 (s, 9H), 3.38 (m, 2H), 3.56 (t, 2H), 4.50 (2xs, 4H), 4.88 (s, br,1H), 7.38 (m, 4H). LRMS: m/z=362 (M+18)$^+$.

Preparation 104 tert-Butyl 2-{[3-(cyanomethyl)benzyl]oxy}ethylcarbamate

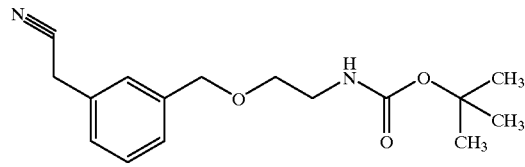

Sodium cyanide (284 mg, 5.78 mmol) and benzyl triethylammonium bromide (63 mg, 0.23 mmol) were added to a solution of tert-butyl 2-{[3-(bromomethyl)benzyl]oxy}ethylcarbamate (preparation 103) (798 mg, 2.31 mmol) in acetonitrile (5 ml), and the reaction stirred at room temperature for 4 days. The mixture was partitioned between water and ethyl acetate and the layers separated. The organic phase was dried over MgSO$_4$ and evaporated under reduced pressure, to afford the desired product as an oil, (654 mg, 97%).

$^1$H NMR (CDCl$_3$, 400 MHz) δ: 1.42 (s, 9H), 3.37 (m, 2H), 3.57 (t, 2H), 3.78 (s, 2H), 4.54 (s, 2H), 4.86 (s, br,1H), 7.26 (m, 3H), 7.37 (m, 1H). LRMS: m/z 291 (M+1)$^+$.

Preparation 105 tert-Butyl 2-{[3-(2-aminoethyl)benzyl]oxy}ethylcarbamate

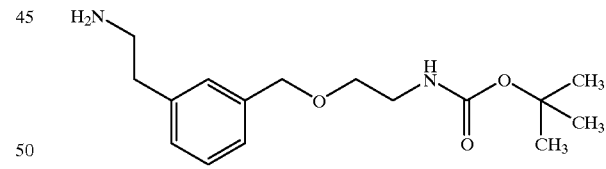

Raney® nickel (170 mg) was added to a solution of tert-butyl 2-{[3-(cyanomethyl)benzyl]oxy}ethylcarbamate (preparation 104) (654 mg, 2.26 mmol) in ethanolic ammonia solution (15 ml), and the mixture hydrogenated at 60 psi and room temperature for 24 hrs. The reaction mixture was filtered through Arbocel®, and the filtrate evaporated under reduced pressure. The residue was purified by column chromatography on silica gel using dichloromethane:methanol:0.88 ammonia (90:10:1) to afford the title compound, (536 mg, 80%).

$^1$H NMR (CDCl$_3$, 300 MHz) δ: 1.25 (s, br,2H), 1.43 (s, 9H), 2.78 (t, 2H), 2.98 (t, 2H), 3.36 (m, 2H), 3.57 (t, 2H), 4.50 (s, 2H), 4.88 (s, br,1H), 7.18 (m, 2H), 7.28 (m, 2H).

Preparation 106

Benzyl 2-[3-{[3-({2-[(tert-butoxycarbonyl)amino]ethoxy}methyl)phenethyl]amino-5-chloro-6-methyl-2-oxo-1(2H)-pyrazinyl]acetate

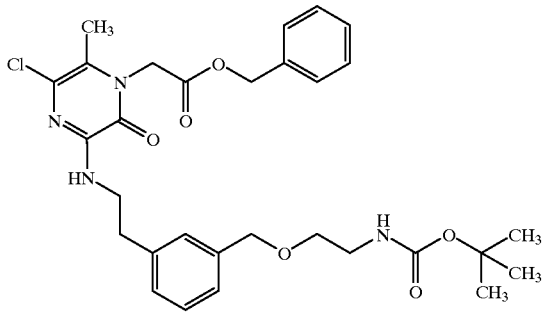

A mixture of tert-butyl 2-[3-(2-aminoethyl)benzyl]oxy}ethylcarbamate (preparation 105) (270 mg, 0.92 mmol), benzyl 2-[3,5-dichloro-2-methyl-6-oxo-1(6H)-pyrazinyl]acetate (preparation 17) (300 mg, 0.92 mmol), and triethylamine (140 ml, 1.01 mmol) in ethyl acetate was heated under reflux overnight. The cooled suspension was diluted with ethyl acetate, then washed with hydrochloric acid (2N), NaHCO₃ solution, brine, then dried over MgSO₄ and evaporated under reduced pressure. The crude product was purified by column chromatography on silica gel using ethyl acetate:pentane (40:60) as eluant, and triturated with ether, to give the title compound as a white solid, (243 mg, 45%). Re-purifiing the ether filtrate by column chromatography on silica gel provided an additional (176 mg, 33%) of the desired product.

$^1$H NMR (CDCl$_3$, 300 MHz) d: 1.42 (s, 9H), 2.20 (s, 3H), 2.95 (t, 2H), 3.36 (m, 2H), 3.56 (t, 2H), 3.68 (m, 2H), 4.50 (s, 2H), 4.80 (s, 2H), 4.99 (m, 1H), 5.21 (s, 2H), 6.12 (s, br,1H), 7.19 (m, 3H), 7.23–7.40 (m, 6H). LRMS: m/z=607 (M+23)$^+$.

Preparation 107

2-[3-{[3-({2-[(tert-Butoxycarbonyl)amino]ethoxy}methyl)phenethyl]amino}-6-methyl-2-oxo-1(2H)-pyrazinyl]acetic acid

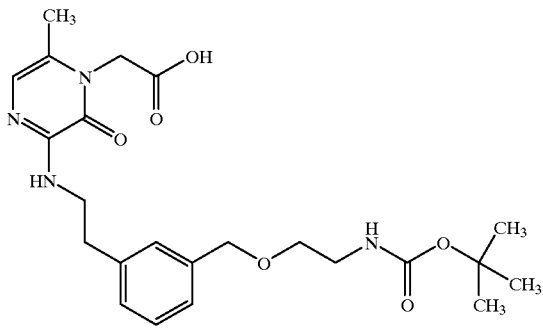

Ammonium formate (425 mg, 6.74 mmol) and 10% palladium on charcoal (200 mg) was added to a solution of benzyl 2-[3-{[3-({2-[(tert-butoxycarbonyl)amino]ethoxy}methyl)phenethyl]amino}-5-chloro-6-methyl-2-oxo-1(2H)-pyrazinyl]acetate (preparation 106) (392 mg, 0.67 mmol) in acetonitrile (10 ml), and the reaction stirred at room temperature overnight. The reaction mixture was filtered through Whatman® fibre, and the filtrate concentrated under reduced pressure. The residue was suspended in dichloromethane, basified using I N NaOH solution, and re-acidified to pH 4, using 1N hydrochloric acid. This solution was extracted with ethyl acetate (3×), and the combined organic extracts dried over MgSO₄ and evaporated under reduced pressure to give the title compound as a white foam, (180 mg, 58%).

$^1$H NMR (d$_6$-DMSO, 400 MHz) δ: 1.37 (s, 9H), 2.02 (s, 3H), 2.82 (t, 2H), 3.10 (t, 2H), 3.40 (t, 2H), 3.46 (m, 2H), 4.42 (m, 4H), 6.60 (s, 1H), 6.74 (t, br,1H), 6.80 (t, br, 1H), 7.15 (m, 3H), 7.24 (m,₁ H). LRMS: m/z=461 (M+1)$^+$.

Preparation 108 tert-Butyl 2-{[3-(2-{[5-methyl-4-(2-{[(3-methyl-1H-indol-5-yl)methyl]amino}-2-oxoethyl)-3-oxo-3,4-dihydro-2-pyrazinyl]amino}ethyl)benzyl]oxy}ethylcarbamate

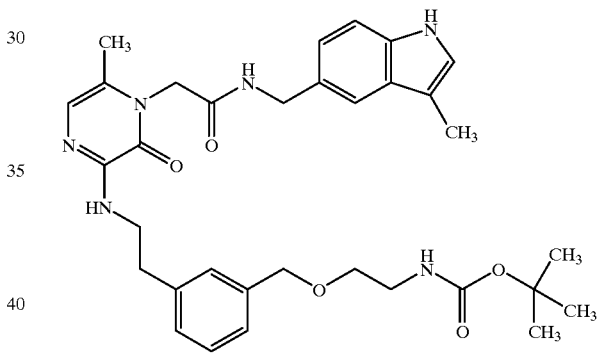

A mixture of 2-[3-{[3-({2-[(tert-butoxycarbonyl)amino]ethoxy}methyl)phenethyl]amino)6-methyl-2-oxo-1(2H)-pyrazinyl]acetic acid (preparation 107) (174 mg, 0.38 mmol), (3-methyl-1H-indol-5-yl)methylamine (preparation 36) (67 mg, 0.42 mmol), HOBT (77 mg, 0.57 mmol), WSCDI.HCl (91 mg, 0.47 mmol) and N-methylmorpholine (124 ml, 1.13 mmol) in N,N-dimethylformamide (5 ml), was stirred at room temperature for 20 hrs. The reaction mixture was partitioned between ethyl acetate and water and the .phases separated. The organic layer was dried over MgSO₄ and evaporated under reduced pressure to give the title compound as a white solid, (220 mg, 96%).

$^1$H NMR (d$_6$-DMSO, 300 MHz) δ: 1.37 (s, 9H), 2.05 (s, 3H), 2.22 (s, 3H), 2.82 (t, 2H), 3.10 (m, 2H), 3.39 (t, 2H), 3.46 (m, 2H), 4.36 (d, 2H), 4.41 (s, 2H), 4.61 (s, 2H), 6.62 (s, 1H), 6.81 (m, 2H), 6.98 (d, 1H), 7.08 (s, 1H), 7.15 (m, 3H), 7.23 (m, 2H), 7.37 (s, 1H), 8.62 (t, br,1H), 10.68 (s, 1H). LRMS: m/z=603 (M+1)$^+$.

Preparation 109

2-[3-({3-[(2-Aminoethoxy)methyl]phenethyl}amino)-6-methyl-2-oxo-1(2H)-pyrazinyl]-N-[(3-methyl-1H-indol-5-yl)methyl]acetamide

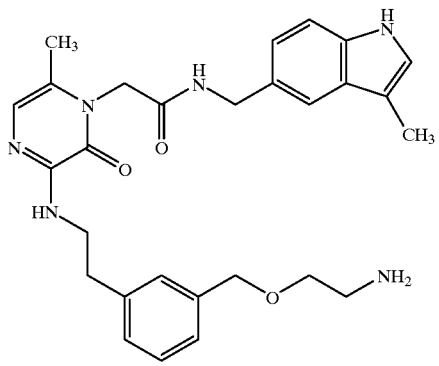

Hydrochloric acid (10 ml, 6N, 60.0 mmol) was added to a solution of tert-butyl 2-{[3-(2-{[5-methyl-4-(2-{[(3-methyl-1H-indol-5-yl)methyl]amino}-2-oxoethyl)-3-oxo-3,4-dihydro-2-pyrazinyl]amino}ethyl)benzyl]oxy}ethylcarbamate (preparation 108) (220 mg, 0.36 mmol) in methanol (10 ml), and the reaction stirred for an hour at room temperature. The mixture was basified using NaOH (1N) solution, and the mixture extracted with ethyl acetate (2×), and dichloromethane (1×). The combined organic extracts were dried over MgSO$_4$ and evaporated under reduced pressure. The crude product was purified by column chromatography on silica gel using dichloromethane:methanol:0.88 ammonia (90:10:1) to afford the title compound as a white solid, (100 mg, 55%).

$^1$H NMR (d$_6$-DMSO, 400 MHz) δ: 2.05 (s, 3H), 2.21 (s, 3H), 2.72 (t, 2H), 2.82 (t, 2H), 3.40 (t, 2H), 3.48 (m, 2H), 4.38 (d, 2H), 4.43 (s, 2H), 4.61 (s, 2H), 6.62 (s, 1H), 6.79 (t, br,1H), 6.98 (d, 1H), 7.06 (s, 1H), 7.15 (m, 3H), 7.24 (m, 2H), 7.37 (s, 1H), 8.60 (t, br,1H), 10.65 (s, 1H). LRMS: m/z=503 (M+1)$^+$.

EXAMPLE 27

N-[(3-Methyl-1H-indol-5-yl)methyl]-2-[6-methyl-3-[(3-{[2-(methylamino)ethoxy]methyl}phenethyl)amino]-2-oxo-1(2H)-pyrazinyl]acetamide

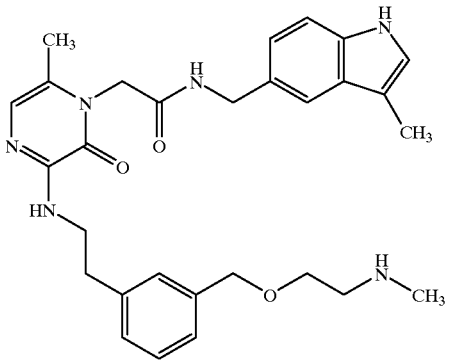

Preparation 110 tert-Butyl methyl[2-({3-[bromomethyl]benzyl}oxy)ethyl]carbamate

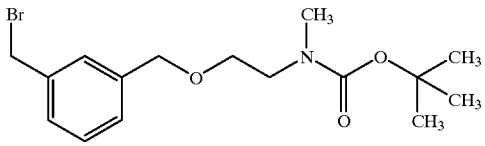

The title compound was obtained (85%) from tert-butyl 2-hydroxyethyl(methyl)carbamate (Synth. Commun. 23;17;1993;2443) and 1,3-bis(bromomethyl)benzene following the procedure described in preparation 103.

$^1$H NMR (CDCl$_3$, 300 MHz) δ: 1.43 (s, 9H), 2.95 (s, 3H), 3.42 (s, br,2H), 3.60 (s, br,2H), 4.50 (2×s, 4H), 7.25 (m, 1H), 7.35 (m, 3H).

Preparation 111 tert-Butyl methyl[2-({3-[cyanomethyl]benzyl}oxy)ethyl]carbamate

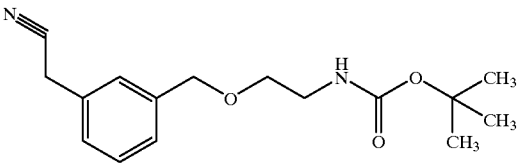

The title compound was obtained (94%) as an oil, from tert-butyl methyl[2-({3-[bromomethyl]benzyl}oxy)ethyl]carbamate (preparation 110), following the procedure described in 104.

$^1$H NMR (CDCl$_3$, 300 MHz) d: 1.41 (s, 9H), 2.95 (s, 3H), 3.42 (s, br,2H), 3.60 (s, br,2H), 3.77 (s, 2H), 4.54 (s, 2H), 7.25 (m, 3H), 7.36 (m, 1H). LRMS: m/z=305 (M+1)$^+$.

Preparation 112 tert-Butyl methyl[2-({3-[2-(methylamino)ethyl]benzyl}oxy)ethyl]carbamate

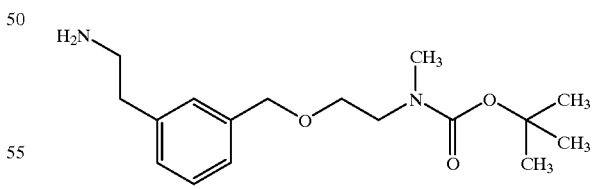

The title compound was obtained as an oil (99%) from tert-butyl methyl[2-({3-[cyanomethyl]benzyl}oxy)ethyl]carbamate (preparation 111), following the procedure described in 105.

$^1$H NMR (CDCl$_3$, 400 MHz) δ: 1.26 (s, br,2H), 1.43 (s, 9H), 2.77 (t, 2H), 2.94 (s, 3H), 2.98 (t, 2H), 3.42 (s, br,2H), 3.60 (s, br,2H), 4.50 (s, 2H), 7.14 (d, 1H), 7.18 (m, 2H), 7.28 (m, 1H). LRMS: m/z=309 (M+1)$^+$.

Preparation 113

Benzyl 2-[3-{[3-({2-[(tert-butoxycarbonyl)(methyl)amino]ethoxy}methyl)phenethyl]amino}-5-chloro-6-methy-2-oxo-1(2H)-pyrazinyl]acetate

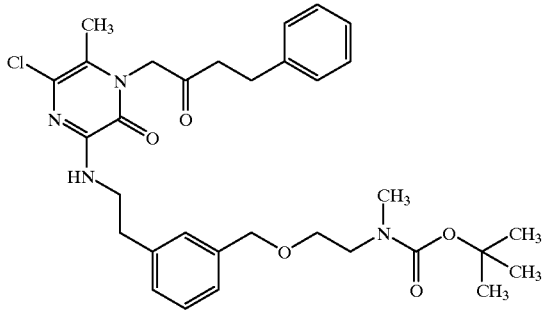

The title compound was obtained as a white crystalline solid (64%) from tert-butyl methyl[2-({3-[2-(methylamino)ethyl]benzyl}oxy)ethyl]carbamate (preparation 112) and benzyl 2-[3,5-dichloro-2-methyl-6-oxo-1(6H)-pyrazinyl]acetate (preparation 17), following the procedure described in preparation 106.

$^1$H NMR (CDCl$_3$, 400 MHz) δ: 1.42 (s, 9H), 2.21 (s, 3H), 2.95 (m, 5H), 3.42 (s, br,2H), 3.60 (s, br,2H), 3.68 (m, 2H), 4.50 (s, 2H), 4.80 (s, 2H), 5.21 (s, 2H), 6.10 (t, br, 1H), 7.17 (d, 1H), 7.20 (m, 2H), 7.26 (m, 1H), 7.36 (m, 5H).

Preparation 114

2-[3-{[3-({2-[(tert-Butoxycarbonyl)(methyl)amino]ethoxy}methyl)phenethyl]amino}-6-methyl-2-oxo-1(2H)-pyrazinyl]acetic acid

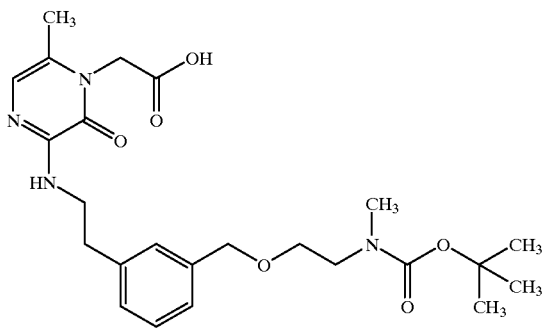

Ammonium formate (368 mg, 5.83 mmol), followed by 10% palladium on charcoal (200 mg), were added to a solution of benzyl 2-[3-{[3-({2-[(tert-butoxycarbonyl)(methyl)amino]ethoxy}methyl)phenethyl]amino-5-chloro-6-methyl- 2-oxo-1(2H)-pyrazinyl]acetate (preparation 113) (350 mg, 0.58 mmol) in methanol (10 ml), and the reaction stirred at room temperature overnight. The reaction mixture was filtered through Whatman® fibre, and the filtrate concentrated under reduced pressure. The residue was triturated with dichloromethane, the resulting suspension filtered again through Whatman® fibre, then through celite, and this filtrate evaporated under reduced pressure. The residual solid was dissolved in dichloromethane, the solution washed with water, brine, then dried over MgSO$_4$ and evaporated under reduced pressure to give the desired product as a gum, (213 mg, 79%).

$^1$H NMR (d$_6$-DMSO, 300 MHz) δ: 1.36 (s, 9H), 1.98 (s, 3H), 2.03 (s, 3H), 2.82 (m, 2H), 3.30 (t, 2H), 3.48 (m, 4H), 4.43 (s, 2H), 4.52 (s, 2H), 6.60 (s, 1H), 6.78 (t, br, 1H), 7.15 (m, 3H), 7.24 (m, 1H). LRMS: m/z=474 (M)$^+$.

Preparation 115 tert-Butyl methyl(2-{[3-(2-{[5-methyl-4-(2-{[(3-methyl-1H-indol-5-yl)methyl]amino}-2-oxoethyl)-3-oxo-3,4-dihydro-2-pyrazinyl]amino}ethyl)benzyl]oxy}ethyl)carbamate

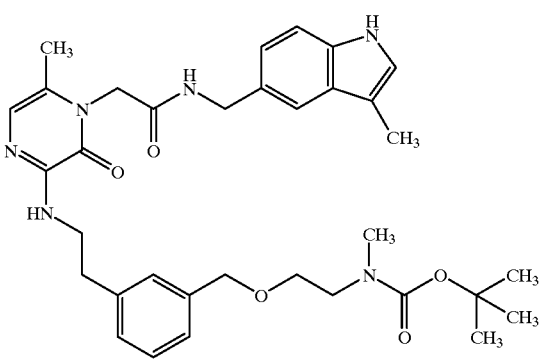

The title compound was obtained as a white solid (97%) from 2-[3-{[3-({2-[(tert-butoxycarbonyl)(methyl)amino]ethoxy}methyl)phenethyl]amino}-6-methyl-2-oxo-1(2H)-pyrazinyl]acetic acid (preparation 114) and (3-methyl-1H-indol-5-yl)methylamine (preparation 36), following a similar procedure to that described in preparation 108.

$^1$H NMR (d$_6$-DMSO, 400 MHz) δ: 1.37 (s, 9H), 2.04 (s, 3H), 2.21 (s, 3H), 2.80 (m, 5H), 3.35 (t, 2H), 3.48 (m, 4H), 4.38 (d, 2H), 4.43 (s, 2H), 4.62 (s, 2H), 6.61 (s, 1H), 6.79 (t, br,1H), 6.98 (d, 1H), 7.06 (s, 1H), 7.15 (m, 3H), 7.24 (m, 2H), 7.37 (s, 1H), 8.80 (t, br,1H), 10.64 (s, 1H). LRMS: m/z=618 (M+1)$^+$.

Preparation 116

N-[(3-Methyl-1H-indol-5-yl)methyl]-2-[6-methyl-3-[(3-{[2-(methylamino)ethoxy]methyl}phenethyl)amino]-2-oxo-1(2H)-pyrazinyl]acetamide

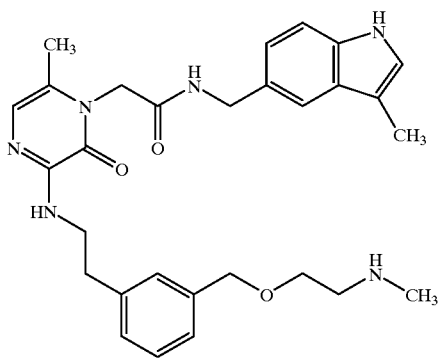

The title compound was obtained as a cream coloured solid, from tert-butyl methyl(2-{[3-(2-[5-methyl-4-(2-{[(3-methyl-1H-indol-5-yl)methyl]amino}-2-oxoethyl)-3-oxo-3,4-dihydro-2-pyrazinyl]amino}ethyl)benzyl]oxy}ethyl)carbamate (preparation 115), following a similar procedure to that described in preparation 109.

¹H NMR (d₆-DMSO, 300 MHz) δ: 2.05 (s, 3H), 2.20 (s, 3H), 2.24 (s, 3H), 2.61 (t, 2H), 2.82 (t, 2H), 3.45 (m, 4H), 4.38 (d, 2H), 4.42 (s, 2H), 4.61 (s, 2H), 6.62 (s, 1H), 6.78 (t, br,1H), 6.98 (d, 1H), 7.05 (s, 1H), 7.14 (m, 3H), 7.22 (m, 2H), 7.38 (s, 1H), 8.80 (t, br,1H), 10.64 (s, 1H). LRMS: m/z=517 (M+1)⁺.

EXAMPLE 28

2-[3-({3-[(1R/S)-1-Amino-2-methoxyethyl]phenethyl}amino)-6-methyl-2-oxo-1(2H)-pyrazinyl]-N-[(3-methyl-1H-indol-5-yl)methyl]acetamide

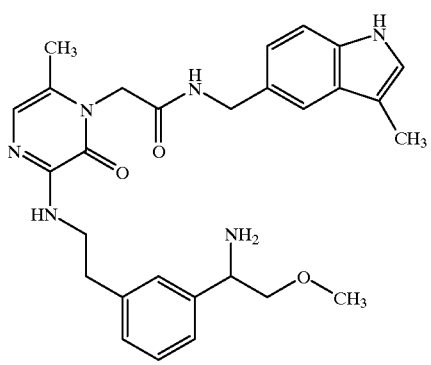

Preparation 117

3-Vinylphenylethylamine

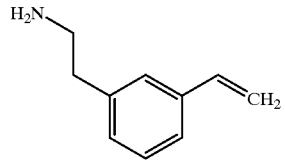

A mixture of 3-bromophenylacetonitrile (3.31 ml, 25.5 mmol), vinyl tributyl tin (16.17 g, 51.0 mmol), bis(triphenylphosphine)palladium(II) chloride (1.48 g, 1.28 mmol) and lithium chloride (3.24 g, 76.5 mmol) in tetrahydrofuran (500 ml), was heated under reflux for 6 hrs, and stirred for a further 18 hrs at room temperature. The reaction mixture was concentrated under reduced pressure, the residue dissolved in ethyl acetate and washed with NaHCO₃ solution (2×), then brine, dried over MGSO, and evaporated under reduced pressure. The crude product was purified by column chromatography on silica gel using ethyl acetate-:hexane (16:84) as eluant to afford a yellow oil.

A solution of aluminum chloride (1.44 g, 10.8 mmol) in tetrahydrofuran (25 ml) was added carefully to lithium aluminum hydride (1.23 g, 32.4 mmol) in tetrahydrofuran (25 ml), and the mixture stirred at room temperature for 10 mins. A solution of the intermediate acetonitrile in tetrahydrofuran (50 ml) was then added and the reaction stirred at room temperature for 3 hrs. The reaction was quenched by the addition of hydrochloric acid, then basified using aqueous NaOH solution. The mixture was extracted with ethyl acetate, the combined organic extracts dried over MgSO₄ and evaporated under reduced pressure. The crude product was redissolved in ethyl acetate, extracted into citric acid, and these aqueous extracts rebasified using aqueous NaHCO₃ solution. This was then re-extracted with ethyl acetate, and the combined extracts evaporated under reduced pressure to provide the title compound as a yellow oil, (1.79 g, 47%).

¹H NMR (CDCl₃, 300 MHz) δ: 1.18 (s, br,2H), 2.75 (t, 2H), 2.97 (t, 2H), 5.22 (d, 1H), 5.76 (d, 1H), 6.70 (dd, 1H), 7.07 (m, 1H), 7.22 (m, 3H).

Preparation 118

Benzyl 3-vinylphenethylcarbamate

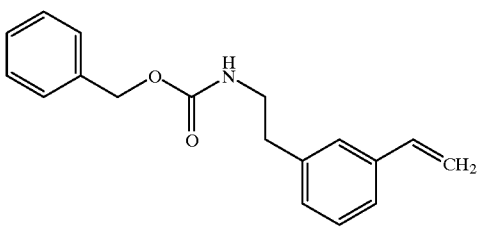

A mixture of 3-vinylphenylethylamine (preparation 117) (1.78 g, 12.1 mmol), N-(benzyloxy)succinimide (3.62 g, 14.52 mmol) and triethylamine (2.53 ml, 18.15 mmol) in dichloromethane (60 ml), was stirred at room temperature under a nitrogen atmosphere overnight. The reaction mixture was washed with citric acid solution, saturated aqueous NaHCO₃, brine, then dried over MgSO₄, and evaporated under reduced pressure. The crude product was purified by column chromatography on silica gel using dichloromethane as eluant to give the desired product as a colourless oil, (1.43 g, 41%).

¹H NMR (CDCl₃, 300 MHz) δ: 2.80 (t, 2H), 3.44 (t, 2H), 4.96 (s, br,1H), 5.12 (s, 2H), 5.24 (d, 1H), 5.78 (d, 1H), 6.70 (dd, 1H), 7.08 (m, 1H), 7.20–7.41 (m, 8H).

Preparation 119

Benzyl 3-{(1R/S)-1-[(tert-butoxycarbonyl)amino]-2-hydroxyethyl}phenethylcarbamate

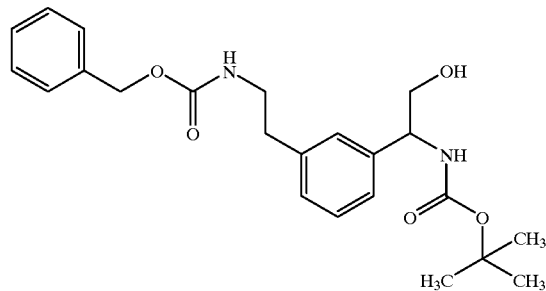

A solution of NaOH (1.22 g, 30.5 mmol) in water (70 ml), followed by hypochlorous acid tert-butyl ester (3.5 ml, 30.5 mmol) were added to a solution of tert-butylcarbamate (3.57 g, 30.5 mmol) in n-propanol (75 ml), in an amber glass flask. This solution was stirred at room temperature for 5 mins, then cooled in an ice-bath. Solutions of (DHQ)₂PHAL (480 mg, 0.6 mmol) in n-propanol (40 ml), and benzyl 3-vinylphenethylcarbamate (preparation 118) (2.81 g, 10 mmol) in n-propanol (70 ml) were added, followed by potassium osmate dihydrate (184 mg, 0.5 mmol) in water (5 ml) and the reaction then stirred at 0° C. for 4 hrs, and at room temperature for a further 18 hrs. Saturated sodium dithionite solution (100 ml) was added, the phases separated, and the aqueous layer extracted with ethyl acetate (2×100 ml). The combined organic extracts were dried over MgSO₄ and evaporated under reduced pressure. The residual brown oil was purified by column chromatography on silica gel twice, using an elution gradient of ethyl acetate:pentane (25:75 to 50:50) to give the desired product as a colourless oil, (603 mg, 15%).

¹H NMR (CDCl₃, 300 MHz) δ: 1.42 (s, 9H), 2.52 (s, br,1H), 2.80 (t, 2H), 3.46 (m, 2H), 3.80 (m, 2H), 4.74 (s, br,1H), 4.84 (s, br,1H), 5.07 (s, 2H), 5.32 (d, 1H), 7.11 (m, 3H), 7.30 (m, 6H).

Preparation 120

Benzyl 3-{(1R/S)-1-[(tert-butoxycarbonyl)amino]-2-methoxyethyl}phenethylcarbamate

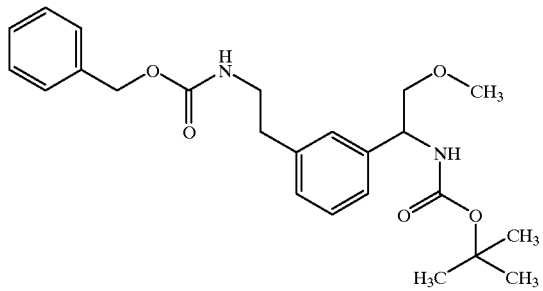

A mixture of methyl iodide (98 ml, 1.57 mmol), benzyl 3-{(1R/S)-1-[(tert-butoxycarbonyl)amino]-2-hydroxyethyl}phenethylcarbamate (preparation 119) (590 mg, 1.4 mmol), benzyltriethylammonium chloride (325 mg, 1.4 mmol) and NaOH solution (185 ml, 10M, 1.85 mmol) in dichloromethane (10 ml), was stirred at room temperature for 3 days. The reaction mixture was partitioned between dichloromethane and water, the phases separated, and the organic layer dried over MgSO₄ and evaporated under reduced pressure. The residual oil was purified by column chromatography on silica gel using an elution gradient of ethyl acetate:pentane (0:100 to 50:50) to provide the title compound as a colourless oil, (289 mg, 47%).

¹H NMR (CD₃OD, 300 MHz) δ: 1.40 (s, 9H), 2.78 (t, 2H), 3.32 (m, 5H), 3.50 (d, 2H), 4.75 (m, 1H), 4.80 (s, 2H), 5.05 (s, 2H), 7.00–7.36 (m, 9H).

Preparation 121 tert-Butyl (1R/S)-1-[3-(2-aminoethyl)phenyl]-2-methoxyethylcarbamate

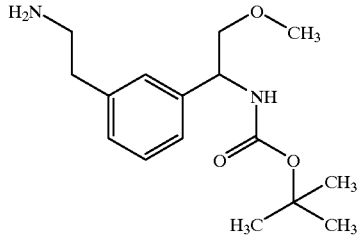

A mixture of benzyl 3-{(1R/S)-1-[(tert-butoxycarbonyl)amino]-2-methoxyethyl}phenethylcarbamate (preparation 120) (289 mg, 0.68 mmol) and 10% palladium on charcoal (30 mg) in methanol (10 ml) was hydrogenated at 15 psi and room temperature for 16 hrs. The reaction mixture was filtered through Arbocel®, and the filtrate evaporated under reduced pressure to give the title compound, (196 mg, 98%).

¹H NMR (CD₃OD, 300 MHz) δ: 1.41 (s, 9H), 2.78 (t, 2H), 2.88 (t, 2H), 3.52 (d, 2H), 4.72–4.80 (m, 5H), 7.11 (d, 1H), 7.18 (m, 2H), 7.24 (m, 1H). LRMS: m/z=295 (M+1)⁺.

Preparation 122

Benzyl 2-[3-[(3-{(1R/S)-1-[(tert-butoxycarbonyl)amino]-2-methoxyethyl}phenethyl)amino]-5-chloro-6-methyl-2-oxo-1(2H)-pyrazinyl]acetate

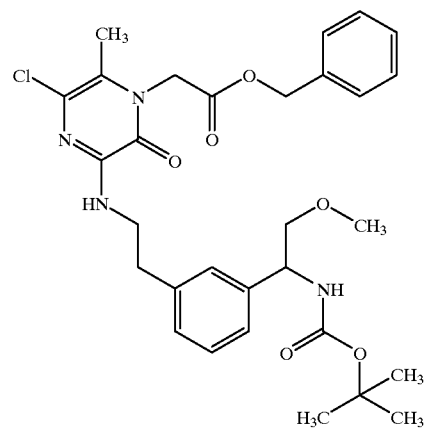

A mixture of tert-butyl (1R/S)-1-[3-(2-aminoethyl)phenyl]-2-methoxyethylcarbamate (preparation 121) (196 mg, 0.67 mmol), benzyl 2-[3,5-dichloro-2-methyl-6-oxo-1 (6H)-pyrazinyl]acetate (preparation 17) (182 mg, 0.56 mmol) and triethylamine (368 ml, 2.78 mmol) in ethyl acetate (5 ml) was heated under reflux for 18 hrs. The cooled mixture was washed with brine (15 ml), dried over MgSO₄ and evaporated under reduced pressure. The residual oil was purified by column chromatography on silica gel using an elution gradient of dichloromethane:methanol (100:0 to 99:1) to afford the title compound as a colourless oil, (248 mg, 76%).

¹H NMR (CDCl₃, 300 MHz) δ: 1.40 (s, 9H), 2.20 (s, 3H), 2.90 (t, 2H), 3.35 (s, 3H), 3.52–3.70 (m, 4H), 4.80 (m, 3H), 5.22 (m, 3H), 6.15 (t, br,1H), 7.17 (m, 3H), 7.24 (m, 1H), 7.37 (m, 5H). LRMS: m/z=585 (M+1)⁺.

Preparation 123

2-[3-[(3-{(1R/S)-1-[(tert-Butoxycarbonyl)amino]-2-methoxyethyl}phenethyl)amino]-6-methyl-2-oxo-1(2H)-pyrazinyl]acetic acid

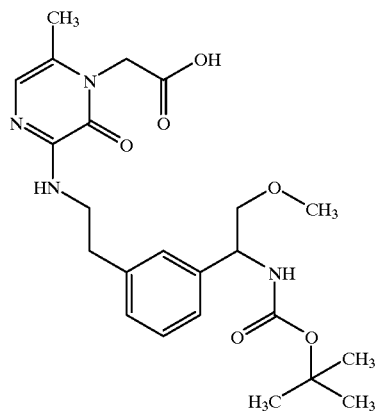

A mixture of benzyl 2-[3-[(3-(1R/S)-1-[(tert-butoxycarbonyl)amino]-2-methoxyethyl}phenethyl)amino]-5-chloro-6-methyl-2-oxo-1(2H)-pyrazinyl]acetate (preparation 122) (248 mg, 0.42 mmol), ammonium formate (265 mg, 4.2 mmol) and 10% palladium on charcoal (100 mg) in methanol (10ml) was heated under reflux for 25 hrs. The cooled reaction was filtered through Arbocel®, and NaOH (420 ml, 10 M, 4.2 mmol) was added to the filtrate. This mixture was evaporated under reduced pressure, triturated and filtered with a dichloromethane:methanol (91:9) solution (3×), and the combined filtrates evaporated under reduced pressure. The crude product was purified by column chromatography on silica gel using an elution gradient of dichloromethane:methanol (100:0 to 93:7) to give the title compound as an oil, (35 mg, 18%).

$^1$H NMR (CD$_3$OD, 300 MHz) δ: 1.40 (s, 9H), 2.18 (s, 3H), 2.90 (m, 2H), 3.35 (s, 3H), 3.55 (m, 4H), 4.60 (s, 2H), 4.80 (m, 1H), 6.66 (s, 1H), 7.17 (m, 2H), 7.24 (m, 2H). LRMS: m/z=483 (M+1)$^+$.

Preparation 124 tert-Butyl (1R/S)-2-methoxy-1-[3-(2-{[5-methyl-4-(2-{[(3-methyl-1H-indol-5-yl)methyl]amino}-2-oxoethyl)-3-oxo-3,4-dihydro-2-pyrazin]amino}ehtyl)phenyl]ethylcarbamate

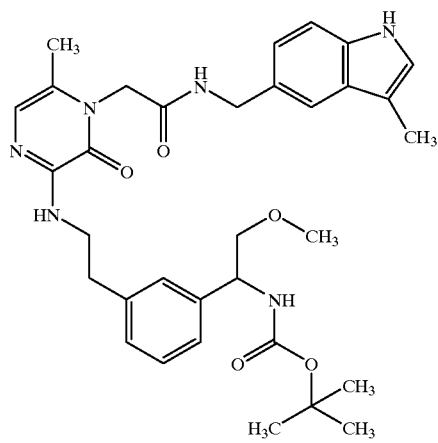

A mixture of 2-[3-[(3-{(1R/S)-1-[(tert-butoxycarbonyl)amino]-2-methoxyethyl}phenethyl)amino]-6-methyl-2-oxo-1(2H)-pyrazinyl]acetic acid (preparation 123) (35 mg, 0.076 mmol), (3-methyl-1H-indol-5-yl)methylamine (preparation 36) (13 mg, 0.08 mmol), HOBT (11 mg, 0.08 mmol), WSCDI.HCl (16 mg, 0.08 mmol) and N-methylmorpholine (16 ml, 0.15 mmol) in N,N-dimethylformamide (2 ml), was stirred at room temperature for 18 hrs. Additional (3-methyl-1H-indol-5-yl)methylamine (preparation 36) (8 mg, 0.038 mmol), was added, and stirring continued for a further 72 hrs at room temperature. The reaction mixture was poured into water (10 ml), and the resulting precipitate filtered, and dried to give the desired product, (26 mg, 57%).

$^1$H NMR (CD$_3$OD,300 MHz) δ: 1.41 (s, 9H), 2.16 (s, 3H), 2.29 (s, 3H), 2.94 (t, 2H), 3.34 (s, 3H), 3.50 (d, 2H), 3.59 (t, 2H), 4.48 (s, 2H), 4.76 (s, 2H), 4.82 (m, 1H), 6.66 (s, 1H), 6.98 (s, 1H), 7.05 (d, 1H), 7.16 (d, 2H), 7.22 (m, 3H), 7.42 (s, 1H). LRMS: mnz=625 (M+23)$^+$.

Preparation 125

2-[3-({3-[(1R/S)-1-Amino-2-methoxyethyl]phenethyl}amino)-6-methyl-2-oxo-1(2H)-pyrazinyl]-N-[(3-methyl-1H-indol-5-yl)methyl]acetamide

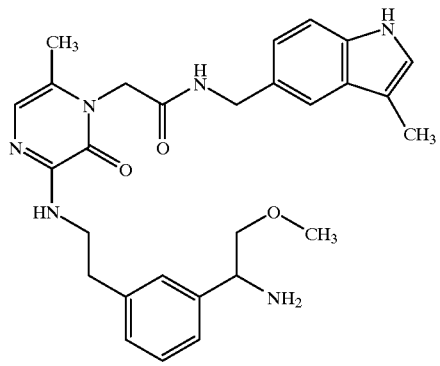

A solution of tert-butyl (1R/S)-2-methoxy-1-[3-(2-{[5-methyl-4-(2-{[(3-methyl-1H-indol-5-yl)methyl]amino}-2-oxoethyl)-3-oxo-3,4-dihydro-2-pyrazinyl]amino}ethyl)phenyl]ethylcarbamate (preparation 124) (26 mg, 0.043 mmol) in hydrochloric acid (2 ml, 6N, 12 mmol) and methanol (2 ml), was stirred under a nitrogen atmosphere for 3 hrs. The reaction mixture was basified to pH 10 using 1N NaOH solution, extracted with dichloromethane (4×10 ml), and ethyl acetate (3×10 ml). The combined organic extracts were dried over MgSO$_4$, and evaporated under reduced pressure to give the title compound as a white solid, (13 mg, 60%). Both R, and S isomers are present although their relative proportions have not been determined.

$^1$H NMR (CD$_3$OD, 300 MHz) δ: 2.13 (s, 3H), 2.26 (s, 3H), 2.90 (t, 2H), 3.35 (s, 3H), 3.41 (m, 1H), 3.49 (m, 1H), 3.58 (m, 2H), 4.06 (m, 1H), 4.45 (s, 2H), 4.74 (s, 2H), 6.64 (s, 1H), 6.98 (s, 1H), 7.02 (d, 1H), 7.18 (m, 2H), 7.24 (m, 3H), 7.42 (s, 1H). LRMS: m/z=503 (M+1)$^+$.

EXAMPLE 29

2-[3-{[2-(2-Aminoethoxy)phenethyl]amino}-6-methyl-2-oxo-1(2H)-pyrazinyl]-N-[(3-methyl-1H-indol-5-yl)methyl]acetamide hydrochloride

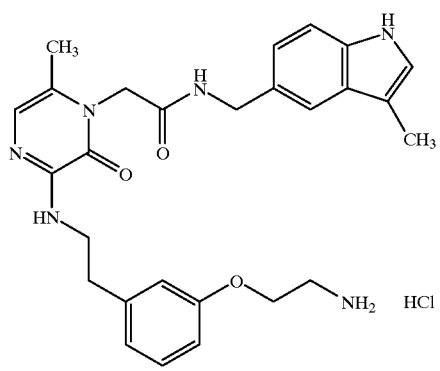

Preparation 126

3-Hydroxyphenyl acetonitrile

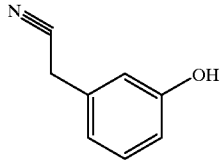

Boron tribromide (68 ml, 1M in dichloromethane, 68 mmol) was added dropwise to an ice-cooled solution of (3-methoxyphenyl)acetonitrile (5.0 g, 34 mmol) in dichloromethane (50 ml), and once addition was complete, the reaction was allowed to warm to room temperature and stirred overnight. The reaction was poured into an ice/water solution, the mixture was basified using NaHCO$_3$ and extracted with dichloromethane. The combined organic extracts were dried over MgSO$_4$ and evaporated under reduced pressure to give the desired product as a brown oil, (4.13 g, 91%).

$^1$H NMR (CDCl$_3$, 300 MHz) δ: 3.72 (s, 3H), 5.99–6.20 (s, br,1H), 6.82 (m, 3H), 7.22 (m, 1H). LRMS: m/z=151 (M+18)$^+$.

Preparation 127 tert-Butyl 2-[2-(cyanomethyl)phenoxy]ethylcarbamate

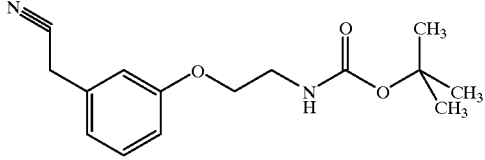

Diethyl azodicarboxylate (6.2 ml, 39.4 mmol) was added dropwise to an ice-cooled solution of 3-hydroxyphenyl acetonitrile (preparation 126) (4.2 g, 31.5 mmol), triphenylphosphine (10.34 g, 39.4 mmol) and tert-butyl 2-hydroxyethylcarbamate (5.4 ml, 34.9 mmol) in tetrahydrofuran (70 ml), and once addition was complete, the reaction was stirred at room temperature overnight. The reaction was diluted with ethyl acetate (400 ml), washed with 1N NaOH solution, water, brine, then dried over MgSO$_4$ and concentrated under reduced pressure. The residue was purified by column chromatography on silica gel using ethyl acetate:pentane (30:70) as eluant to give the desired product as a yellow/green oil, that crystallised on standing, (5.88 g, 68%).

$^1$H NMR (CDCl$_3$, 300 MHz) δ: 1.44 (s, 9H), 3.59 (m, 2H), 3.68 (s, 2H), 4.10 (t, 2H), 5.08 (s, br,1H), 6.86 (d, 1H), 6.98 (m, 1H), 7.34 (m, 2H). LMS: m/z=299 (M+23)$^+$.

Preparation 128 tert-Butyl 2-[2-(aminomethyl)phenoxy]ethylcarbamate

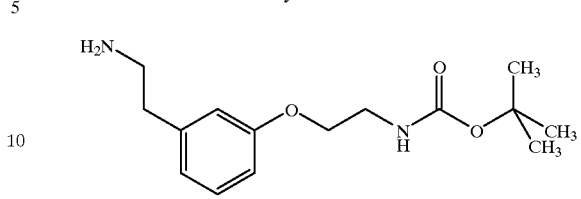

The title compound was obtained as a pale yellow crystalline solid, (51%) from tert-butyl 2-[2-(cyanomethyl)phenoxy]ethylcarbamate (preparation 127), following the procedure described in preparation 105.

$^1$H NMR (CDCl$_3$, 300 MHz) δ: 1.43 (s, 9H), 1.54 (s, br,2H), 2.80 (t, 2H), 2.98 (t, 2H), 3.58 (m, 2H), 4.02 (t, 2H), 5.28 (s, br,1H), 6.81 (d, 1H), 6.92 (m, 1H), 7.18 (m, 2H). LRMS: m/z=281 (M+1)$^+$.

Preparation 129

Benzyl 2-[3-({2-[(tert-butoxycarbonyl)amino]ethoxy})phenethyl]amino}-5-chloro-6-methyl-2-oxo-1(2H)-pyrazinyl]acetate

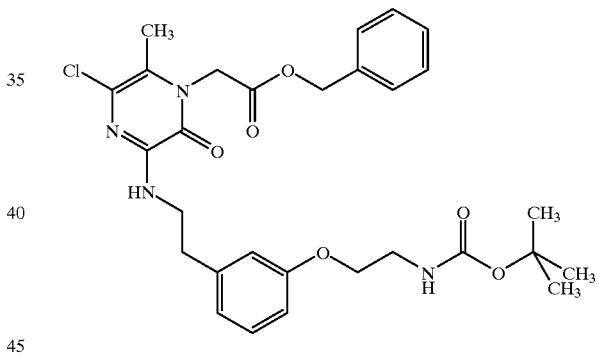

A mixture of benzyl 2-[3,5-dichloro-2-methyl-6-oxo-1(6H)-pyrazinyl]acetate (preparation 17) (300 mg, 0.92 mmol), tert-butyl 2-[2-(aminomethyl)phenoxy]ethylcarbamate (preparation 128), (257 mg, 0.92 mmol) and triethylamine (140 ml, 1.0 mmol) in ethyl acetate (6 ml) was heated under reflux for 18 hrs. The cooled mixture was partitioned between ethyl acetate (80 ml) and hydrochloric acid (2N, 30 ml) and the phases separated. The organic layer was washed consecutively with hydrochloric acid (2N), saturated NaHCO$_3$ solution, brine, then dried over MgSO$_4$, and evaporated under reduced pressure. The crude product was purified by column chromatography on silica gel using ethyl acetate:pentane (50:50) as eluant to give the title compound as an orange foam, (500 mg, 95%).

$^1$H NMR (CDCl$_3$, 300 MHz) δ: 1.40 (s, 9H), 2.20 (s, 3H), 2.98 (t, 2H), 3.60 (m, 4H), 4.10 (t, 2H), 4.80 (s, 2H), 5.21 (s, 2H), 5.68 (s, br,1H), 6.57 (s, br,1H), 6.68–6,88 (m, 2H), 7.18 (m, 2H), 7.37 (m, 5H). LRMS: m/z=571, 573 (M+1)$^+$.

Preparation 130

2-[3-{[3-({2-[(tert-Butoxycarbonyl)amino]ethoxy})phenethyl]amino}-6-methyl-2-oxo-1(2H)-pyrazinyl]acetic acid

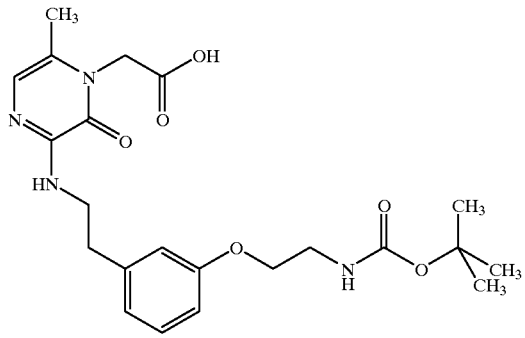

10% Palladium on charcoal (125 mg), followed by ammonium formate (553 mg, 8.77 mmol) were added to a solution of benzyl 2-[3-{[3-({2-[(tert-butoxycarbonyl)amino]ethoxy})phenethyl]amino}-5-chloro-6-methyl-2-oxo-1(2H)-pyrazinyl]acetate (preparation 129) (500 mg, 0.88 mmol) in methanol (10 ml), and the reaction stirred at room temperature overnight. The reaction mixture was filtered through Whatman® fibre, NaOH solution (8.77 ml, 1N, 8.77 mmol) was added to the filtrate, and the solution evaporated under reduced pressure. The residue was triturated with a 10% methanol:dichloromethane solution, the suspension filtered, the filtrate dried over MgSO$_4$ and evaporated under reduced pressure to give the title compound as a white solid, (289 mg, 69%).

$^1$H NMR (d$_6$-DMSO, 300 MHz) δ: 1.37 (s, 9H), 2.01 (s, 3H), 2.80 (t, 2H), 3.35 (t, 2H), 3.41 (t, 2H), 3.94 (t, 2H), 4.19 (s, 2H), 6.55 (s, 1H), 6.80–6.92 (m, 2H), 7.14 (m, 2H).

Preparation 131 tert-Butyl 2-[2-(2-{[5-methyl-4-(2-{[(3-methyl-1H-indol-5-yl)methyl]amino}-2-oxoethyl)-3-oxo-3,4-dihydro-2-pyrazinyl]amino}ethyl)phenoxy]ethylcarbamate

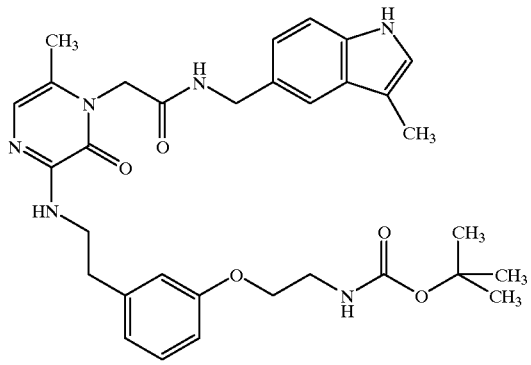

A mixture of 2-[3-{[3-({2-[(tert-Butoxycarbonyl)amino]ethoxy})phenethyl]amino}-6-methyl-2-oxo-1(2H)-pyrazinyl]acetic acid (preperation 130) (268 mg, 0.60 mmol), and (3-Methyl-1H-indol-5-yl)methylamine (preparation 36) (106 mg, 0.66 mmol) was added to a solution of HOBT (122 mg, 0.90 mmol), WSCDI.HCl (144 mg, 0.75 mmol) and N-methylmorpholine (198 ml, 1.8 mmol) in N,N-dimethylformamide (5 ml), and the reaction stirred at room temperature for 20 hrs. The mixture was poured into water (100 ml), with vigorous stirring, and the resulting precipitate filtered off. This solid was washed well with water, triturated with ether and dried under vacuum, to afford the title compound, (315 mg, 89%).

$^1$H NMR (d$_6$-DMSO, 300 MHz) δ: 1.37 (s, 9H), 2.04 (s, 3H), 2.22 (s, 3H), 2.82 (t, 2H), 3.37 (m, 2H), 3.43 (m, 2H), 3.95 (t, br,2H), 4.37 (d, 2H), 4.62 (s, 2H), 6.61 (s, 1H), 6.78 (t, br,1H), 6.83 (m, 1H), 6.90 (d, 1H), 6.98 (d, 1H), 7.04–7.19 (m, 4H), 7.24 (d, 1H), 7.38 (s, 1H), 8.60 (t, br,1H), 10.66 (s, 1H). LRMS: m/z=589 (M+1)$^+$.

Preparation 132

2-[3-{12-(2-Aminoethoxy)phenethyl]amino}-6-methyl-2-oxo-1(2H)-pyrazinyl]-N-[(3-methyl-1H-indol-5-yl)methyl]acetamide hydrochloride

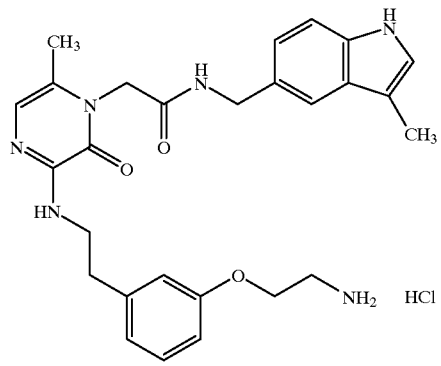

Hydrochloric acid (10 ml, 6N, 60 mmol) was added to a solution of tert-butyl 2-[2-(2-{[5-methyl-4-(2-{[[(3-methyl-1H-indol-5-yl)methyl]amino}-2-oxoethyl)-3-oxo-3,4-dihydro-2-pyrazinyl]amino}ethyl)phenoxy]ethylcarbamate (preparation 131) (315 mg, 0.54 mmol) in methanol (10 ml), and the reaction stirred at room temperature for 1½ hrs. The reaction mixture was basified using NaOH (2N), and the resulting precipitate filtered off. This yellow solid was pre-adsorbed onto silica gel, and purified by column chromatography on silica gel using dichloromethane:methanol:0.88 ammonia (92:7:1) as eluant, to give a cream coloured solid, 169 mg.

This was dissolved in a 10% methanol:dichloromethane solution, hydrochloric acid (1N, 1 equiv) was added, the solution stirred for 5 minutes then evaporated under reduced pressure. The product was triturated with a methanol:ether solution, to give the title compound as a white solid, (153 mg, 54%).

$^1$H NMR (d$_6$-DMSO, 300 MHz) δ: 2.05 (s, 3H), 2.22 (s, 3H), 2.88 (t, 2H), 3.32 (m, 2H), 3.42 (t, 2H), 4.18 (t, 2H), 4.38 (d, 2H), 4.62 (s, 2H), 6.63 (s, 1H), 6.96 (m, 4H), 7.08 (s, 1H), 7.19 (m, 2H), 7.23 (d, 1H), 7.38 (s, 1H), 8.17 (s, br,3H), 8.66 (t, br,1H), 10.70 (s, 1H). LRMS: m/z=489 (M+1)$^+$; Found: C, 59.78; H, 6.47; N, 15.54. C$_{27}$H$_{32}$N$_6$O$_3$;HCl;H$_2$O requires C, 59.71; H, 6.51; N, 15.47%.

EXAMPLE 30

N-[(3-Methyl-1H-indol-5-yl)methyl]-2-[6-methyl-2-oxo-3-({3-[(2R)pyrrolidinylmethoxy]phenethyl}amino)-1(2H)-pyrazinyl]acetamide

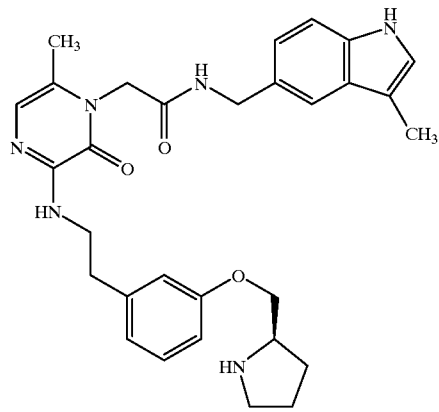

Preparation 133 tert-Butyl (2R)-2-{[3-(cyanomethyl)phenoxy]methyl}-1-pyrrolidinecarboxylate

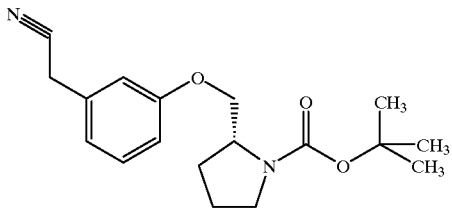

Diethyl azodicarboxylate (3.92 g, 22.5 mmol) was added dropwise to a solution of 3-hydroxyphenyl acetonitrile (3.0 g, 22.5 mmol), triphenylphosphine (5.90 g, 22.5 mmol) and Boc-(R)prolinol (4.53 g, 22.5 mmol) in tetrahydrofuran (30 ml), and the reaction stirred at room temperature for 18 hrs. The mixture was evaporated under reduced pressure and the residue partitioned between dichloromethane and water. The layers were separated, the organic phase washed with water, dried over MgSO$_4$ and concentrated under reduced pressure. The crude product was purified by column chromatography on silica gel using an elution gradient of dichloromethane-:pentane:methanol (80:20 to 100:0:0 to 95:0:5) to give the title compound, (2.69 g, 38%).

$^1$H NMR (d$_6$-DMSO, 300 MHz) δ: 1.39 (s, 9H), 1.77–2.00 (m, 4H), 3.24 (m, 2H), 3.88 (m, 1H), 4.00 (m, 4H), 6.94 (m, 3H), 7.27 (m, 1H). LRMS: m/z=339 (M+23)$^+$.

Preparation 134 tert-Butyl (2R)-2-{[3-(2-aminoethyl)phenoxy]methyl}-1-pyrrolidinecarboxylate

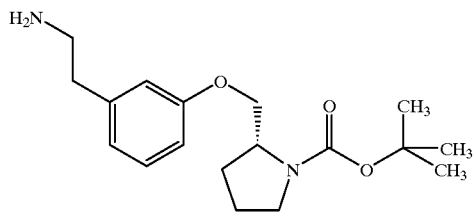

A mixture of tert-butyl (2R)-2-{[3-(cyanomethyl)phenoxy]methyl}-1-pyrrolidinecarboxylate (preparation 133) (2.70 g, 8.54 mmol), and Raney® nickel (400 mg) in saturated ethanolic ammonia solution (100 ml), was hydrogentaed at 60 psi and room temperature for 20 hrs. The reaction mixture was filtered through a glass microfibre filter, and the filtrate evaporated under reduced pressure. The crude product was purified by column chromatography on silica gel using an elution gradient of dichloromethane:methanol:0.88 ammonia (95:5:0.5 to 90:10:1) to afford the title compound, (1.54 g, 56%).

$^1$H NMR (d$_6$-DMSO, 300 MHz) δ: 1.38 (s, 9H), 1.78 (m, 1H), 1.90 (m, 3H), 2.59 (t, 2H), 2.75 (t, 2H), 3.23 (m, 2H), 3.81 (t, 1H), 3.99 (m, 2H), 6.77 (m, 3H), 7.18 (m, 1H). LRMS: m/z=321 (M+1)$^+$.

Preparation 135 tert-Butyl (2R)-2-({3-[2-({4-[2-(benzyloxy)-2-oxoethyl]-6-chloro-5-methyl-3-oxo-3,4-dihydro-2-pyrazinyl}amino)ethyl]phenoxy}methyl)-1-pyrrolidinecarboxylate

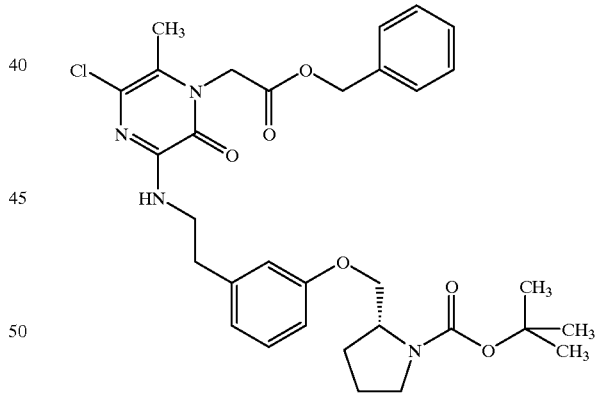

Triethylamine (0.51 ml, 3.67 mmol) was added to a solution of tert-butyl (2R)-2-{[3-(2-aminoethyl)phenoxy]methyl}-1-pyrrolidinecarboxylate (preparation 134) (588 mg, 1.84 mmol) and benzyl 2-[3,5-dichloro-2-methyl-6-oxo-1(6H)-pyrazinyl]acetate (preparation 17) (60 mg, 1.83 mmol) in ethyl acetate (10 ml), and the reaction heated under reflux for 6 hrs. The cooled mixture was partitioned between water and ethyl acetate, and the layers separated. The organic phase was washed with water, then brine, dried over MgSO$_4$ and evaporated under reduced pressure to give the title compound, (1.07 g, 94%).

$^1$H NMR (d$_6$-DMSO, 300 MHz) δ: 1.40 (s, 9H), 1.75–2.20 (m, 6H), 2.81 (t, 2H), 3.26 (m, 5H), 3.45 (m, 2H), 3.82 (m, 1H), 4.88 (s, 2H), 5.20 (s, 2H), 6.80 (m, 3H), 7.18 (m, 1H), 7.38 (m, 5H), 7.48 (m, 1H). LRMS: m/z=612 (M+1)⁺.

Preparation 136

2-[3-[(3-{[(2R)-1-(tert-Butoxycarbonyl)pyrrolidinyl] methoxy}phenethyl)amino]-6-methyl-2-oxo-1(2H)-pyrazinyl]acetic acid

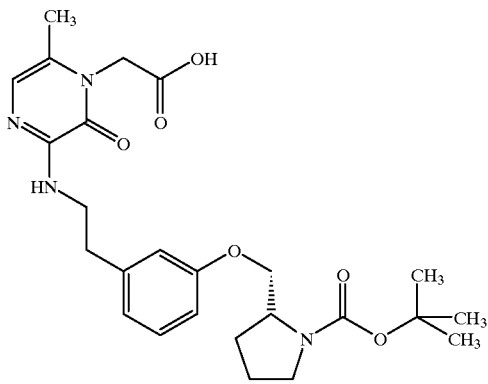

10% Palladium on charcoal (125 mg) and ammonium formate (515 mg, 8.17 mmol) were added to a solution of tert-butyl (2R)-2-({3-[2-({4-[2-(benzyloxy)-2-oxoethyl]-6-chloro-5-methyl-3-oxo-3,4-dihydro-2-pyrazinyl}amino) ethyl]phenoxy}methyl)-1-pyrrolidinecarboxylate (preparation 135) (500 mg, 0.82 mmol) in methanol (10 ml), and the reaction stirred at room temperature under a nitrogen atmosphere for 18 hrs, followed by a further 24 hrs, at 50° C. The cooled mixture was filtered through Whatman® fibre, and NaOH (327 mg, 8.17 mmol) in water was added to the filtrate. This solution was evaporated under reduced pressure and the residue purified by column chromatography on silica gel using an elution gradient of dichloromethane:methanol:0.88 ammonia (90:10:1 to 85:15:2) to provide the desired product, (67 mg, 11%).

¹H NMR (d₆-DMSO, 400 MHz) δ: 1.38 (s, 9H), 1.78 (m, 1H), 1.91 (m, 3H), 2.01 (s, 2H), 2.80 (t, 2H), 3.33 (s, br,3H), 3.43 (m, 2H), 3.82 (m, 1H), 4.00 (m, 2H), 4,38 (s, 2H), 6.58 (s, 1H), 6.63 (m, 1H), 6.78 (m, 3H), 7.18 (m, 1H). LRMS: m/z=487 (M+1)⁺.

Preparation 137 tert-Butyl (2R)-2-{[3-(2-{[5-methyl-4-(2-{[(3-methyl-1H-indol-5-yl)methyl-amino}-2-]oxoethyl)-3-oxo-3,4-dihydro-2-pyrazinyl]amino}ethyl) phenoxy]methyl}-1-pyrrolidinecarboxylate

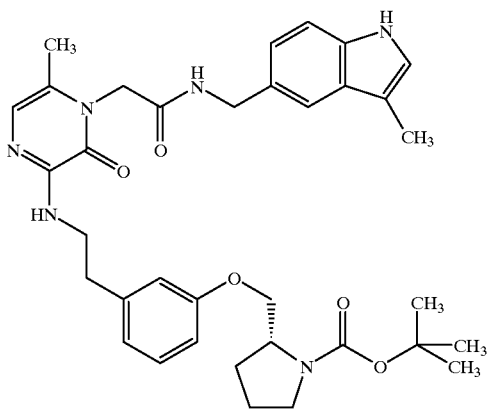

A mixture of 2-[3-[(3{[(2R)-1-(tert-butoxycarbonyl) pyrrolidinyl]methoxy}phenethyl)amino]-6-methyl-2-oxo-1 (2H)-pyrazinyl]acetic acid (preparation 136) (65 mg, 0.13 mmol), (3-methyl-1H-indol-5-yl)methylamine (preparation 36) (25 mg, 0.16 mmol), HOBT (20 mg, 0.15 mmol), WSCDI.HCl (31 mg, 0.16 mmol) and N-methylmorpholine (40 mg, 0.40 mmol) in N,N-dimethylformamide (2.5 ml), was stirred at room temperature for 20 hrs. The reaction mixture was partitioned between ethyl acetate and water and the phases separated. The organic layer was washed with water, brine, then dried over MgSO₄ and evaporated under reduced pressure to give the title compound, (84 mg, 100%).

¹H NMR (d₆-DMSO, 400 MHz) δ: 1.38 (s, 9H), 1.78 (m, 1H), 1.90 (m, 3H), 2.02 (s, 3H), 2.20 (s, 3H), 2.80 (t, 2H), 3.25 (m, 2H), 3.45 (m, 2H), 3.82 (m, 1H), 4.00 (m, 2H), 4.38 (d, 2H), 4.60 (s, 2H), 6.61 (s, 1H), 6.78 (m, 3H), 6.98 (d,1H), 7.05 (s, 1H), 7.18 (m, 1H), 7.24 (d, 1H), 7.36 (s, 1H), 7.96 (s, 1H), 8.60 (m, 1H), 10.64 (s, 1H). LRMS: m/z=629 (M+1)⁺.

Preparation 138

N-[(3-Methyl-1H-indol-5-yl)methyl]-2-[6-methyl-2-oxo-3-({3-[(2R)pyrrolidinylmethoxy] phenethyl}amino)-1(2H)-pyrazinyl]acetamide

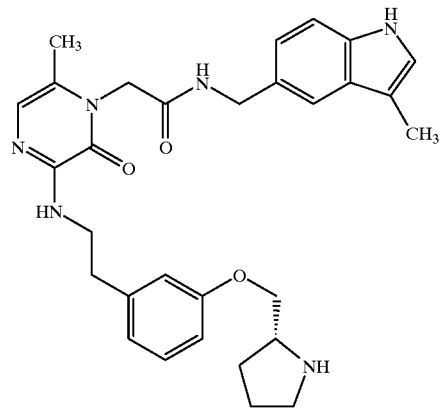

Hydrochloric acid (4 ml, 6N, 24 mmol) was added dropwise to a solution of tert-butyl (2R)-2-{[3-(2-{[5-methyl-4-(2-{[(3-methyl-1H-indol-5-yl)methyl]amino}-2-oxoethyl)-3-oxo-3,4-dihydro-2-pyrazinyl]amino}ethyl) phenoxy]methyl}-1-pyrrolidinecarboxylate (preparation 137) (84 mg, 0.13 mmol) in methanol (4 ml), and the reaction stirred at room temperature for 2½ hrs. The reaction mixture was basified to pH 9 using NaOH solution, and the resulting precipitate filtered off. This solid was purified by column chromatography on silica gel using dichloromethane:methanol:0.88 ammonia (90:10:0.5) as eluant to afford the title compound, (30 mg, 41%).

¹H NMR (d₆-DMSO, 300 MHz) δ: 1.44 (m, 1H), 1.66 (m, 2H), 1.83 (m, 1H), 2.05 (s, 3H), 2.22 (s, 3H), 2.80 (m, 4H), 3.39 (m, 1H), 3.46 (m, 2H), 3.80 (d, 2H), 4.38 (d, 2H), 4.60 (s, 2H), 6.62 (s, 1H), 6.97 (m, 4H), 6.98 (d, 1H), 7.05 (s, 1H), 7.18 (m, 1H), 7.25 (d, 1H), 7.37 (s, 1H), 8.60 (m, 1H), 10.66 (s, 1H). LRMS: m/z=529 (M+1)⁺.

EXAMPLE 31

N-(1H-Indol-5-ylmethyl)-2-[3-({[(2R)-1-isobutylpyrrolidinyl]methyl}amino)-6-methyl-2-oxo-1(2H)-pyrazinyl]acetamide

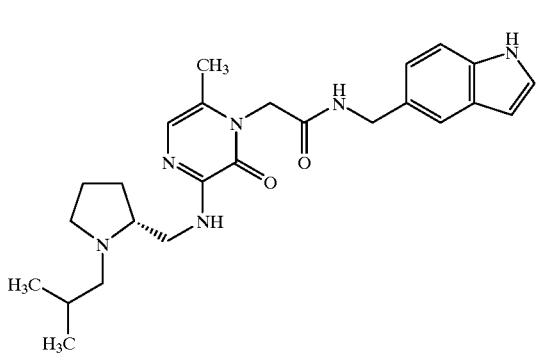

Preparation 139

N-(1H-Indol-5-ylmethyl)-2-[3-({[(2R)-1-isobutylpyrrolidinyl]methyl}amino)-6-methyl-2-oxo-1(2H)-pyrazinyl]acetamide

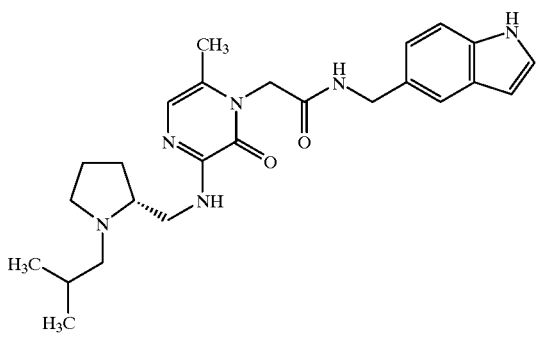

HOBT (24 mg, 0.18 mmol), WSCDI.HCl (29 mg, 0.15 mmol), N-methylmorpholine (39 ml, 0.36 mmol) and 1H-indol-5-ylmethylamine (preparation 8) (19 mg, 0.13 mmol) were added to a solution of 2-[3-({[(2R)-1-isobutylpyrrolidinyl]methyl}amino)-6-methyl-2-oxo-1(2H)-pyrazinyl]acetic acid (preparation 62) (38 mg, 0.12 mmol) in N,N-dimethylformamide (2 ml), and the reaction was stirred at room temperature overnight. The mixture was evaporated under reduced pressure and the residue purified by column chromatography on silica gel using dichloromethane:methanol:0.88 ammonia (95:5:0.5) as eluant. The product was re-purified using a Biotage™ (KP-Sil™ 60 Å silica gel) cartridge and dichloromethane:methanol:0.88 ammonia (95:5:0.5) as eluant to afford the title compound, (16 mg, 30%).

$^1$H NMR (CDCl$_3$, 400 MHz) δ: 0.83 (d, 3H), 0.90 (d, 3H), 1.56–1.78 (m, 5H), 1.82 (m, 1H), 2.07 (m, 2H), 2.24 (s, 3H), 2.60 (m, 1H), 3.16 (m, 1H), 3.21 (m, 1H), 3.52 (m, 1H), 4.50 (d, 2H), 4.63 (s, 2H), 6.42 (m, 1H), 6.50 (s, 1H), 6.63 (s, br,1H), 6.70 (s, 1H), 7.05 (d, 1H), 7.20 (m, 1H), 7.34 (d, 1H), 7.49 (s, 1H), 8.20 (s, br,1H). LRMS: m/z=450 (M)$^+$.

EXAMPLE 32

2-[3-({[(2R)-1-(Cyclopropylmethyl)pyrrolidinyl]methyl}amino)-6-methyl-2-oxo-1(2H)-pyrazinyl]-N-(1H-indol-5-ylmethyl)acetamide

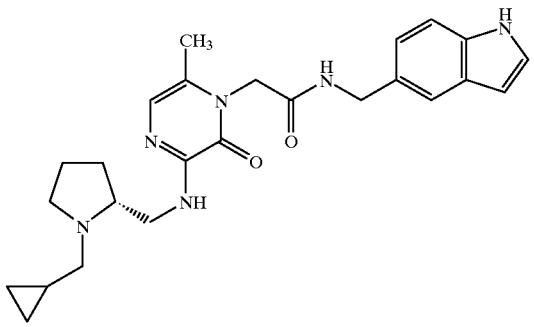

Preparation 140

2-[3-({[(2R)-1-(Cyclopropylmethyl)pyrrolidinyl]methyl}amino)-6-methyl-2-oxo-1(2H)-pyrazinyl]-N-(1H-indol-5-ylmethyl)acetamide

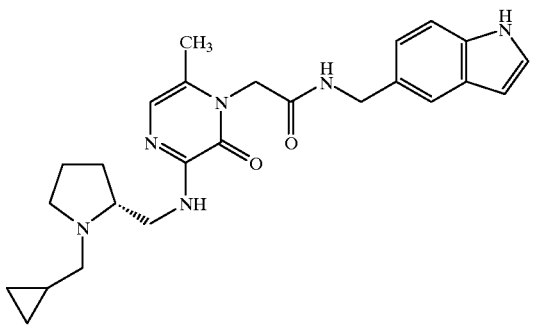

The title compound was obtained as a partially crystallised oil (32%), from 2-[3-({[(2R)-1-(cyclopropylmethyl)pyrrolidinyl]methyl}amino)-6-methyl-2-oxo-1(2H)-pyrazinyl]acetic acid (preparation 48) and 1H-indol-5-ylmethylamine (preparation 8), using the procedure described in preparation 45.

$^1$H NMR (CD$_3$OD, 300 MHz) δ: 0.17 (m, 2H), 0.50 (m, 2H), 0.94 (m, 1H), 1.62 (m, 1H), 1.78 (m, 2H), 1.94 (m, 1H), 2.08 (m, 4H), 2.32 (m, 1H), 2.75 (m, 2H), 3.28 (m, 2H), 3.57 (m, 1H), 4.44 (s, 2H), 4.70 (s, 2H), 6.40 (d, 1H), 6.62 (s, 1H), 7.03 (d, 1H), 7.20 (d, 1H), 7.34 (d, 1H), 7.46 (s, 1H).

EXAMPLE 33

2-[3-({[(2R)-1-(Cyclopentyl)pyrrolidinyl]methyl}amino)-6-methyl-2-oxo-1(2H)-pyrazinyl]-N-(1H-indol-5-ylmethyl)acetamide

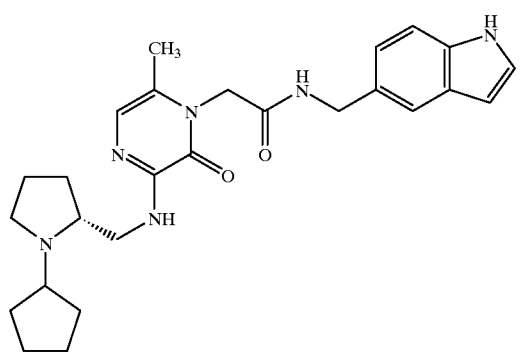

Preparation 142

(2R)-1-Cyclopentyl-2-pyrrolidinecarboxamide

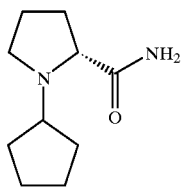

Cyclopentanone (388 ml, 4.38 mmol), acetic acid (251 ml, 4.38 mmol) and sodium triacetoxyborohydride (1.4 g, 6.6 mmol) were added consecutively to a solution of (2R) pyrrolidinecarboxamide (500 mg, 4.38 mmol) in dichloromethane (10 ml), and the solution stirred at room temperature for 4 hrs. Saturated NaHCO$_3$ solution (100 ml), was added and the mixture extracted with ethyl acetate. The combined organic extracts were washed with water, brine, then dried over MgSO$_4$ and concentrated under reduced pressure. The residue was triturated with ether, to afford the title compound as a white solid, (320 mg, 40%).

$^1$H NMR (CDCl$_3$, 400 MHz) d: 1.39–1.81 (m, 10H),1.95 (m, 1H), 2.10 (m, 1H), 2.42 (m, 1H), 2.86 (t, 1H), 3.17 (m, 2H), 5.36 (s, br,1H), 7.38 (s, br,1H). LRMS: mlz=183 (M+1)$^+$.

Preparation 143

[(2R)-1-Cyclopentyl pyrrolidinyl]methylamine

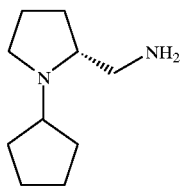

Lithium aluminum hydride (2.63 ml, 1M in tetrahydrofuran, 2.63 mmol) was added dropwise to a solution of (2R)-1-cyclopentyl-2-pyrrolidinecarboxamide (preparation 142) (320 mg, 1.76 mmol) in tetrahydrofuran (5 ml), and once addition was complete, the reaction was stirred at room temperature for 4 hrs. Water was added to quench the reaction, the mixture diluted with ethyl acetate and dried over MgSO$_4$ This mixture was filtered through Whatman® fibre, and the filtrate evaporated under reduced pressure. The residue was purified by chromatography using a Biotage™ (KP-Sil™ 60 Å silica gel) cartridge and an elution gradient of dichloromethane:methanol:0.88 ammonia (95:5:0.5 to 90:10:1) to give the desired product as a clear oil, (208 mg, 71%).

$^1$H NMR (CDCl$_3$, 400 MHz) δ: 1.19 (s, br,2H), 1.40–1.94 (m, 12H), 2.44 (dd, 1H), 2.57–2.77 (m, 3H), 2.88 (m, 1H), 3.00 (m, 1H). LRMS: m/z=169 (M+1)$^+$.

Preparation 144

Benzyl 2-[3-chloro-5-({[(2R)-1-cyclopentylpyrrolidinyl]methyl}amino)-2-methyl-6-oxo-1(6H)-pyrazinyl]acetate

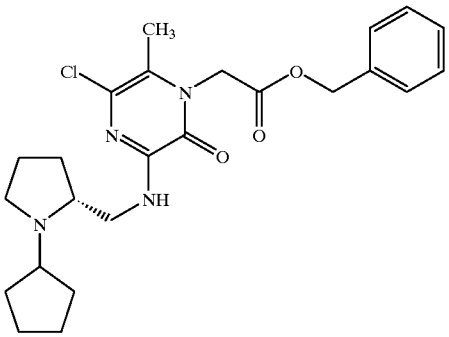

Benzyl 2-[3,5-dichloro-2-methyl-6-oxo-1(6H)-pyrazinyl] acetate (preparation 17) (404 mg, 1.23 mmol) was added to a solution of [(2R)-1-cyclopentylpyrrolidinyl]methylamine (preparation 143) (208 mg, 1.23 mmol) in ethyl acetate (10 ml), followed by triethylamine (190 ml, 1.36 mmol), and the reaction heated under reflux overnight under a nitrogen atmosphere. The cooled mixture was diluted with ethyl acetate, washed with water, brine, then dried over MgSO$_4$ and concentrated under reduced pressure. The crude product was purified by chromatography using a Biotage™ (KP-Sil™ 60 Å silica gel) cartridge and an elution gradient of dichloromethane:methanol:0.88 ammonia (100:0:0 to 95:5:0.5) to give the desired product as a cream solid, (450 mg, 80%).

$^1$H NMR (CDCl$_3$, 400 MHz) δ: 1.42–1.59 (m, 10H), 1.86 (m, 2H), 2.20 (s, 3H), 2.47 (m 1H), 2.90 (m, 1H), 2.98 (m, 1H), 3.04 (m, 1H), 3.22 (m, 1H), 3.54 (m, 1H), 4.80 (s, 2H), 5.21 (s, 2H), 6.58 (s, br,1H), 7.37 (m, 5H). LRMS: m/z=458, 460 (M+1)$^+$.

Preparation 145

2-[3-({[(2R)-1-Cyclopentylpyrrolidinyl] methyl}amino)-6-methyl-2-oxo-1(2H)-pyrazinyl] acetic acid hydrochloride

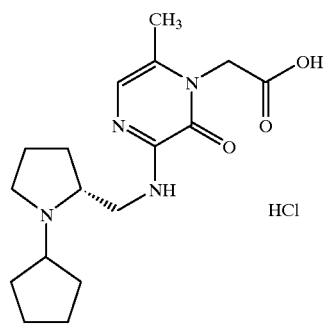

A mixture of benzyl 2-[3-({[(2R)-1-cyclopentylpyrrolidinyl]methyl}amino)-6-methyl-2-oxo-1 (2H)-pyrazinyl]acetate (preparation 144) (450 mg, 0.98 mmol), and palladium hydroxide (200 mg) in methanol was hydrogenated at 60 psi and room temperature overnight. The mixture was filtered through Whatman® fibre, and the filtrate concentrated under reduced pressure. The residue was azeotroped with dichloromethane several times to give the title compound as a green foam, (370 mg, 100%).

$^1$H NMR (d$_6$-DMSO, 400 MHz) δ: 1.50 (m, 2H), 1.69 (m, 4H), 1.82 (m, 2H), 1.96 (m, 4H), 2.06 (s, 3H), 3.08 (m, 1H), 3.20–3.62 (m, 4H), 3.78 (m, 1H), 4.62 (s, 2H), 6.63 (s, 1H), 7.36 (s, br, 1H). LRMS: m/z=335 (M+1)$^+$.

Preparation 146

2-[3-({[(2R)-1-Cyclopentylpyrrolidinyl]methyl}amino)-6-methyl-2-oxo-1(2H)-pyrazinyl]-N-(1H-indol-5-ylmethyl)acetamide

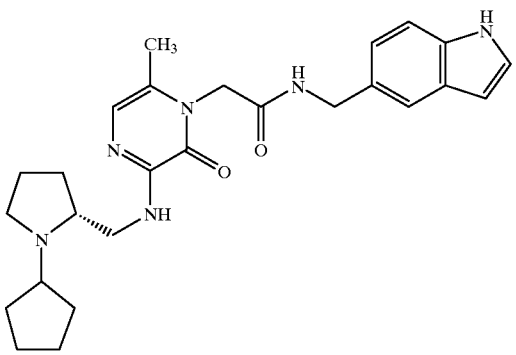

The title compound was prepared from 2-[3-({[(2R)-1-cyclopentylpyrrolidinyl]methyl}amino)6-methyl-2-oxo-1(2H)-pyrazinyl]acetic acid hydrochloride (preparation 145) and 1H-indol-5-ylmethylamine (preparation 8), following the procedure described in preparation 45. The crude product was purified by chromatography using a Biotage™ (KP-Sil™ 60 Å silica gel) cartridge and dichloromethane:methanol:0.88 ammonia (95:5:0.5) as eluant. The product was further purified using preparative tlc and dichloromethane:methanol:0.88 ammonia (90:10:1) as eluant to afford the title compound, (11 mg, 16%).

$^1$H NMR (CD$_3$OD, 400 MHz) δ: 1.50–1.62 (m, 4H), 1.65–1.82 (m, 5H), 1.83–2.00 (m, 3H), 2.18 (s, 3H), 2.60 (m, 1H), 3.00–3.17 (m, 3H), 3.26 (m, 1H), 3.57 (m, 1H), 4.50 (s, 2H), 4.78 (s, 2H), 6.43 (d, 1H), 6.70 (s, 1H), 7.10 (d, 1H), 7.24 (d, 1H), 7.38 (d, 1H), 7.54 (s, 1H). LRMS: m/z=463 (M+1)$^+$.

EXAMPLE 34

2-[3-({[(2R)-1-(Cyclohexyl)pyrrolidinyl]methyl}amino)-6-methyl-2-oxo-1(2H)-pyrazinyl]-N-(1H-indol-5-ylmethyl)acetamide

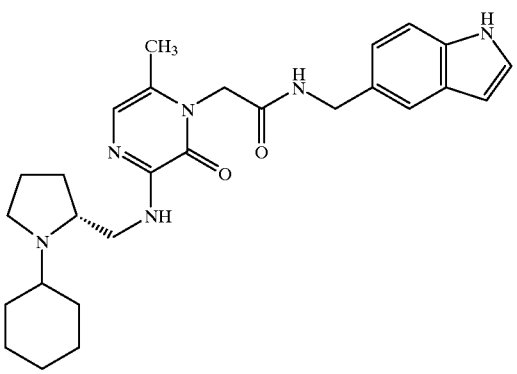

Preparation 147

(2R)-1-Cyclohexyl-2-pyrrolidinecarboxamide

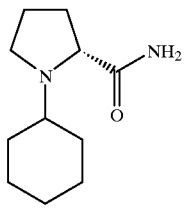

The title compound was obtained as a white solid (55%) from cyclohexanone and (2R)-pyrrolidinecarboxamide, following the procedure described in preparation 142.

$^1$H NMR (CDCl$_3$, 400 MHz) δ: 1.02–1.25 (m, 6H), 1.77 (m, 5H), 1.92 (m, 2H), 2.02 (m, 1H), 2.36 (m, 1H), 2.50 (m, 1H), 3.08 (t, 1H), 3.24 (dd, 1H), 5.38 (s, br, 1H), 7.39 (s, br, 1H).

Preparation 148

[(2R)-1-Cyclohexylpyrrolidinyl]methylamine

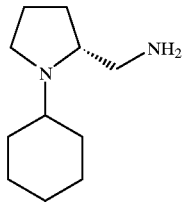

Lithium aluminum hydride (7.3 ml, 1M in tetrahydrofuran, 7.3 mmol) was added dropwise to a solution of (2R)-1-cyclohexyl-2-pyrrolidinecarboxamide (preparation 147) (950 mg, 4.85 mmol) in tetrahydrofuran (15 ml) and once addition was complete, the reaction was heated under reflux for 20 hrs. The cooled mixture was carefully quenched with water, and extracted with ethyl acetate. The combined organic extracts were then dried over MgSO$_4$ and evaporated under reduced pressure. The residue was suspended in dichloromethane, filtered through Whatman® fibre and the filtrate evaporated under reduced pressure to give the desired product as an oil (849 mg, 96%).

$^1$H NMR (CDCl$_3$, 400 MHz) δ: 1.03–1.54 (m, 8H), 1.54–1.90 (m, 8H), 2.40 (m, 1H), 2.45–2.63 (m, 3H), 2.79 (m, 1H), 2.94 (m, 1H). LRMS: m/z 183 (M+1)$^+$.

Preparation 149

Benzyl 2-[3-chloro-5-({[(2R)-1-cyclohexylpyrrolidinyl]methyl}amino)-2-methyl-6-oxo-1(6H)-pyrazinyl]acetate

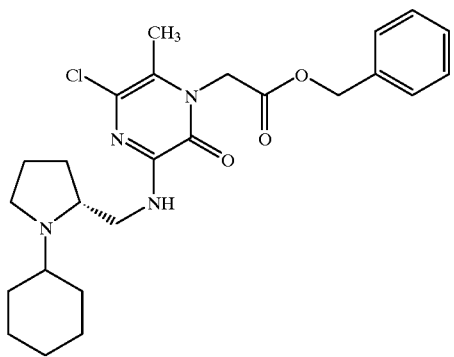

The title compound was obtained as a pale brown solid (60%), from [(2R)-1-cyclohexylpyrrolidinyl]methylamine (preparation 148) and benzyl 2-[3,5-dichloro- 2-methyl-6-oxo-1(6H)-pyrazinyl]acetate (preparation 17), following the procedure described in preparation 144.

$^1$H NMR (CDCl$_3$, 400 MHz) δ: 1.07–1.34 (m, 6H), 1.58–1.83 (m, 7H), 1.92 (m, 1H), 2.20 (s, 3H), 2.43 (m, 1H), 2.58 (m, 1H), 2.98 (m, 1H), 3.16 (m, 2H), 3.48 (m, 1H), 4.80 (s, 2H), 5.21 (s, 2H), 6.58 (s, br,1H), 7.38 (m, 5H). LRMS: mz=473, 475 (M+1)$^+$.

Preparation 150

2-[3-({[(2R)-1-Cyclohexylpyrrolidinyl]methyl}amino)-6-methyl-2-oxo-1(2H)-pyrazinyl]acetic acid hydrochloride

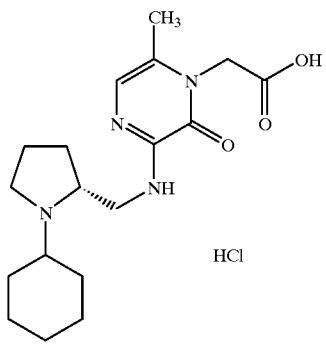

HCl

The title compound was obtained (100%) from benzyl 2-[3-chloro-5-({[(2R)-1-cyclohexylpyrrolidinyl]methyl}amino)-2-methyl-6-oxo-1(6H)-pyrazinyl]acetate (preparation 149) following a similar procedure to that described in preparation 145.

$^1$H NMR (d$_6$-DMSO, 400 MHz) δ: 1.01–1.29 (m, 4H), 1.38 (m, 2H), 1.58 (m, 1H), 1.75–2.17 (m, 8H), 3.04–3.39 (m, 5H), 3.58 (m, 2H), 3.83 (m, 1H), 4.62 (s, 2H), 6.62 (s, 1H), 7.38 (s, br,1H).

Preparation 151

2-[3-({[(2R)-1-(Cyclohexyl)pyrrolidinyl]methyl}amino)-6-methyl-2-oxo-1(2H)-pyrazinyl]-N-(1H-indol-5-ylmethyl)acetamide

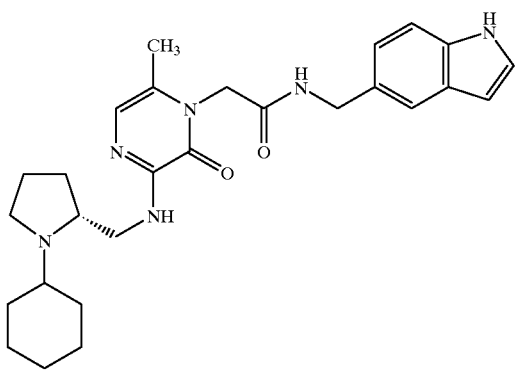

The title compound was obtained as a white powder after trituration with ether (40%), from 2-[3-({[(2R)-1-cyclohexylpyrrolidinyl]methyl}amino)-6-methyl-2-oxo-1 (2H)-pyrazinyl]acetic acid hydrochloride (preparation 150) and 1H-indol-5-ylmethylamine (preparation 8), following a similar procedure to that described in preparation 139.

$^1$H NMR (CD$_3$OD, 400 MHz) δ: 1.12–1.34 (m, 5H), 1.60–1.82 (m, 7H), 1.92 (m, 1H), 1.98 (m, 1H), 2.14 (s, 3H), 2.52 (m, 1H), 2.61 (m, 1H), 2.98 (m, 1H), 3.20 (m, 2H), 3.42 (m, 1H), 4.44 (s, 2H), 4.75 (s, 2H), 6.40 (d, 1H), 6.64 (s, 1H), 7.04 (d, 1H), 7.20 (d, 1H), 7.34 (d, 1H), 7.48 (s, 1H). LRMS: m/z=476 (M+1)$^+$.

EXAMPLE 35

2-[3-({[1-({(2R)-1-Methylcyclopropyl}methyl)pyrrolidinyl]methyl}amino)-6-methyl-2-oxo-1(2H)-pyrazinyl]-N-(1H-indol-5-ylmethyl)acetamide

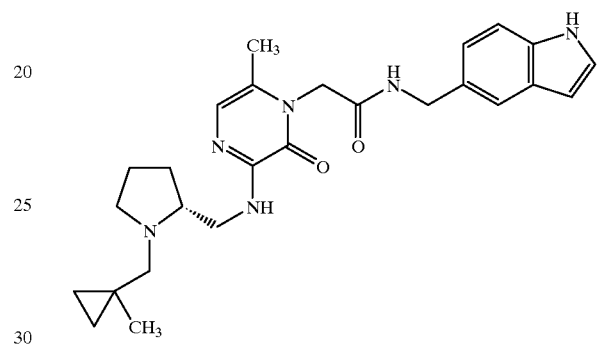

Preparation 152

(2R)-1-[(1-Methylcyclopropyl)methyl]-2-pyrrolidinecarboxamide

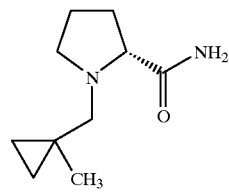

(2R)-Pyrrolidinecarboxamide (1.0 g, 8.73 mmol) was added to a solution of 1-methylcyclopropanecarbaldehyde (preparation 58) (412 ml, 0.04M, 17.6 mmol in dichloromethane) and the solution stirred at room temperature for 30 mins. Acetic acid (502 ml, 8.73 mmol) followed by sodium triacetoxyborohydride (2.8 g, 13.2 mmol) were added and the reaction stirred at room temperature overnight. The mixture was concentrated under reduced pressure to a volume of 200 ml, then basified using saturated NaHCO$_3$ solution, and the phases separated. The organic layer was dried over MgSO$_4$ and evaporated under reduced pressure. The crude product was purified by chromatography using a Biotage™ (KP-Sil™ 60 Å silica gel) cartridge with dichloromethane:methanol:0.88 ammonia (95:5:0.5) as eluant to give the desired product, (771 mg, 48%).

$^1$H NMR (CDCl$_3$, 300 MHz) δ: 0.22 (m, 2H), 0.36 (m, 2H), 1.13 (s, 3H), 1.72–1.97 (m, 4H), 2.07–2.28 (m, 2H), 2.98 (m, 2H), 3.31 (m, 1H), 5.38 (s, br,1H), 7.24 (s, br,1H), LRMS: m/z=182 (M)$^+$.

Preparation 153

{(2R)-1-[(1-Methylcyclopropyl)methyl]pyrrolidinyl}methylamine

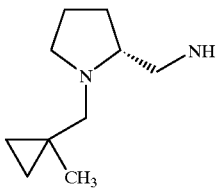

The title compound was obtained as an oil (72%) from (2R)-1-[(1-methylcyclopropyl)methyl]-2-pyrrolidinecarboxamide (preparation 152) following the procedure described in preparation 148.

$^1$H NMR (CDCl$_3$, 400 MHz) δ: 0.19 (m, 2H), 0.32 (m, 2H), 1.06 (s, 3H), 1.26 (s, br,2H), 1.52 (d, 1H), 1.56–1.82 (m, 4H), 2.05 (dd, 1H), 2.34 (m, 1H), 2.60 (d,$_1$ H), 2.76 (dd, 1H), 2.97 (d, 1H), 3.23 (m, 1H). LRMS: m/z=168 (M)$^+$.

Preparation 154

Benzyl 2-[3chloro-2-methyl-5-[({(2R)-1-[(1-methylcyclopropyl)methyl]-2-pyrrolidinyl}methyl)amino]-6-oxo-1(6H) pyrazinyl]acetate

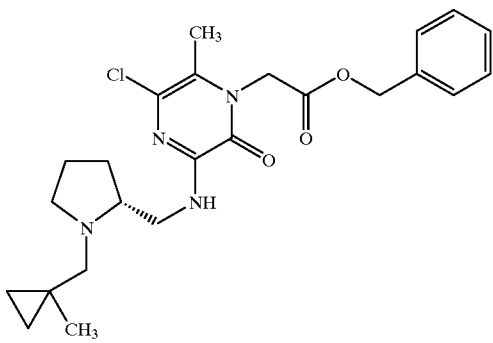

The title compound was obtained as a yellow oil (81%), from {(2R)-1-[(1-methylcyclopropyl)methyl]-2-pyrrolidinyl}methylamine (preparation 153) and benzyl 2-[3,5-dichloro-2-methyl-6-oxo-1(6H)-pyrazinyl]acetate (preparation 17), following a similar procedure to that described in preparation 144.

$^1$H NMR (CDCl$_3$, 300 MHz) δ: 0.20 (m, 2H), 0.34 (m, 2H), 1.11 (s, 3H), 1.56–1.90 (m, 5H), 2.11 (m, 1H), 2.20 (s, 3H), 2.61 (m, 1H), 3.00 (d, 1H), 3.30 (m, 2H), 3.60 (m, 1H), 4.80 (s, 2H), 5.20 (s, 2H), 6.75 (m, 1H), 7.38 (m, 5H). LRMS: m/z=459, 461 (M+1)$^+$.

Preparation 155

2-[2-Methyl-5-[({(2R)-1-[(1-methylcyclopropyl)methyl]-2-pyrrolidinyl}methyl)amino]-6-oxo-1(6H)-pyrazinyl]acetic acid hydrochloride

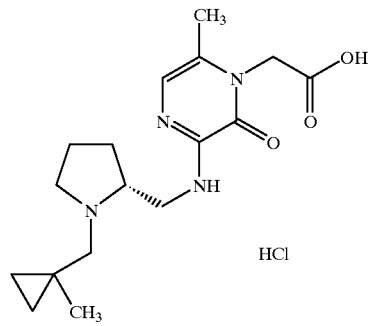

The title compound was obtained as a yellow oil (100%) from benzyl 2-[3-chloro-2-methyl-5-[({(2R)-1-[(1-methylcyclopropyl)methyl]-2-pyrrolidinyl}methyl)amino]-6-oxo-1(6H)-pyrazinyl]acetate (preparation 154), following the procedure described in preparation 145.

$^1$H NMR (d$_6$-DMSO, 400 MHz) δ: 0.39 (m, 2H), 0 50 (m, 1H), 0.59 (m, 1H), 1.18 (s, 3H), 1.70–1.97 (m, 3H), 2.02 (m, 4H), 2.78 (m, 1H), 3.05 (m, 1H), 3.20–3.65 (m, 5H), 4.65 (s, 2H), 6.62 (s, 1H), 7.40 (s, br,1H). LRMS: m/z=335 (M+1)$^+$.

Preparation 156

N-(1H-Indol-5-ylmethyl)-2-[6-methyl-3-[({(2R)-1-[(1-methylcyclopropyl)methyl]-2-pyrrolidinyl}methyl)amino]-2-oxo-1(2H)-pyrazinyl]acetamide

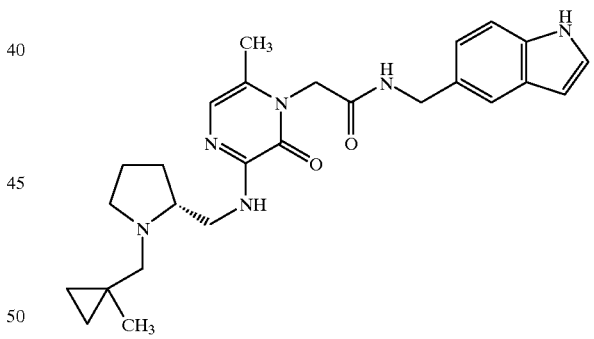

The title compound was prepared from 2-[2-methyl-5-[({(2R)-1-[(1-methylcyclopropyl)methyl]-2-pyrrolidinyl}methyl)amino]-6-oxo-1(6H)-pyrazinyl]acetic acid hydrochloride (preparation 155) using the method described in preparation 139. The product was further purified by column chromatography on silica gel using hexane:i-propanol:0.88 ammonia (75:25:2) as eluant to afford the title compound as a white foam, (99 mg, 48%).

$^1$H NMR (CDCl$_3$, 400 MHz) δ: 0.18 (m, 2H), 0.30 (m, 2H), 1.02 (s, 3H), 1.50–1.84 (m, 5H), 2.08 (m, 1H), 2.20 (s, 3H), 2.60 (s, br,1H), 2.99 (d, 1H), 3.28 (m, 2H), 3.54 (m, 1H), 4.52 (d, 2H), 4.62 (s, 2H), 6.45 (m, 2H), 6.61 (s, br,1H), 6.70 (s, 1H), 7.04 (d, 1H), 7.20 (s, 1H), 7.34 (d, 1H), 7.48 (s, 1H), 8.18 (s, br,1H). LRMS: m/z 463 (M+1)$^+$.

EXAMPLE 36

N-(1H-Indol-5-ylmethyl)-2-[6-methyl-2-oxo-3-({[(2R)-1-tetrahydro-2H-pyran-4-2-pyrrolidinyl]methyl}amino)-1(2H)-pyrazinyl]acetamide

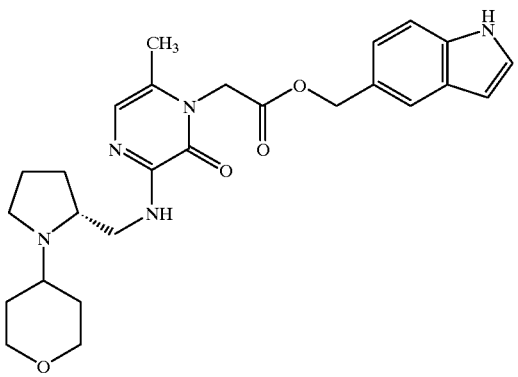

Preparation 157

[(2R)-1-Tetrahydro-2H-pyran-4-yl-2-pyrrolidinyl]methylamine

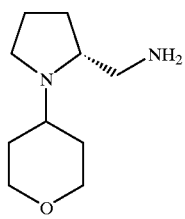

Tetrahydro-4H-pyran-4-one (291 ml, 3.15 mmol) and acetic acid (181 ml, 3.15 mmol) were added to a slurry of (2R)-pyrrolidinecarboxamide (360 mg, 3.15 mmol) in tetrahydrofuran (8 ml), followed by sodium triacetoxyborohydride (1.0 g, 4.73 mmol), and the reaction stirred at room temperature overnight. Water was added, the mixture extracted with ethyl acetate, and the combined organic extracts evaporated under reduced pressure. The residue was purified by column chromatography on silica gel using dichloromethane:methanol (95:5) as eluant to give a white solid. Lithium aluminum hydride (5 ml, 1M in tetrahydrofuran 5.0 mmol) was added to a solution of the intermediate amide in tetrahydrofuran (8 ml), and the reaction heated under reflux overnight. The cooled reaction was quenched with water (1.5 ml), dried over MgSO$_4$, filtered, and the filter pad washed well with ethyl acetate. The combined filtrates were evaporated under reduced pressure to give the title compound as an oil, (460 mg, 79%).

$^1$H NMR (CDCl$_3$, 400 MHz) δ: 1.39–1.84 (m, 9H), 2.50–2.73 (m, 3H), 2.81 (m, 1H), 2.98 (m, 1H), 3.38 (m, 2H), 4.00 (m, 2H). LRMS: m/z=185 (M+1)$^+$.

Preparation 158

Benzyl 2-[3-chloro-2-methyl-6-oxo-5-({[(2R)-1-tetrahydro-2H-pyran-4-yl-2-pyrrolidinyl]methyl}amino)-1(6H)-pyrazinyl]acetate

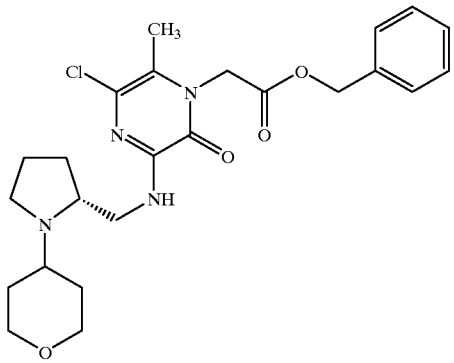

A mixture of [(2R)-1-tetrahydro-2H-pyran-4-yl-2-pyrrolidinyl]methylamine (preparation 157) (460 mg, 2.50 mmol), benzyl 2-[3,5-dichloro-2-methyl-6-oxo-1(6H)-pyrazinyl]acetate (preparation 17), and triethylamine (870 ml, 6.24 mmol) in ethyl acetate (8 ml) was heated under reflux for 18 hrs, then cooled. Water (1.5 ml) was added, the reaction mixture dried over MgSO$_4$, and filtered through celite, washing the filter pad well with ethyl acetate. The combined filtrates were concentrated under reduced pressure and the residue purified by column chromatography on silica gel using hexane:ethyl acetate (50:50) as eluant to give the desired product as a white solid, (970 mg, 82%).

$^1$H NMR (CDCl$_3$, 400 MHz) δ: 1.55–1.94 (m, 8H), 2.20 (s, 3H), 2.58(m, 1H), 2.71 (m, 1H), 3.00 (m, 1H), 3.16 (m, 2H), 3.38 (m, 2H), 3.52 (m, 1H), 4.00 (m, 2H), 4.80 (s, 2H), 5.20 (s, 2H), 6.48 (s, 1H), 7.37 (m, 5H). LRMS: m/z=475 (M+1)$^+$.

Preparation 159

2-[6-Methyl-2-oxo-3-({[(2R)-1-tetrahydro-2H-pyran-4-yl-2-pyrrolidinyl]methyl}amino)-1(2H)-pyrazinyl]acetic acid hydrochloride

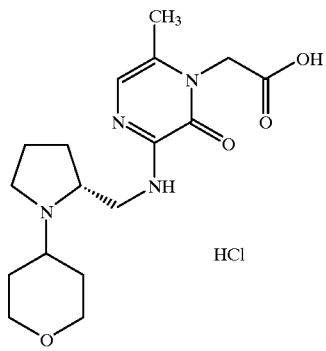

A mixture of benzyl 2-[3-chloro-2-methyl-6-oxo-5-({[(2R)-1-tetrahydro-2H-pyran-4-yl-2-pyrrolidinyl]methyl}amino)-1(6H)-pyrazinyl]acetate (preparation 158) (970 mg, 2.04 mmol) and palladium hydroxide (80 mg) in ethanol (8 ml) was hydrogenated at 15 psi and room temperature for 20 hrs. The reaction mixture was filtered through Whatman® fibre, and the filtrate evaporated under reduced pressure to give the desired compound, (680 mg, 95%).

LRMS: m/z=351 (M+1)$^+$.

EXAMPLE 37

2-[5-({[(2R,4R)-1-Cyclopentyl-4-methylpiperidinyl]methyl}amino)-2-methyl-6-oxo-1(6H)pyrazinyl]-N-(1H-indol-4-ylmethyl)acetamide

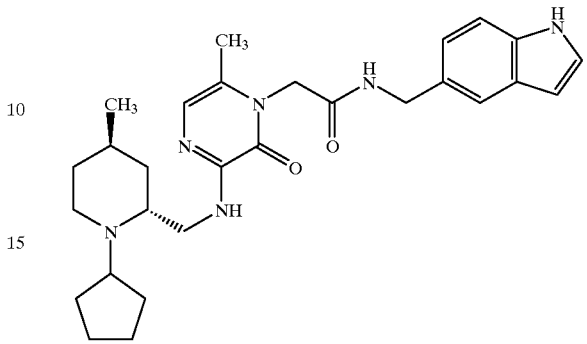

Preparation 160

N-(1H-Indol-5-ylmethyl)-2-[6-methyl-2-oxo-3-({[(2R)-1-tetrahydro-2H-pyran-4-yl-2-pyrrolidinyl]methylamino)-1(2H)-pyrazinyl]acetamide

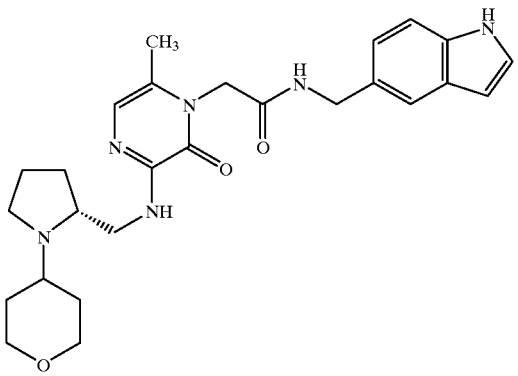

The title compound was obtained as a white powder (31%), from 2-[6-Methyl-2-oxo-3-({[(2R)-1-tetrahydro-2H-pyran-4-yl-2-pyrrolidinyl]methyl}amino)-1( 2H-pyrazinyl] acetic acid hydrochloride (preparation 159) and 1H-indol-5-ylmethylamine (preparation 8), using a similar procedure to that described in preparation 45.

$^1$H NMR (CDCl$_3$, 400 MHz) δ: 1.54–1.84 (m, 8H), 2.23 (s, 3H), 2.57 (m, 1H), 2.70 (m, 1H), 2.99 (m, 1H), 3.15 (m, 2H), 3.37 (m, 2H), 3.46 (m, 1H), 3.99 (m, 2H), 4.52 (d, 2H), 4.63 (s, 2H), 6.27 (s, br,1H), 6.52 (s, 1H), 6.59 (s, br,1H), 6.73 (s, 1H), 7.06 (d, 1H), 7.20 (s, 1H), 7.37 (d, 1H), 7.50 (s, 1H), 8.22 (s, br,1H). LRMS: m/z=478 (M)$^+$.

Preparation 161

Benzyl 2-[3-chloro-5-({[(2R,4R)-1-cyclopentyl-4-methylpiperidinyl]methyl}amino)-2-methyl-6-oxo-1(6H)-pyrazinyl]acetate

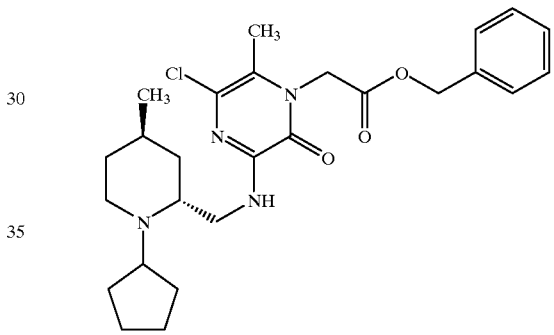

A mixture of (2R,4R)-4-methyl-2-piperidinecarboxamide (prepared as in preparation 86) (5.0 g, crude), cyclopentanone (3.1 ml, 35 mmol), sodium triacetoxyborohydride (9.5 g, 45.5 mmol) and acetic acid (2 ml, 35 mmol) in tetrahydrofuran (30 ml), was stirred at room temperature overnight. The reaction mixture was evaporated under reduced pressure, to give the crude carboxamide (6 g).

This intermediate (3 g) was suspended in tetrahydrofuran (20 ml), lithium aluminum hydride (17 ml, 1M in tetrahydrofuran, 17 mmol) added, and the reaction heated under reflux for 18 hrs. Water was added to the cooled reaction, the mixture dried over MgSO$_4$, and filtered, washing well with ethyl acetate. The combined filtrates were concentrated under reduced pressure and the residue re-dissolved in ethyl acetate (12 ml). Triethylamine (1.3 ml, 9 mmol) and benzyl 2-[3,5-dichloro-2-methyl-6-oxo-1(6H)-pyrazinyl]acetate (preparation 17), (2.0 g, 6.11 mmol) were added, and the reaction heated under reflux for 20 hrs. The cooled mixture was concentrated under reduced pressure and the residue purified by column chromatography on silica gel using ethyl acetate:pentane (5:95) as eluant to afford the title compound as a white solid, (850 mg, 12%).

$^1$H NMR (CDCl$_3$, 400 MHz) δ: 0.88 (d, 3H), 1.20–1.60 (m, 8H), 1.70 (m, 3H), 1.85 (m, 1H), 1.97 (m, 1H), 2.20 (s, 3H), 2.61 (m, 1H), 2.81 (m, 1H), 3.17 (m, 2H), 3.42 (m, 1H), 3.58 (m, 1H), 4.80 (s, 2H), 5.20 (s, 2H), 6.50 (s, br,1H), 7.36 (m, 5H) LRMS: m/z=487, 489 (M+1)$^+$.

Preparation 162

2-[5-({[(2R,4R)-1-Cyclopentyl-4-methylpiperidinyl]methyl}amino)-2-methyl-6-oxo-1(6H)-pyrazinyl-N-(1H-indol-4-ylmethyl)acetamide

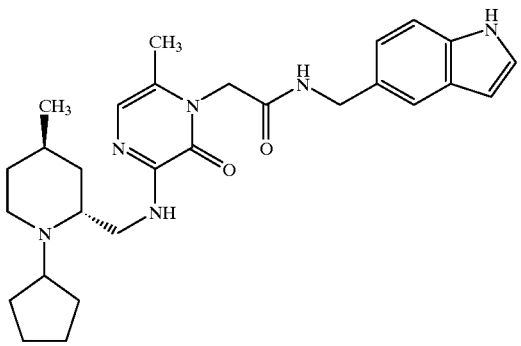

A mixture of benzyl 2-[3-chloro-5-({[(2R,4R)-1-cyclopentyl-4-methylpiperidinyl]methyl}amino)-2-methyl-6-oxo-1(6H)-pyrazinyl]acetate (preparation 161) (320 mg, 0.66 mmol), and palladium hydroxide (85 mg) in methanol (6 ml) was hydrogenated at 15 psi and room temperature overnight. The incomplete reaction was filtered, the filtrate evaporated under reduced pressure and the residue re-dissolved in methanol (8 ml). Palladium hydroxide (85 mg) was added and the reaction hydrogenated at 30 psi and room temperature overnight. The reaction mixture was filtered through Whatman® fibre, and the filtrate evaporated under reduced pressure to afford an oil, 200 mg, A mixture of 1H-indol-5-ylmethylamine (preparation 8) (85 mg, 0.56 mmol), HOBT (78 mg, 0.56 mmol), WSCDI·HCl (111 mg, 0.56 mmol) and N-methylmorpholine (96 ml, 0.87 mmol), were added to a solution of the intermediate acid in dichloromethane (6 ml), and the reaction stirred at room temperature for 20 hrs. The reaction mixture was loaded directly onto a silica column and purified using dichloromethane:methanol:0.88 ammonia 995:5;0.5) as eluant, to give the title compound as a white powder, (22 mg, 8%).

$^1$H NMR (CDCl$_3$, 400 MHz) δ: 0.86 (d, 3H), 1.20–1.99 (m, 13H), 2.28 (s, 3H), 2.60 (m, 1H), 2.81 (m, 1H), 3.16 (m, 2H), 3.40 (m, 1H), 3.55 (m, 1H), 4.50 (d, 2H), 4.63 (m, 2H), 6.42 (s, br, 1H), 6.52 (m, 2H), 7.04 (d, 1H), 7.20 (m, 1H), 7.35 (d, 1H), 7.50 (s, 1H), 8.24 (s, br,1H).

EXAMPLE 38

N-(1H-Benzimidazol-6-ylmethyl)-2-[3-({[(2R)-1-isobutylpyrrolidinyl]methyl}amino)-6-methyl-2-oxo-1(2H)-pyrazinyl]acetamide

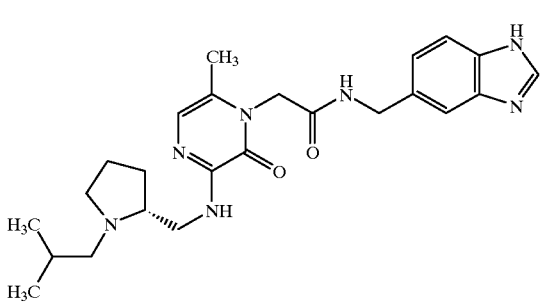

Preparation 163

N-(1H-Benzimidazol-6-ylmethyl)-2-[3-({([(2R)-1-isobutylpyrrolidinyl]methyl}amino)-6-methyl-2-oxo-1(2H)-pyrazinyl]acetamide

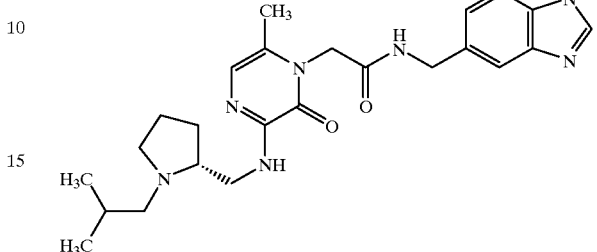

HOBT (25 mg, 0.19 mmol), WSCDI.HCl (31 mg, 0.16 mmol), N-methylmorpholine (41 ml, 0.37 mmol) and 1H-benzimidazol-6-ylmethylamine (21 mg, 0.1 4 mmol) were added to a solution of 2-[3-({[(2R)-1-isobutylpyrrolidinyl]methyl}amino)-6-methyl-2-oxo-1(2H)-pyrazinyl]acetic acid (preparation 62) (40 mg, 0.12 mmol) in N,N-dimethylformamide (2 ml), and the reaction was stirred at room temperature overnight. The mixture was evaporated under reduced pressure and the residue preadsorbed on to silica gel, and then purified by column chromatography on silica gel using dichloromethane:methanol:0.88 ammonia (95:5:0.5) as eluant to provide the title compound (6 mg, 10%).

$^1$H NMR (CDCl$_3$, 400 MHz) δ: 0.82 (d, 3H), 0.87 (d, 3H), 1.52–1.84 (m, 5H), 2.07 (m, 2H), 2.22 (s, 3H), 2.30 (m, 1H), 2.60 (m, 1H), 3.14 (m, 1H), 3.20 (m, 1H), 3.48 (m, 1H), 4.53 (m, 2H), 4.62 4.78 (m, 2H), 6.40 (s, br,1H), 6.74 (s, 1H), 7.10 (m, 2H), 7.28–7.70 (m, 2H), 8.00 (s, 1H). LRMS: m/z 452 (M+1)$^+$.

EXAMPLE 39

N-(1H-Benzimidazol-6-ylmethyl)-2-[3-({[(2R)-1-cyclopentylpyrrolidinyl]methyl}amino)-6-methyl-2-oxo-1(2H)-pyrazinyl]acetamide

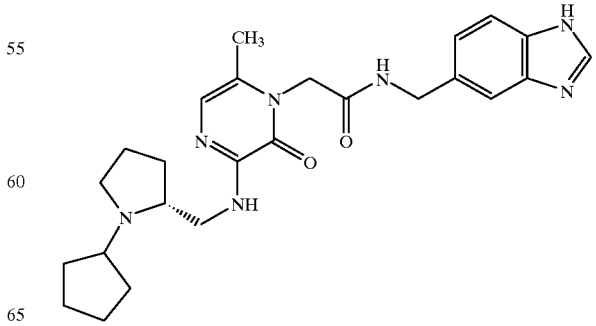

Preparation 164

N-(1H-Benzimidazol-6-ylmethyl)-2-[3-({[(2R)-1-cyclopentylpyrrolidinyl]methyl}amino)-6-methyl-2-oxo-1(2H)-pyrazinyl]acetamide

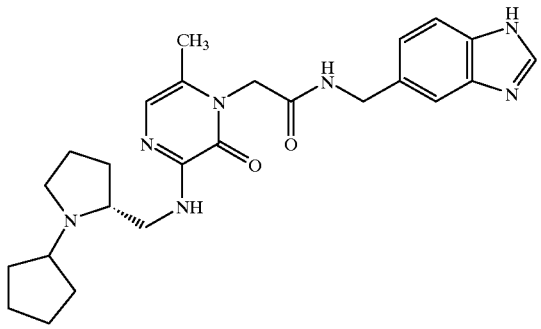

The title compound as obtained as a white foam (42%) from 2-[3-({[(2R)-1-cyclopentyl-2-pyrrolidinyl] methyl}amino)-6-methyl-2-oxo-1(2H)-pyrazinyl]acetic acid hydrochloride (preparation 145) and 1H-benzimidazol-6-ylmethylamine following the procedure described in preparation 163.

$^1$H NMR (CDCl$_3$, 400 MHz) δ: 1.40–1.92 (m, 10H), 2.21 (s, 3H), 2.38 (m, 1H), 2.50 (m, 1H), 2.92 (m, 1H), 3.00 (m, 2H), 3.20 (m, 2H), 3.42 (m, 1H), 4.54 (d, 2H), 4.66 (s, 2H), 6.35 (s, br,1H), 6.69 (s, 1H), 7.04–7.20 (m, 2H), 7.38–7.60 (m, 2H), 7.98 (s, 1H). LRMS: m/z=463 (M+1)$^+$.

Abbreviations

DIBAL Diisobutylaluminium hydride
HOBT 1-Hydroxybenzotriazole hydrate
LRMS Low resolution mass spectroscopy
TFA Trifluoroacetic acid
TMSCN Trimethylsilyl cyanide
WSCDI.HCl 1-(3-Dimethylaminopropyl)-3-ethylcarbodiimide hydrochloride The biological activities of the compounds of the present invention were determined by the following test methods.

Chromogenic Assays

The inhibition of thrombin, trypsin, plasmin or factor Xa is measured in 96 well plate chromogenic assays. The percentage inhibition and IC$_{50}$ are calculated from triplicate samples of an 8 concentration dose-response curve. From the substrate Km and IC$_{50}$, the Ki for each inhibitor is calculated. All assays are carried out in a total incubation of 200 μl of 50 mM HEPES and 150 mM NaCl at pH 8.0, and all compound dilutions are preincubated with enzyme at room temperature for 15 minutes prior to addition of substrate. After 30 minutes incubation at 30° C., the O.D. is measured at 405 nM in a 96 well plate reader. Thrombin activity is measured using bovine thrombin and S2238 (H-D-Phe-Pip-Arg-pNA), bovine pancreatic trypsin is assayed with S2222 (Benz-Isoleu-Glu-Gly-Arg-pNA), bovine plasma plasmin is assayed with Chromozym PL (Tosyl-Gly-Pro-Lys-pNA) and bovine factor Xa is assayed in 50 mM Tris, 150 mM NaCl, pH 7.5 buffer with S2222.

Clotting Assays

Thrombin time (TT) and activated partial thromboplastin time (APTT) are measured using Instrumentation Laboratories (IL) Test TT reagent and IL Test APTT (ellagic acid) reagent respectively in an Automated Coagulation Laboratory (ACL), according to the manufacturer's instructions.

In Vitro

To 1 ml aliquots of rat pooled plasma (citrated), a $^1/_{100}$ volume of a range of compound concentrations is added and the resulting mixtures preincubated at room temperature for 15 minutes, after which the TT and APTT are measured.

Ex Vivo

Compounds are dosed per os, intravenously or intraduodenally to rats. Pre- and post-dose blood samples are taken into citrate solution and plasma prepared. TT and APTT are measured as for in vitro assays.

All compounds specifically exemplified exhibited measured in vitro inhibitory activities against thrombin with Ki<3×10$^{-7}$ M and in vitro inhibitory potency versus trypsin with Ki>1×10$^{-5}$ M

What is claimed is:

1. A compound of formula 1

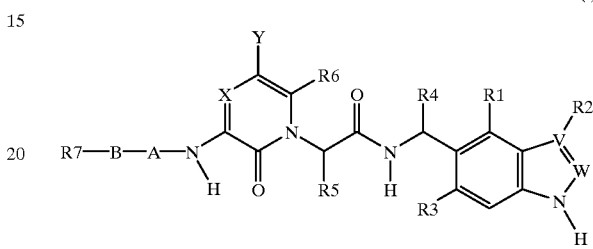

(I)

wherein:

$R^1$ is hydrogen, C$_1$–C$_4$ alkyl, perfluoro C$_1$–C$_4$ alkyl, OC$_1$–C$_4$ alkyl, fluoro or chloro;

$R^2$ is hydrogen, CH$_3$, or CF$_3$;

$R^3$ is hydrogen, C$_1$–C$_4$ alkyl, perfluoro C$_1$–C$_4$alkyl, OC$_1$–C$_4$ alkyl, fluoro or chloro;

$R^4$ is hydrogen, C$_1$–C$_4$ alkyl;

$R^5$ is hydrogen or C$_1$–C$_4$ alkyl;

$R^6$ is hydrogen, fluoro or chloro;

C$_1$–C$_6$ alkyl, C$_3$–C$_6$ carbocyclic, C$_3$–C$_6$ carbocyclic, or C$_1$–C$_4$ alkyl wherein the alkyl and carbocyclic may optionally be substiututed by C$_1$–C$_4$ alkyl or fluoro, and wherein the carbocycle contains zero, one or more double bonds;

or $R^5$ and $R^6$ together form a bridging chain containing 2 or 3 carbon atoms;

Y is hydrogen, chloro, fluoro, bromo, methyl or CF$_3$;

V is C or N;

W is CH, CF, CCl, or N, and X is N;

B—A— is any one of the following fragments:
B—C(R$^8$)(R$^9$)—
B—CH$_2$—C(R$^8$)(R$^9$)—
B—C(R$^8$)(R$^9$)—CH$_2$—
B—CH$_2$—(R$^8$)(R$^9$)—CH$_2$—
B—C(R$^8$)(R$^9$)—CH$_2$—CH$_2$—
B—CH$_2$—CH$_2$—C(R$^8$)(R$^9$)— wherein:
$R^8$ and $R^9$ are independently hydrogen, —(CH$_2$)$_m$N(R$^{10}$)(R$^{11}$), —CH$_2$O—(CH$_2$)$_2$N(R$^{10}$)(R$^{11}$), or $R^8$ and $R^9$ together form a 4 to 6 membered ring containing N(R$^{12}$); and m is 0, 1 and 2 except where A represents —C(R$^8$)(R$^9$)— when m is 1 or 2;

$R^{10}$ and $R^{11}$ are independently selected from hydrogen or C$_1$–C$_4$ alkyl optionally containing an oxygen in the chain or at the end of the chain;

or $R^{10}$ and $R^{11}$ together with the nitrogen atom to which they are bonded form a 4 to 6 membered saturated heterocyclic ring wherein when the ring is six membered it may optionally contain one oxygen or an additional nitrogen atom present as N(R$^{12}$);

$R^{12}$ is hydrogen or $C_1$–$C_4$ alkyl optionally containing an oxygen atom in the chain or at the end of the chain;

B is phenyl or a 5 to 6 membered aromatic heterocyclic ring containing up to two heteroatoms independently selected from oxygen, sulphur and nitrogen; when B is phenyl or an aromatic heterocycle, $R^7$ is one or more of hydrogen, $C_1$–$C_6$ alkyl, perfluoro $C_1$–$C_6$ alkyl, $OC_1$–$C_6$ alkyl perfluoro $OC_1$–$C_6$ alkyl, fluoro, chloro, or any one of the following fragments:

$(CH_2)_p$—O—$(CH_2)_2N(R^{10})(R^{11})$ where $R^{10}$ and $R^{11}$ are as defined above, p is 0 or 1;

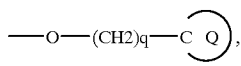

where Q, together with the C atom to which it is joined, is a 5 or 6 membered heterocyclic ring containing one nitrogen atom, said heterocyclic ring being optionally substituted by $C_1$–$C_4$ alkyl, and q is 1 or 2;

—$(CH_2)_r$—$C(R^{13})(R^{14})$—$(CH_2)_s$—$N(R^{15})(R^{16})$ where r and s are independently=0, 1 or 2 $R^{13}$ and $R^{14}$ are independently hydrogen or $C_1$–$C_4$ alkyl optionally containing one oxygen atom in the chain or at the end of the chain, or $R^{13}$ and $R^{14}$ together with the carbon atom to which they are bonded form a 4 to 6 membered carbocyclic saturated ring;

$R^{15}$ and $R^{16}$ are independently selected from hydrogen or $C_1$–$C_4$ alkyl optionally containing an oxygen atom in the chain or at the end of the chain, or $R^{15}$ and $R^{16}$ together with the nitrogen atom to which they are bonded form a 4 to 6 membered saturated heterocyclic ring;

or one of $R^{13}$ or $R^{14}$ and one of $R^{15}$ or $R^{16}$ together with the carbon and nitrogen atoms to which they are bonded form a 4 to 6 membered saturated heterocyclic ring in which case the other of $R^{13}$ or $R^{14}$ is hydrogen or $C_1$–$C_4$ alkyl, and the others of $R^{15}$ or $R^{16}$ is hydrogen or $C_1$–$C_4$ alkyl optionally containing an oxygen atom in the chain or at the end of the chain;

or wherein $R^7$—B represents the following bicyclic fragments where $R^{12}$ is as defined above

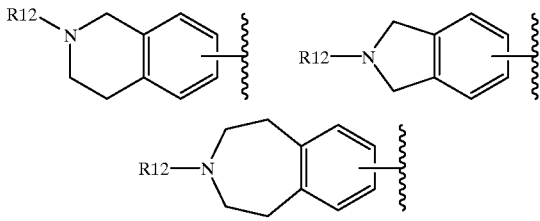

with the proviso that $R^7$, $R^8$ and $R^9$ cannot all be hydrogen, and only one of $R^7$, $R^8$ and $R^9$ contains one nitrogen atom or, when $R^8$ and $R^9$ together form a ring, said ring contains only one nitrogen atom with the proviso that one of $R^8$ or $R^9$ may be the following fragment which contains two nitrogen atoms:

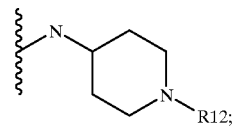

or, B is a 4 to 7 membered saturated or partially saturated heterocyclic ring containing one or two heteroatoms wherein at least one is a nitrogen and the other is independently selected from oxygen, sulphur and nitrogen; and wherein B is a saturated or partially saturated heterocycle, $R^7$ is one or more of $C_1$–$C_6$ alkyl or $C_1$–$C_6$ carbocyclic or $C_3$–$C_6$ carbocyclic $C_1$–$C_4$ alkyl said carbocyclic containing zero, one or more double bonds wherein said alkyl and cycloalkyl optionally contain one heteratom selected from oxygen, sulphur and nitrogen and are further optionally substituted by one or more fluoro, or $C_1$–$C_4$ alkyl optionally containing an oxygen in the alkyl chain or at the end of the chain;

and pharmaceutically acceptable salts thereof.

2. A compound as claimed in claim 1 wherein $R^1$ is hydrogen or methyl.

3. A compound a claimed in claims 1 or 2 wherein $R^2$ is hydrogen or methyl.

4. A compound as claimed in claim 1 wherein $R^3$ is hydrogen or methyl.

5. A compound as claimed in claim 1 wherein $R^4$ is hydrogen.

6. A compound as claimed in claim 1 wherein $R^5$ is hydrogen.

7. A compound as claimed in claim 1 wherein $R^6$ is $C_1$–$C_6$ alkyl, $C_3$–$C_6$ carbocyclic optionally substituted by fluoro, or $R^5$ and $R^6$ together form a bridging chain containing 2 or 3 carbon atoms.

8. A compound as claimed in claim 1 wherein Y is hydrogen, chloro or bromo.

9. A compound as claimed in claim 1 wherein W is CH or N.

10. A compound as claimed in claim 1 wherein B—A— represents B—$CH_2$–$C(R^8)(R^9)$ where $R^8$ and $R^9$ are independently hydrogen, —$(CH_2)_mN(R^{10})(R^{11})$, —$CH_2O$—$(CH_2)_2N(R^{10})(R^{11})$, or $R^8$ and $R^9$ together form a 4 to 6 membered ring containing $N(R^{12})$ and m is 0, 1 and 2 except where A represents —$C(R^8)(R^9)$— when m is 1 or 2.

11. A compound as claimed in claim 10 wherein when C* is chiral, then B—$CH_2$—$C^*(R^8)(R^9)$ represents the S-enantiomer.

12. A compound as claimed in claim 10 wherein B is phenyl.

13. A compound as claimed in claim 1 wherein m is 1.

14. A compound as claimed in claim 1 wherein $R^{10}$ and $R^{11}$ independently represent hydrogen, $C_1$–$C_4$ alkyl optionally containing an oxygen atom in the chain, or $R^{10}$ and $R^{11}$ together with the nitrogen to which they are bonded form a 5 to 6 membered heterocyclic ring wherein when the ring is six membered it optionally contains one oxygen or a nitrogen atom.

15. A compound as claimed in claim 1 wherein $R^{12}$ is hydrogen or $C_1$–$C_4$ alkyl optionally containing an oxygen atom in the chain or at the end of the chain.

16. A compound as claimed in claim 1 wherein B is phenyl or a six membered aromatic heterocyclic ring containing one nitrogen atom, wherein said phenyl or heterocyclic ring may be substituted by fluoro, chloro, $C_1$–$C_4$ alkyl or $OC_1$–$C_4$ alkyl.

17. A compound as claimed in claim 1 wherein B is phenyl $R^7$ is —$(CH_2)_r$—$C(R^{13})(R^{14})$—$(CH_2)_s$—$N(R^{15})(R^{16})$ wherein r, s, and $R^{13}$ to $R^{16}$ are define in claim 1.

18. A compound as claimed in claim 1 wherein B is a saturated or partially saturated 4 to 7 membered heterocyclic ring containing one or two heteroatoms wherein at least one is nitrogen and the other is independently selected from oxygen, sulphur and nitrogen; and $R^7$ is $R^{17}$ which is substituted on the nitrogen of the heterocyclic ring and is selected from one or more of $C_1$–$C_6$ alkyl, $C_3$–$C_6$ carbocyclic or $C_3$–$C_6$ carbocyclic $C_1$–$C_4$ alkyl, said carbocyclic containing zero, one or more double bonds wherein said alkyl and carbocyclic optionally contain one heteroatom selected from oxygen, sulphur and nitrogen and are further optionally substituted by one or more fluoro, or $C_1$–$C_4$ alkyl optionally containing an oxygen in the alkyl chain or at the end of the chain.

19. A compound as claimed in claim 18 wherein the saturated or partially saturated heterocyclic ring is furthermore optionally substituted by $R^{18}$ which is independently selected from one or more of $C_1$–$C_6$ alkyl and perfluoro $C_1$–$C_6$ alkyl wherein said alkyl optionally contains an oxygen atom in the chain or at the end of the chain.

20. A compound as claimed in claim 18 wherein $R_{17}$ is cyclopropylmethyl.

21. A compound as claimed in claim 18 wherein the heterocyclic ring is a 5 to 6 membered saturated heterocyclic ring.

22. A compound as claimed in claim 18 wherein B—A is B—$C(R^8)(R^9)$.

23. A compound as claimed in claim 1 wherein $R^7$—B—A is selected from the following radicals:

(a)

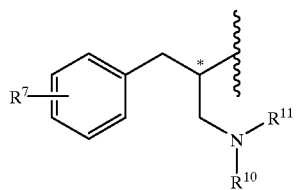

wherein R10 and R11 are as defined in claim 1 and R7 is hydrogen, C1–C4 alkyl, perfluoro C1–C4 alkyl, OC1–C4 alkyl, perfluoro OC1–C4 alkyl, fluoro or chloro;

(b)

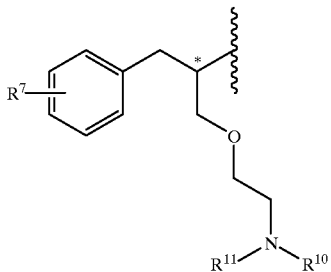

wherein R10 and R11 are as defined in claim 1;

(c)

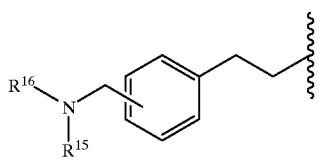

wherein R15 and R16 are as defined in claim 1;

(d)

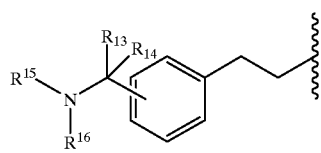

wherein R13 to R16 are as defined in claim 1;

(e)

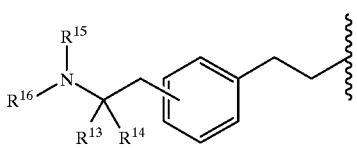

wherein R13 to R16 are as defined in claim 1;

(f)

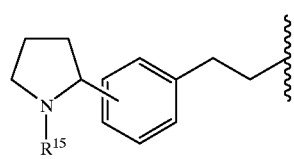

wherein R15 is hydrogen or C1–C4 alkyl optionally containing oxygen in the chain or at the end of the chain;

(g)

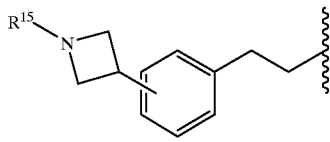

wherein R15 is hydrogen or C1–C4 alkyl optionally containing oxygen in the chain or at the end of the chain; and (h)

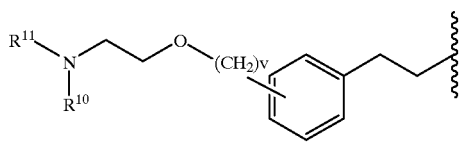

wherein R10 and R11 are as defined in claim 1, and v is 0 or 1;

(i)

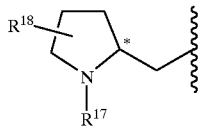

(j)

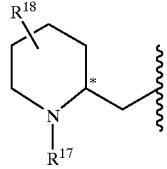

(k)
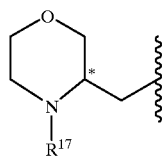
Wherein R17 and R18 in (i), (j) and (k) are as defined in claims 19 to 21.
24. A compound as claimed in claim 23 wherein radical (a) to (k) is selected from:
radical (a)
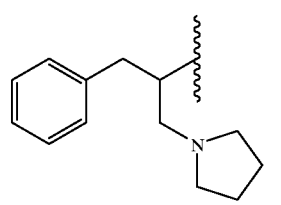
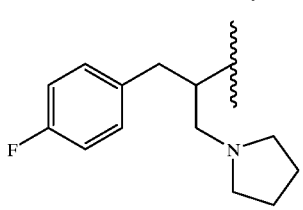
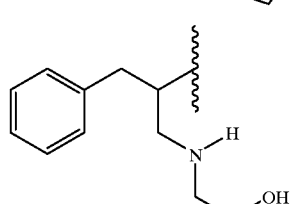
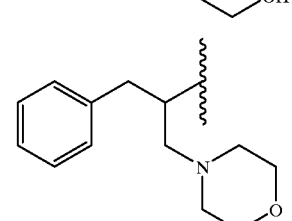
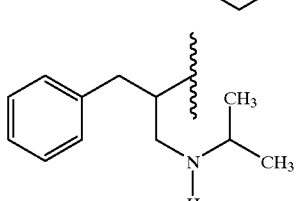
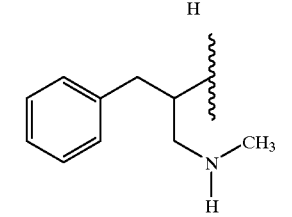
radical (b)
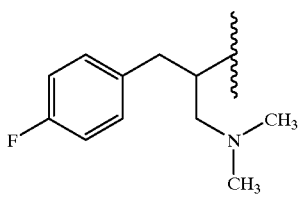
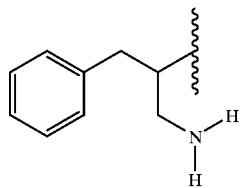
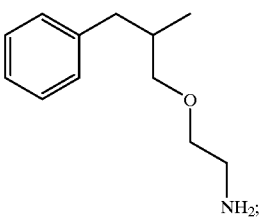
radical (c)
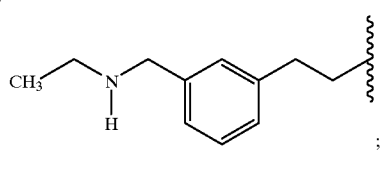
;
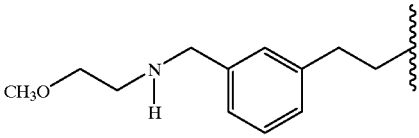
;
;
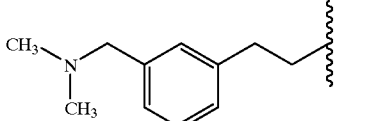
;
radical (d)
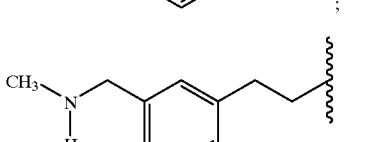
;
radical (e)
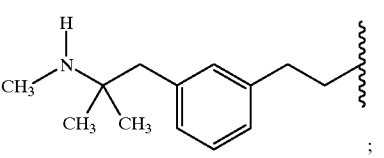
;

-continued radical (f)

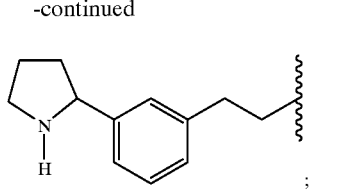

radical (g)

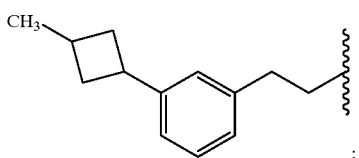

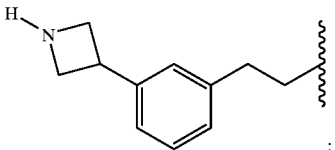

radical (h)

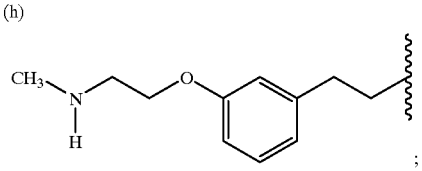

radical (i)

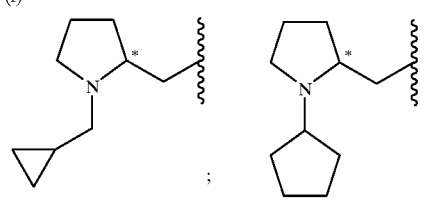

radical (j)

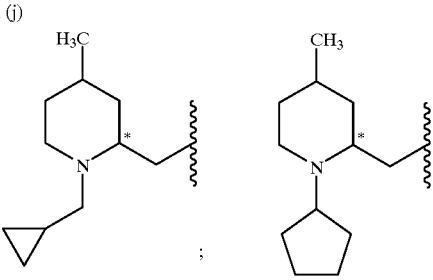

radical (k)

25. A compound as claimed in claim 1 selected from the group consisting of:

2-[3-(3-[(dimethylamino)methyl]phenethylamino)-6-methyl-2-oxo-1(2H)-pyrazinyl]-N-(1H-indol-5-ylmethyl)acetamide;

2-[3-chloro-5-(3-[(dimethylamino)methyl]phenethylamino)-2-methyl-6-oxo-1(6H)-pyrazinyl]-N-(1H-indol-5-ylmethyl)acetamide;

2-[3-[(1S)-1-benzyl-2-(dimethylamino)ethyl]amino-6-methyl-2-oxo-1(2H)-pyrazinyl]-N-(1H-indol-5-ylmethyl)acetamide;

2-[3-[(1S)-1-benzyl-2-(dimethylamino)ethyl]amino-5-chloro-6-methyl-2-oxo-1(2H)-pyrazinyl]-N-(1H-indol-5-ylmethyl)acetamide;

2-[3-{[(2R,S)-3-(dimethylamino)-2-phenylpropyl]amino}-6-methyl-2-oxo-1(2H)-pyrazinyl]-N-(1H-indol-5-ylmethyl)acetamide;

N-[(3-Methyl-1H-indol-5-yl)methyl]-2-[6-methyl-3-([3-[(methylamino)methyl]phenethyl]amino)-2-oxo-1(2H)-pyrazinyl]acetamide;

2-[3-{[(1S)-1-benzyl-2-(dimethylamino)ethyl]amino}-6-methyl-2-oxo-1(2H)-pyrazinyl]-N-[(6-methyl-1H-indazol-5-yl)methyl]acetamide;

2-[3-{[3-(3-azetidinyl)phenethyl]amino}-6-methyl-2-oxo-1(2H)-pyrazinyl]-N-[(3methyl-1H-indol-5-yl)methyl]acetamide;

N-[(3-methyl-1H-indol-5-yl)methyl]-2-[6-methyl-3-{[3-(1-methyl-3-azetidinyl)phenethyl]amino}-2-oxo-1(2H)-pyrazinyl]acetamide;

2-[3-[(3-{[(2-methoxyethyl)amino]methyl}phenethyl)amino]-6-methyl-2-oxo-1(2H)-pyrazinyl]-N-[(3-methyl-1H-indol-5-yl)methyl]acetamide;

2-[3-({[(2R)-1-(cyclopropylmethyl)pyrrolidinyl]methyl}amino)-6-methyl-2-oxo-1(2H)-pyrazinyl]-N-[(3-methyl-1H-indol-5-yl)methyl]acetamide;

2-[3-({[(2R)-1-cyclopentyl pyrrolidinyl]methyl}amino)-6-methyl-2-oxo-1(2H)-pyrazinyl]-N-[(3-methyl-1H-indol-5-yl)methyl]acetamide;

N-[(3-methyl-1H-indol-5-yl)methyl]-2-[6-methyl-2-oxo-3-({[(2R)-1-tetrahydro-2H-pyran-4-ylpyrrolidinyl]methyl}amino)-1(2H)-pyrazinyl]acetamide;

N-[(3-methyl-1H-indol-5-yl)methyl]-2-[6-methyl-3-[({(2R)-1-[(1-methylcyclopropyl)methyl]pyrrolidinyl}methyl)amino]-2-oxo-1(2H)-pyrazinyl]acetamide;

2-[3-({[(2R)-1-(2-methoxyethyl)pyrrolidinyl]methyl}amino)-6-methyl-2-oxo-1(2)H-pyrazinyl]-N-[(3-methyl-1H-indol-5-yl)methyl]acetamide;

N-[(3-methyl-1H-indol-5-yl)methyl]-2-[6-methyl-3-({[(2R)-1-neopentylpyrrolidinyl]methyl}amino)-2-oxo-1(2H)-pyrazinyl]acetamide;

2-[3-({[(2R)-1-isobutylpyrrolidinyl]methyl}amino)-6-methyl-2-oxo-1(2H)-pyrazinyl]-N-[(3-methyl-1H-indol-5-yl)methyl]acetamide;

2-[3-({[(2R)-1-(2-methoxyethyl)pyrrolidinyl]methyl}amino)-6-methyl-2-oxo-1(2H)-pyrazinyl]-N-[(3-methyl-1H-indol-5-yl)methyl]acetamide;

2-[3-({[(2R)-1-cyclopentyl pyrrolidinyl]methyl}amino)-6-methyl-2-oxo-1(2H)-pyraziny]-N-[(3-methyl-1H-indol-5-yl)methyl]acetamide;

2-[3-({[(2R)-1-(cyclopropylmethyl)piperidinyl]methyl}amino)-6-methyl-2-oxo-1(2H)-pyrazinyl]-N-[(3-methyl-1H-indol-5-yl)methyl]acetamide;

and pharmaceutically acceptable salts thereof.

26. A compound as claimed in claim 26 selected from the group consisting of:

2-[3-(3-[(dimethylamino)methyl]phenethylamino)-6-methyl-2-oxo-1(2H)-pyrazinyl]-N-(1H-indol-5-ylmethyl)acetamide;

2-[3-[(1S)-1-benzyl-2-(dimethylamino)ethyl]amino-6-methyl-2-oxo-1(2H)-pyrazinyl]-N-(1H-indol-5-ylmethyl)acetamide;

N-[(3-Methyl-1H-indol-5-yl)methyl]-2-[6-methyl-3-([3-[(methylamino)methyl]phenethyl]amino)-2-oxo-1(2H)-pyrazinyl]acetamide;

2-[3-[(3-[(2-methoxyethyl)amino]methyl}phenethyl)
amino]-6-methyl-2-oxo-1(2H)-pyrazinyl]-N-[(3-
methyl-1H-indol-5-yl)methyl]acetamide;

2-[3-({[(2R)-1-(cyclopropylmethyl)pyrrolidinyl]
methyl}amino)-6-methyl-2-oxo-1(2H)-pyrazinyl]-N-
[(3-methyl-1H-indol-5-yl)methyl]acetamide;

2-[3-({[(2R)-1-cyclopentyl pyrrolidinyl]methyl}amino)-
6-methyl-2-oxo-1(2H)-pyrazinyl]-N-[(3-methyl-1H-
indol-5-yl)methyl]acetamide;

2-[3-({[(2R)-1-isobutylpyrrolidinyl]methyl}amino)-6-
methyl-2-oxo-1(2H)-pyrazinyl]-N-[(3-methyl-1H-
indol-5-yl)methyl]acetamide;

and pharmaceutically acceptable salts thereof.

27. A pharmaceutical composition comprising a compound of formula (1) or a pharmaceutically acceptable salt thereof as claimed in claim 1 together with a pharmaceutically acceptable carrier.

28. A compound of a formula (I) or a pharmaceutically acceptable salt thereof as claimed in claim 1 for use in medicine.

29. A method of treating a mammal for deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts restenosis and occlusion following angioplasty; neurodegenerative disorders; inflammatory disorders; or scarring; which comprises treating said mammal with an effective amount of a compound of formula (I) or a pharmaceutically acceptable salt thereof as claimed claim 1.

* * * * *